United States Patent
Fukushima et al.

(10) Patent No.: US 9,793,486 B2
(45) Date of Patent: Oct. 17, 2017

(54) POLYMER COMPOUND AND LIGHT-EMITTING ELEMENT USING THE SAME

(75) Inventors: Daisuke Fukushima, Tsukuba (JP); Tomoyasu Yoshida, Tsukuba (JP); Yoshihiro Kawada, Tsukuba (JP); Takashi Kuragano, Tsukuba (JP); Makoto Anryu, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 1005 days.

(21) Appl. No.: 14/006,977

(22) PCT Filed: Mar. 16, 2012

(86) PCT No.: PCT/JP2012/057658
§ 371 (c)(1),
(2), (4) Date: Sep. 24, 2013

(87) PCT Pub. No.: WO2012/133256
PCT Pub. Date: Oct. 4, 2012

(65) Prior Publication Data
US 2014/0014935 A1 Jan. 16, 2014

(30) Foreign Application Priority Data
Mar. 25, 2011 (JP) .................. 2011-067565

(51) Int. Cl.
| H01L 51/00 | (2006.01) |
| C07C 17/093 | (2006.01) |
| C08G 61/12 | (2006.01) |
| C09D 165/00 | (2006.01) |
| C07C 17/16 | (2006.01) |
| C07C 17/263 | (2006.01) |
| C07C 17/32 | (2006.01) |
| C07F 5/02 | (2006.01) |
| H01L 51/50 | (2006.01) |

(52) U.S. Cl.
CPC ........ *H01L 51/0043* (2013.01); *C07C 17/093* (2013.01); *C07C 17/16* (2013.01); *C07C 17/263* (2013.01); *C07C 17/32* (2013.01); *C07F 5/025* (2013.01); *C08G 61/12* (2013.01); *C08G 61/122* (2013.01); *C09D 165/00* (2013.01); *H01L 51/0035* (2013.01); *H01L 51/0039* (2013.01); *C07C 2602/06* (2017.05); *C07C 2603/18* (2017.05); *C08G 2261/124* (2013.01); *C08G 2261/314* (2013.01); *C08G 2261/3142* (2013.01); *C08G 2261/3162* (2013.01); *C08G 2261/3245* (2013.01); *C08G 2261/5222* (2013.01); *C08G 2261/95* (2013.01); *H01L 51/5012* (2013.01)

(58) Field of Classification Search
CPC .................................................. H01L 51/0043
See application file for complete search history.

(56) References Cited

U.S. PATENT DOCUMENTS

| 4,709,006 A | 11/1987 | Tsai et al. |
| 6,297,351 B1 | 10/2001 | Murayama et al. |
| 6,361,887 B1 | 3/2002 | Shi et al. |
| 2002/0122899 A1* | 9/2002 | Doi .......... C09K 11/06 428/1.1 |
| 2003/0092878 A1 | 5/2003 | Sato et al. |
| 2004/0062930 A1 | 4/2004 | Roberts et al. |
| 2010/0289014 A1 | 11/2010 | Ito et al. |
| 2013/0112966 A1 | 5/2013 | Sassa |
| 2013/0122625 A1 | 5/2013 | Sassa et al. |

FOREIGN PATENT DOCUMENTS

| CN | 1777629 A | 5/2006 |
| CN | 1863838 A | 11/2006 |
| CN | 1946758 A | 4/2007 |
| CN | 101511904 A | 8/2009 |
| JP | 2001-181619 A | 7/2001 |
| JP | 2002-356674 A | 12/2002 |

(Continued)

OTHER PUBLICATIONS

Office Action dated Nov. 13, 2015 in CN Application No. 201280023927.6.
Office Action dated Mar. 18, 2015 in CN Application No. 201280023927.6.
Office Action dated May 25, 2015 in TW Application No. 101110059.
Int'l Search Report dated Jun. 26, 2012 in Int'l Application No. PCT/JP2012/057658.
Bai et al, "New Carbon Dioxide-Selective Membranes Based on Sulfonated Polybenzimidazole (SPBI) Copolymer Matrix for Fuel Cell Applications," Ind. Eng. Chem. Res., vol. 48, pp. 2344-2354 (2009).

*Primary Examiner* — Robert Vetere
(74) *Attorney, Agent, or Firm* — Panitch Schwarze Belisario & Nadel LLP

(57) ABSTRACT

A polymer compound is provided having a constitutional unit represented by the following formula (1):

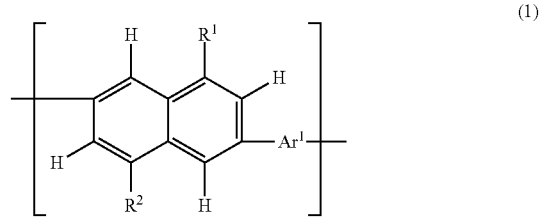

wherein: $R^1$ and $R^2$ represent an alkyl group, an aryl group, a mono-valent aromatic heterocyclic group, an alkoxy group or an aryloxy group, and $Ar^1$ represents an arylene group or a di-valent condensed polycyclic aromatic heterocyclic group.

18 Claims, No Drawings

(56) References Cited

FOREIGN PATENT DOCUMENTS

| | | | |
|---|---|---|---|
| JP | 2003-183362 A | | 7/2003 |
| JP | 2009-057307 A | | 3/2009 |
| JP | 2009057307 A | * | 3/2009 |
| JP | 2010-143841 A | | 7/2010 |
| TW | 555833 B | | 10/2003 |
| WO | 2012011418 A1 | | 1/2012 |
| WO | 2012011441 A1 | | 1/2012 |

* cited by examiner

POLYMER COMPOUND AND LIGHT-EMITTING ELEMENT USING THE SAME

CROSS-REFERENCE TO RELATED APPLICATION

This application is a Section 371 of International Application No. PCT/JP2012/057658, filed Mar. 16, 2012, which was published in the Japanese language on Oct. 4, 2012, under International Publication No. WO 2012/133256 A1, and the disclosure of which is incorporated herein by reference.

TECHNICAL FIELD

The present invention relates to a polymer compound, more particularly a naphthalene polymer compound and a light emitting device using the same.

BACKGROUND ART

Light emitting devices such as organic electroluminescent devices and the like are suitable for use in displays and the like owing to properties such as driving at low voltage, high luminance and the like, and recently attract attention. For production of this light emitting device, light emitting materials and charge transporting materials are used. As the light emitting material and the charge transporting material, there is a suggestion, for example, on polymer compounds containing a constitutional unit derived from unsubstituted naphthalene, a constitutional unit derived from naphthalene in which the 1,5-position is substituted by a hexyloxy group or a constitutional unit derived from naphthalene in which the 1,5-position is substituted by a methyloctyloxyphenyl group (JP-A No. 2002-356674).

SUMMARY OF THE INVENTION

However, when the above-described polymer compound is used in fabrication of a light emitting device, the resulting light emitting device shows no sufficient luminance life.

Then, the present invention has an object of providing a polymer compound which, when used in alight emitting device, gives excellent luminance life of the resulting light emitting device.

In a first aspect, the present invention provides a polymer compound comprising a constitutional unit represented by the following formula (1).

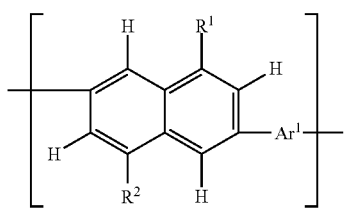

(in the formula (1), $R^1$ and $R^2$ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.

$Ar^1$ represents an unsubstituted or substituted arylene group, an unsubstituted or substituted di-valent condensed polycyclic aromatic heterocyclic group or a di-valent aromatic amine residue represented by the following formula (2).

Here, the skeleton of a ring linked to a naphthalene ring in the above-described unsubstituted or substituted di-valent condensed polycyclic aromatic heterocyclic group consists only of carbon atoms.)

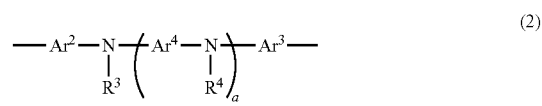

(in the formula (2), $Ar^2$, $Ar^3$ and $Ar^4$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups.

$R^3$ and $R^4$ represent each independently a hydrogen atom, an unsubstituted or substituted alkyl group, an unsubstituted or substituted aryl group or an unsubstituted or substituted mono-valent aromatic heterocyclic group.

a is 0 or 1.).

In a second aspect, the present invention provides a composition comprising at least one material selected from the group consisting of hole transporting materials, electron transporting materials and light emitting materials, and the above-described polymer compound.

In a third aspect, the present invention provides a liquid composition comprising the above-described polymer compound and a solvent.

In a fourth aspect, the present invention provides a film comprising the above-described polymer compound.

In a fifth aspect, the present invention provides a light emitting device having electrodes consisting of an anode and a cathode, and a layer containing the above-described polymer compound disposed between the electrodes.

In a sixth aspect, the present invention provides a compound represented by the following formula (a).

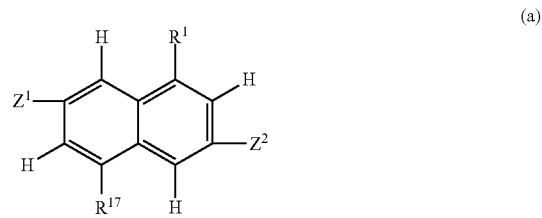

(in the formula (a), $R^1$ represents the same meaning as described above.

$R^{17}$ represents a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.

$Z^1$ and $Z^2$ represent each independently a borate residue or a boric acid residue.).

In a seventh aspect, the present invention provides a compound represented by the following formula (b).

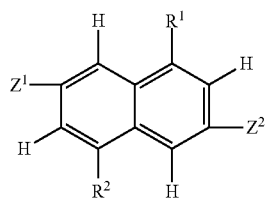

(in the formula (b), $R^1$, $R^2$, $Z^1$ and $Z^2$ represent the same meaning as described above.).

In an eighth aspect, the present invention provides a method of producing a compound represented by the above-described formula (a), comprising reacting a compound represented by the following formula (c) with at least one compound selected from the group consisting of a compound represented by the following formula (d) and a compound represented by the following formula (e).

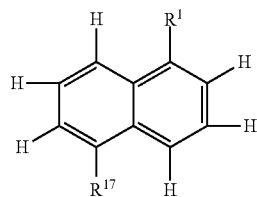

(in the formula (c), $R^1$ and $R^{17}$ represent the same meaning as described above.)

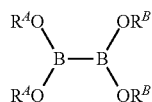

(in the formula (d), $R^A$ and $R^B$ represent each independently a hydrogen atom, an unsubstituted or substituted alkyl group or an unsubstituted or substituted aryl group. A plurality of $R^A$s may be the same or different, and two $R^A$s may be mutually linked to form a ring structure. A plurality of $R^B$s may be the same or different, and two $R^B$s may be mutually linked to form a ring structure.)

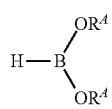

(in the formula (e), $R^A$ represents the same meaning as described above. A plurality of $R^A$s may be the same or different, and two $R^A$s may be mutually linked to form a ring structure.).

In a ninth aspect, the present invention provides a method of producing a compound represented by the above-described formula (b), comprising reacting a compound represented by the following formula (f) with at least one selected from the group consisting of a compound represented by the following formula (d) and a compound represented by the following formula (e).

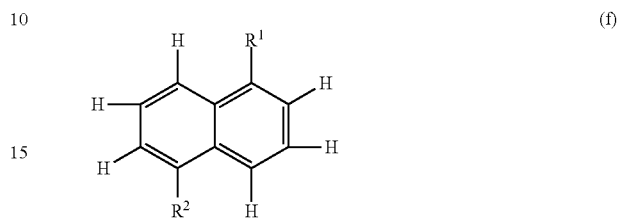

(in the formula (f), $R^1$ and $R^2$ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.).

In a tenth aspect, the present invention provides a method of producing a compound represented by the following formula (g), comprising reacting a compound represented by the above-described formula (a) with a halogenating agent.

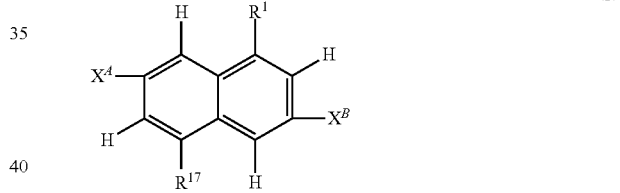

(in the formula (g), $R^1$ and $R^{17}$ represent the same meaning as described above.

$X^A$ and $X^B$ represent each independently a fluorine atom, a chlorine atom, a bromine atom or an iodine atom.).

In an eleventh aspect, the present invention provides a method of producing a compound represented by the following formula (h), comprising reacting a compound represented by the above-described formula (b) with a halogenating agent.

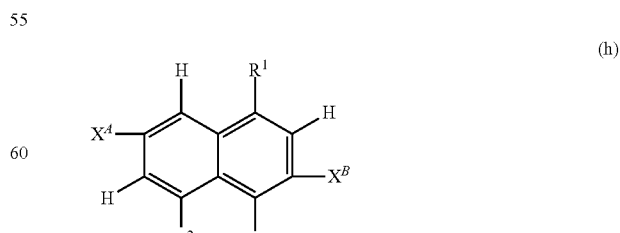

(in the formula (h), $R^1$, $R^2$, $X^A$ and $X^B$ represent the same meaning as described above.).

MODES FOR CARRYING OUT THE INVENTION

Suitable embodiments of the present invention will be illustrated below.

First, terms used in this specification will be explained.

"Constitutional unit" means at least one unit present in a polymer compound.

"n-Valent aromatic heterocyclic group" (n is 1 or 2) means a group obtained by removing n hydrogen atoms from a heterocyclic compound having aromaticity.

"Heterocyclic compound" means an organic compound having a cyclic structure in which elements constituting the ring include not only a carbon atom but also a hetero atom such as an oxygen atom, a sulfur atom, a nitrogen atom, a phosphorus atom, a boron atom and the like contained in the ring.

"Arylene group" means an atomic group obtained by removing two hydrogen atoms from an aromatic hydrocarbon.

"Aryl group" means an atomic group obtained by removing one hydrogen atom from an aromatic hydrocarbon, and includes groups having a condensed ring and groups obtained by linking two or more moieties selected from independent benzene rings and condensed rings.

The boric acid residue means a group represented by —B(OH)$_2$.

The borate residue means, for example, a group represented by the following formulae.

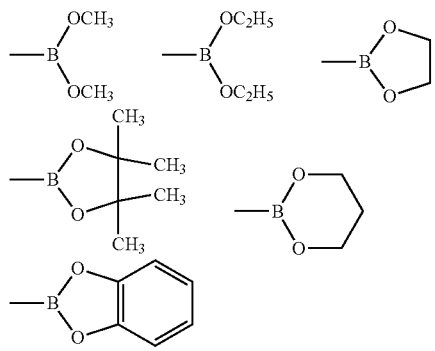

[Polymer Compound]

Polymer compounds according to suitable embodiments will be explained below.

<Constitutional Unit Represented by the Formula (1)>

The polymer compound of the present invention comprises a constitutional unit represented by the above-described formula (1).

In the above-described formula (1), $R^1$ and $R^2$ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, and owing to more excellent luminance life of the resultant light emitting device, preferably an unsubstituted or substituted alkyl group, an unsubstituted or substituted aryl group or an unsubstituted or substituted alkoxy group, more preferably an unsubstituted or substituted alkyl group or an unsubstituted or substituted aryl group, further preferably an unsubstituted or substituted alkyl group, particularly preferably an unsubstituted alkyl group.

The unsubstituted or substituted alkyl group represented by $R^1$ and $R^2$ may be any of linear, branched or cyclic. The number of carbon atoms of the linear and branched alkyl groups is usually 1 to 50, preferably 3 to 30, more preferably 4 to 20, not including the number of carbon atoms of a substituent. The number of carbon atoms of the cyclic alkyl group is usually 3 to 50, preferably 3 to 30, more preferably 4 to 20, not including the number of carbon atoms of a substituent.

The unsubstituted or substituted alkyl group represented by $R^1$ and $R^2$ includes, for example, unsubstituted alkyl groups such as a methyl group, an ethyl group, a n-propyl group, an isopropyl group, a n-butyl group, an isobutyl group, a tert-butyl group, a n-pentyl group, an isoamyl group, a 2-ethylbutyl group, a n-hexyl group, a cyclohexyl group, a n-heptyl group, a cyclohexylmethyl group, a cyclohexylethyl group, a n-octyl group, a 2-ethylhexyl group, a 3-n-propylheptyl group, a n-decyl group, a 3,7-dimethyloctyl group, a 2-ethyloctyl group, a 2-n-hexyldecyl group and the like; substituted alkyl groups such as a trifluoromethyl group, a pentafluoroethyl group, a perfluorobutyl group, a perfluorohexyl group, a perfluorooctyl group, a 3-phenylpropyl group, a 3-(4-methylphenyl)propyl group, a (3,5-di-n-hexylphenylpropyl group), a 6-ethyloxyhexyl group and the like, and owing to more excellent luminance life of the resultant light emitting device, preferably unsubstituted alkyl groups, more preferably a methyl group, an ethyl group, a n-propyl group, a n-butyl group, an isobutyl group, a n-pentyl group, an isoamyl group, a 2-ethylbutyl group, a n-hexyl group, a n-heptyl group, a cyclohexylethyl group, a n-octyl group, a 2-ethylhexyl group, a 3-n-propylheptyl group, a n-decyl group, a 3,7-dimethyloctyl group, a 2-ethyloctyl group and a 2-n-hexyldecyl group, further preferably a n-butyl group, an isobutyl group, a n-pentyl group, an isoamyl group, a 2-ethylbutyl group, a n-hexyl group, a n-heptyl group, a cyclohexylethyl group, a n-octyl group, a 2-ethylhexyl group, a 3-n-propylheptyl group, a n-decyl group, a 3,7-dimethyloctyl group, a 2-ethyloctyl group and a 2-n-hexyldecyl group, particularly preferably a cyclohexylethyl group, a n-octyl group, a 2-ethylhexyl group, a 3-n-propylheptyl group, a n-decyl group, a 3,7-dimethyloctyl group and a 2-ethyloctyl group.

The number of carbon atoms of the unsubstituted or substituted aryl group represented by $R^1$ and $R^2$ is usually 6 to 60, preferably 6 to 20, more preferably 6 to 10, further preferably, not including the number of carbon atoms of a substituent.

The unsubstituted or substituted aryl group represented by $R^1$ and $R^2$ includes, for example, a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group and a 4-phenylphenyl group, and groups obtained by substituting a hydrogen atom in these groups by an alkyl group, an alkoxy group, an aryl group, a fluorine atom and the like, and owing to an improvement in solubility of a polymer compound in an organic solvent and heat resistance thereof in good balance, preferably a phenyl group substituted by an alkyl group and a phenyl group substituted by an aryl group.

The phenyl group substituted by an alkyl group includes, for example, a 2-methylphenyl group, a 3-methylphenyl group, a 4-methylphenyl group, a 3-n-butylphenyl group, a 4-n-butylphenyl group, a 4-tert-butylphenyl group, a 3-n-hexylphenyl group, a 4-n-hexylphenyl group, a 4-n-octylphenyl group, a 3,5-dimethylphenyl group, a 3-n-hexyl-5- methylphenyl group, a 3,5-di-n-hexylphenyl group and a 4-n-butyl-2,6-dimethylphenyl group.

The phenyl group substituted by an aryl group includes a 4-phenylphenyl group, a 4-tert-butylphenylphenyl group, a 3,5-bis(4-tert-butylphenyl)phenyl group and a 3,5-bis(3,5-di-n-hexylphenyl)phenyl group.

The number of carbon atoms of the unsubstituted or substituted mono-valent aromatic heterocyclic group represented by $R^1$ and $R^2$ is usually 2 to 60, preferably 4 to 60, more preferably 4 to 20, not including the number of carbon atoms of a substituent.

The unsubstituted or substituted mono-valent aromatic heterocyclic group represented by $R^1$ and $R^2$ includes, for example, a thienyl group, a pyrrolyl group, a furyl group, a pyridyl group, a piperidyl group, a quinolyl group, an isoquinolyl group, a pyrimidyl group and a triazinyl group, and groups obtained by substituting a hydrogen atom in these groups by an alkyl group, an alkoxy group and the like, preferably a thienyl group, a pyridyl group, a quinolyl group, an isoquinolyl group, a pyrimidyl group and a triazinyl group, and groups obtained by substituting a hydrogen atom in these groups by an alkyl group and an alkoxy group, more preferably a pyridyl group, a pyrimidyl group and a triazinyl group, and groups obtained by substituting a hydrogen atom in these groups by an alkyl group and an alkoxy group.

The unsubstituted or substituted alkoxy group represented by $R^1$ and $R^2$ may be any of linear, branched or cyclic. The number of carbon atoms of the linear or branched alkoxy group is usually 1 to 40, preferably 2 to 20, more preferably 4 to 10, not including the number of carbon atoms of a substituent. The number of carbon atoms of the cyclic alkoxy group is usually 3 to 40, preferably 3 to 20, more preferably 4 to 10, not including the number of carbon atoms of a substituent.

The unsubstituted or substituted alkoxy group represented by $R^1$ and $R^2$ includes, for example, a methoxy group, an ethoxy group, a n-propyloxy group, an isopropyloxy group, a n-butyloxy group, an isobutyloxy group, a tert-butyloxy group, a n-pentyloxy group, a n-hexyloxy group, a cyclohexyloxy group, a n-heptyloxy group, a n-octyloxy group, a 2-ethylhexyloxy group, a n-nonyloxy group, a n-decyloxy group, a 3,7-dimethyloctyloxy group and a lauryloxy group, and owing to an improvement in solubility of a polymer compound in an organic solvent and heat resistance thereof in good balance, preferable are a n-butyloxy group, a n-pentyloxy group, a n-hexyloxy group, a n-octyloxy group, a 2-ethylhexyloxy group, a n-decyloxy group and a 3,7-dimethyloctyloxy group.

The number of carbon atoms of the unsubstituted or substituted aryloxy group represented by $R^1$ and $R^2$ is usually 6 to 60, preferably 7 to 48, not including the number of carbon atoms of a substituent.

The unsubstituted or substituted aryloxy group represented by $R^1$ and $R^2$ includes, for example, a phenoxy group, a 1-naphthyloxy group, a 2-naphthyloxy group, a 1-anthracenyloxy group, a 9-anthracenyloxy group and a 1-pyrenyloxy group, and groups obtained by substituting a hydrogen atom in these groups by an alkyl group, an alkoxy group, a fluorine atom and the like.

In the above-described formula (1), $Ar^1$ represents an unsubstituted or substituted arylene group, an unsubstituted or substituted di-valent condensed polycyclic aromatic heterocyclic group or a di-valent aromatic amine residue represented by the above-described formula (2). Here, the skeleton of a ring linked to a naphthalene ring in the above-described unsubstituted or substituted di-valent condensed polycyclic aromatic heterocyclic group consists only of carbon atoms. $Ar^1$ represents preferably an unsubstituted or substituted arylene group from the standpoint of luminance life of the resultant light emitting device and represents preferably a di-valent aromatic amine residue represented by the above-described formula (2) from the standpoint of balance between hole transportability and luminance life of the resultant light emitting device.

The number of carbon atoms of the unsubstituted or substituted arylene group represented by $Ar^1$ is usually 6 to 60, preferably 6 to 30, more preferably 6 to 18, further preferably 10 to 14, not including the number of carbon atoms of a substituent.

The unsubstituted or substituted arylene group represented by $Ar^1$ includes, for example, unsubstituted or substituted phenylene groups such as an unsubstituted or substituted 1,4-phenylene group, an unsubstituted or substituted 1,3-phenylene group, an unsubstituted or substituted 1,2-phenylene group and the like; unsubstituted or substituted naphthalenediyl groups such as an unsubstituted or substituted 1,4-naphthalenediyl group, an unsubstituted or substituted 1,5-naphthalenediyl group, an unsubstituted or substituted 2,6-naphthalenediyl group and the like; unsubstituted or substituted phenanthrenediyl groups such as an unsubstituted or substituted 2,7-phenanthrenediyl group and the like; unsubstituted or substituted dihydrophenanthrenediyl groups such as an unsubstituted or substituted 9,10-dihydro-2,7-phenanthrenediyl group and the like; unsubstituted or substituted naphthacenediyl groups such as an unsubstituted or substituted 1,7-naphthacenediyl group, an unsubstituted or substituted 2,8-naphthacenediyl group, an unsubstituted or substituted 5,12-naphthacenediyl group and the like; unsubstituted or substituted fluorenediyl groups such as an unsubstituted or substituted 2,7-fluorenediyl group, an unsubstituted or substituted 3,6-fluorenediyl group and the like; unsubstituted or substituted perylenediyl groups such as an unsubstituted or substituted 3,9-perylenediyl group, an unsubstituted or substituted 3,10-perylenediyl group and the like; and unsubstituted or substituted chrysenediyl groups such as an unsubstituted or substituted 6,12-chrysenediyl group, an unsubstituted or substituted 2,8-chrysenediyl group and the like. Preferable are an unsubstituted or substituted phenylene group, an unsubstituted or substituted naphthalenediyl group and an unsubstituted or substituted fluorenediyl group, more preferable are an unsubstituted or substituted naphthalenediyl group and an unsubstituted or substituted fluorenediyl group.

The substituent which can be carried on the arylene group represented by $Ar^1$ includes, for example, an unsubstituted or substituted alkyl group, an unsubstituted or substituted aryl group, an unsubstituted or substituted mono-valent aromatic heterocyclic group, an unsubstituted or substituted alkoxy group and an unsubstituted or substituted aryloxy group, and preferable are an unsubstituted or substituted alkyl group, an unsubstituted or substituted aryl group and an unsubstituted or substituted alkoxy group, more preferable are an unsubstituted or substituted alkyl group and an unsubstituted or substituted aryl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

The number of carbon atoms of the unsubstituted or substituted di-valent condensed polycyclic aromatic heterocyclic group represented by $Ar^1$ is usually 6 to 60, preferably 8 to 30, more preferably 8 to 20, particularly preferably 9 to 15, not including the number of carbon atoms of a substituent.

The unsubstituted or substituted di-valent condensed polycyclic aromatic heterocyclic group represented by $Ar^1$ is an atomic group remaining after removing two hydrogen atoms from a condensed polycyclic aromatic ring group obtained by condensation of a hydrocarbon ring and a hetero ring. Here, in unsubstituted or substituted di-valent condensed polycyclic aromatic heterocyclic group represented by $Ar^1$, the above-described hydrocarbon ring is linked to a naphthalene ring having $R^1$ and $R^2$. That is, in the unsubstituted or substituted di-valent condensed polycyclic aromatic heterocyclic group represented by $Ar^1$, the skeleton of a ring linked to a naphthalene ring consists only of a carbon atom.

The unsubstituted or substituted di-valent condensed polycyclic aromatic heterocyclic group represented by $Ar^1$ is preferably a group represented by the following formula (12), or a group represented by the following formula (12) further having a substituent.

(12)

(in the formula (12), the ring 12A represents a ring having a skeleton consisting only of carbon atoms, linked to a naphthalene ring having $R^1$ and $R^2$ in the formula (1).

The ring 12B is condensed with the ring 12A, and represents a monocyclic or condensed polycyclic aromatic hetero ring.).

The unsubstituted or substituted di-valent condensed polycyclic aromatic heterocyclic group represented by $Ar^1$ includes, for example, groups represented by the following formulae (12-1) to (12-12) and groups represented by the following formulae (12-1) to (12-12) further having a substituent, and preferable are groups represented by the following formulae (12-9) to (12-12) and groups represented by the following formulae (12-9) to (12-12) further having a substituent, further preferable are groups represented by the following formula (12-12). Here, $R^b$ represents an unsubstituted or substituted alkyl group, an unsubstituted or substituted aryl group or an unsubstituted or substituted mono-valent aromatic heterocyclic group.

(12-1)

(12-2)

(12-3)

(12-4)

(12-5)

(12-6)

(12-7)

(12-7)

(12-8)

(12-9)

(12-10)

(12-11)

(12-12)

The substituent which can be carried on the di-valent condensed polycyclic aromatic heterocyclic group represented by $Ar^1$ includes, for example, an unsubstituted or substituted alkyl group, an unsubstituted or substituted aryl group, an unsubstituted or substituted mono-valent aromatic heterocyclic group, an unsubstituted or substituted alkoxy group and an unsubstituted or substituted aryloxy group, and preferable are an unsubstituted or substituted alkyl group, an unsubstituted or substituted aryl group and an unsubstituted or substituted alkoxy group, more preferable are an unsubstituted or substituted alkyl group and an unsubstituted or substituted aryl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

In the above-described formula (2), $Ar^2$, $Ar^3$ and $Ar^4$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups.

The number of carbon atoms of the unsubstituted or substituted arylene group represented by $Ar^2$, $Ar^3$ and $Ar^4$ is usually 6 to 60, preferably 6 to 30, more preferably 6 to 18, further preferably 6 to 10, particularly preferably 6, not including the number of carbon atoms of a substituent.

The unsubstituted arylene group represented by $Ar^2$, $Ar^3$ and $Ar^4$ includes, for example, phenylene groups such as a 1,3-phenylene group, a 1,4-phenylene group and the like; naphthalenediyl groups such as a 1,4-naphthalenediyl group, a 2,6-naphthalenediyl group and the like; anthracenediyl groups such as a 9,10-anthracenediyl group and the like; phenanthrenediyl groups such as a 2,7-phenanthrenediyl group and the like; dihydrophenanthrenediyl groups such as a 9,10-dihydro-2,7-phenanthrenediyl group and the like; naphthacenediyl groups such as a 5,12-naphthacenediyl group and the like; fluorenediyl groups such as a 2,7-fluorenediyl group and the like; perylenediyl groups such as a 3,8-perylenediyl group and the like; and chrysenediyl groups such as a 2,8-chrysenediyl group, a 6,12-chrysenediyl group and the like.

The number of carbon atoms of the unsubstituted or substituted di-valent aromatic heterocyclic group represented by $Ar^2$, $Ar^3$ and $Ar^4$ is usually 2 to 60, preferably 4 to 60, more preferably 4 to 20, further preferably 4 to 9, particularly preferably 4 or 5, not including the number of carbon atoms of a substituent.

The unsubstituted di-valent aromatic heterocyclic group represented by $Ar^2$, $Ar^3$ and $Ar^4$ includes, for example, pyrrolediyl groups such as a N-methyl-2,5-pyrrolediyl group and the like; furandiyl groups such as a 2,5-furandiyl group and the like; pyridinediyl groups such as a 2,5-pyridinediyl group, a 2,6-pyridinediyl group and the like; quinolinediyl groups such as a 2,4-quinolinediyl group, a 2,6-quinolinediyl group and the like; isoquinolinediyl groups such as a 1,4-isoquinolinediyl group, a 1,5-isoquinolinediyl group and the like; phenoxazinediyl groups such as a 3,7-phenoxazinediyl group and the like; and carbazolediyl groups such as a 3,6-carbazolediyl group and the like.

The group obtained by linking two or more groups selected from the group consisting of unsubstituted or substituted arylene groups and unsubstituted or substituted di-valent aromatic heterocyclic groups represented by $Ar^2$, $Ar^3$ and $Ar^4$ means a group obtained by linking (namely, directly bonding) two or more groups selected from the group consisting of unsubstituted or substituted arylene groups and unsubstituted or substituted di-valent aromatic heterocyclic groups described above, and examples thereof include groups represented by the following formulae (13-1) to (13-4), preferably groups represented by the following formulae (13-1) to (13-3), more preferably groups represented by the following formula (13-1). A hydrogen atom in these arylene group and di-valent aromatic heterocyclic group constituting a group represented by the following formulae (13-1) to (13-4) may be substituted by a substituent which can be carried on the group represented by $Ar^2$, $Ar^3$ and $Ar^4$ described later.

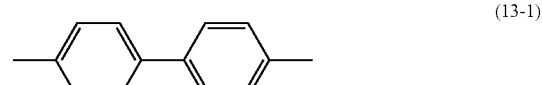

(13-1)

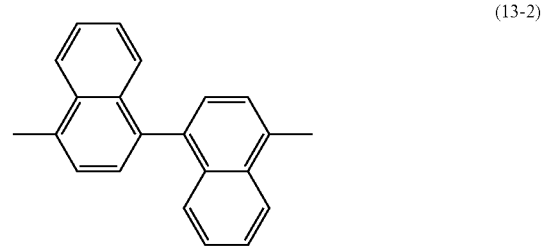

(13-2)

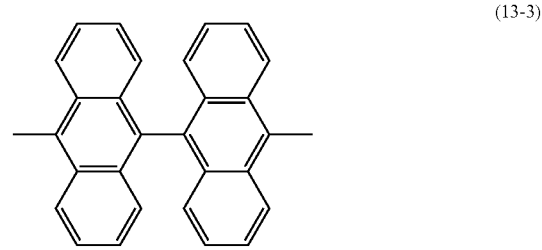

(13-3)

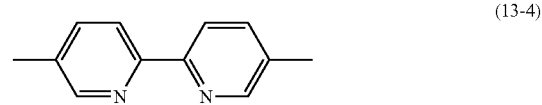

(13-4)

$Ar^2$ and $Ar^3$ represent preferably an unsubstituted or substituted arylene group, more preferably an unsubstituted or substituted 1,4-phenylene group or an unsubstituted or substituted 1,4-naphthalenediyl group, further preferably an unsubstituted or substituted 1,4-phenylene group.

$Ar^4$ represents preferably an unsubstituted or substituted arylene group or a group obtained by linking two or more groups selected from the group consisting of unsubstituted or substituted arylene groups and unsubstituted or substituted di-valent aromatic heterocyclic groups, more preferably an unsubstituted or substituted 1,4-phenylene group, an unsubstituted or substituted 1,4-naphthalenediyl group, an unsubstituted or substituted 2,7-fluorenediyl group, a 9,10-anthracenediyl group, an unsubstituted or substituted 9,10-dihydro-2,7-phenanthrenediyl group, an unsubstituted or substituted group represented by the above-described formula (13-1), further preferably an unsubstituted or substituted 1,4-phenylene group, an unsubstituted or substituted 2,7-fluorenediyl group, an unsubstituted or substituted 9,10-dihydro-2,7-phenanthrenediyl group, an unsubstituted or substituted group represented by the above-described formula (13-1), particularly preferably an unsubstituted 1,4-phenylene group, a substituted 2,7-fluorenediyl group, an unsubstituted or substituted 9,10-dihydro-2,7-phenanthrenediyl group or an unsubstituted group represented by the above-described formula (13-1).

The substituent which can be carried on the group represented by Ar², Ar³ and Ar⁴ is preferably an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, more preferably an unsubstituted or substituted alkyl group or an unsubstituted or substituted aryl group, further preferably an unsubstituted or substituted alkyl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

Some of the substituents which can be carried on the group represented by Ar², Ar³ and Ar⁴ may be mutually linked to form a ring.

In the above-described formula (2), $R^3$ and $R^4$ represent each independently a hydrogen atom, an unsubstituted or substituted alkyl group, an unsubstituted or substituted aryl group or an unsubstituted or substituted mono-valent aromatic heterocyclic group. $R^3$ and $R^4$ represent preferably an unsubstituted or substituted alkyl group or an unsubstituted or substituted aryl group, more preferably a substituted aryl group.

The definitions and examples of the unsubstituted or substituted alkyl group, the unsubstituted or substituted aryl group and the unsubstituted or substituted mono-valent aromatic heterocyclic group represented by $R^3$ and $R^4$ are the same as the definitions and examples of the unsubstituted or substituted alkyl group, the unsubstituted or substituted aryl group and the unsubstituted or substituted mono-valent aromatic heterocyclic group represented by $R^1$ and $R^2$.

In the above-described formula (2), a is 0 or 1, preferably 1.

The di-valent aromatic amine residue represented by the above-described formula (2) includes, for example, groups represented by the following formulae (2A-1) to (2A-36). Of them, groups represented by the formulae (2A-3) to (2A-7), the formulae (2A-12) to (2A-17), the formulae (2A-25) to (2A-28) and the formulae (2A-31) to (2A-36) are preferable, groups represented by the formulae (2A-6) to (2A-7), the formulae (2A-14) to (2A-17), the formula (2A-26), the formula (2A-28) and the formulae (2A-33) to (2A-35) are more preferable, owing to excellent luminance life of the resulting light emitting device.

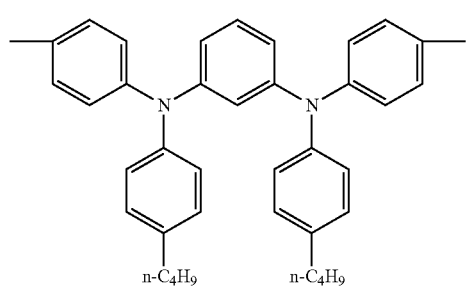

(2A-1)

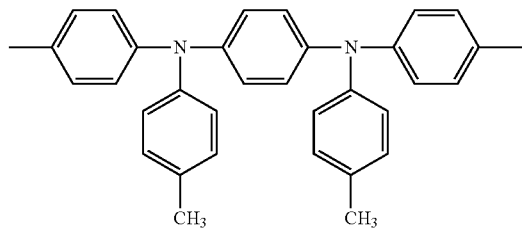

(2A-2)

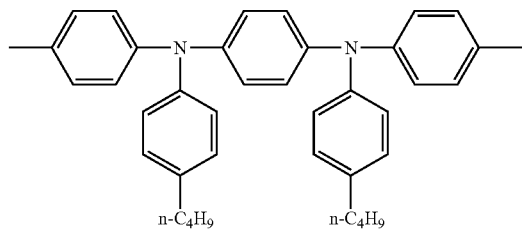

(2A-3)

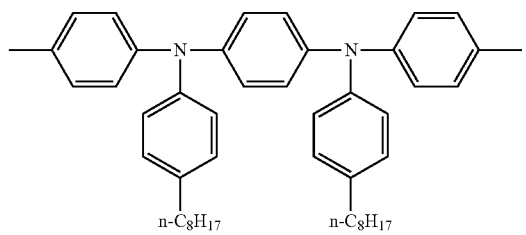

(2A-4)

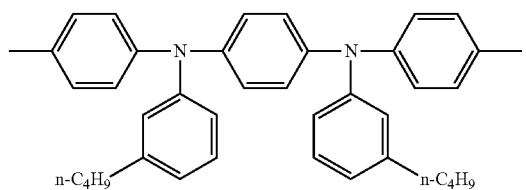

(2A-5)

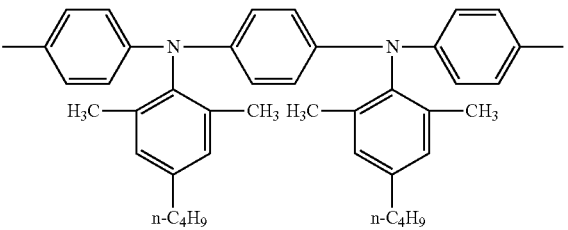

(2A-6)

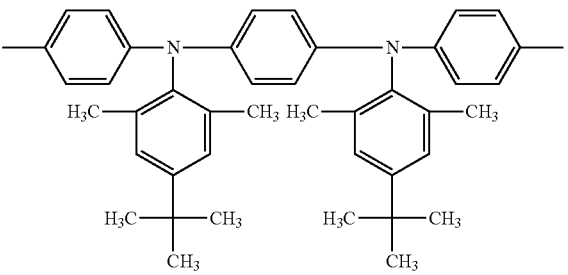

(2A-7)

(2A-8)
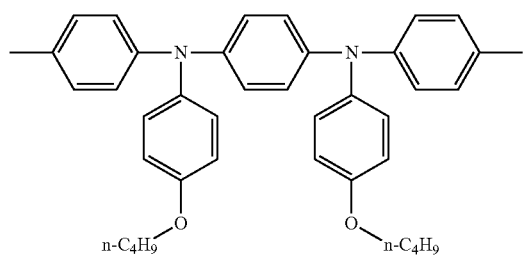
(2A-9)
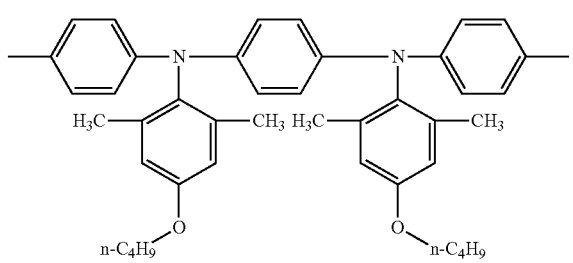
(2A-10)
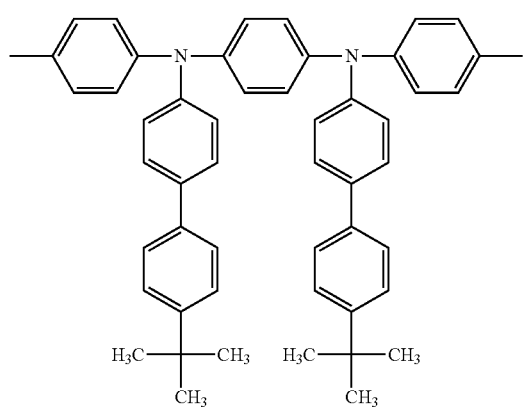
(2A-11)
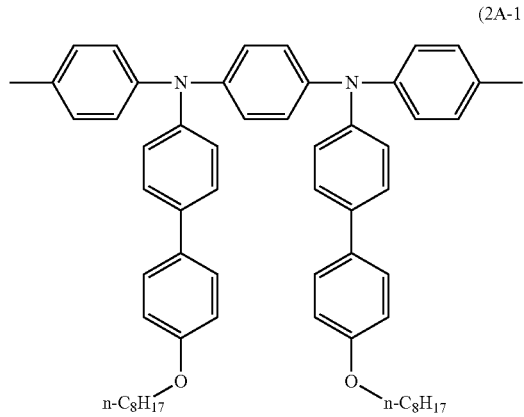
(2A-12)
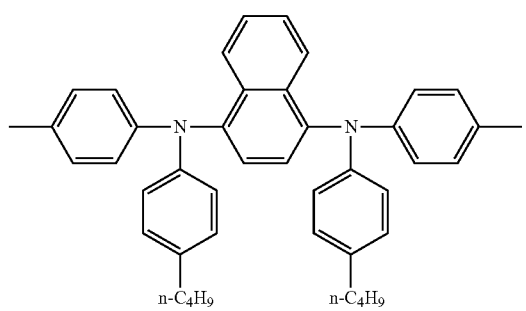
(2A-13)
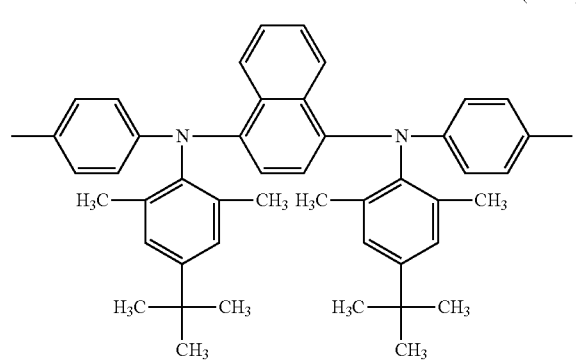
(2A-14)
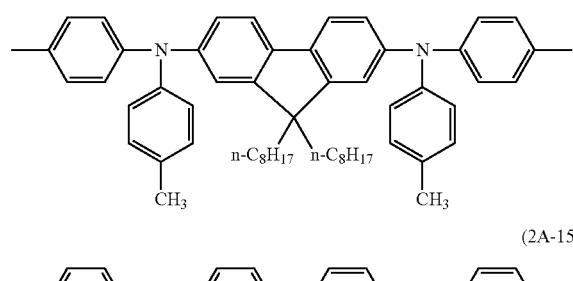
(2A-15)
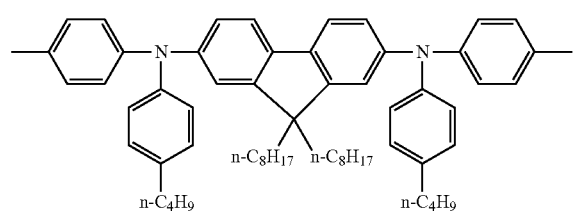
(2A-16)
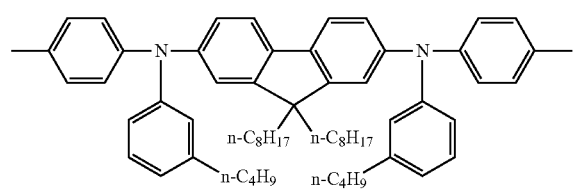
(2A-17)
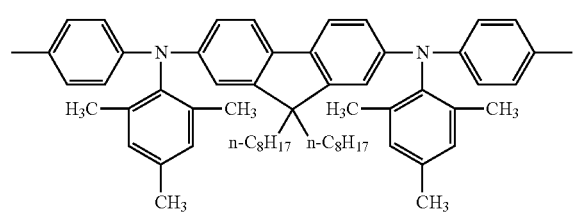

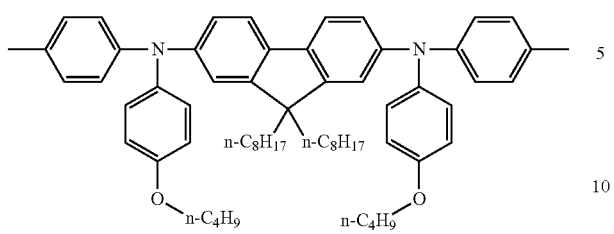
(2A-18)
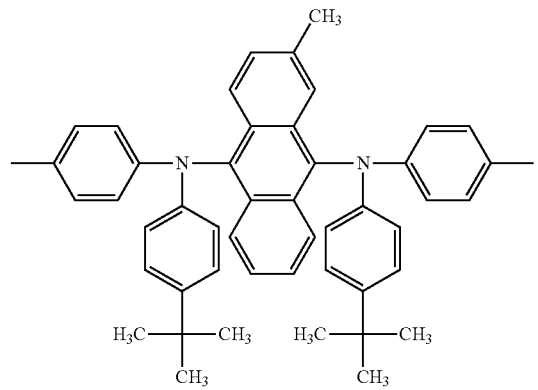
(2A-22)
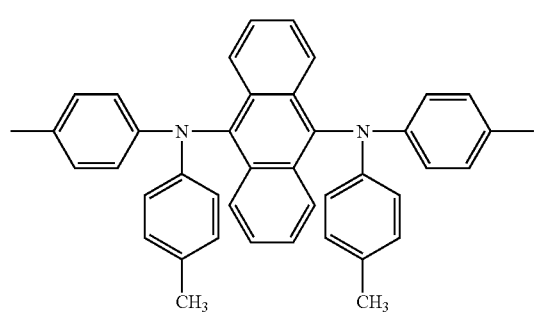
(2A-19)
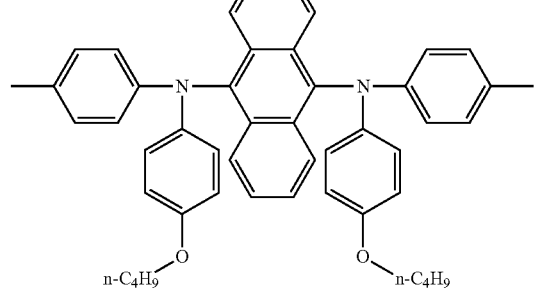
(2A-23)
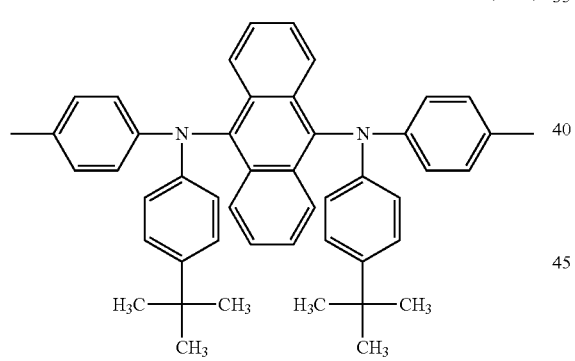
(A-20)
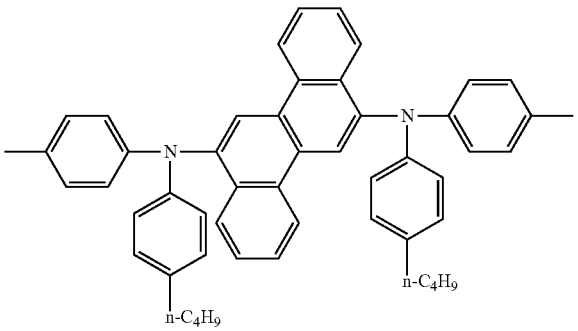
(2A-24)
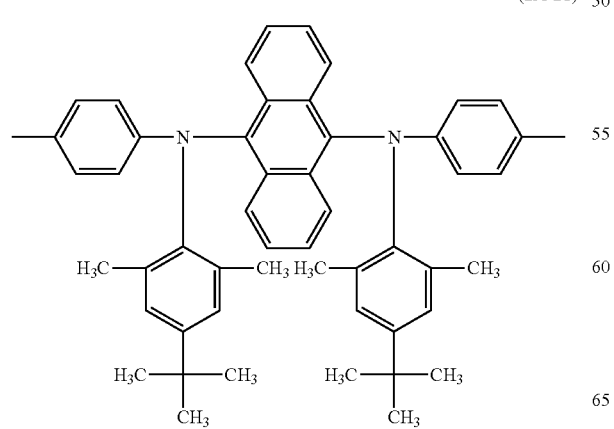
(2A-21)
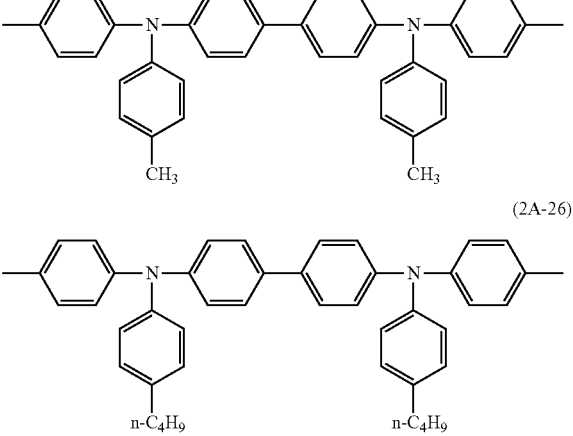
(2A-25)
(2A-26)

(2A-27)
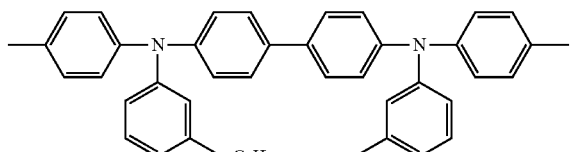
(2A-28)
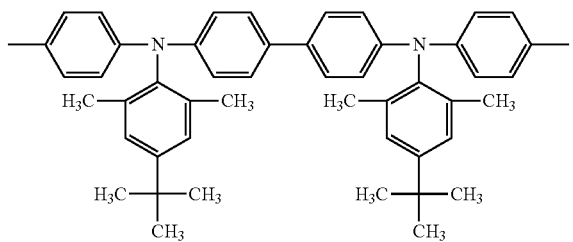
(2A-29)
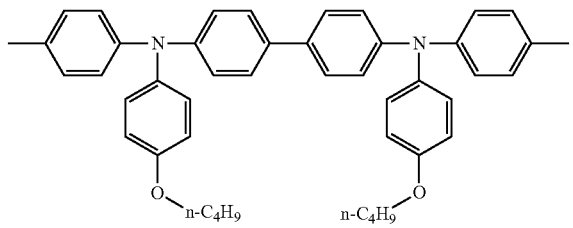
(2A-30)
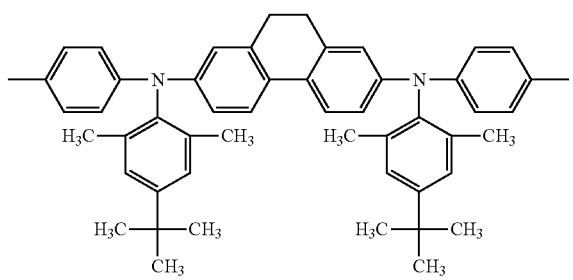
(2A-31)
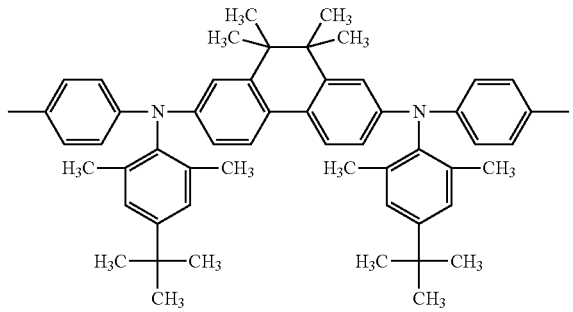
(2A-32)
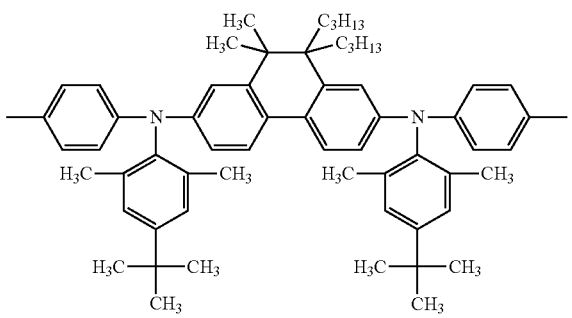
(2A-33)
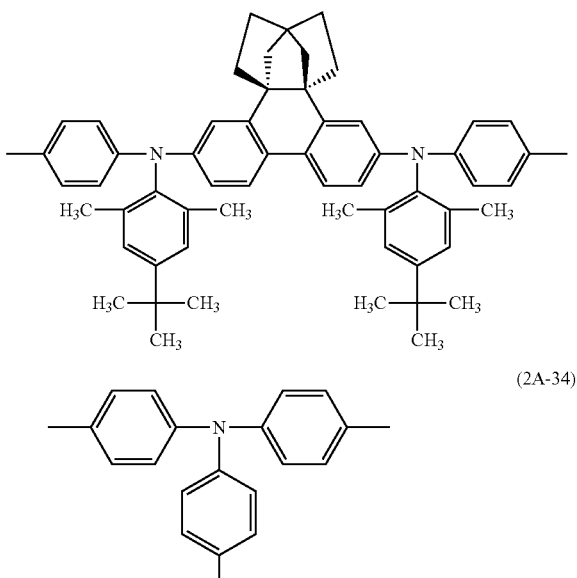
(2A-34)
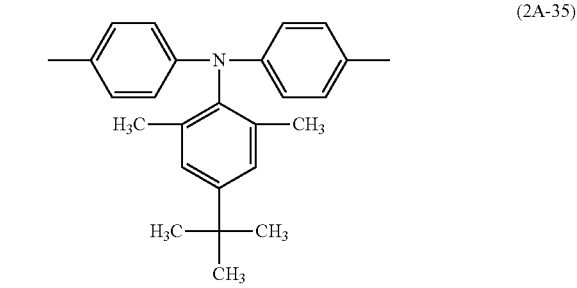
(2A-35)
(2A-36)
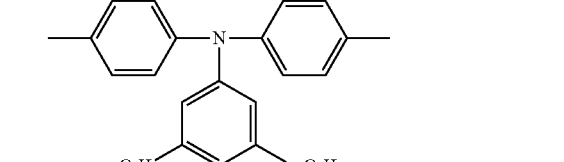
The constitutional unit represented by the above-described formula (1) is preferably a constitutional unit represented by the following formula (3), from the standpoint of luminance life of the resultant light emitting device.

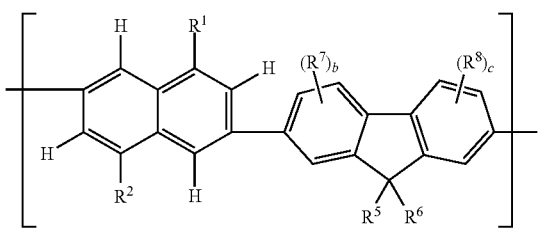

(3)

(in the formula (3),

R¹ and R² represent the same meaning as described above.

R⁵ and R⁶ represent each independently a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.

R⁷ and R⁸ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group. When a plurality of R⁷s and R⁸s are present, each of them may be the same or different.

b and c represent each independently an integer of 0 to 3).

In the above-described formula (3), the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by R⁵ and R⁶ are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by R¹ and R². R⁵ and R⁶ may be mutually linked to form a ring structure together with the carbon atom to which they are attached.

R⁵ and R⁶ represent preferably an unsubstituted or substituted alkyl group or an unsubstituted or substituted aryl group. The combination of R⁵ and R⁶ is preferably a combination in which both moieties are an unsubstituted or substituted alkyl group or one is an unsubstituted or substituted alkyl group and the other is an unsubstituted or substituted aryl group, more preferably a combination in which one is an unsubstituted or substituted alkyl group and the other is an unsubstituted or substituted aryl group.

In the above-described formula (3), R⁷ and R⁸ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, preferably, an unsubstituted or substituted alkyl group or an unsubstituted or substituted aryl group. The definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by R⁷ and R⁸ are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by R¹ and R².

In the above-described formula (3), b and c represent each independently an integer of 0 to 3, preferably 0 or 1, more preferably 0.

In the constitutional unit represented by the above-described formula (1), Ar¹ is preferably a di-valent aromatic amine residue represented by the above-described formula (2), from the standpoint of balance of hole transportability and luminance life of the resultant light emitting device.

The constitutional unit represented by the above-described formula (1) includes, for example, constitutional units represented by the following formulae (1A-1) to (1A-68). Of them, constitutional units represented by the formulae (1A-3) to (1A-14), the formulae (1A-17) to (1A-39) and the formulae (1A-52) to (1A-68) are preferable, constitutional units represented by the formulae (1A-8) to (1A-13), the formulae (1A-19) to (1A-32), the formulae (1A-35) to (1A-39) and the formulae (1A-52) to (1A-68) are more preferable, because of excellent luminance life of the resultant light emitting device.

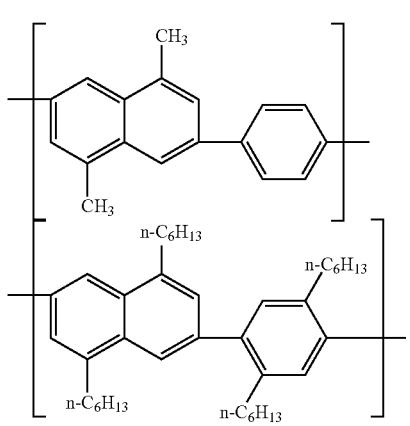

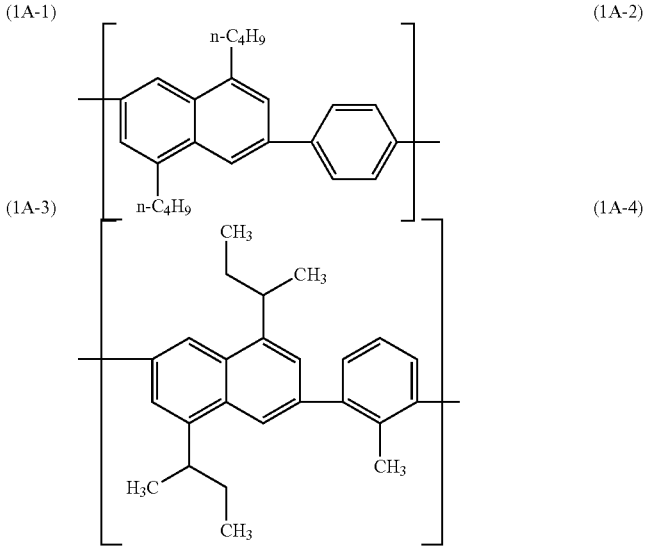

-continued
(1A-5)
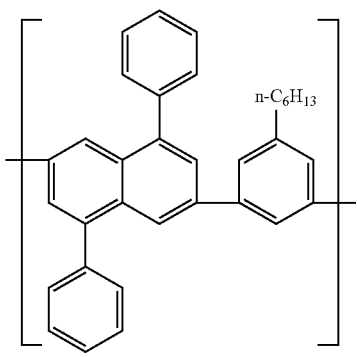
(1A-6)
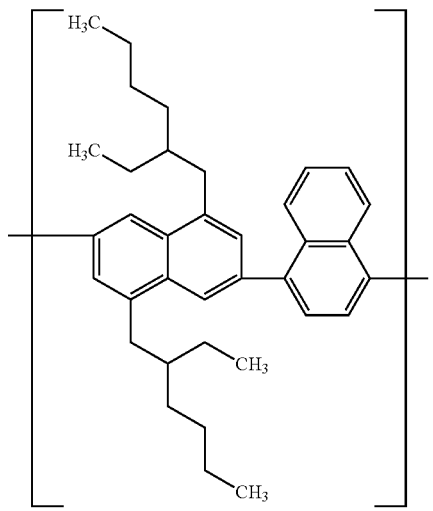
(1A-7)
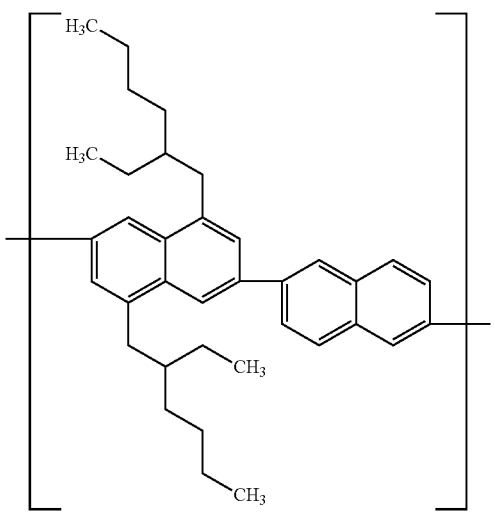
(1A-8)
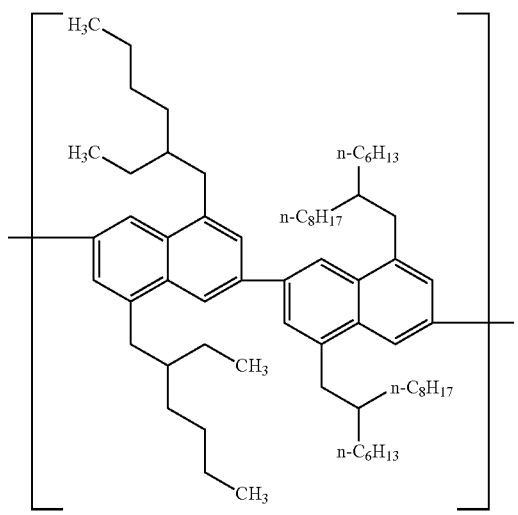
(1A-9)
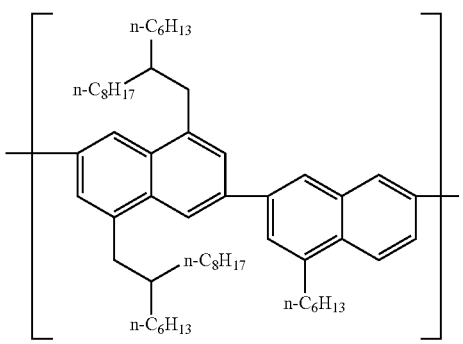
(1A-10)
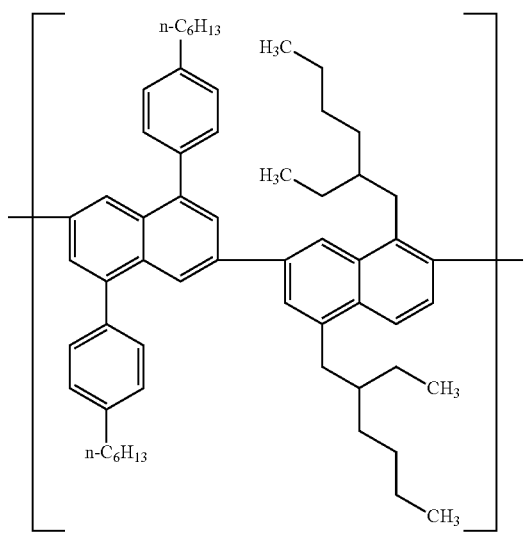

-continued
(1A-11)
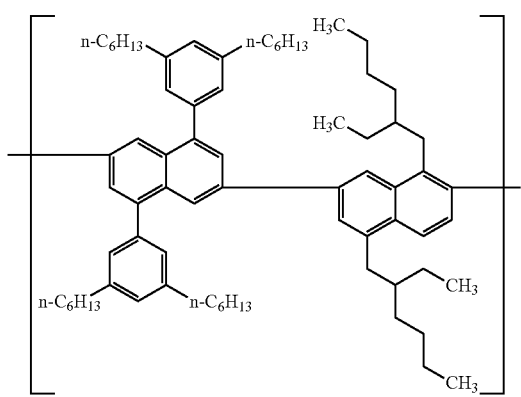
(1A-12)
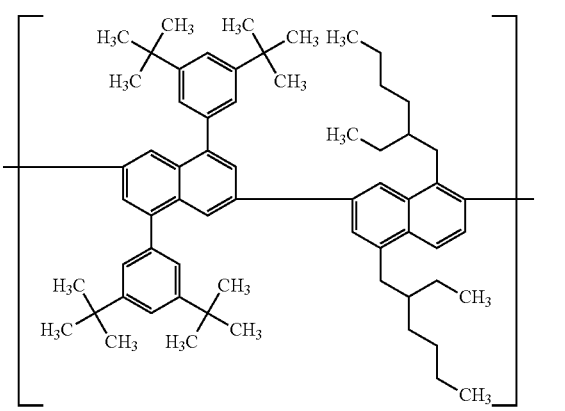
(1A-13)
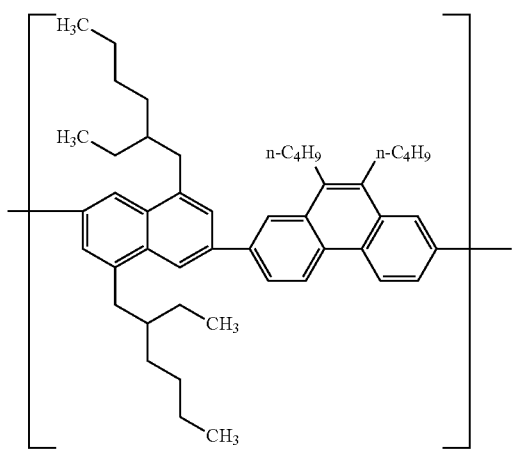
(1A-14)
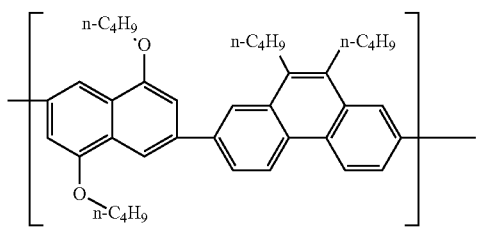
(1A-15)
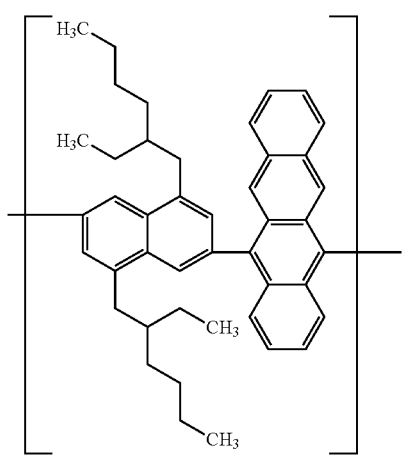
(1A-16)
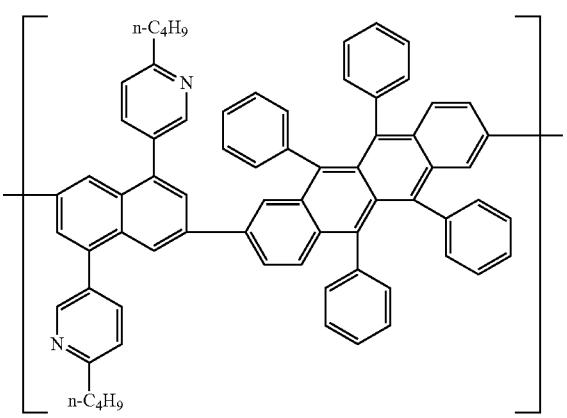

-continued
(1A-17)
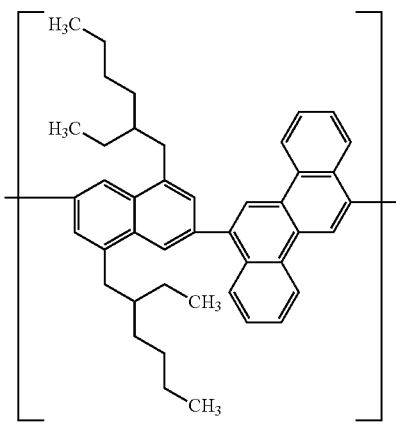
(1A-18)
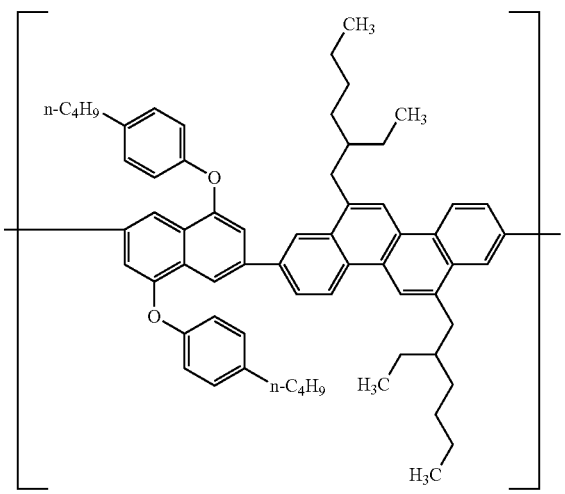
(1A-19)
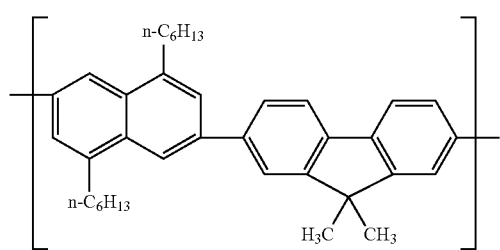
(1A-20)
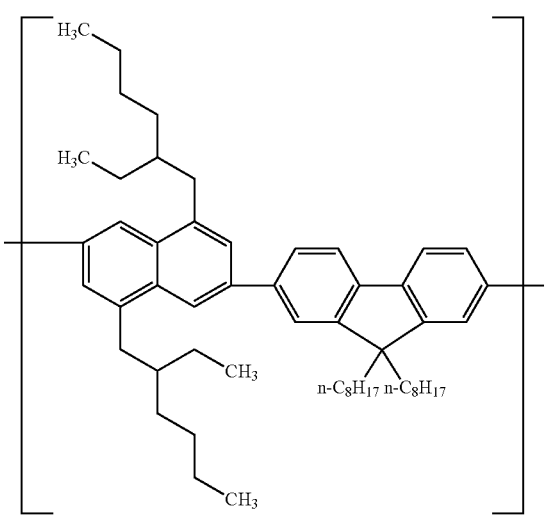
(1A-21)
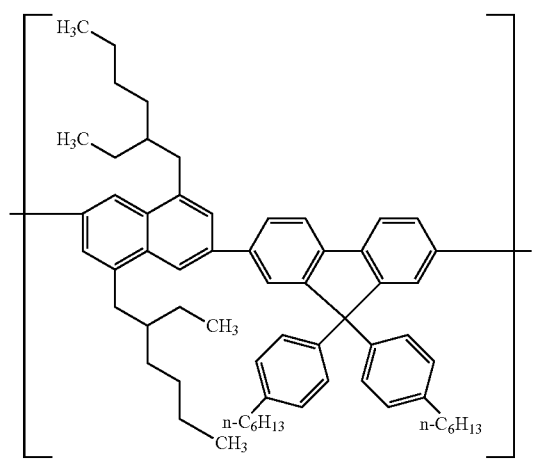
(1A-22)
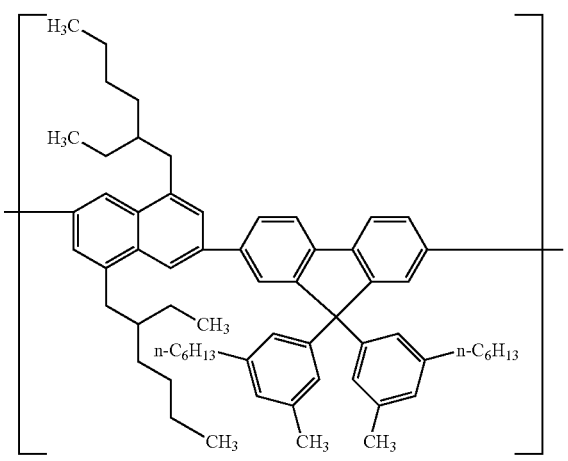

-continued
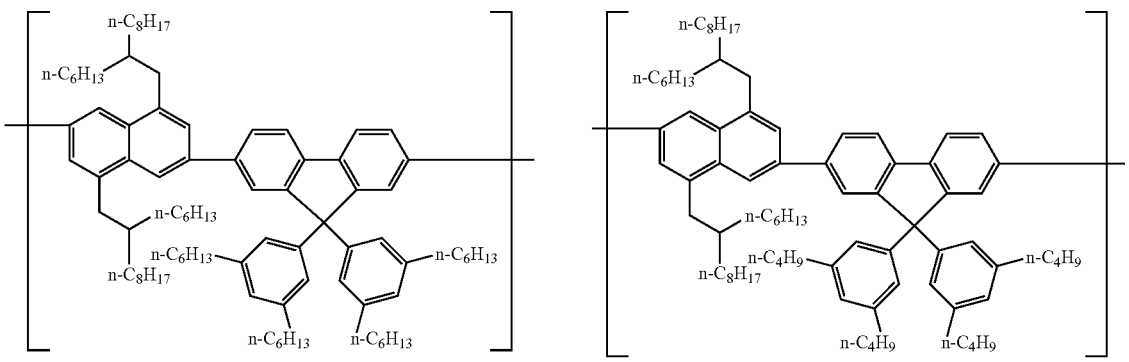
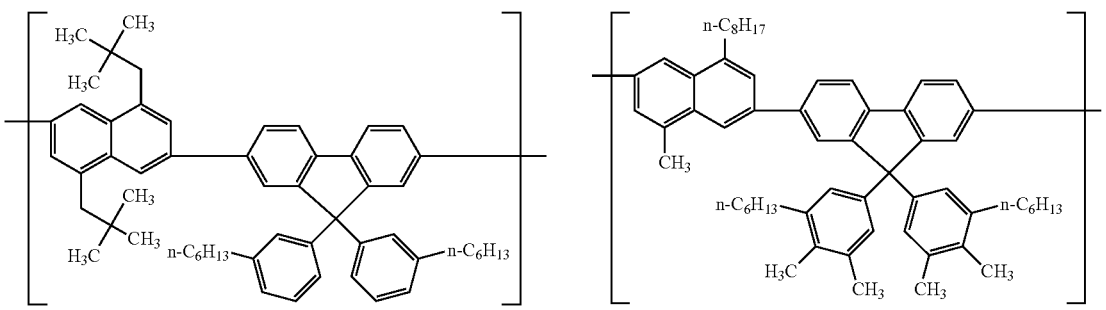
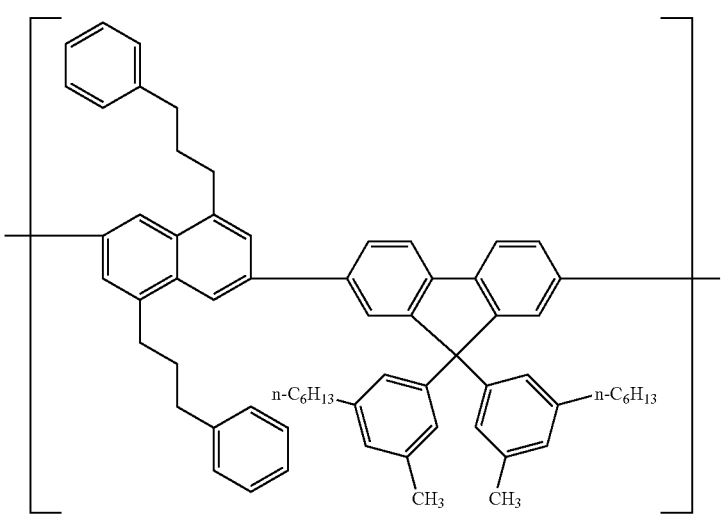

-continued
(1A-28)
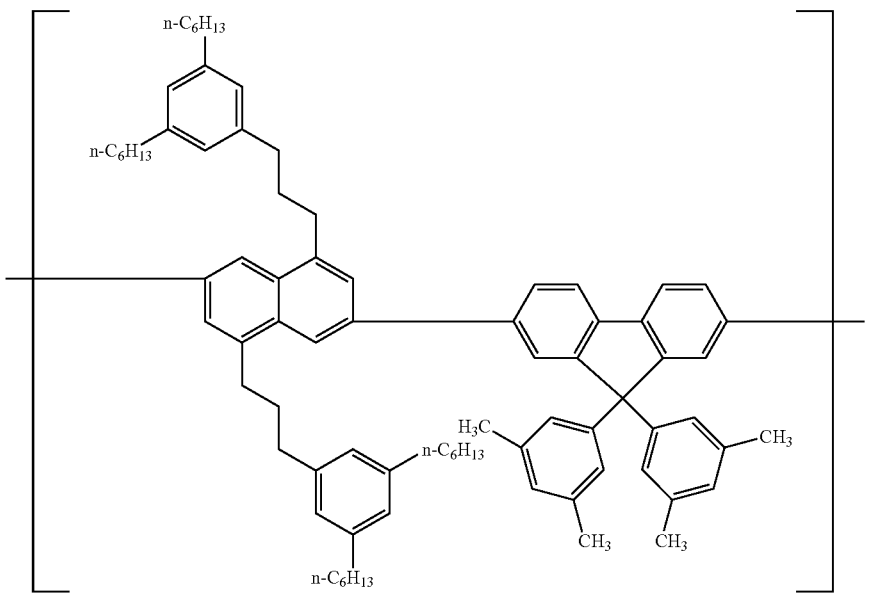
(1A-29)
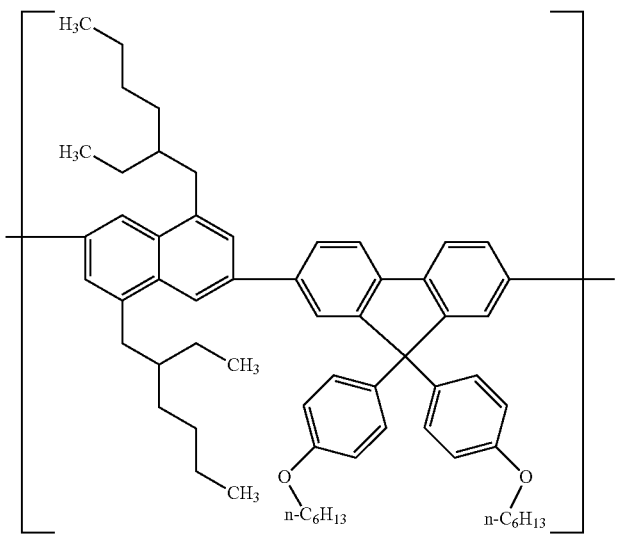
(1A-30)
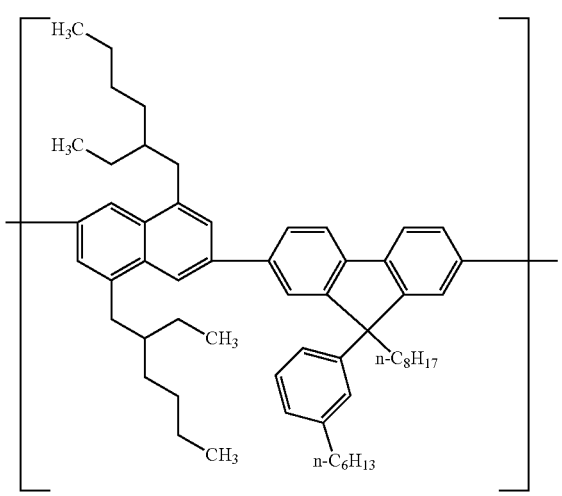
(1A-31)
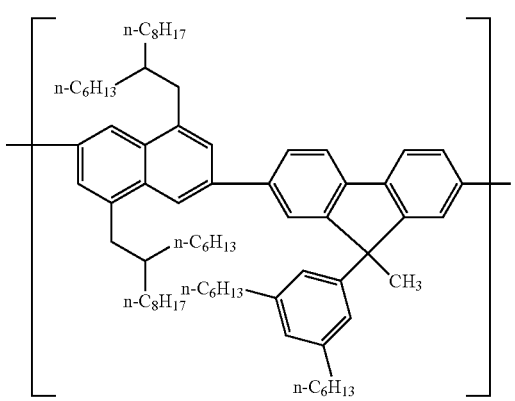

(1A-32)
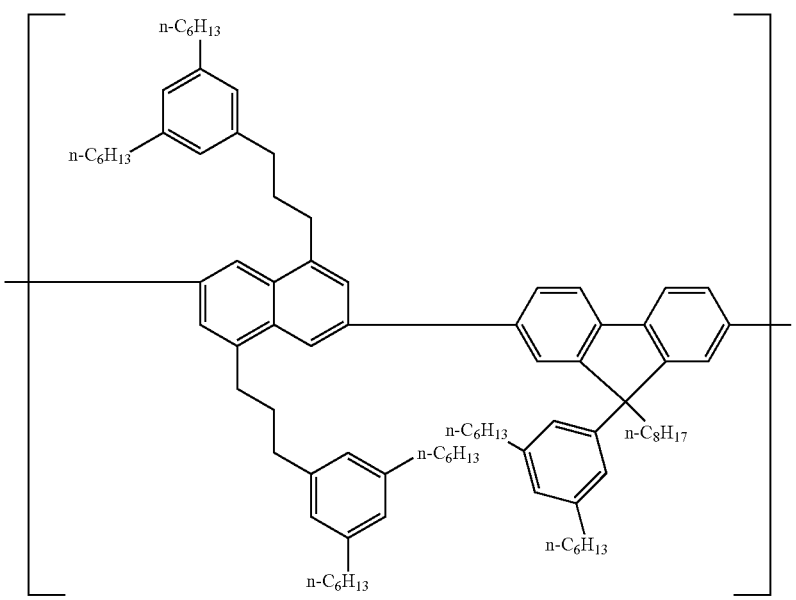
(1A-33)
(1A-34)
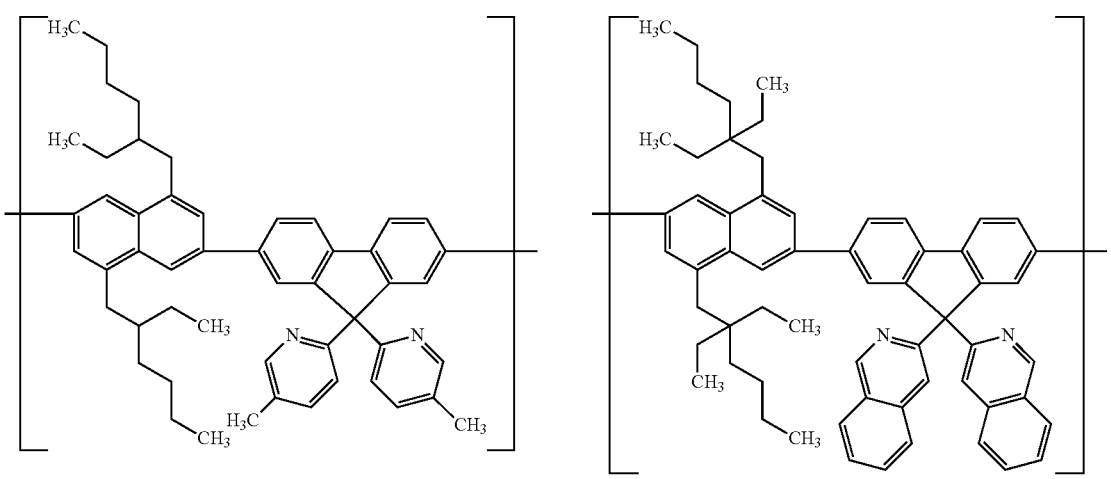
(1A-35)
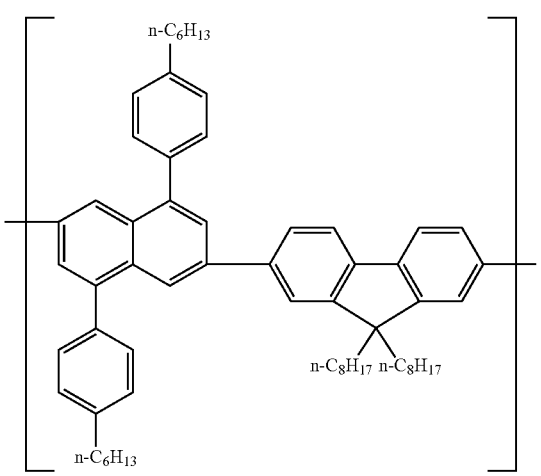

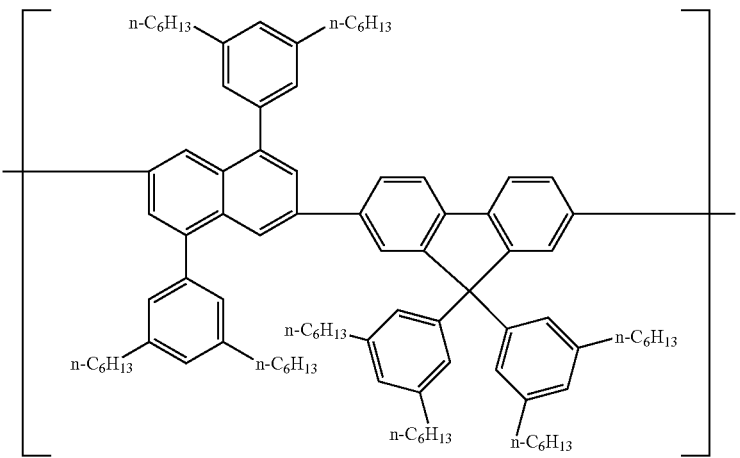
(1A-36)
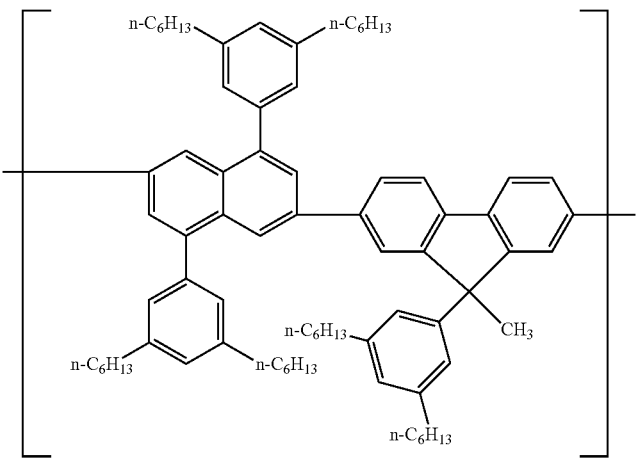
(1A-37)
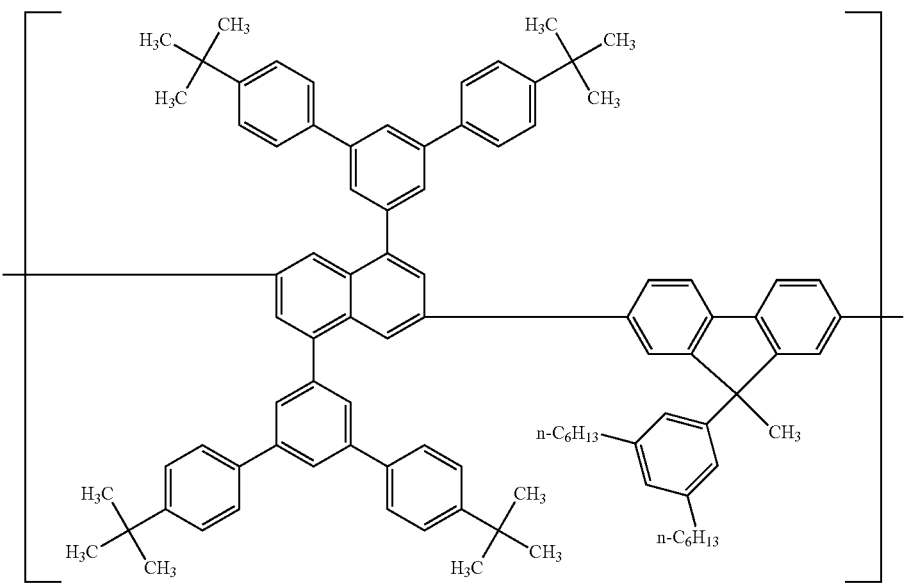
(1A-38)

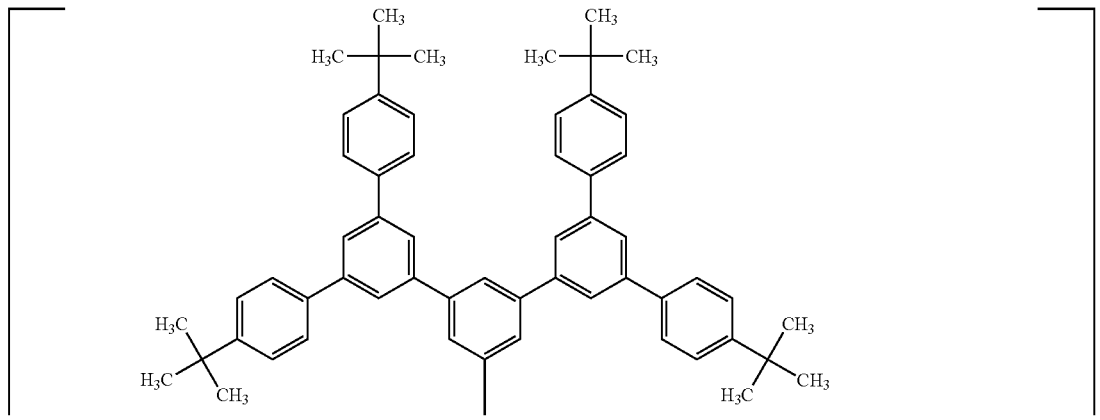
(1A-39)
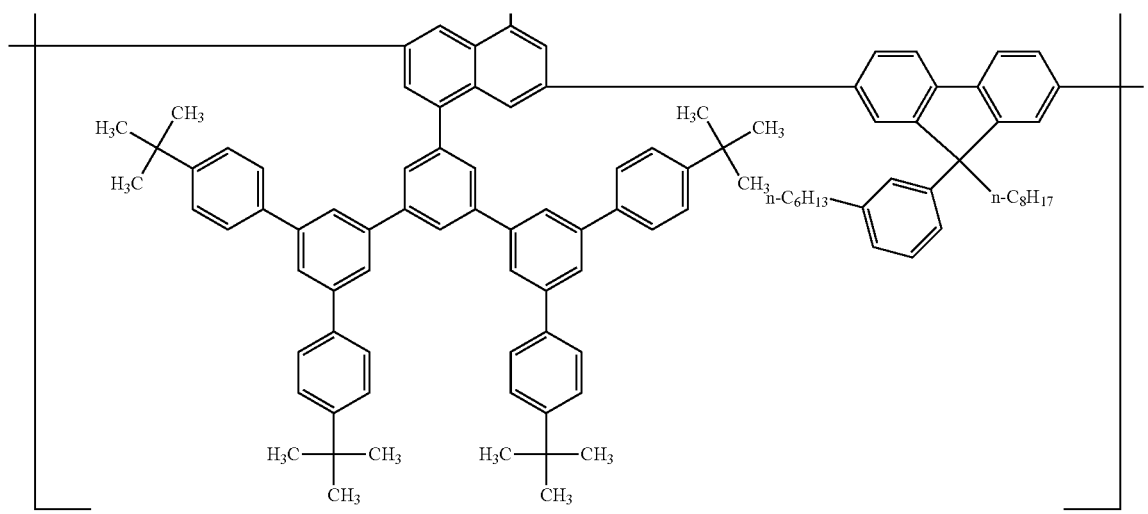
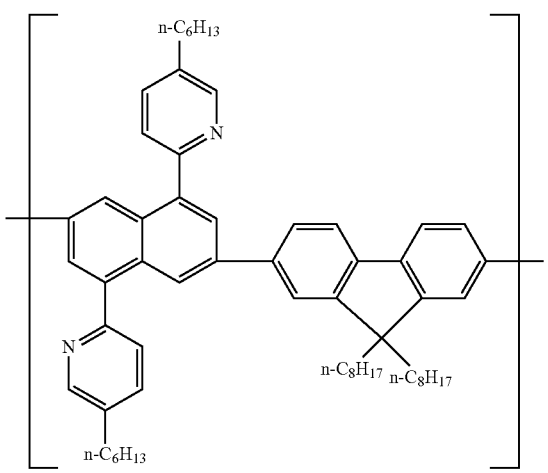
(1A-40)

-continued
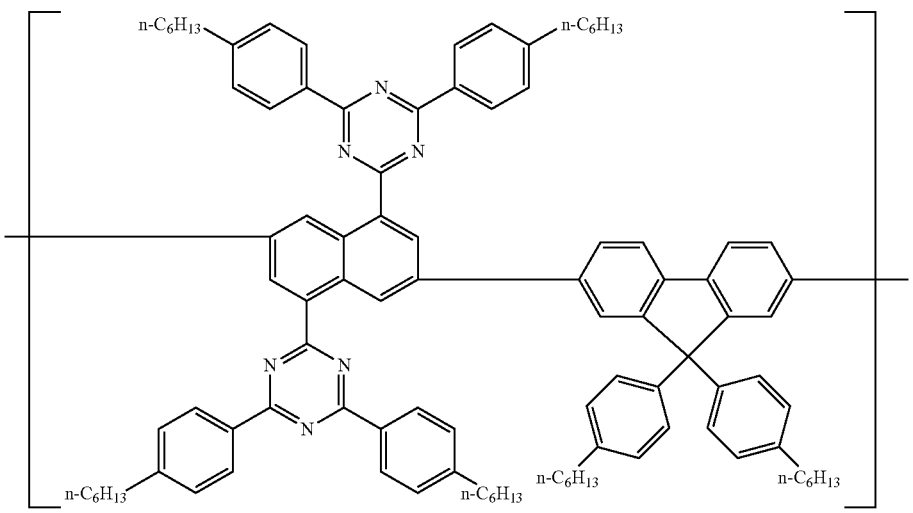
(1A-41)
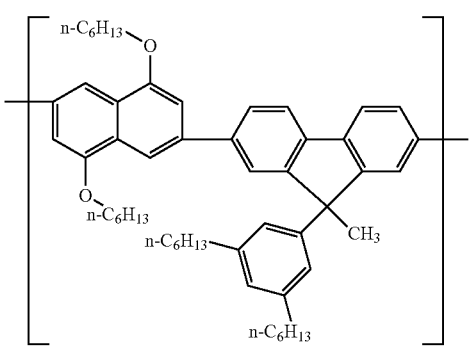
(1A-42)
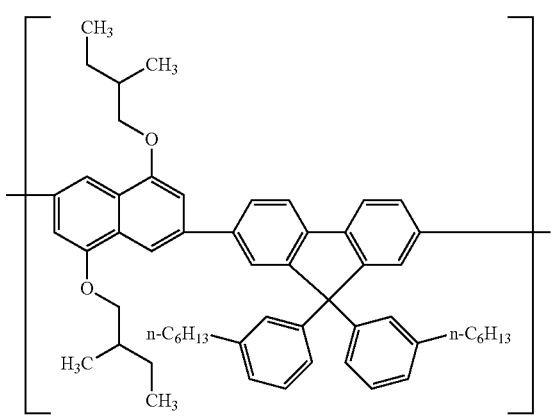
(1A-43)
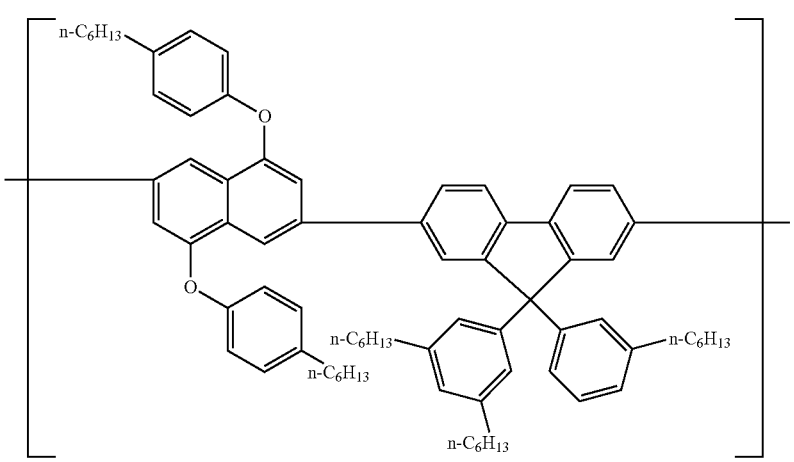
(1A-44)

-continued
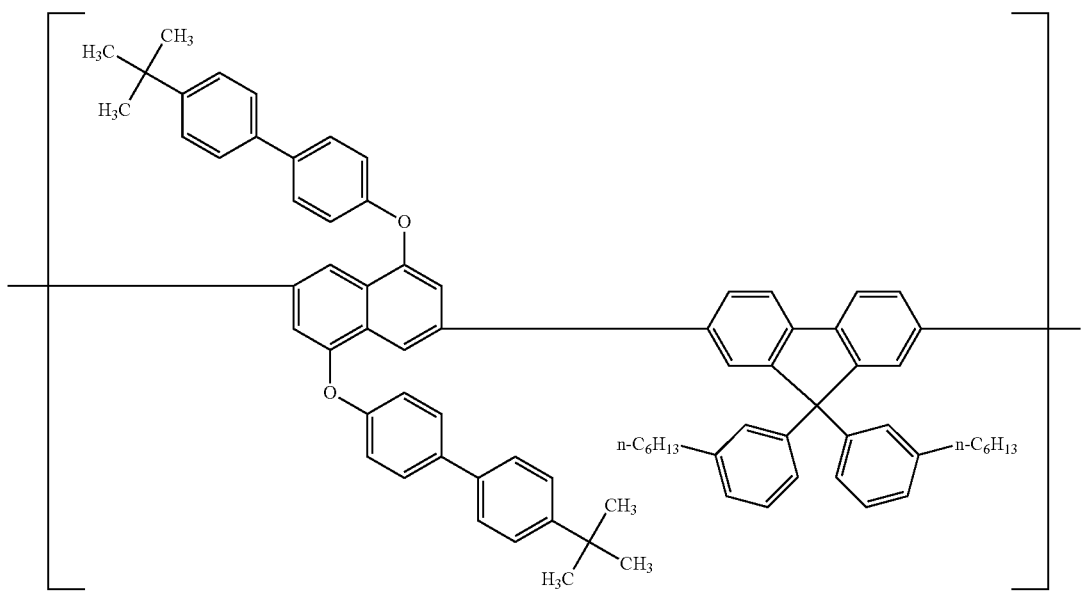
(1A-45)
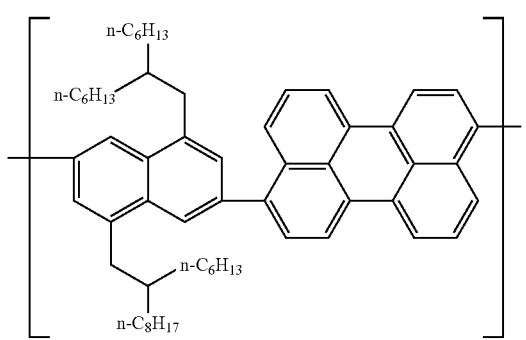
(1A-46)
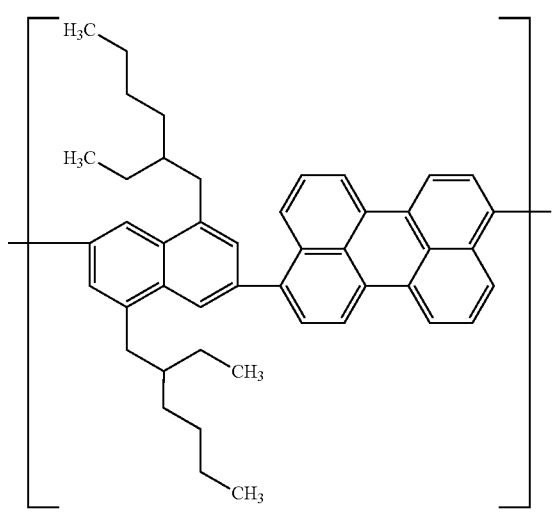
(1A-47)
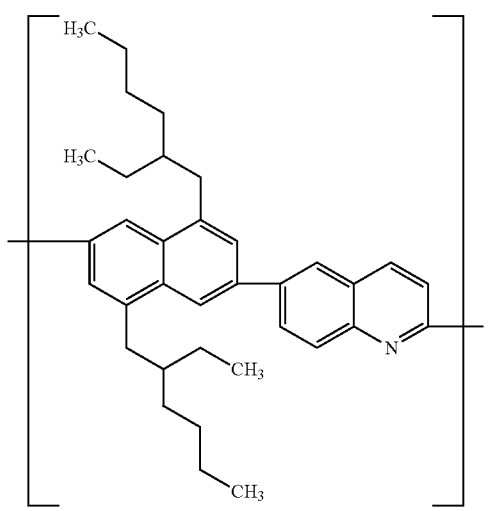
(1A-48)
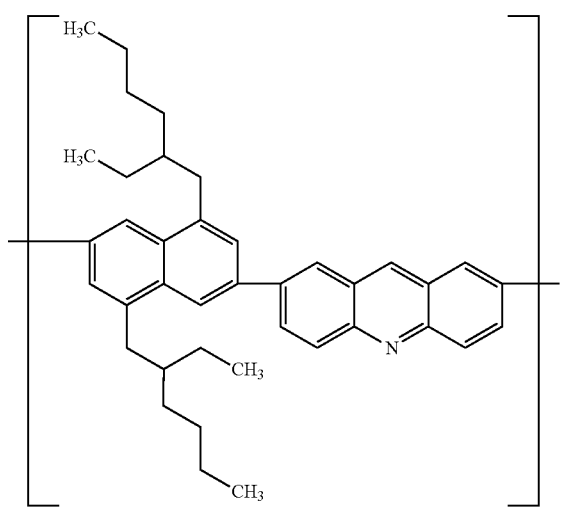
(1A-49)

-continued
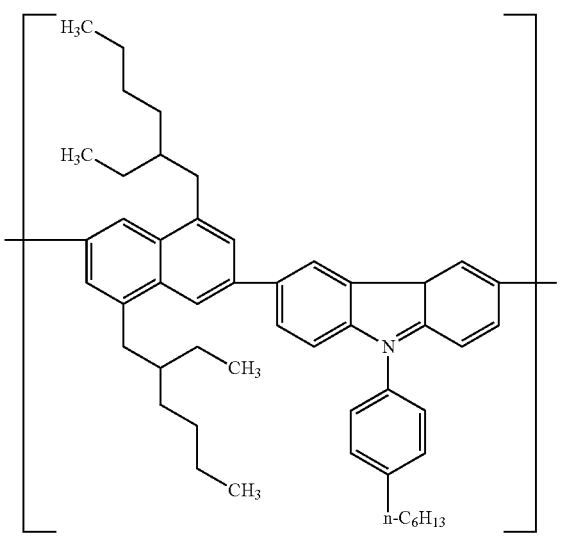
(1A-50)
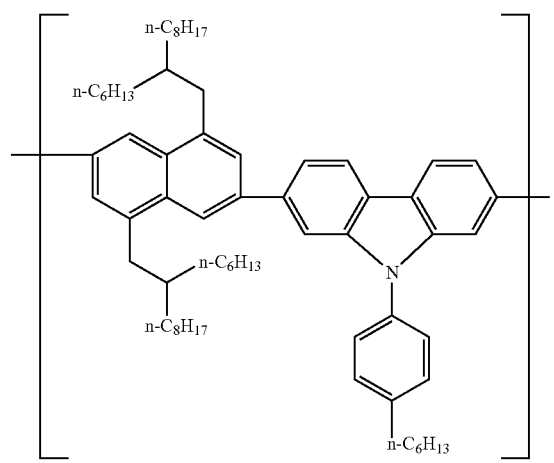
(1A-51)
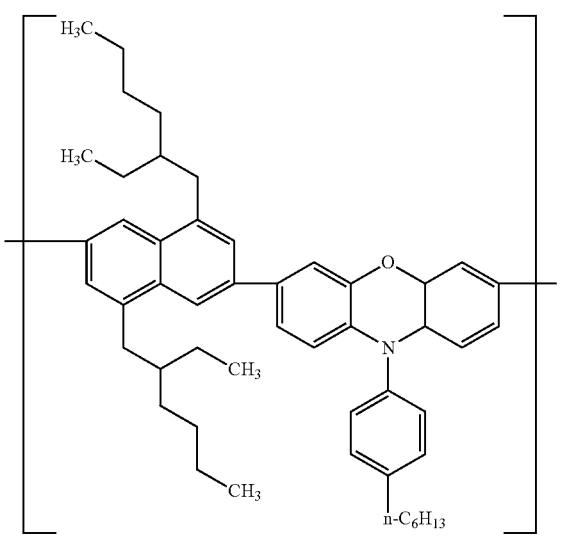
(1A-52)
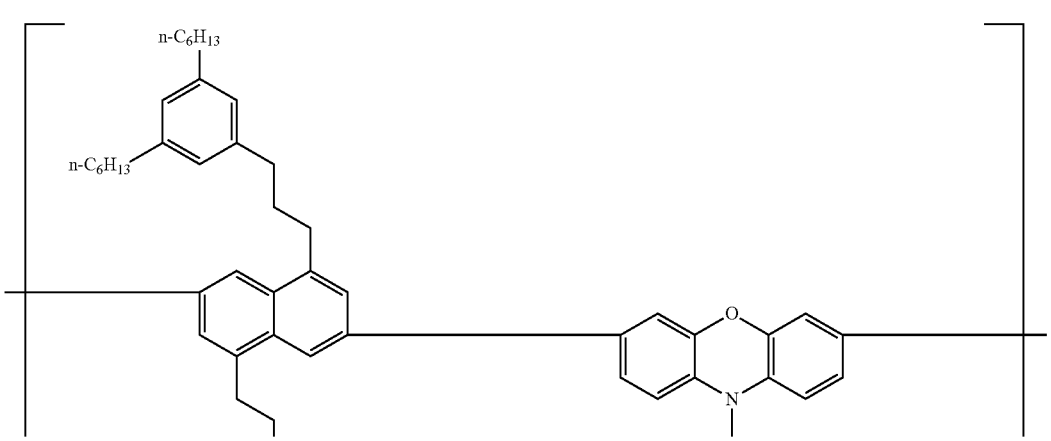
(1A-53)

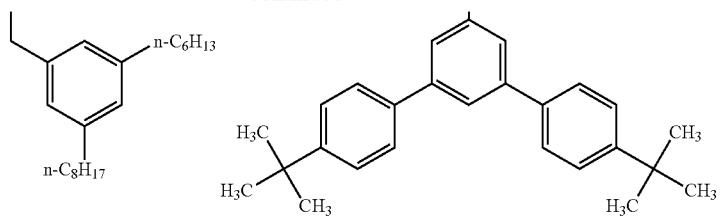
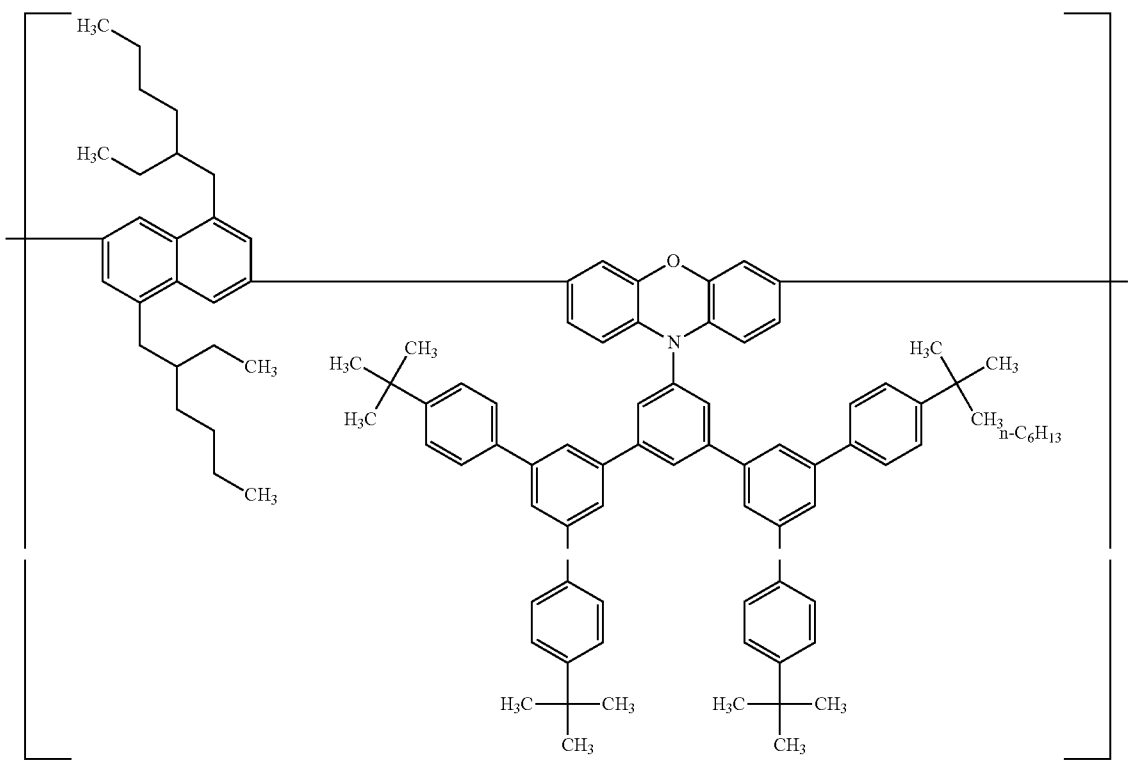
(1A-54)
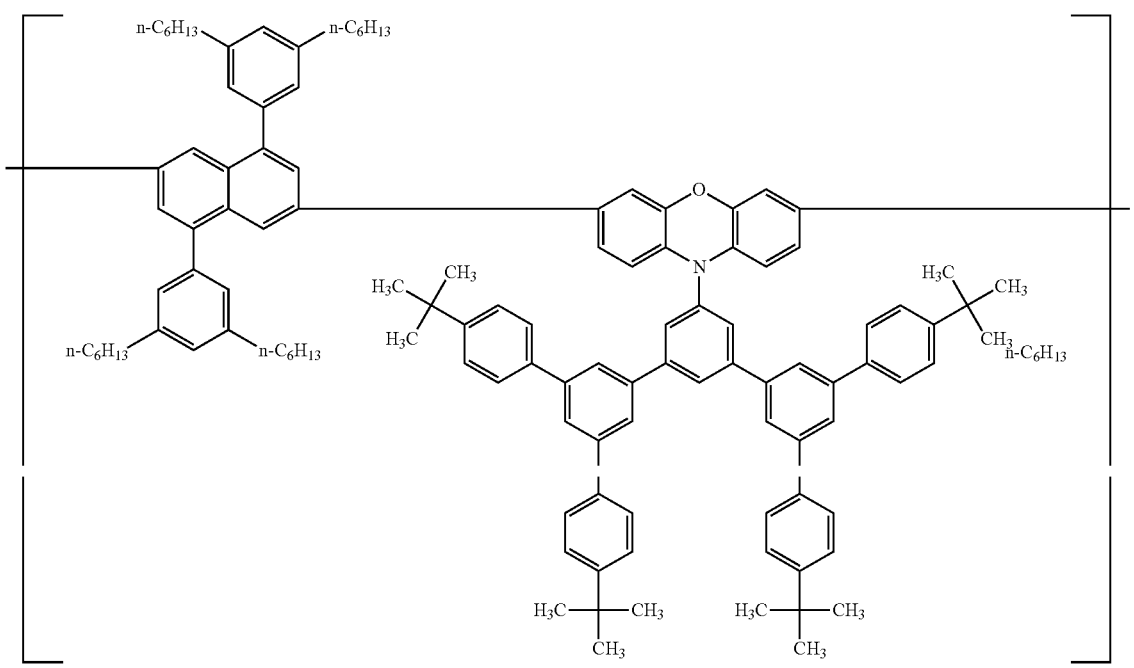
(1A-55)

-continued
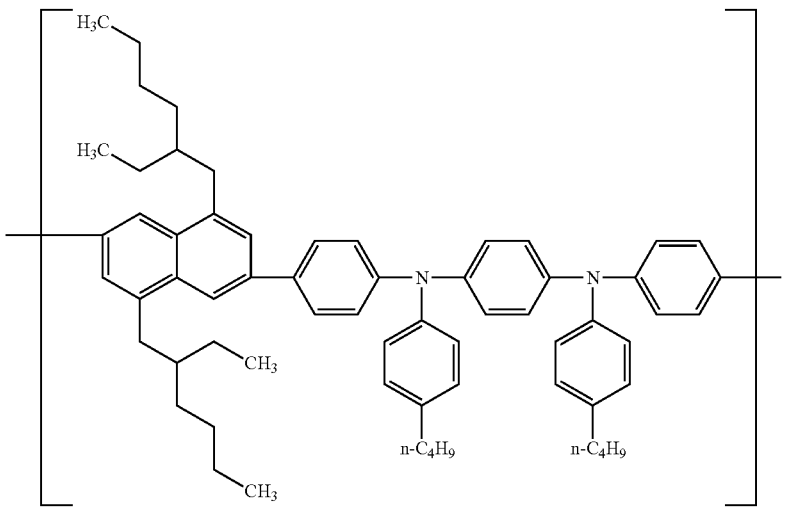
(1A-56)
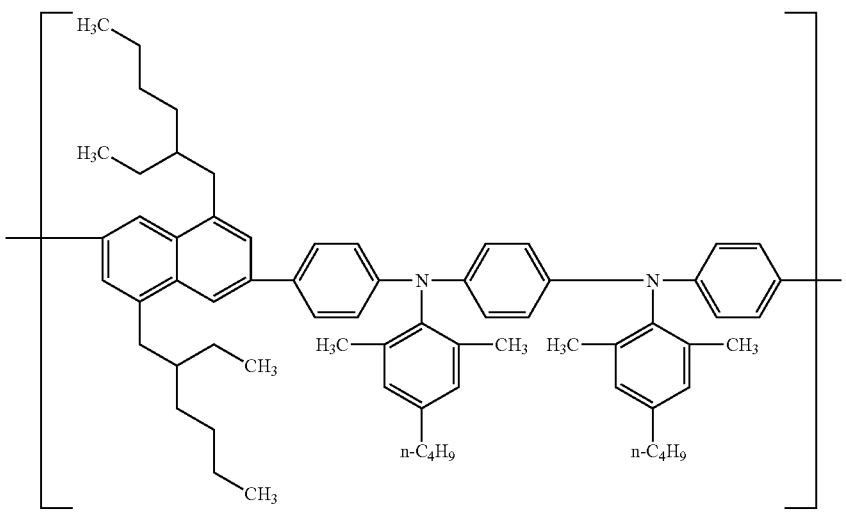
(1A-57)
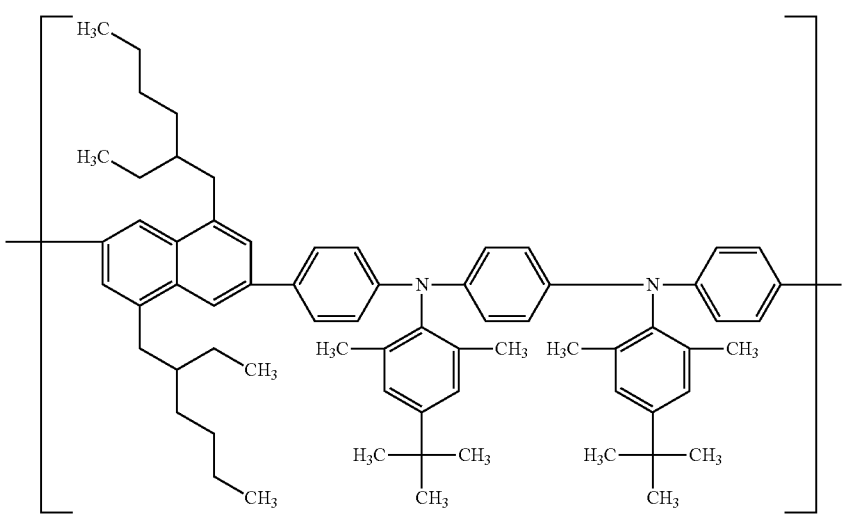
(1A-58)

-continued
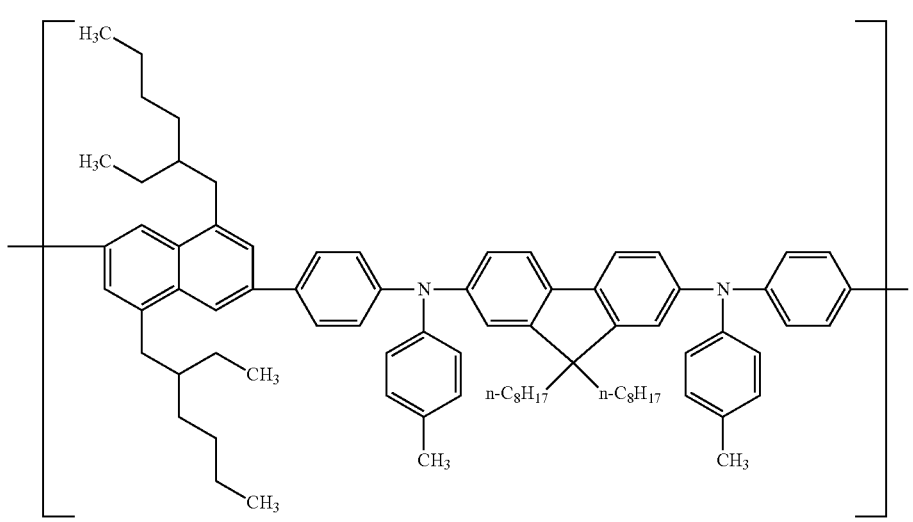
(1A-59)
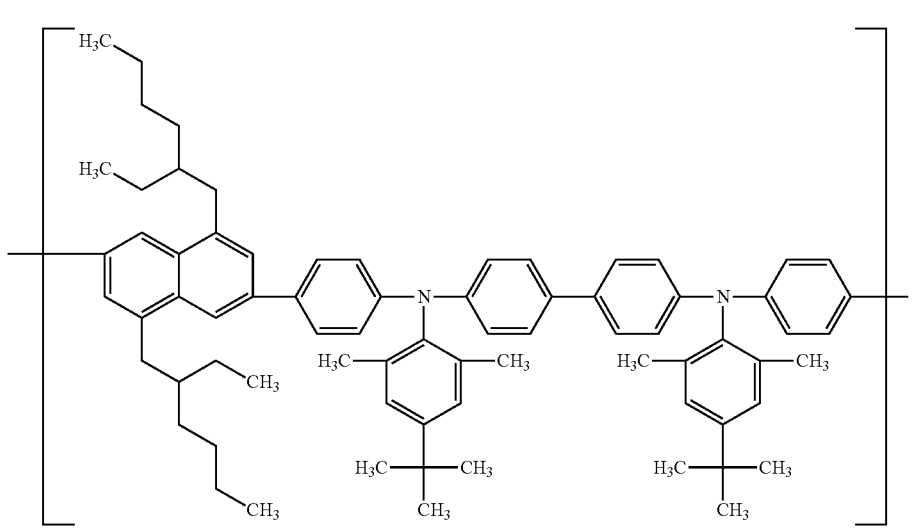
(1A-60)
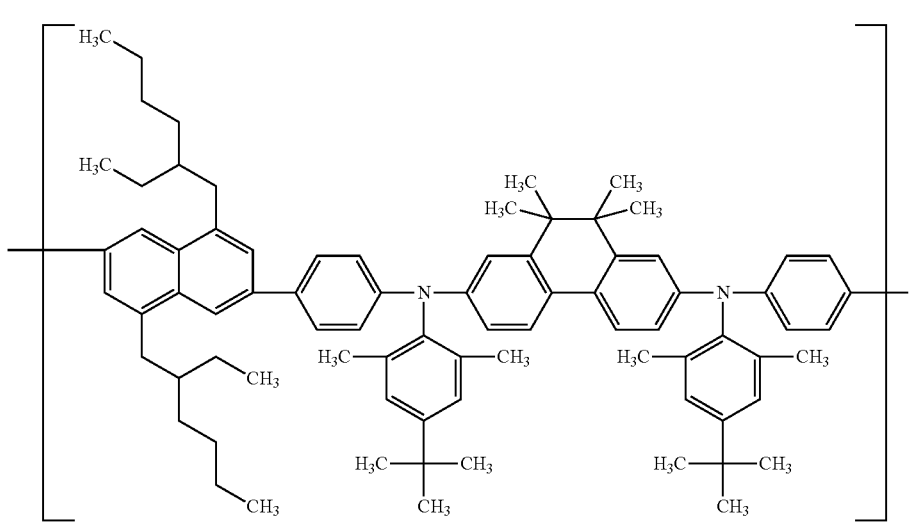
(1A-61)

-continued
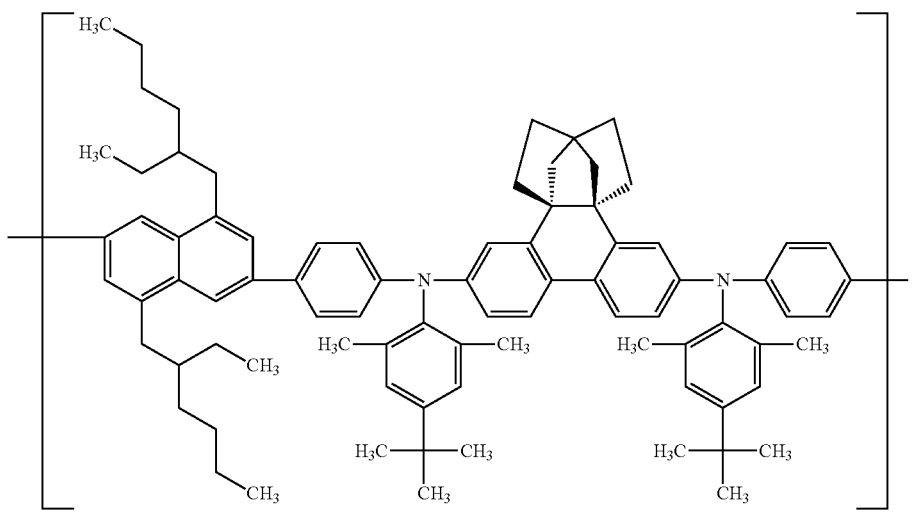
(1A-62)
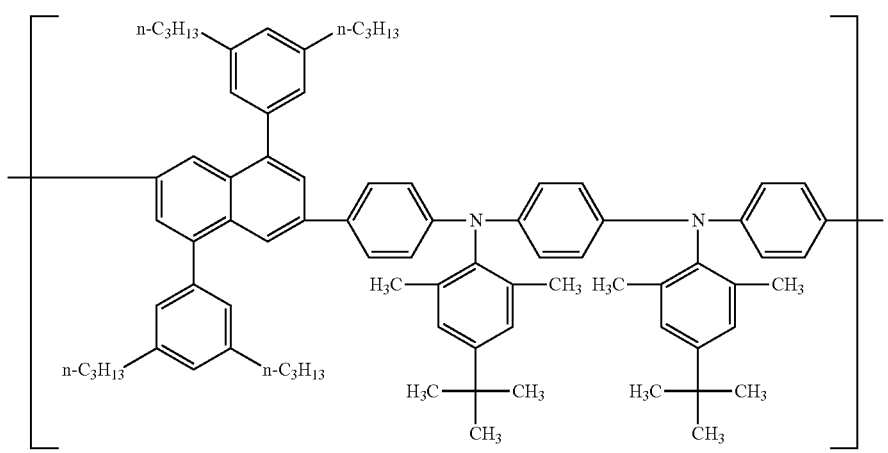
(1A-63)
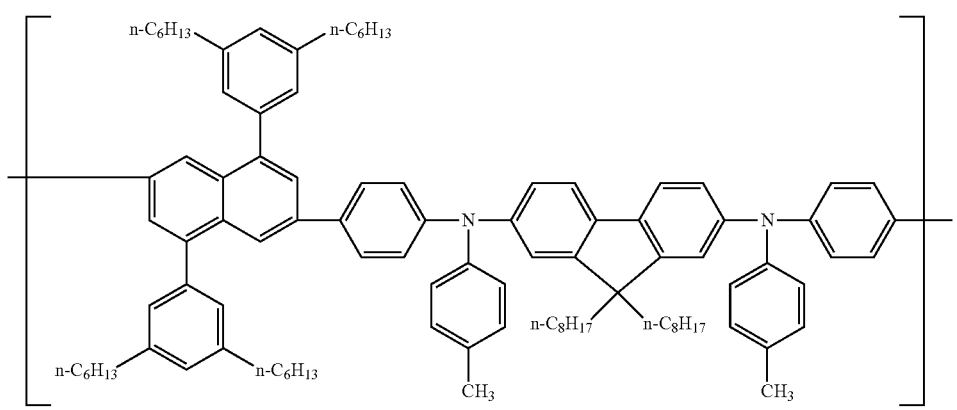
(1A-64)

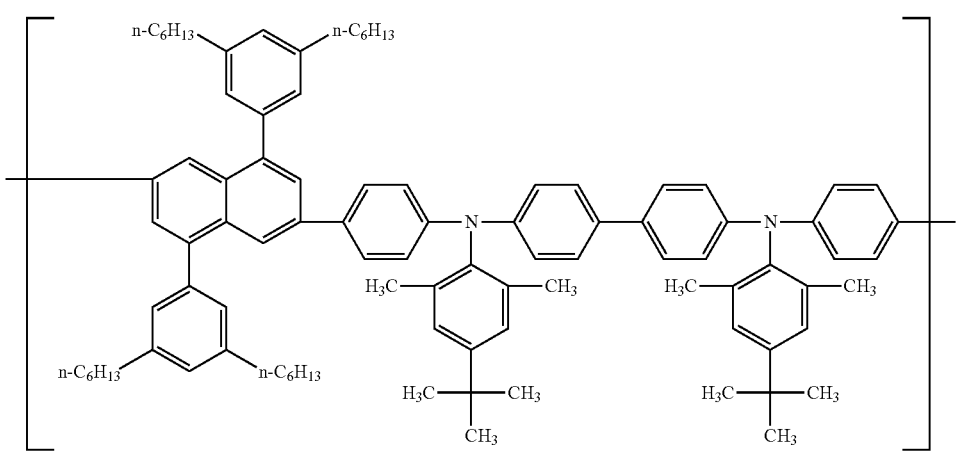
(1A-65)
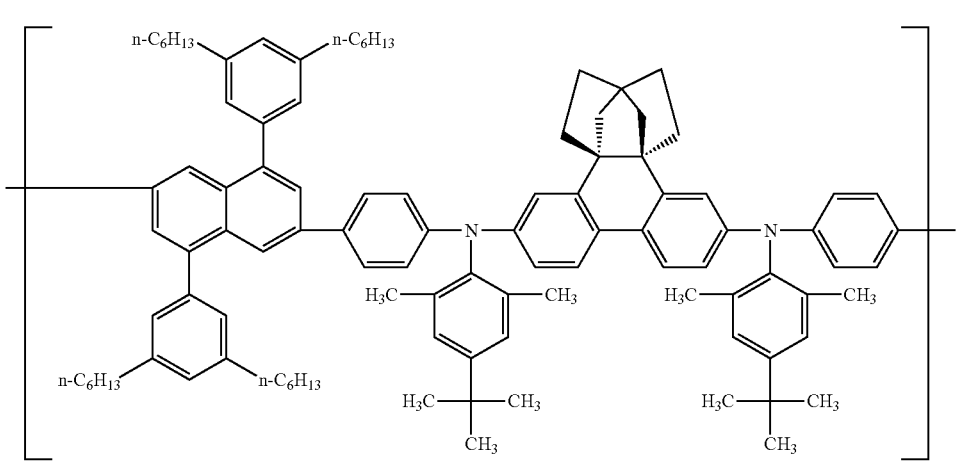
(1A-66)
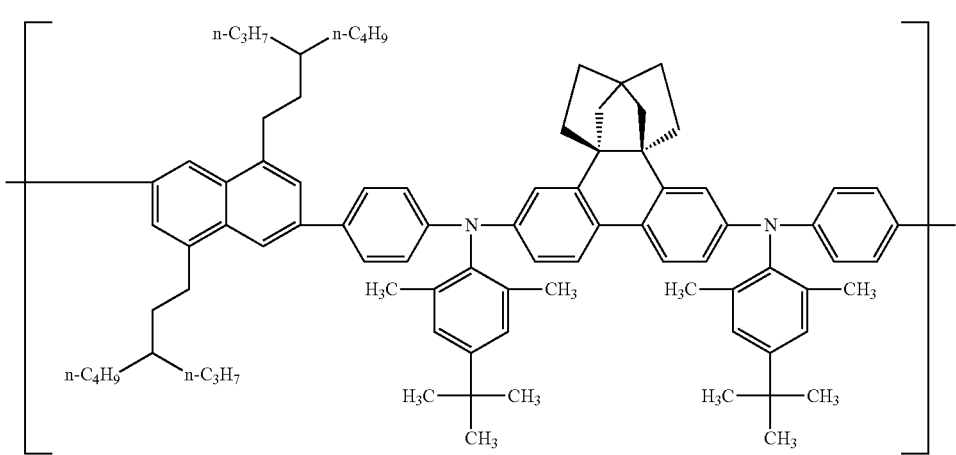
(1A-67)

(1A-68)

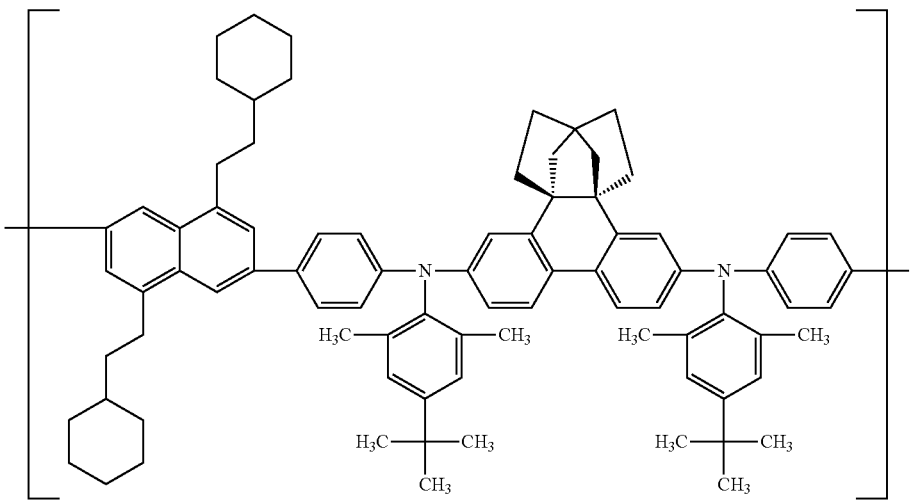

From the standpoint of solubility, the polymer compound of the present invention is preferably [1] a polymer compound comprising a constitutional unit represented by the above-described formula (1), and at least one constitutional unit selected from the group consisting of a constitutional unit represented by the following formula (4), a constitutional unit represented by the following formula (5) and a constitutional unit represented by the following formula (6), more preferably [2] a polymer compound consisting of a constitutional unit represented by the above-described formula (1), and at least one constitutional unit selected from the group consisting of a constitutional unit represented by the following formula (4), a constitutional unit represented by the following formula (5) and a constitutional unit represented by the following formula (6), further preferably [3] a polymer compound consisting of a constitutional unit represented by the above-described formula (1), and at least one constitutional unit selected from the group consisting of a constitutional unit represented by the following formula (4) and a constitutional unit represented by the following formula (6).

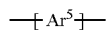 (4)

(in the formula (4), $Ar^5$ represents an unsubstituted or substituted arylene group.)

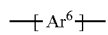 (5)

(in the formula (5), $Ar^6$ represents an unsubstituted or substituted di-valent aromatic heterocyclic group.)

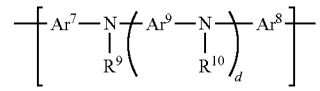 (6)

(in the formula (6), $Ar^7$, $Ar^8$ and $Ar^9$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups.

$R^9$ and $R^{10}$ represent each independently a hydrogen atom, an unsubstituted or substituted alkyl group, an unsubstituted or substituted aryl group or an unsubstituted or substituted mono-valent aromatic heterocyclic group.

d is 0 or 1.).

The unsubstituted or substituted arylene group represented by $Ar^5$ in the formula (4) includes, for example, unsubstituted or substituted phenylene groups such as an unsubstituted or substituted 1,4-phenylene group, an unsubstituted or substituted 1,3-phenylene group, an unsubstituted or substituted 1,2-phenylene group and the like; unsubstituted or substituted naphthalenediyl groups such as an unsubstituted or substituted 1,4-naphthalenediyl group, an unsubstituted or substituted 1,5-naphthalenediyl group, an unsubstituted or substituted 2,6-naphthalenediyl group and the like; unsubstituted or substituted phenanthrenediyl groups such as an unsubstituted or substituted 2,7-phenanthrenediyl group and the like; unsubstituted or substituted anthracenediyl groups such as a 1,4-anthracenediyl group, a 1,5-anthracenediyl group, a 2,6-anthracenediyl group, a 9,10-anthracenediyl group and the like; unsubstituted or substituted naphthacenediyl groups such as an unsubstituted or substituted 1,7-naphthacenediyl group, an unsubstituted or substituted 2,8-naphthacenediyl group, an unsubstituted or substituted 5,12-naphthacenediyl group and the like; unsubstituted or substituted fluorenediyl groups such as an unsubstituted or substituted 2,7-fluorenediyl group, an unsubstituted or substituted 3,6-fluorenediyl group and the like; unsubstituted or substituted pyrenediyl groups such as an unsubstituted or substituted 1,6-pyrenediyl group, an unsubstituted or substituted 1,8-pyrenediyl group, an unsubstituted or substituted 2,7-pyrenediyl group, an unsubstituted or substituted 4,9-pyrenediyl group and the like; unsubstituted or substituted perylenediyl groups such as an unsubstituted or substituted 3,9-perylenediyl group, an unsubstituted or substituted 3,10-perylenediyl group and the like; and unsubstituted or substituted chrysenediyl groups such as an unsubstituted or substituted 6,12-chrysenediyl group, an unsubstituted or substituted 2,8-chrysenediyl group and the like, preferably an unsubstituted or substituted phenylene group, an unsubstituted or substituted naphthalenediyl group, an unsubstituted or substituted anthracenediyl group and an unsubstituted or substituted fluorenediyl group, more preferably an unsubstituted or substituted phenylene group, an unsubstituted or substituted naphthalenediyl group and an unsubstituted or substituted fluorenediyl group.

The substituent which can be carried on the arylene group represented by $Ar^5$ includes, for example, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, preferably an unsubstituted or substituted alkyl group, an unsubstituted or substituted aryl group or an unsubstituted or substituted alkoxy group, more preferably an unsubstituted or substituted alkyl group or an unsubstituted or substituted aryl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

The constitutional unit represented by the above-described formula (4) is preferably a constitutional unit represented by the following formula (7), a constitutional unit represented by the following formula (8) or a constitutional unit represented by the following formula (9), more preferably a constitutional unit represented by the following formula (8) or a constitutional unit represented by the following formula (9), further preferably a constitutional unit represented by the following formula (9), because of more excellent luminance life of the resultant light emitting device.

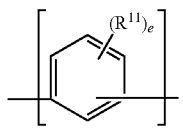
(7)

(in the formula (7), $R^{11}$ represents an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group. When a plurality of $R^{11}$s are present, these may be the same or different.

e represents an integer of 0 to 4.)

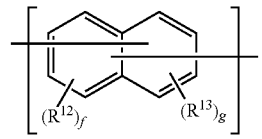
(8)

(in the formula (8), $R^{12}$ and $R^{13}$ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group. When a plurality of $R^{12}$s and $R^{13}$s are present, each of them may be the same or different.

f and g represent each independently an integer of 0 to 4. Here, f+g is 6 or less.)

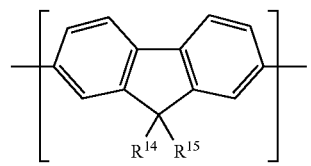
(9)

(in the formula (9), $R^{14}$ and $R^{15}$ represent each independently a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.).

The definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^{11}$ in the above-described formula (7) are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$. $R^{11}$ represents preferably an unsubstituted or substituted alkyl group or an unsubstituted or substituted aryl group.

In the above-described formula (7), e is preferably 0 or 1.

The constitutional unit represented by the above-described formula (7) includes, for example, constitutional units represented by the following formulae (7A-1) to (7A-9) and constitutional units represented by the following formulae (7B-1) to (7B-12). Of them, constitutional units represented by the formulae (7A-4) to (7A-9) and the formulae (7B-2) to (7B-10) are preferable, constitutional units represented by the formulae (7A-5) to (7A-8), the formula (7B-4) and the formula (7B-6) are more preferable, because of excellent luminance life of the resultant light emitting device.

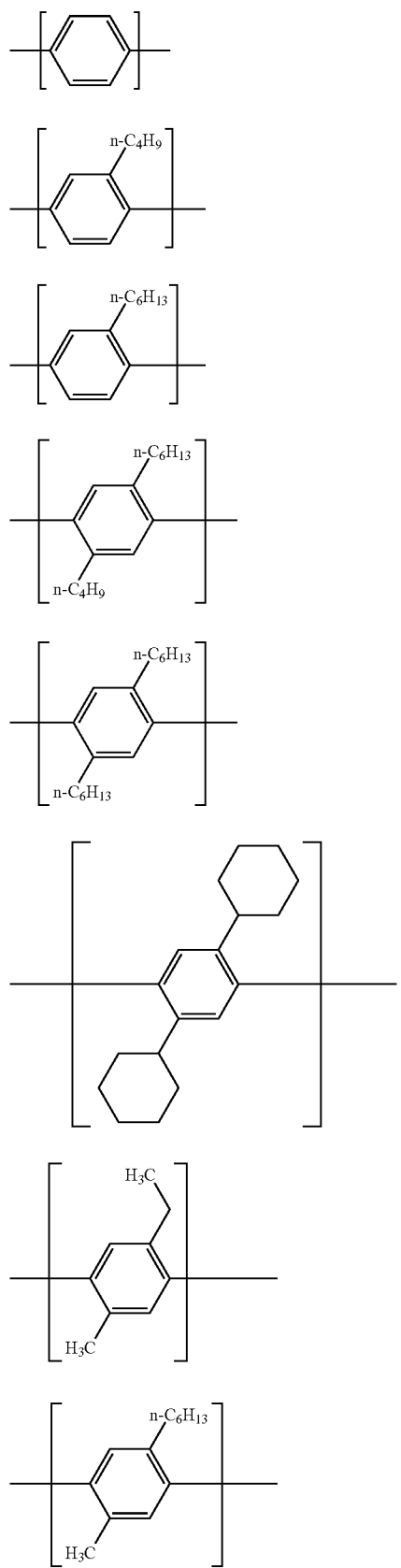
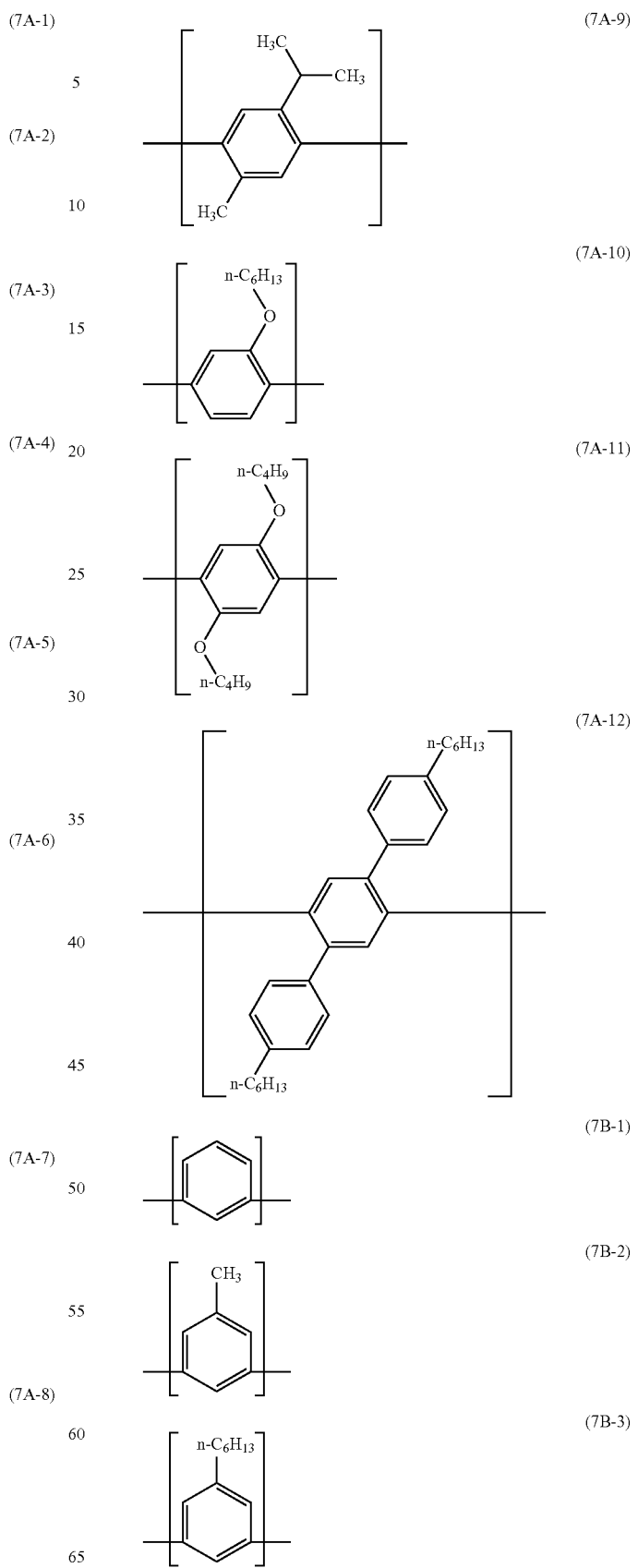

-continued

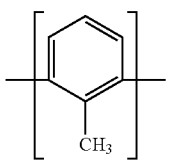
(7B-4)

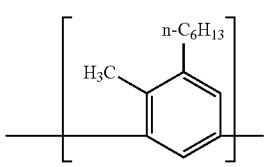
(7B-5)

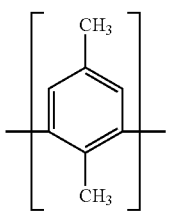
(7B-6)

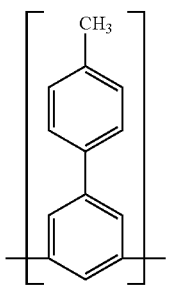
(7B-7)

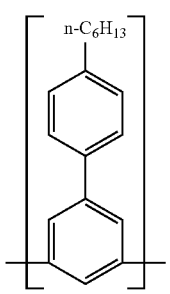
(7B-8)

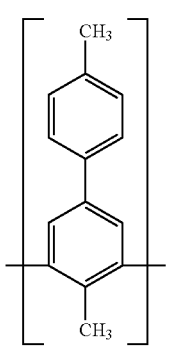
(7B-9)

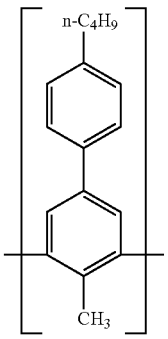
(7B-10)

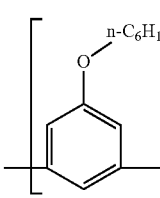
(7B-11)

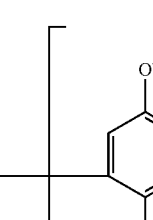
(7B-12)

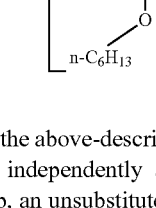

In the above-described formula (8), $R^{12}$ and $R^{13}$ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, preferably an unsubstituted or substituted alkyl group, an unsubstituted or substituted aryl group or an unsubstituted or substituted alkoxy group, more preferably an unsubstituted or substituted alkyl group or an unsubstituted or substituted aryl group, further preferably an unsubstituted or substituted alkyl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

In the above-described formula (8), f and g represent each independently preferably 0 or 1, more preferably 1, and further preferably, both f and g are 1.

The constitutional unit represented by the above-described formula (8) is preferably a constitutional unit represented by the following formula (8a).

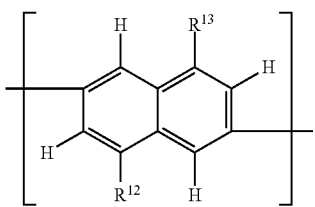

(8a)

(in the formula (8a), $R^{12}$ and $R^{13}$ represent the same meaning as described above.).

The constitutional unit represented by the above-described formula (8) includes, for example, constitutional units represented by the following formulae (8A-1) to (8A-23). Of them, constitutional units represented by the formulae (8A-1) to (8A-3) and the formulae (8A-10) to (8A-19) are preferable, constitutional units represented by the formulae (8A-11) to (8A-19) are more preferable, because of excellent luminance life of the resultant light emitting device.

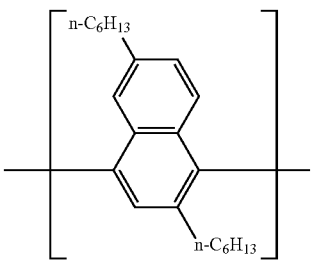

(8A-1)

(8A-2)

(8A-3)

(8A-4)

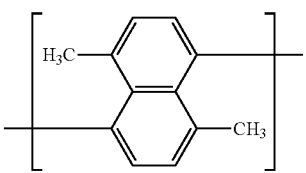

(8A-5)

(8A-6)

(8A-7)

(8A-8)

(8A-9)

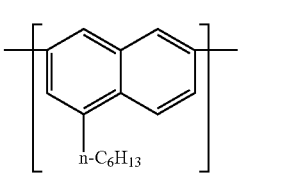

(8A-10)

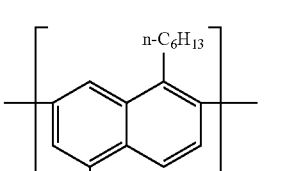

(8A-11)

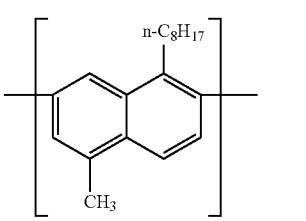

(8A-12)

(8A-13)
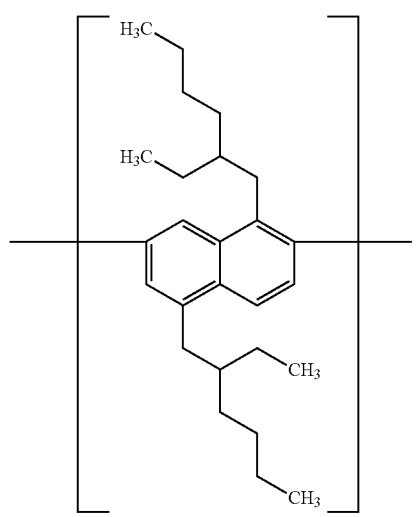
(8A-16)
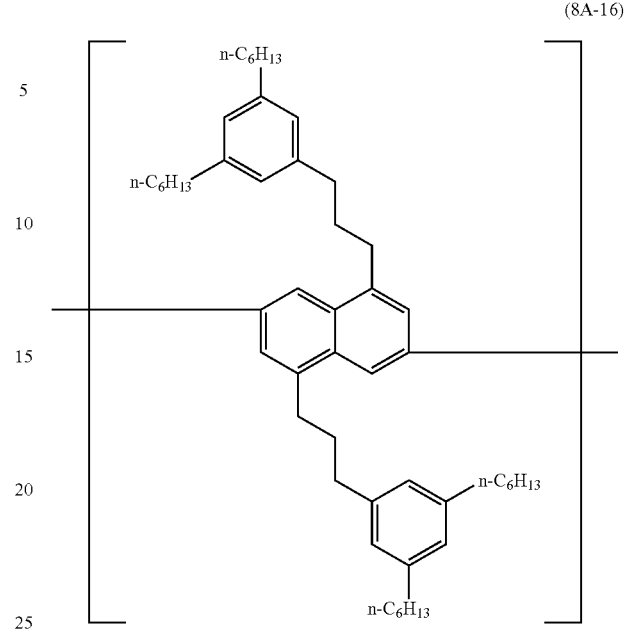
(8A-14)
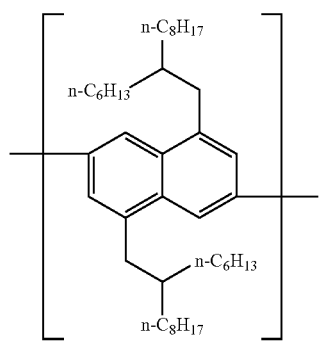
(8A-17)
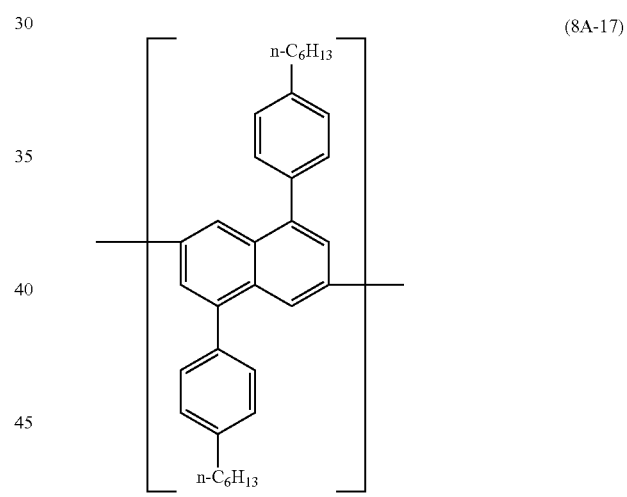
(8A-15)
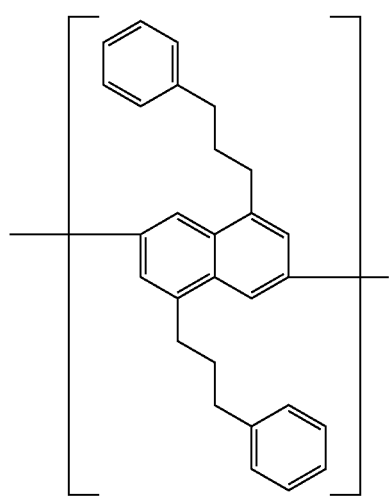
(8A-18)
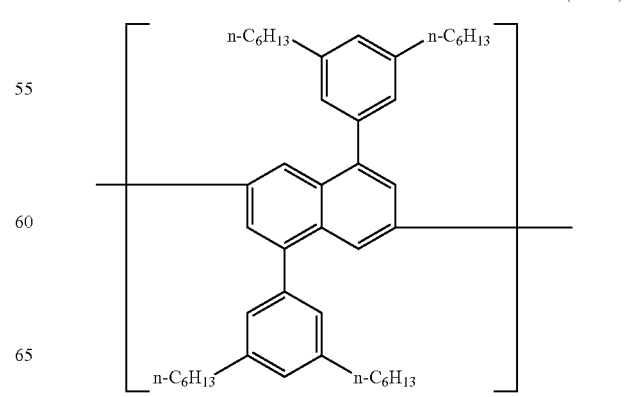

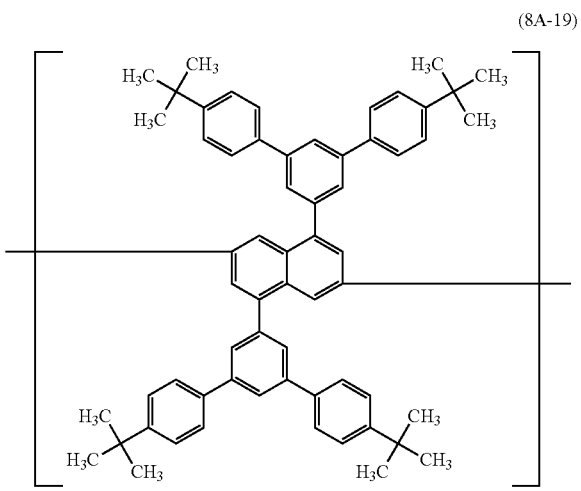

(8A-19)

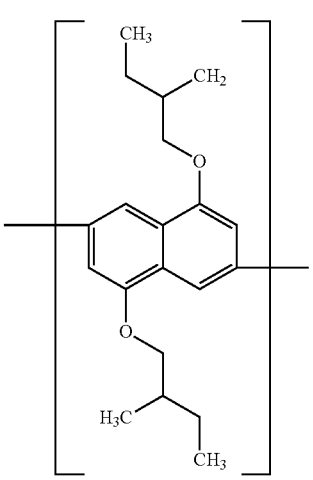

(8A-22)

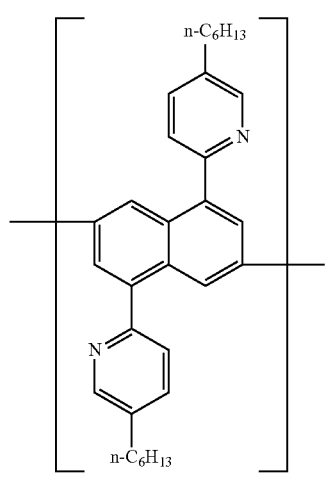

(8A-20)

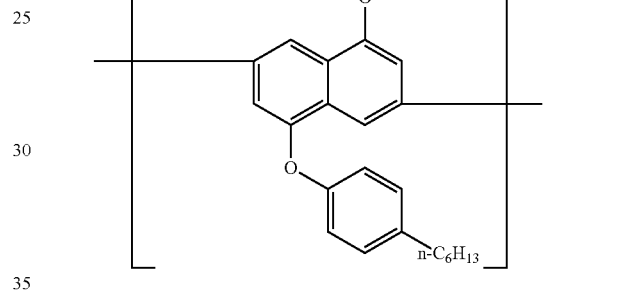

(8A-23)

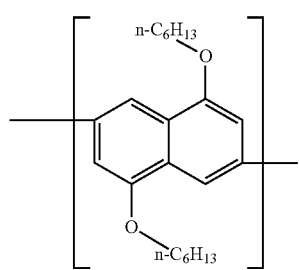

(8A-21)

In the above-described formula (9), $R^{14}$ and $R^{15}$ represent each independently a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, preferably an unsubstituted or substituted alkyl group, an unsubstituted or substituted aryl group or an unsubstituted or substituted alkoxy group, more preferably an unsubstituted or substituted alkyl group or an unsubstituted or substituted aryl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$. $R^{14}$ and $R^{15}$ may be mutually linked to form a ring structure together with the carbon atom to which they are attached.

The constitutional unit represented by the above-described formula (9) includes, for example, constitutional units represented by the following formulae (9A-1) to (9A-19). Of them, constitutional units represented by the formulae (9A-4) to (9A-17) are preferable, constitutional units represented by the formulae (9A-10) to (9A-17) are more preferable, because of excellent luminance life of the resultant light emitting device.

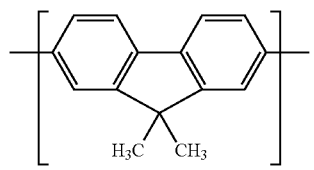
(9A-1)
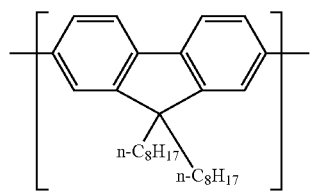
(9A-2)
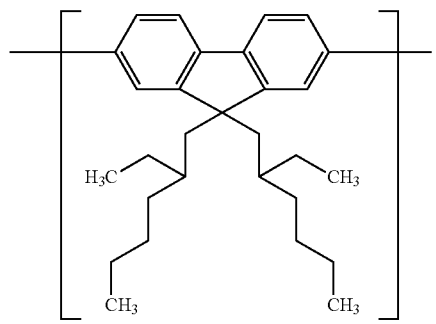
(9A-3)
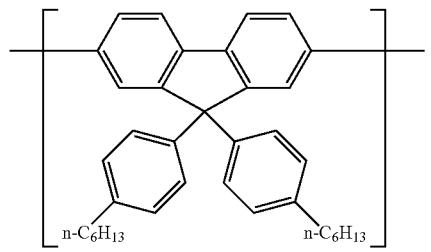
(9A-4)
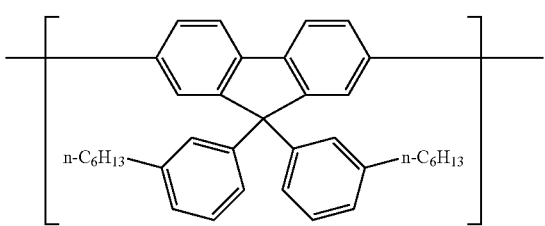
(9A-5)
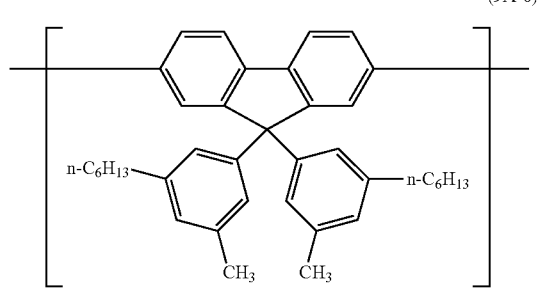
(9A-6)
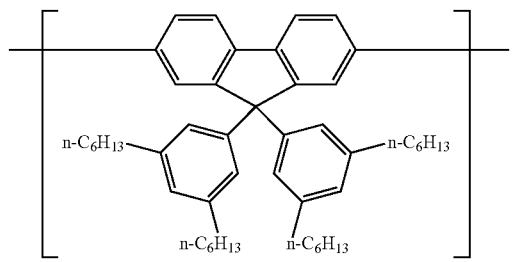
(9A-7)
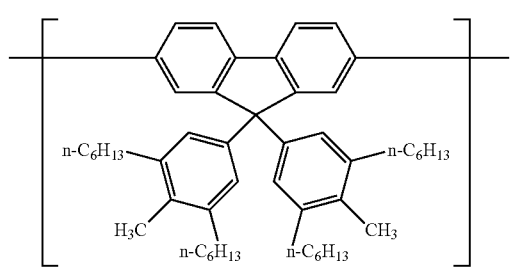
(9A-8)
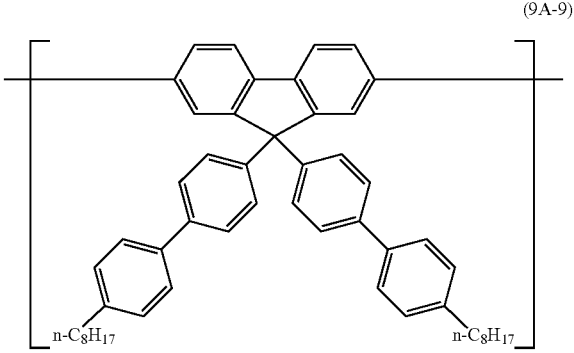
(9A-9)
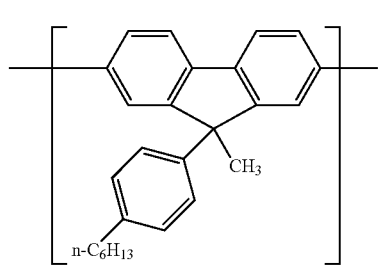
(9A-10)
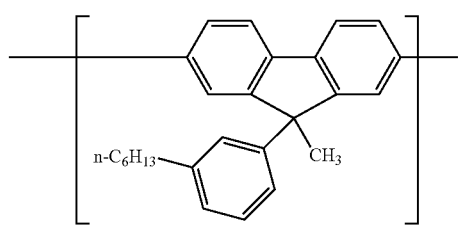
(9A-11)

(9A-12)
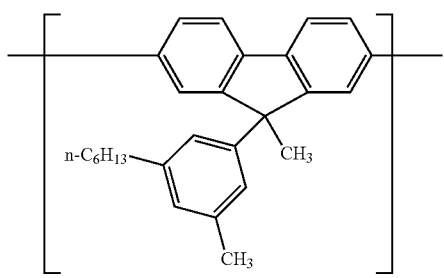

(9A-13)
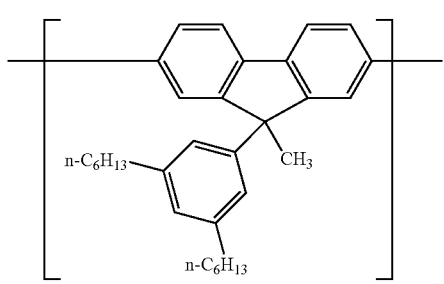

(9A-14)
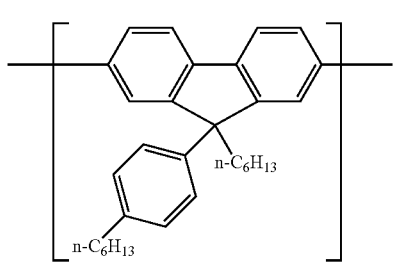

(9A-15)
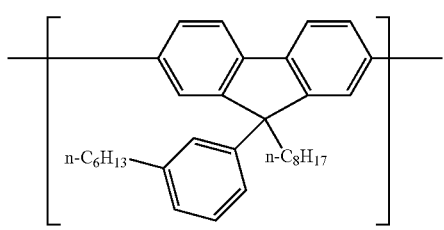

(9A-16)
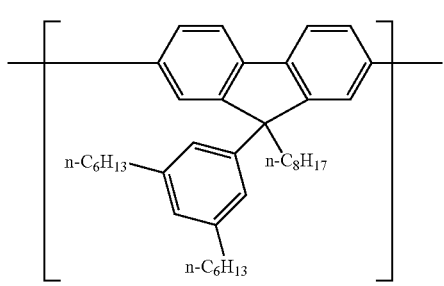

(9A-17)
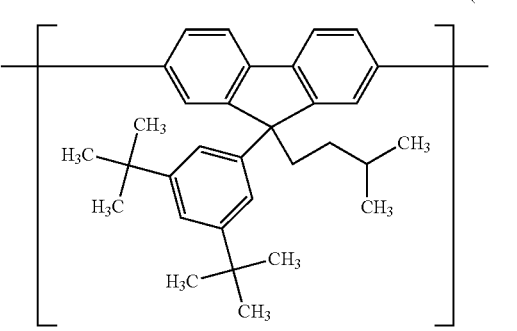

(9A-18)
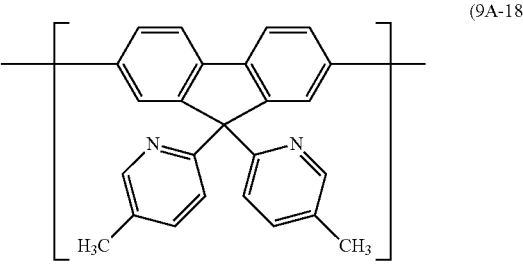

(9A-19)
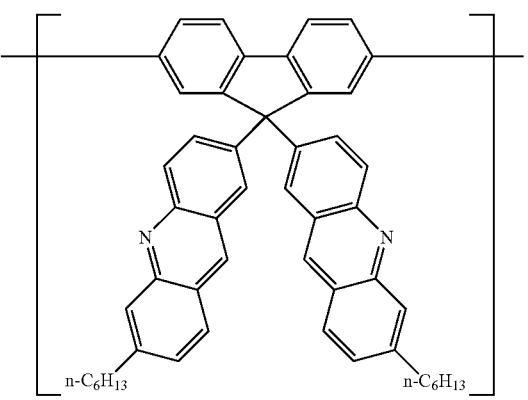

The unsubstituted or substituted di-valent aromatic heterocyclic group represented by $Ar^6$ in the above-described formula (5) includes, for example, unsubstituted or substituted pyridinediyl groups such as an unsubstituted or substituted 2,5-pyridinediyl group, an unsubstituted or substituted 2,6-pyridinediyl group and the like; unsubstituted or substituted furandiyl groups such as an unsubstituted or substituted 2,5-furandiyl group and the like; unsubstituted or substituted triazinediyl groups such as an unsubstituted or substituted 1,3,5-triazinediyl group and the like; unsubstituted or substituted quinolinediyl groups such as an unsubstituted or substituted 2,6-quinolinediyl group and the like; unsubstituted or substituted isoquinolinediyl groups such as an unsubstituted or substituted 1,4-isoquinolinediyl group, an unsubstituted or substituted 1,5-isoquinolinediyl group and the like; unsubstituted or substituted quinoxalinediyl groups such as an unsubstituted or substituted 5,8-quinoxalinediyl group and the like; unsubstituted or substituted carbazolediyl groups such as an unsubstituted or substituted 2,7-carbazolediyl group, an unsubstituted or substituted 3,6-carbazolediyl group and the like; unsubstituted or substituted phenoxazinediyl groups such as an unsubstituted or substituted 3,7-phenoxazinediyl group and the like, unsubstituted or substituted phenothiazinediyl groups such as an unsubstituted or substituted 3,7-phenothiazinediyl group and the like; and unsubstituted or substituted dibenzosilolediyl groups such as an unsubstituted or substituted 2,7-dibenzosilolediyl group and the like, preferably an unsubstituted or substituted triazinediyl group, an unsubstituted or substituted carbazolediyl group and an unsubstituted or substituted phenoxazinediyl group, more preferably an unsubstituted or substituted carbazolediyl group and an unsubstituted or substituted phenoxazinediyl group, further preferably an unsubstituted or substituted phenoxazinediyl group.

The substituent which can be carried on the unsubstituted or substituted di-valent aromatic heterocyclic group represented by $Ar^6$ includes, for example, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, preferably an unsubstituted or substituted alkyl group, an unsubstituted or substituted aryl group or an unsubstituted or substituted alkoxy group, more preferably an unsubstituted or substituted alkyl group or an unsubstituted or substituted aryl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

The constitutional unit represented by the above-described formula (5) is preferably a constitutional unit represented by the following formula (10), because of more excellent light emission efficiency of the resultant light emitting device.

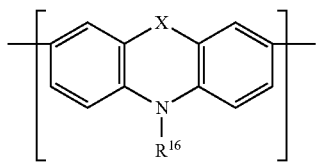
(10)

(in the formula (10), $R^{16}$ represents an unsubstituted or substituted alkyl group, an unsubstituted or substituted aryl group or an unsubstituted or substituted mono-valent aromatic heterocyclic group.

X represents a single bond, —O—, —S—, or —C($R^a$)$_2$—. $R^a$ represents an unsubstituted or substituted alkyl group or an unsubstituted or substituted aryl group. Two $R^a$s may be the same or different.).

In the above-described formula (10), $R^{16}$ represents an unsubstituted or substituted alkyl group, an unsubstituted or substituted aryl group or an unsubstituted or substituted mono-valent aromatic heterocyclic group, preferably an unsubstituted or substituted alkyl group or an unsubstituted or substituted aryl group, more preferably an unsubstituted or substituted aryl group. The definitions and examples of these unsubstituted or substituted alkyl group, unsubstituted or substituted aryl group and unsubstituted or substituted mono-valent aromatic heterocyclic group are the same as the definitions and examples of the unsubstituted or substituted alkyl group, the unsubstituted or substituted aryl group and the unsubstituted or substituted mono-valent aromatic heterocyclic group represented by $R^1$ and $R^2$.

In the above-described formula (10), X represents preferably —O— or —C($R^a$)$_2$—, more preferably —O—.

The constitutional unit represented by the above-described formula (10) includes, for example, constitutional units represented by the following formulae (10A-1) to (10A-8). Of them, constitutional units represented by the formulae (10A-1) to (10-5) and the formulae (10-12) to (10A-14) are preferable, constitutional units represented by the formulae (10A-3) to (10A-5) are more preferable, because of excellent luminance life of the resultant light emitting device.

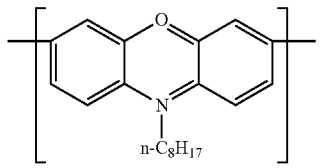
(10A-1)

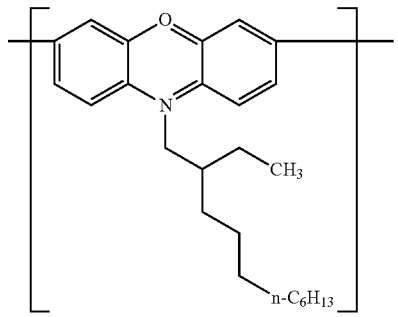
(10A-2)

-continued
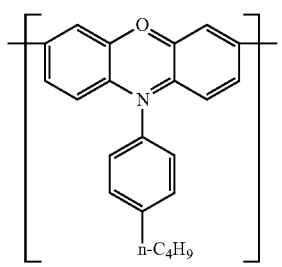 (10A-3)
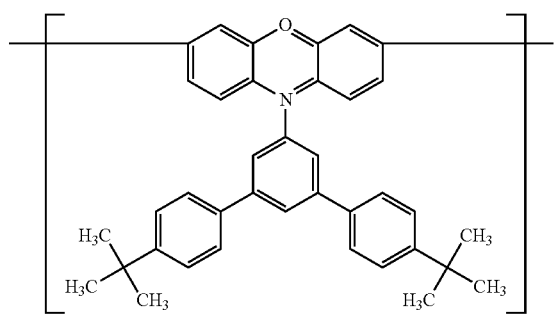 (10A-4)
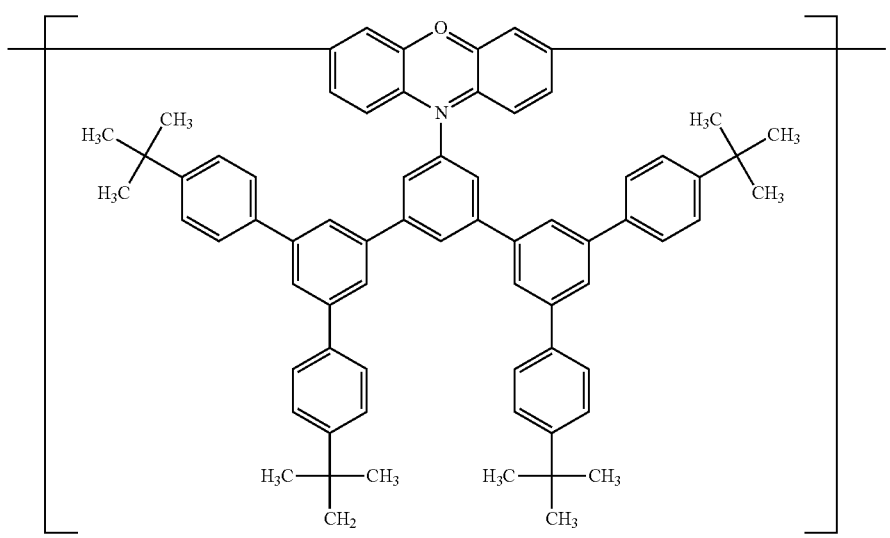 (10A-5)
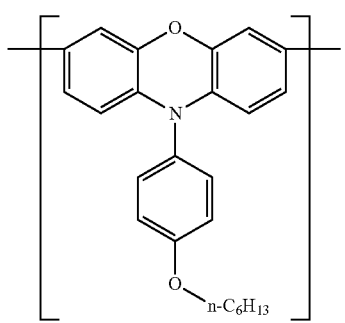 (10A-6)
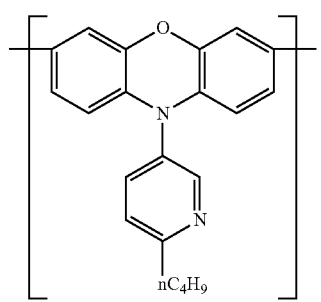 (10A-7)
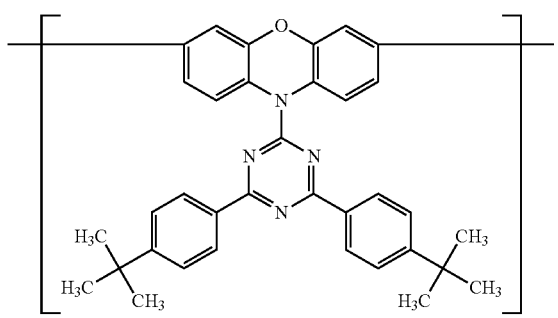 (10A-8)
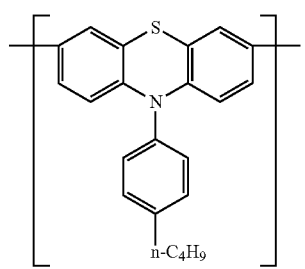 (10A-9)

(10A-10)
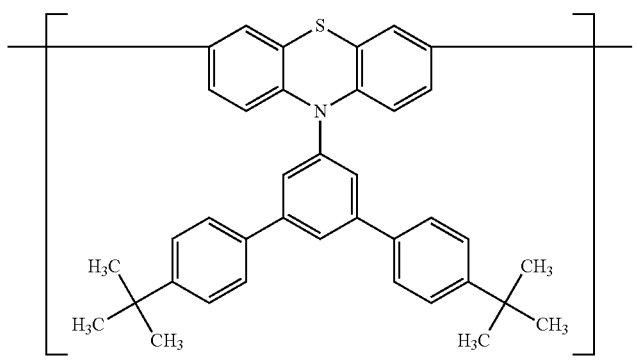
(10A-11)
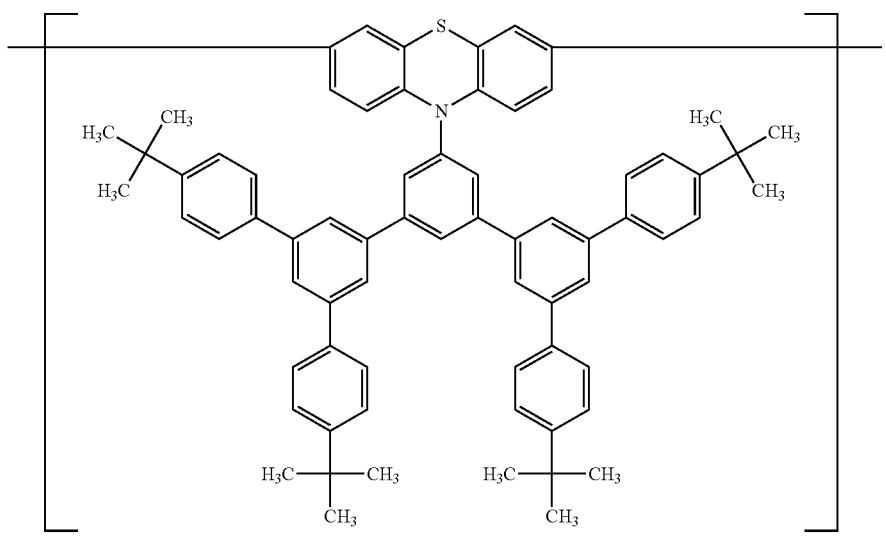
(10A-12)
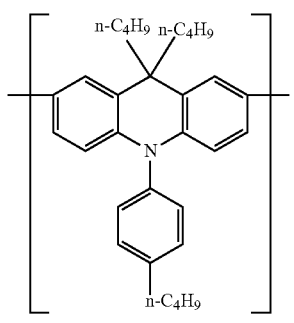
(10A-13)
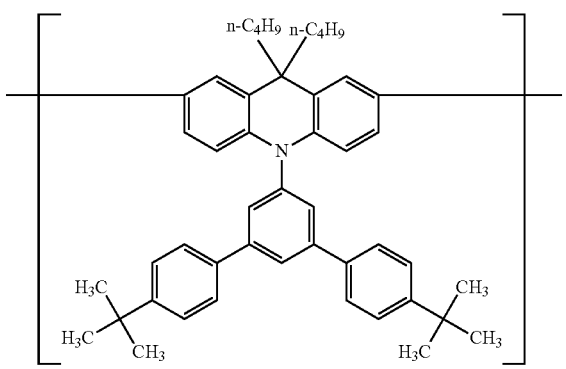

-continued

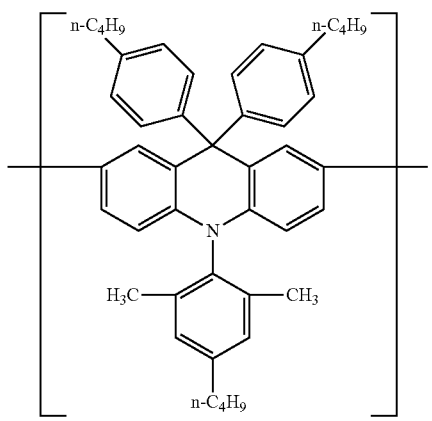
(10A-14)

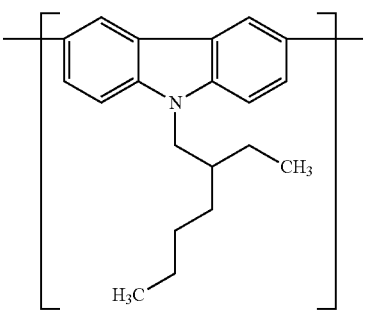
(10A-15)

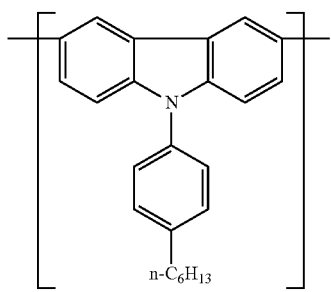
(10A-16)

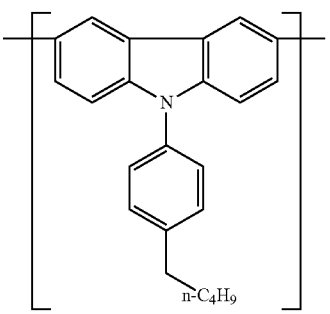
(10A-17)

In the above-described formula (6), $Ar^7$, $Ar^8$ and $Ar^9$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups. The definitions and examples of these unsubstituted or substituted arylene group, unsubstituted or substituted di-valent aromatic heterocyclic group and group obtained by linking two or more groups selected from the group consisting of unsubstituted or substituted arylene groups and unsubstituted or substituted di-valent aromatic heterocyclic groups are the same as the definitions and examples of the unsubstituted or substituted arylene group, the unsubstituted or substituted di-valent aromatic heterocyclic group and the group obtained by linking two or more groups selected from the group consisting of unsubstituted or substituted arylene groups and unsubstituted or substituted di-valent aromatic heterocyclic groups represented by $Ar^2$, $Ar^3$ and $Ar^4$.

$Ar^7$ and $Ar^8$ represent preferably an unsubstituted or substituted arylene group, more preferably an unsubstituted or substituted 1,4-phenylene group or an unsubstituted or substituted 1,4-naphthalenediyl group, further preferably an unsubstituted or substituted 1,4-phenylene group.

$Ar^9$ represents preferably an unsubstituted or substituted arylene group or a group obtained by linking two or more groups selected from the group consisting of unsubstituted or substituted arylene groups and unsubstituted or substituted di-valent aromatic heterocyclic groups, more preferably an unsubstituted or substituted 1,4-phenylene group, an unsubstituted or substituted 1,4-naphthalenediyl group, an unsubstituted or substituted 2,7-fluorenediyl group, a 9,10-anthracenediyl group, an unsubstituted or substituted 9,10-dihydro-2,7-phenanthrenediyl group or an unsubstituted or substituted group represented by the above-described formula (13-1), further preferably an unsubstituted or substituted 1,4-phenylene group, an unsubstituted or substituted 2,7-fluorenediyl group, an unsubstituted or substituted 9,10-dihydro-2,7-phenanthrenediyl group or an unsubstituted or substituted group represented by the above-described formula (13-1), particularly preferably an unsubstituted 1,4-phenylene group, a substituted 2,7-fluorenediyl group, an unsubstituted or substituted 9,10-dihydro-2,7-phenanthrenediyl group or an unsubstituted group represented by the above-described formula (13-1).

The substituent which can be carried on the group represented by $Ar^7$, $Ar^8$ and $Ar^9$ includes preferably an unsubstituted or substituted alkyl group, an unsubstituted or substituted aryl group, an unsubstituted or substituted mono-valent aromatic heterocyclic group, an unsubstituted or substituted alkoxy group and an unsubstituted or substituted aryloxy group, more preferably an unsubstituted or substituted alkyl group and an unsubstituted or substituted aryl group, further preferably an unsubstituted or substituted alkyl group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

The substituents which can be carried on the group represented by $Ar^7$, $Ar^8$ and $Ar^9$ may be mutually linked to form a ring structure.

The definitions and examples of the unsubstituted or substituted alkyl group, the unsubstituted or substituted aryl group and the unsubstituted or substituted mono-valent aromatic heterocyclic group represented by $R^9$ and $R^{10}$ in the above-described formula (6) are the same as the definitions and examples of the unsubstituted or substituted alkyl group, the unsubstituted or substituted aryl group and the unsubstituted or substituted mono-valent aromatic heterocyclic group represented by $R^1$ and $R^2$. $R^9$ and $R^{10}$ represent preferably an unsubstituted or substituted alkyl group or an unsubstituted or substituted aryl group, more preferably a substituted aryl group.

In the above-described formula (6), d is 0 or 1, preferably 1.

The constitutional unit represented by the above-described formula (6) includes, for example, constitutional units represented by the above-described the formulae (2A-1) to (2A-36). Of them, constitutional units represented by the formulae (2A-3) to (2A-7), the formulae (2A-12) to (2A-17), the formulae (2A-25) to (2A-28) and the formulae (2A-31) to (2A-36) are preferable, constitutional units represented by the formulae (2A-6) to (2A-7), the formulae (2A-14) to (2A-17), the formula (2A-26), the formula (2A-28) and the formulae (2A-33) to (2A-35) are more preferable, because of excellent luminance life of the resultant light emitting device.

In the polymer compound of the present invention, the proportion of the total mole number of a constitutional unit represented by the formula (1), a constitutional unit represented by the formula (4), a constitutional unit represented by the formula (5) and a constitutional unit represented by the formula (6) with respect to the total mole number of all constitutional units is preferably 80 to 100%, more preferably 90 to 100%, further preferably 95 to 100%, particularly preferably 100%.

In the polymer compound of the present invention, the proportion of the total mole number of a constitutional unit represented by the formula (1) with respect to the total mole number of all constitutional units is preferably 1 to 100%, more preferably 30 to 100%, further preferably 50 to 100%, particularly preferably 60 to 100%.

The polymer compound of the present invention is, when used in the form of a composition described later, preferably a polymer compound consisting of a constitutional unit represented by the following formula (11).

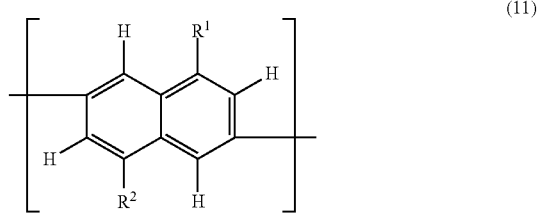

(11)

(in the formula (11), $R^1$ and $R^2$ represent the same meaning as described above.).

The polymer compound consisting of at least one constitutional units represented by the formula (11) may be a polymer compound consisting of only one constitutional unit such as a polymer compound (P-4) and the like or a polymer compound consisting of two constitutional units such as a polymer compound (P-5) and the like, described later.

The polymer compound of the present invention has a polystyrene-equivalent number-average molecular weight according to gel permeation chromatography (hereinafter, referred to as "GPC") of usually $1 \times 10^3$ to $1 \times 10^6$, preferably $1 \times 10^4$ to $1 \times 10^6$. The polymer compound has a polystyrene-equivalent weight-average molecular weight of usually $2 \times 10^3$ to $2 \times 10^2$, and because of excellent film formability, preferably $2 \times 10^4$ to $2 \times 10^6$, more preferably $3 \times 10^4$ to $1 \times 10^6$, further preferably $5 \times 10^4$ to $5 \times 10^5$.

It is preferable that the end group of the polymer compound of the present invention is a stable group. The end group is preferably a group having a conjugated bond to the main chain, and includes groups having bonding to an aryl group or a mono-valent aromatic heterocyclic group via a carbon-carbon bond.

The polymer compound of the present invention may be a homopolymer, or a copolymer such as a block copolymer, a random copolymer, an alternate copolymer, a graft copolymer and the like, or may be another embodiment.

Suitable polymer compounds include the following polymer compounds (P-1) to (P-15). Q1 to Q18 represent the molar ratio of the repeating unit in brackets to all constitutional units in the polymer compound.

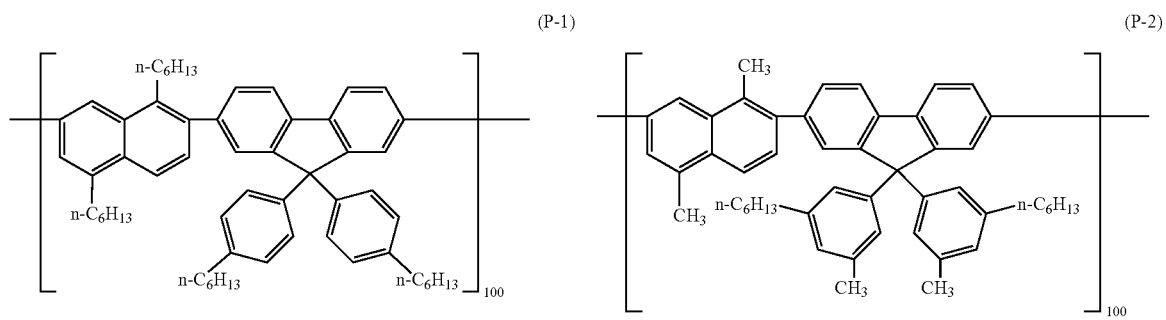

-continued
(P-3)
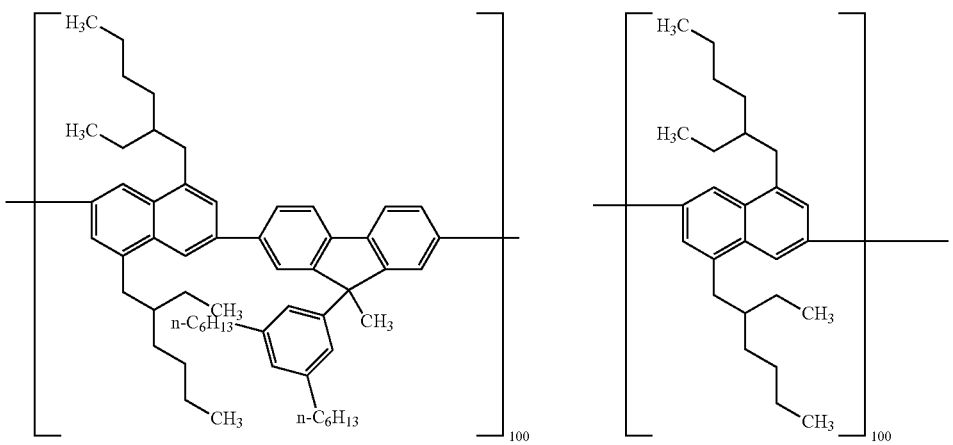
(P-4)
(P-5)
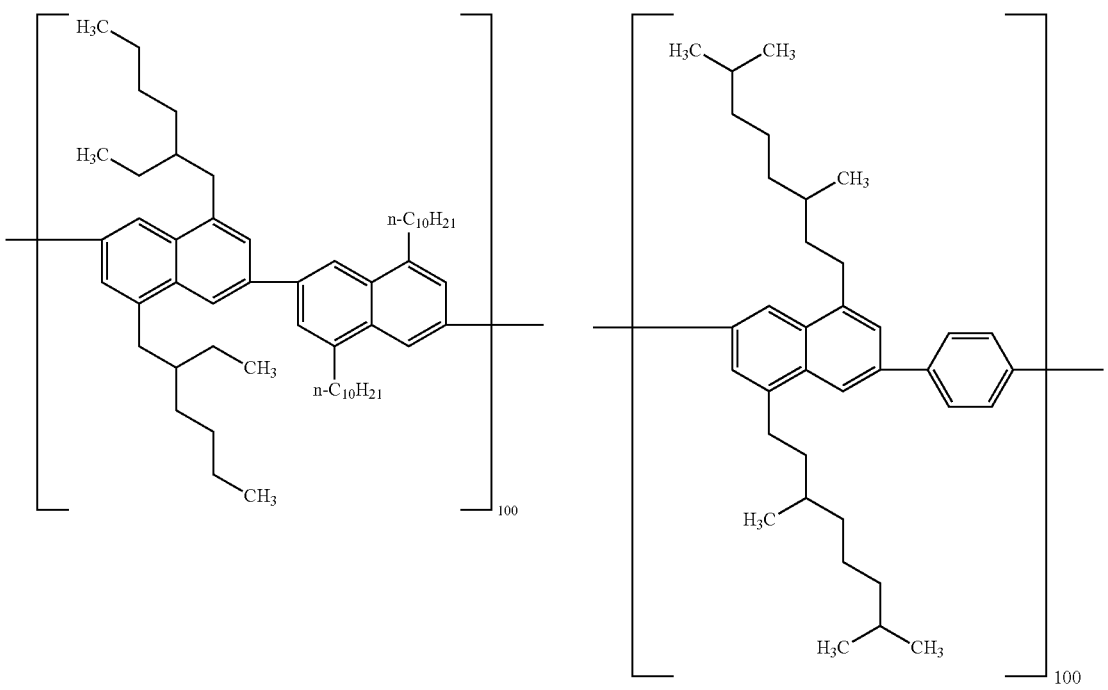
(P-6)

-continued
(P-7)
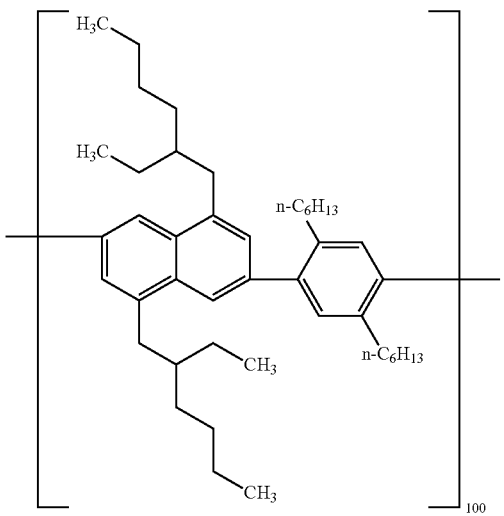
(P-8)
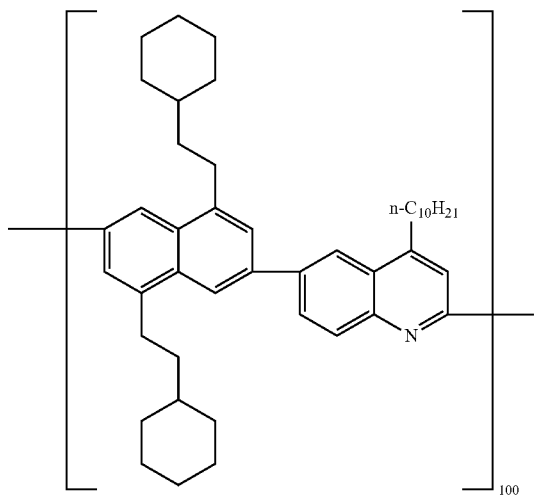
(P-9)
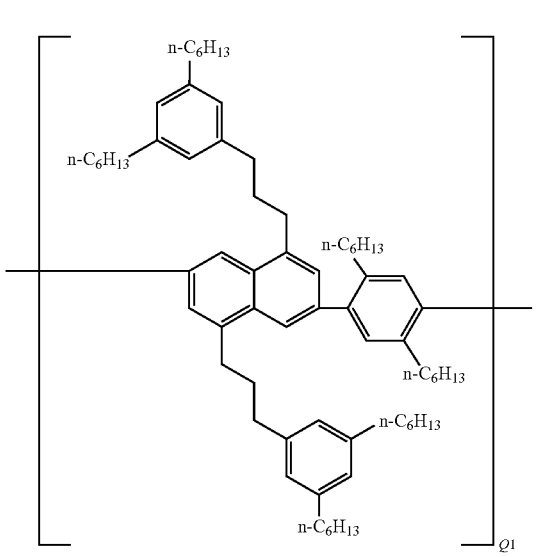 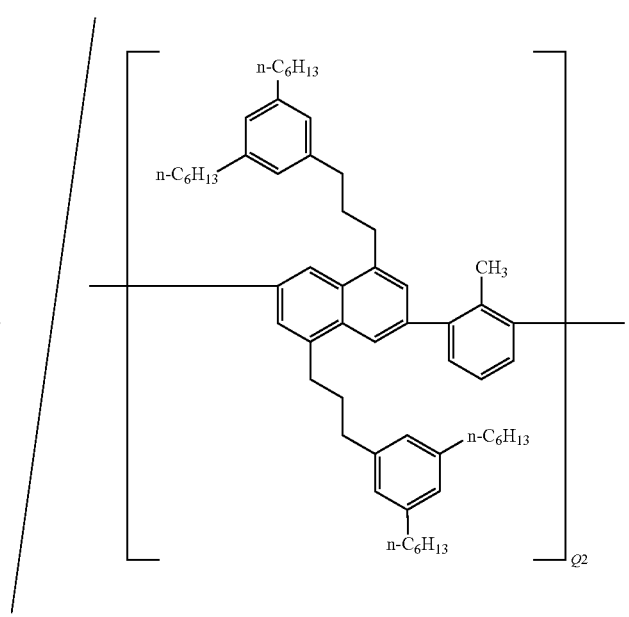

(wherein, Q1 represents a number of 10 to 90, and Q2 represents a number of 10 to 90. Here, Q1+Q2 is 100.)
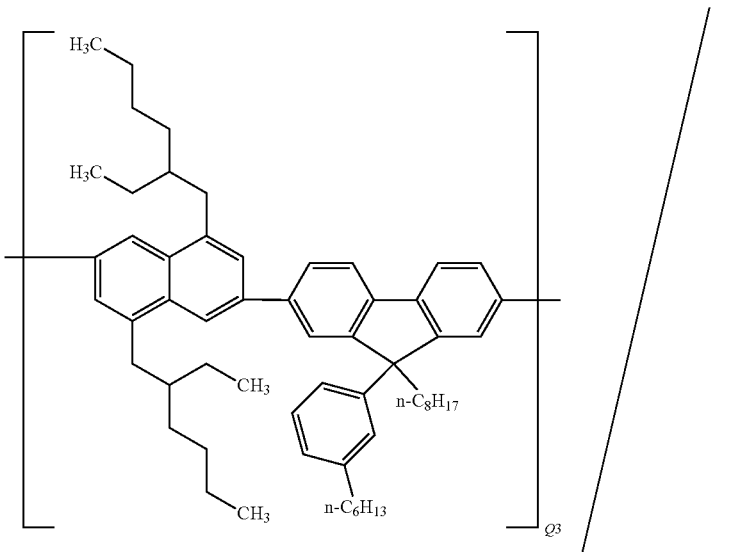
(P-10)
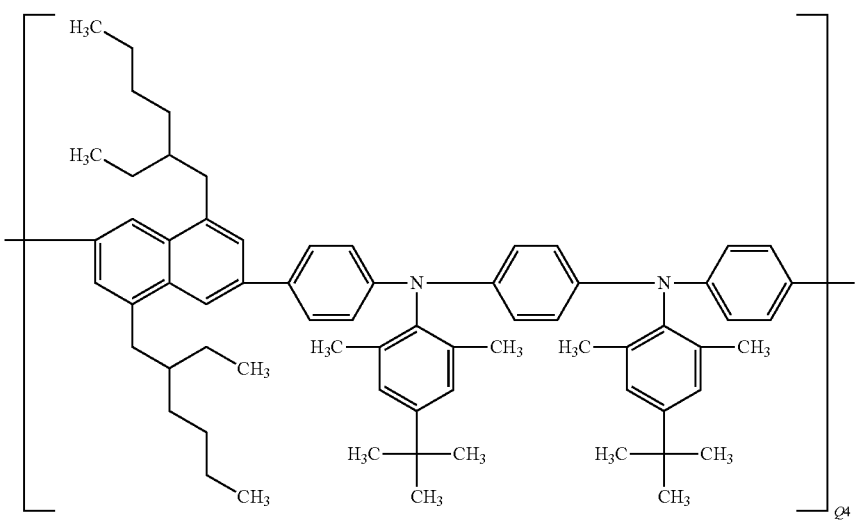

(wherein, Q3 represents a number of 80 to 96, and Q4 represents a number of 4 to 20. Here, Q3+Q4 is 100.)
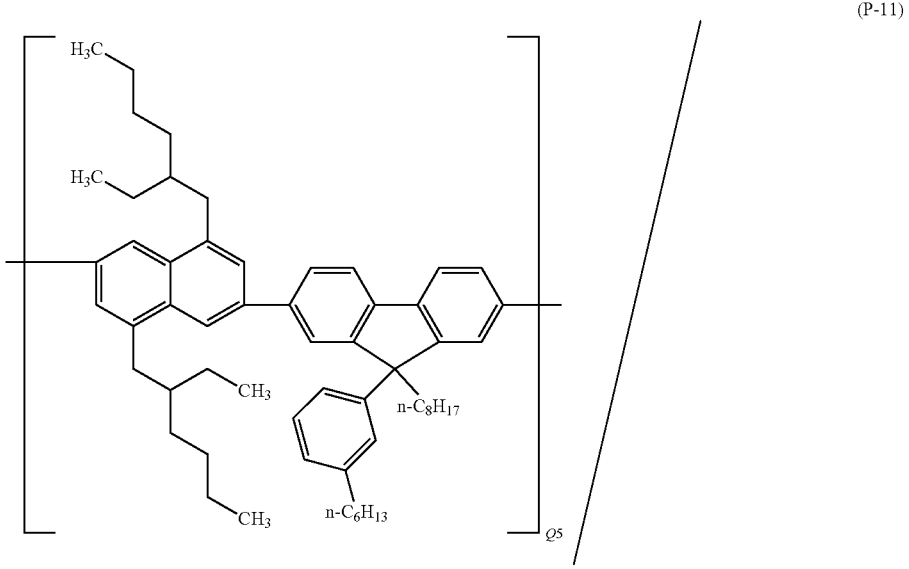
(P-11)
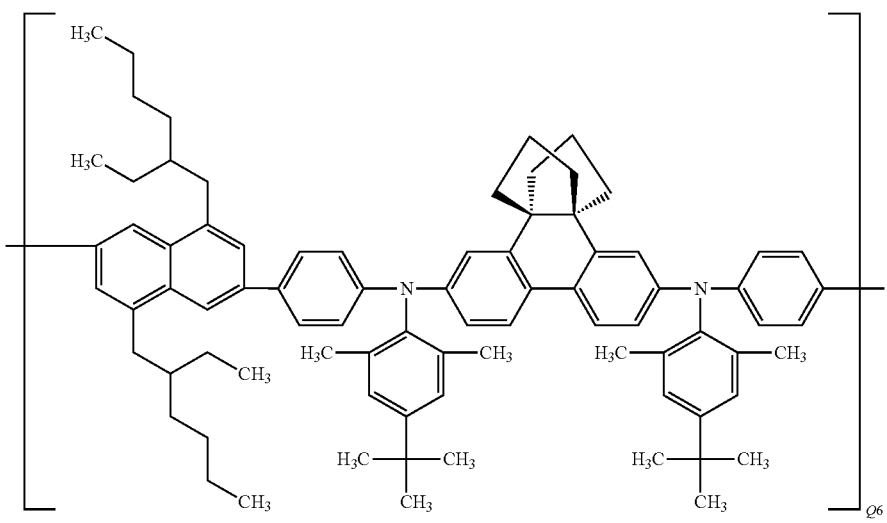

(wherein, Q5 represents a number of 80 to 96, and Q6 represents a number of 4 to 20. Here, Q5+Q6 is 100.)
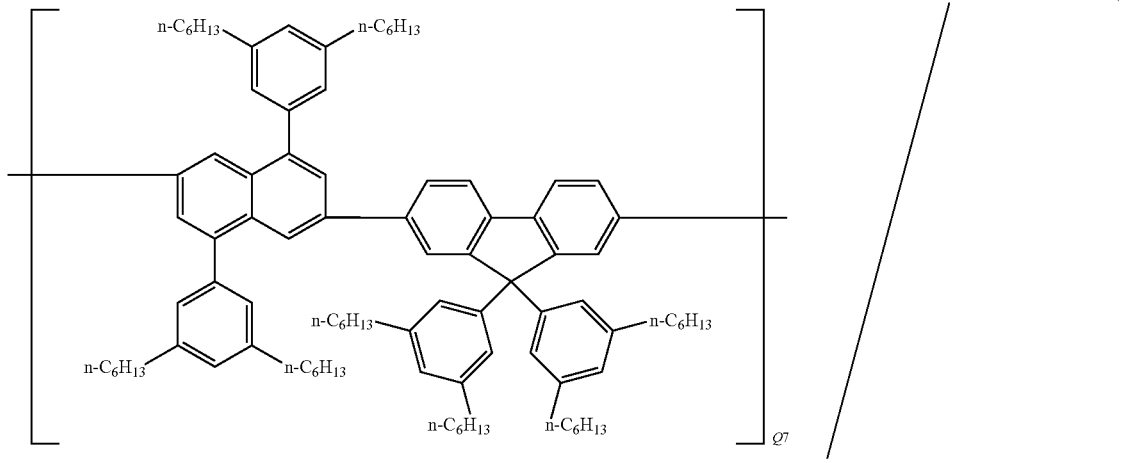
(P-12)
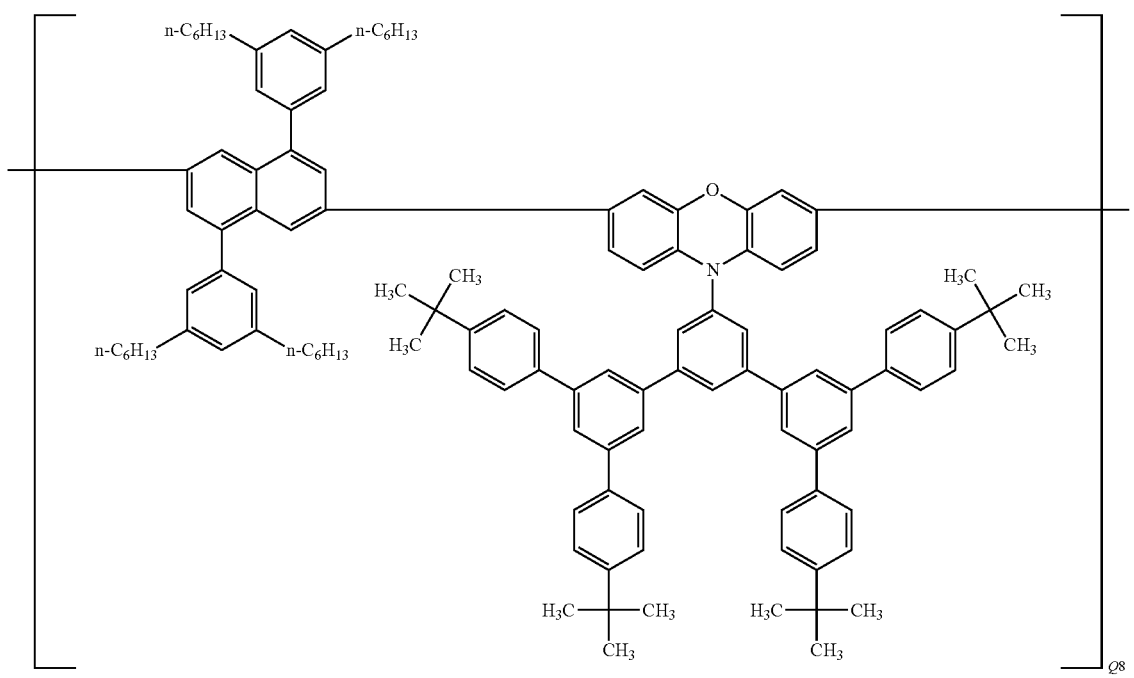

(wherein, Q7 represents a number of 80 to 96, and Q8 represents a number of 4 to 20. Here, Q7+Q8 is 100.)
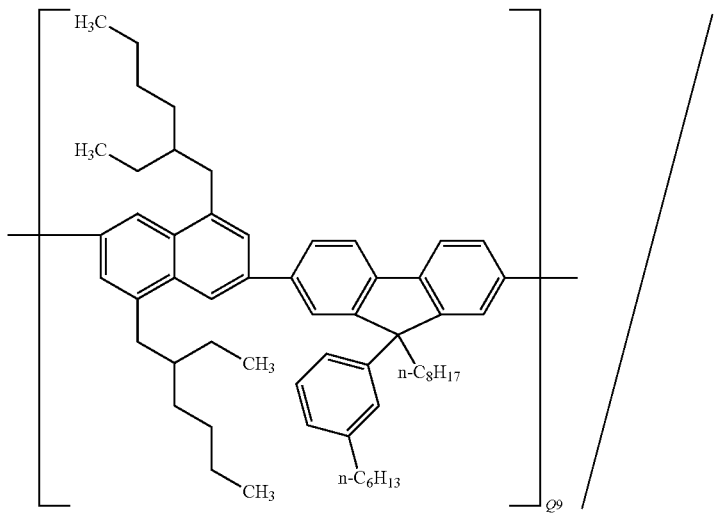
(P-13)
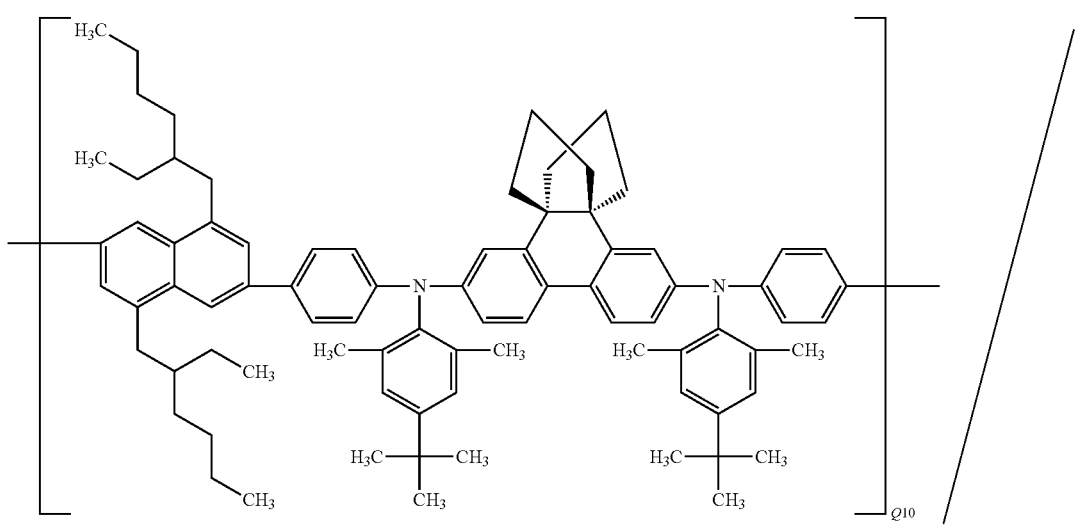

-continued
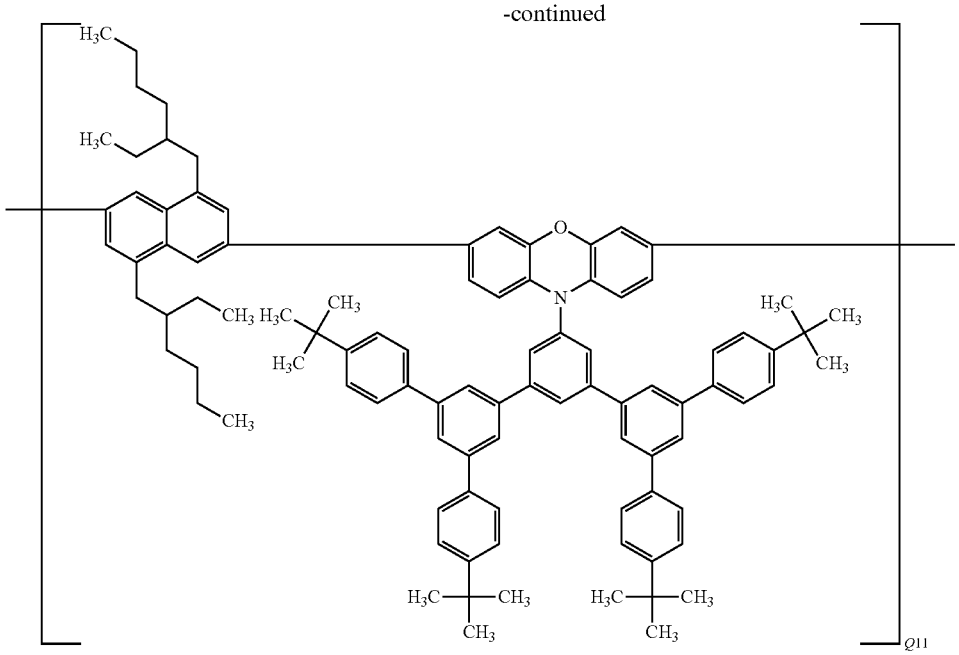
(wherein, Q9 represents a number of 70 to 95, Q10 represents a number of 4 to 20, and Q11 represents a number of 1 to 10. Here, Q9+Q10+Q11 is 100.)
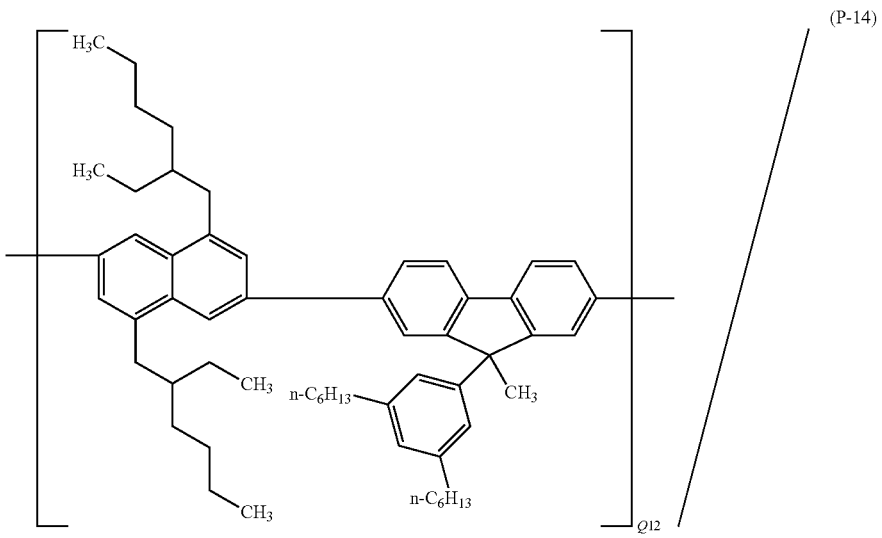
(P-14)

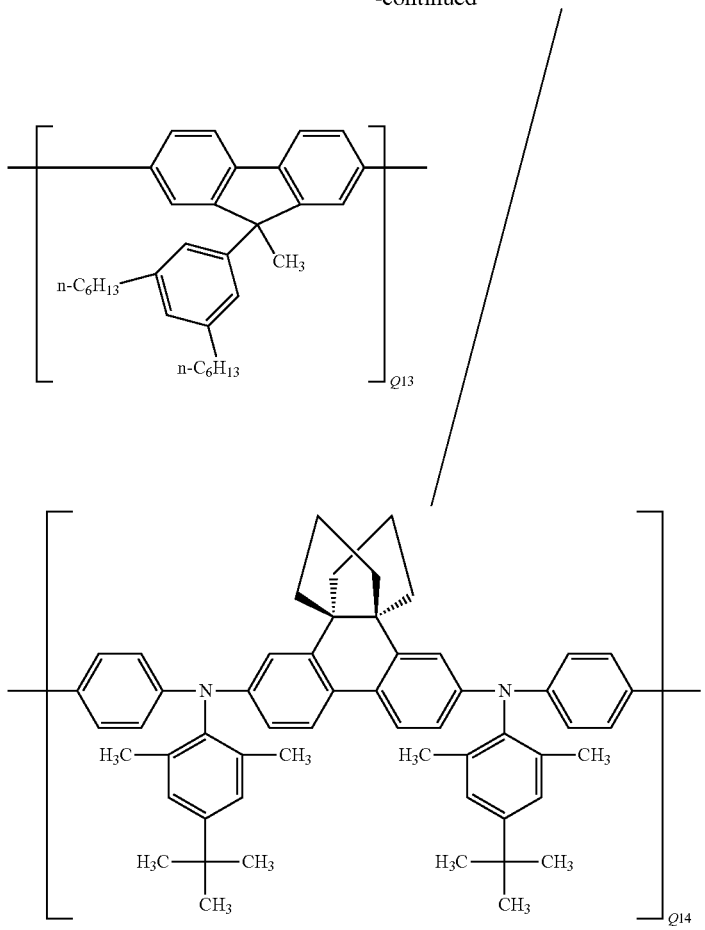
(wherein, Q12 represents a number of 60 to 90, Q13 represents a number of 5 to 20, and Q14 represents a number of 5 to 20. Here, Q12+Q13+Q14 is 100.)
(P-15)
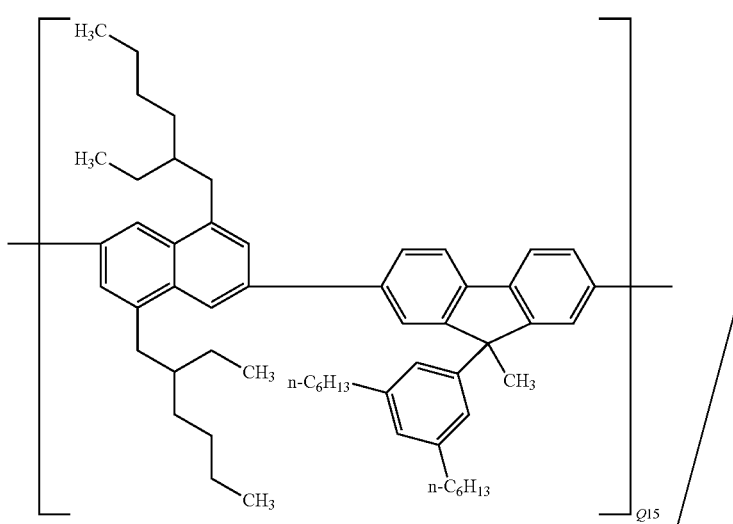

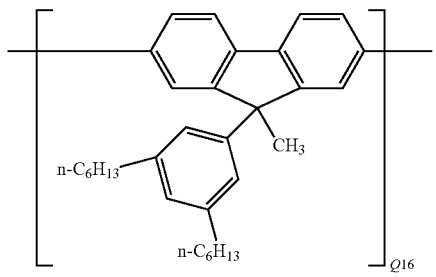
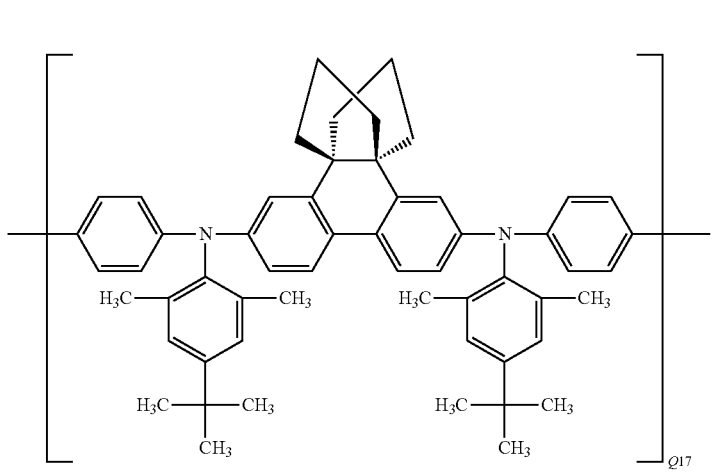
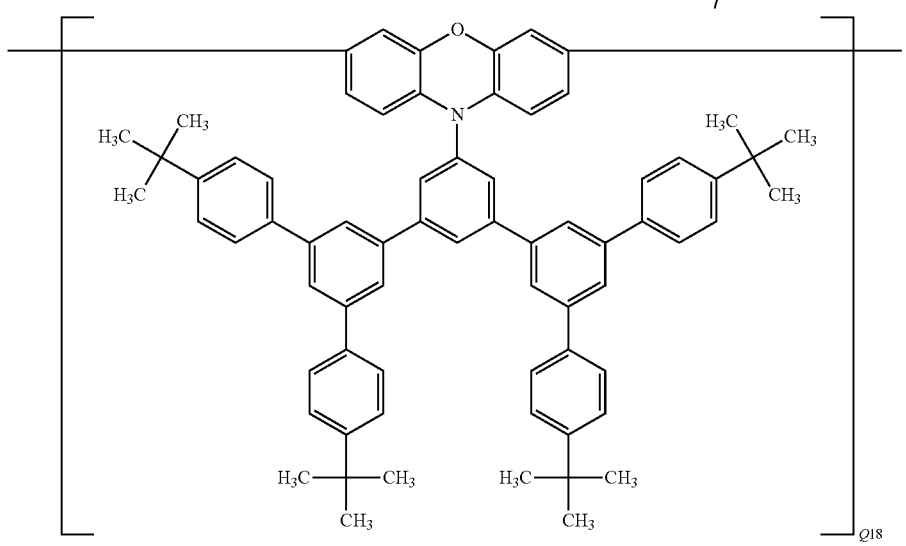

(wherein, Q15 represents a number of 60 to 90, Q16 represents a number of 5 to 20, Q17 represents a number of 3 to 15, and Q18 represents a number of 0.5 to 8. Here, Q15+Q16+Q17+Q18 is 100.)

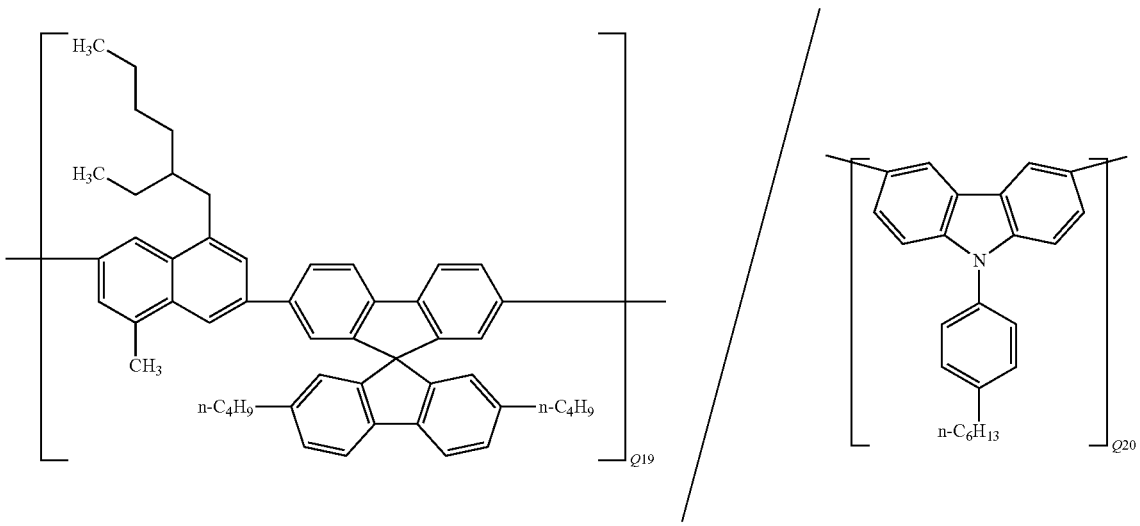

(P-16)

(wherein, Q19 represents a number of 50 to 95, and Q20 represents a number of 50 to 5. Here, Q19+Q20 is 100.)

[Production Method of Polymer Compound]

The polymer compound of the present invention may be produced by any method, and can be produced, for example, by

[1] condensation-polymerizing a compound represented by the following formula (M-1) (preferably, a compound represented by the above-described formula (b)) and a compound represented by the following formula (M-2) by a cross-coupling reaction, or

[2] condensation-polymerizing a compound represented by the following formula (M-3) and a compound represented by the following formula (M-4) by a cross-coupling reaction.

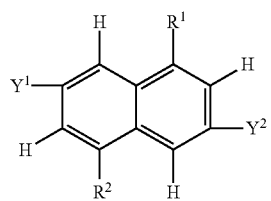
(M-1)

(in the formula (M-1), $R^1$ and $R^2$ represent the same meaning as described above.

$Y^1$ and $Y^2$ represent each independently a borate residue, a boric acid residue, a group represented by the following formula (a-2), a group represented by the following formula (a-3) or a group represented by the following formula (a-4).)

—MgX$^C$      (a-2)

(in the formula (a-2), X$^C$ represents a chlorine atom, a bromine atom or an iodine atom.)

—ZnX$^C$      (a-3)

(in the formula (a-3), X$^C$ represents the same meaning as described above.)

—Sn(R$^T$)$_3$      (a-4)

(in the formula (a-4), R$^T$ represents an unsubstituted or substituted alkyl group or an unsubstituted or substituted aryl group. A plurality of R$^T$s may be the same or different.)

X$^D$—Ar$^1$—X$^E$      (M-2)

(in the formula (M-2),

Ar$^1$ represents the same meaning as described above.

X$^D$ and X$^E$ represent each independently a chlorine atom, a bromine atom, an iodine atom or a group represented by the following formula (a-1).)

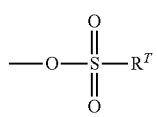
(a-1)

(wherein, R$^T$ represents the same meaning as described above.)

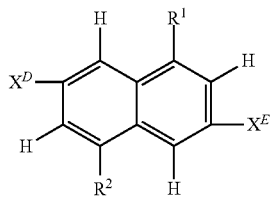
(M-3)

(in the formula (M-3), R$^1$, R$^2$, X$^D$ and X$^E$ represent the same meaning as described above.)

Y$^1$—Ar$^1$—Y$^2$      (M-4)

(in the formula (M-4), Ar$^1$, Y$^1$ and Y$^2$ represent the same meaning as described above.).

The definitions and examples of the unsubstituted or substituted alkyl group and the unsubstituted or substituted aryl group represented by $R^T$ in the formula (a-4) are the same as the definitions and examples of the unsubstituted or substituted alkyl group and the unsubstituted or substituted aryl group represented by $R^1$ and $R^2$.

The group represented by the formula (a-1) includes, for example, a methyl sulfonate group, a trifluoromethyl sulfonate group, a phenyl sulfonate group and a 4-methylphenyl sulfonate group.

The group represented by the formula (a-4) includes, for example, a trimethylstannyl group, a triethylstannyl group and a tributylstannyl group.

In the formulae (M-1) and (M-4), $Y^1$ and $Y^2$ represent preferably a borate residue or a boric acid residue, since then synthesis and handling of the compound are easy.

In the formulae (M-2) and (M-3), $X^D$ and $X^E$ represent preferably a bromine atom, since then reactivity is excellent.

As the compound represented by the formulae (M-1), (M-2), (M-3) and (M-4), those synthesized and isolated previously can be used, or those prepared in the reaction system can be used as they are.

In the case of the above-described condensation polymerization [1], the proportion of the compound represented by the formula (M-2) is usually 0.1 to 1000 parts by mol, preferably 1 to 500 parts by mol, more preferably 50 to 150 parts by mol, with respect to 100 parts by mol of the compound represented by the formula (M-1).

In the case of the above-described condensation polymerization [2], the proportion of the compound represented by the formula (M-4) is usually 0.1 to 1000 parts by mol, preferably 1 to 500 parts by mol, more preferably 50 to 150 parts by mol, with respect to 100 parts by mol of the compound represented by the formula (M-3).

The condensation polymerization method includes, for example, methods of reacting the compound represented by the formulae (M-1), (M-2), (M-3) and (M-4) using a suitable catalyst or a suitable base.

The catalyst includes, for example, catalysts composed of a transition metal complex such as palladium complexes such as dichlorobis(triphenylphosphine)palladium, dichlorobis(tris-o-methoxyphenylphosphine)palladium, palladium [tetrakis(triphenylphosphine)], [tris(dibenzylideneacetone)]dipalladium, palladium acetate and the like, nickel complexes such as nickel[tetrakis(triphenylphosphine)], [1,3-bis(diphenylphosphino)propane]dichloronickel, [bis(1,4-cyclooctadiene)]nickel and the like, etc. and, if necessary, further, a ligand such as triphenylphosphine, tri(tert-butylphosphine), tricyclohexylphosphine, diphenylphosphinopropane, bipyridyl and the like. As the catalyst, those synthesized previously can be used, or those prepared in the reaction system can be used as they are. These catalysts may be used singly or two or more of them may be used in combination.

In the case of use of a catalyst, the use amount thereof is preferably 0.00001 to 3 molar equivalents, more preferably 0.00005 to 0.5 molar equivalents, further preferably 0.0001 to 0.2 molar equivalents, in terms of the amount of a transition metal with respect to the sum of the mole numbers of the compounds represented by the formulae (M-1), (M-2), (M-3) and (M-4).

The base includes, for example, inorganic bases such as sodium carbonate, potassium carbonate, cesium carbonate, potassium fluoride, cesium fluoride, tripotassium phosphate and the like, and organic bases such as tetrabutylammonium fluoride, tetrabutylammonium chloride, tetrabutylammonium bromide, tetrabutylammonium hydroxide and the like.

These bases may be used singly or two or more of them may be used in combination.

In the case of use of a base, the use amount thereof is preferably 0.5 to 20 molar equivalents, more preferably 1 to 10 molar equivalents, with respect to the sum of the mole numbers of the compounds represented by the formulae (M-1), (M-2), (M-3) and (M-4).

Condensation polymerization is carried out usually in the presence of a solvent such as an organic solvent and the like.

The organic solvent varies depending on the kind of the compound represented by the formula (M-1), (M-2), (M-3) or (M-4) and the reaction thereof, and examples thereof include toluene, xylene, mesitylene, tetrahydrofuran, 1,4-dioxane, dimethoxyethane, N,N-dimethylacetamide and N,N-dimethylformamide. For suppressing side reactions, it is desirable to subject these solvents to a deoxidation treatment. The solvents may be used singly or two or more of them may be used in combination.

The use amount of an organic solvent is such an amount that the total concentration of compounds represented by the formulae (M-1), (M-2), (M-3) and (M-4) is usually 0.1 to 90% by weight, preferably 1 to 50% by weight, more preferably 2 to 30% by weight.

The reaction temperature of condensation polymerization is preferably −100 to 200° C., more preferably −80 to 150° C., further preferably 0 to 120° C. The reaction time is usually 1 hour or more, preferably 2 to 500 hours, depending on conditions such as the reaction temperature and the like.

Condensation polymerization is preferably carried out under anhydrous conditions when $Y^1$ and/or $Y^2$ is a group represented by the formula (a-2).

The above-described condensation polymerization method includes, for example, a method of polymerization by the Suzuki reaction (Chemical Reviews (Chem. Rev.), vol. 95, p. 2457 (1995)), a method of polymerization by the Grignard reaction (Kyoritsu Publication, Polymer Functional Material Series, vol. 2, Synthesis and Reaction of Polymer (2), pp. 432 to 433) and a method of polymerization by the Yamamoto Polymerization method (Progressive Polymer Science (Prog. Polym. Sci.), vol. 17, pp. 1153 to 1205, 1992).

The post-treatment of condensation polymerization can be carried out by a known method such as a method of adding the reaction solution obtained in condensation polymerization to a lower alcohol such as methanol and the like to cause deposition of a precipitate and filtrating and drying the precipitate, and the like.

The polymer compound obtained by the post-treatment can be, if necessary, purified by a usual method such as re-crystallization, continuous extraction with a soxhlet extractor, column chromatography and the like.

[Composition]

The composition of the present invention is a composition containing at least one material selected from the group consisting of hole transporting materials, electron transporting materials and light emitting materials and a polymer compound of the present invention. The composition of the present invention can be used as, for example, a light emitting material or a charge transporting material.

The hole transporting material includes hole transporting materials contained in a hole transporting layer when a light emitting device of the present invention has the hole transporting layer, explained in the section of [light emitting device] described later, and a polymer compound consisting of at least one constitutional unit selected from the group consisting of a constitutional unit represented by a constitutional unit represented by the formula (5), a constitutional unit represented by the formula (6) and a constitutional unit represented by the formula (9).

The electron transporting material includes electron transporting materials contained in an electron transporting layer when a light emitting device of the present invention has the electron transporting layer, explained in the section of [light emitting device] described later, and a polymer compound consisting of at least one constitutional unit selected from the group consisting of a constitutional unit represented by a constitutional unit represented by the formula (5), a constitutional unit represented by the formula (6) and a constitutional unit represented by the formula (9).

The light emitting material includes light emitting materials which may be contained in a light emitting device of the present invention, explained in the section of [light emitting device] described later, and a polymer compound consisting of at least one constitutional unit selected from the group consisting of a constitutional unit represented by a constitutional unit represented by the formula (5), a constitutional unit represented by the formula (6) and a constitutional unit represented by the formula (9).

The at least one material selected from the group consisting of hole transporting materials, electron transporting materials and light emitting materials is preferably a polymer compound consisting of at least one constitutional unit selected from the group consisting of a constitutional unit represented by the formula (5), a constitutional unit represented by the formula (6) and a constitutional unit represented by the formula (9), more preferably a polymer compound consisting of at least one constitutional unit selected from the group consisting of a constitutional unit represented by the formula (10), a constitutional unit represented by the formula (6) and a constitutional unit represented by the formula (9), further preferably a polymer compound consisting of at least one constitutional unit selected from the group consisting of a constitutional unit represented by the formula (6) and a constitutional unit represented by the formula (9), since then the resultant light emitting device shows more excellent luminance life.

Of the compositions of the present invention, preferable is a composition comprising a polymer compound consisting of a constitutional unit represented by the formula (11), and a polymer compound consisting of at least one constitutional unit selected from the group consisting of a constitutional unit represented by the formula (5), a constitutional unit represented by the formula (6) and a constitutional unit represented by the formula (9), as the at least one material selected from the group consisting of hole transporting materials, electron transporting materials and light emitting materials.

The content ratio of the at least one material selected from the group consisting of hole transporting materials, electron transporting materials and light emitting materials to the polymer compound of the present invention may advantageously be determined depending on its use application. When the composition of the present invention is used in a light emitting layer of a light emitting device, the proportion of the polymer compound of the present invention is usually 1 to 99 parts by weight with respect to 100 parts by weight of the whole composition.

When $Ar^1$ in the polymer compound of the present invention is a di-valent aromatic amine residue represented by the formula (2) and/or when the polymer compound of the present invention contains at least one constitutional unit selected from the group consisting of a constitutional unit represented by the formula (6) and a constitutional unit represented by the formula (10), the proportion of the polymer compound of the present invention is preferably 20 to 99 parts by weight, more preferably 40 to 95 parts by weight with respect to 100 parts by weight of the whole composition.

When the polymer compound of the present invention is a polymer compound consisting of a constitutional unit represented by the formula (11), the proportion of the polymer compound of the present invention is preferably 1 to 20 parts by weight, more preferably 5 to 20 parts by weight with respect to 100 parts by weight of the whole composition.

The composition of the present invention has a polystyrene-equivalent number-average molecular weight of usually $1\times10^3$ to $1\times10^8$, preferably $1\times10^4$ to $1\times10^6$. The composition of the present invention has a polystyrene-equivalent weight-average molecular weight of usually $1\times10^3$ to $1\times10^8$, and because of good film formability and excellent light emission efficiency of the resultant device, preferably $1\times10^4$ to $5\times10^6$. The average molecular weight of the composition means a value obtained by analyzing the composition by GPC.

The liquid composition of the present invention is a composition comprising a polymer compound of the present invention and a solvent. The liquid composition of the present invention is called a solution, an ink or an ink composition in some cases.

The liquid composition of the present invention is useful for fabrication of a device by coating according to a printing method and the like typified by an inkjet print method. The liquid composition of the present invention may contain a hole transporting material, an electron transporting material, a light emitting material, a stabilizer, a thickening agent, a compound of low molecular weight for lowering viscosity, a surfactant, an antioxidant and the like, as other components.

The proportion of the polymer compound of the present invention in the liquid composition of the present invention is usually 0.1 to 99.9 parts by weight, preferably 0.1 to 10 parts by weight, more preferably 0.2 to 7 parts by weight, further preferably 0.5 to 2 parts by weight with respect to 100 parts by weight of the liquid composition.

The viscosity of the liquid composition of the present invention may advantageously be regulated by the kind of a printing method, and when a solution passes through a discharging apparatus such as in an inkjet print method and the like, it is preferably in the range of 1 to 20 mPa·s at 25° C. for preventing clogging and curved flying in discharging.

The compound of high molecular weight used as a thickening agent may advantageously be one which is soluble in the same solvent as for the polymer compound of the present invention and does not disturb light emission and charge transportation, and for example, polystyrene of high molecular weight and polymethyl methacrylate of high molecular weight can be used. These compounds of high molecular weight have a polystyrene-equivalent weight-average molecular weight of preferably 500000 or more, more preferably 1000000 or more.

By adding a small amount of a poor solvent for solid components in the liquid composition of the present invention as a thickening agent, viscosity can be enhanced. When a poor solvent is added as a thickening agent, the kind and the addition amount of the poor solvent may advantageously be selected so that solid components in the liquid composition do not deposit, and if also storage stability is taken into consideration, the proportion of the poor solvent is preferably 50 parts by weight or less, more preferably 30 parts by weight or less with respect to 100 parts by weight of the liquid composition.

The antioxidant may advantageously be one which is soluble in the same solvent as for the polymer compound of the present invention and does not disturb light emission and charge transportation, and examples thereof include phenol antioxidants and phosphorus-based antioxidants.

As the solvent in the liquid composition of the present invention, those capable of dissolving or uniformly dispersing solid components in the liquid composition are preferable. Examples of the solvent include chlorine-based solvents such as chloroform, methylene chloride, 1,2-dichloroethane, 1,1,2-trichloroethane, chlorobenzene, o-dichlorobenzene and the like, ether solvents such as tetrahydrofuran, dioxane, anisole, 4-methylanisole and the like, aromatic hydrocarbon solvents such as toluene, xylene, mesitylene, ethylbenzene, n-hexylbenzene, cyclohexylbenzene and the like, aliphatic hydrocarbon solvents such as cyclohexane, methylcyclohexane, n-pentane, n-hexane, n-heptane, n-octane, n-nonane, n-decane and the like, ketone solvents such as acetone, methyl ethyl ketone, cyclohexanone, benzophenone, acetophenone and the like, ester solvents such as ethyl acetate, butyl acetate, ethylcellosolve acetate, methyl benzoate, phenyl acetate and the like, polyhydric alcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol and the like and derivatives thereof, alcohol solvents such as methanol, ethanol, propanol, isopropanol, cyclohexanol and the like, sulfoxide solvents such as dimethyl sulfoxide and the like, and amide solvents such as N-methyl-2-pyrrolidone, N,N-dimethylformamide and the like. These solvents may be used singly or two or more of them may be used in combination.

Of them, aromatic hydrocarbon solvents, ether solvents, aliphatic hydrocarbon solvents, ester solvents and ketone solvents are preferable, toluene, xylene, ethylbenzene, diethylbenzene, trimethylbenzene, n-propylbenzene, isopropylbenzene, n-butylbenzene, isobutylbenzene, sec-butylbenzene, n-hexylbenzene, cyclohexylbenzene, 1-methylnaphthalene, tetralin, anisole, 4-methylanisole, ethoxybenzene, cyclohexane, bicyclohexyl, cyclohexenyl-cyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexyl ketone, acetophenone and benzophenone are more preferable, since solubility of a polymer compound, uniformity in film formation and a viscosity property can be improved.

It is preferable to use two or more of these solvents in combination, it is more preferable to use two to three of these solvents in combination, it is particularly preferable to use two of these solvents in combination, since film formability and a device property are enhanced.

When two solvents are contained in the liquid composition of the present invention, one of them may be solid at 25° C. One solvent has a boiling point of preferably 180° C. or higher, more preferably 200° C. or higher, since film formability is enhanced. It is preferable that a polymer compound is dissolved at a concentration of 1% by weight or more at 60° C. in any of two solvents, and it is preferable that a polymer compound is dissolved at a concentration of 1% by weight or more at 25° C. in one of two solvents, since good viscosity is obtained.

When two or more solvents are contained in the liquid composition of the present invention, it is preferable that the proportion of a solvent having the highest boiling point is 40 to 90% by weight, more preferably 50 to 90% by weight, further preferably 65 to 85% by weight based on all solvents in the liquid composition, since excellent viscosity and film formability are obtained.

The number of the polymer compound of the present invention contained in the liquid composition of the present invention may be one or two or more. A compound of high molecular weight other than the polymer compound of the present invention may be contained in a range not deteriorating a device property and the like.

The liquid composition of the present invention may contain water, a metal and a salt thereof in an amount of 1 to 1000 ppm by weight. Examples of the metal include lithium, sodium, calcium, potassium, iron, copper, nickel, aluminum, zinc, chromium, manganese, cobalt, platinum and iridium. Further, the liquid composition of the present invention may contain silicon, phosphorus, fluorine, chlorine, bromine and the like in an amount of 1 to 1000 ppm by weight.

[Film]

The film of the present invention comprises a polymer compound of the present invention, and examples thereof include a luminous film, an electrically conductive film and an organic semiconductor film.

The film of the present invention can be fabricated, for example, by a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method, a capillary coat method and a nozzle coat method, preferably by a screen printing method, a flexo printing method, an offset printing method and an inkjet print method.

The thickness of the film of the present invention is usually 1 nm to 10 µm, preferably 5 nm to 1 µm, more preferably 10 nm to 500 nm, further preferably 10 nm to 200 nm.

When the film is fabricated using a liquid composition of the present invention, it can be heated at a temperature of 100° C. or higher since the glass transition temperature of a polymer compound of the present invention contained in a solution is high.

[Light Emitting Device]

The light emitting device of the present invention is a light emitting device having electrodes consisting of an anode and a cathode and a layer containing a polymer compound of the present invention disposed between the electrodes.

The layer containing a polymer compound of the present invention is preferably at least one layer among a light emitting layer, a hole transporting layer, a hole injection layer, an electron transporting layer, an electron injection layer and an interlayer layer, more preferably at least one layer among an electron transporting layer, an electron injection layer and a light emitting layer, more preferably a light emitting layer.

The light emitting layer means a layer having a function of light emission.

The hole transporting layer means a layer having a function of transporting holes.

The electron transporting layer means a layer having a function of transporting electrons.

The interlayer layer means a layer which is present adjacent to a light emitting layer between the light emitting layer and an anode, and having a function of insulating the light emitting layer and the anode, or having a function of insulating the light emitting layer and a hole injection layer or hole transporting layer.

The electron transporting layer and the hole transporting layer are generically called a charge transporting layer, and the electro injection layer and the hole injection layer are generically called a charge injection layer. The light emitting layer, the hole transporting layer, the hole injection layer, the electron transporting layer, the electron injection layer and the interlayer layer may each be composed of a single layer or two or more layers.

When the layer containing a polymer compound of the present invention is a light emitting layer, the light emitting layer may further contain a material selected from a hole transporting material, an electron transporting material, a light emitting material which shows fluorescence and/or phosphorescence and is difference from the polymer compound of the present invention, and an additive for elongating luminance life of a light emitting device.

When the layer containing a polymer compound of the present invention contains further a hole transporting material, the proportion of the hole transporting material with respect to 100 parts by weight of the sum of the polymer compound of the present invention and the hole transporting material is usually 1 to 80 parts by weight, preferably 5 to 60 parts by weight.

When the layer containing a polymer compound of the present invention contains further an electron transporting material, the proportion of the electron transporting material with respect to 100 parts by weight of the sum of the polymer compound of the present invention and the electron transporting material is usually 1 to 80 parts by weight, preferably 5 to 60 parts by weight.

When the layer containing a polymer compound of the present invention contains further a light emitting material (which may show any of fluorescence and phosphorescence), the proportion of the light emitting material with respect to 100 parts by weight of the sum of the polymer compound of the present invention and the light emitting material is usually 1 to 80 parts by weight, preferably 5 to 60 parts by weight.

When the layer containing a polymer compound of the present invention contains further two or more materials selected from the group consisting of a hole transporting material, an electron transporting material and a light emitting material, the proportion of the light emitting material with respect to 100 parts by weight of the sum of these materials is usually 1 to 50 parts by weight, preferably 5 to 40 parts by weight. The total proportion of the hole transporting material and the electron transporting material with respect to 100 parts by weight of the sum of these materials is usually 1 to 50 parts by weight, preferably 5 to 40 parts by weight.

As the hole transporting material and the electron transporting material, hole transporting materials and electron transporting materials described later can be used. As the light emitting material, for example, triplet light emitting complexes can be used.

The triplet light emitting complex includes, for example, a complex containing iridium as the central metal: Ir(ppy)$_3$, Btp$_2$Ir(acac), FIrpic, COM-1, COM-2, COM-3, COM-4, COM-5, COM-6, COM-7, COM-8, ADS066GE commercially available from American Dye Source, a complex containing platinum as the central metal: PtOEP, and a complex containing europium as the central metal: Eu(TTA)$_3$phen. These triple light emitting complexes are those represented by the following chemical formulae.

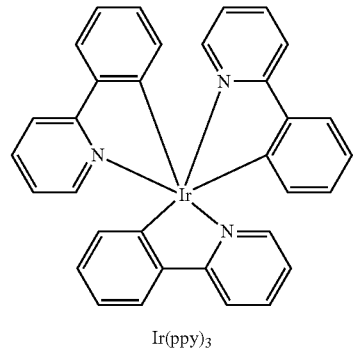

Ir(ppy)$_3$

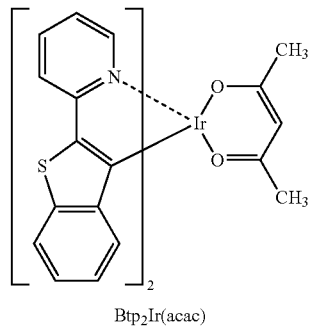

Btp$_2$Ir(acac)

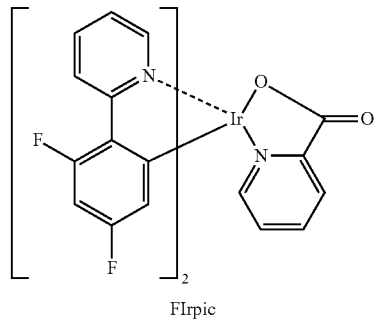

FIrpic

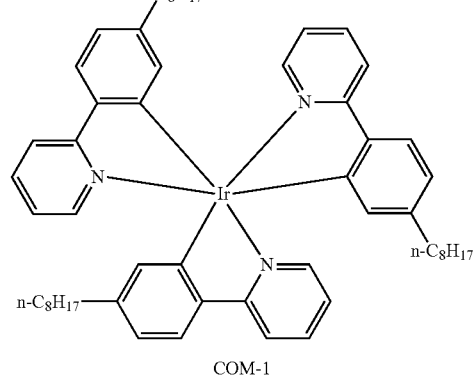

COM-1

-continued
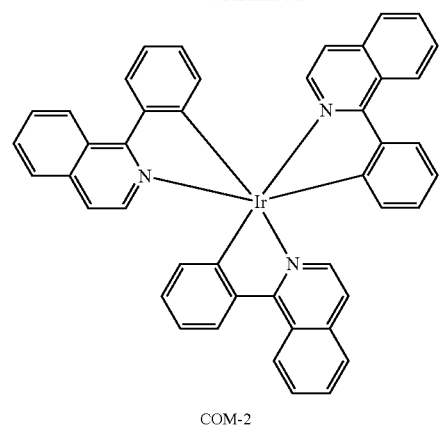
COM-2
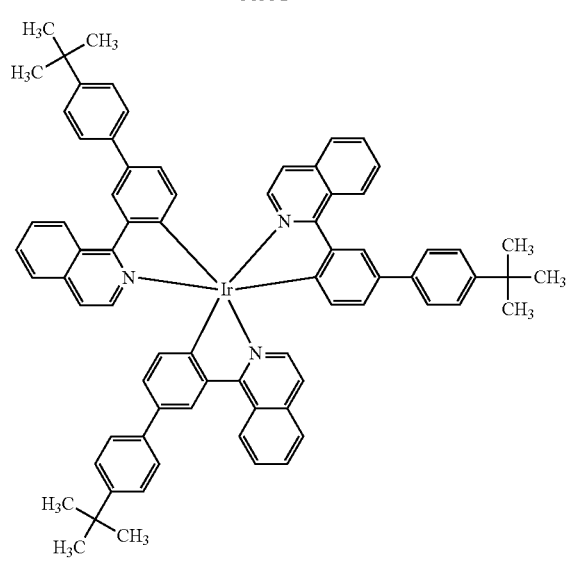
COM-3
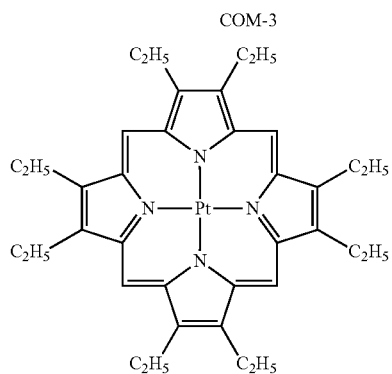
PtOEP
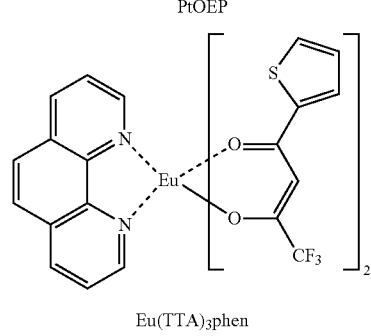
Eu(TTA)₃phen
-continued
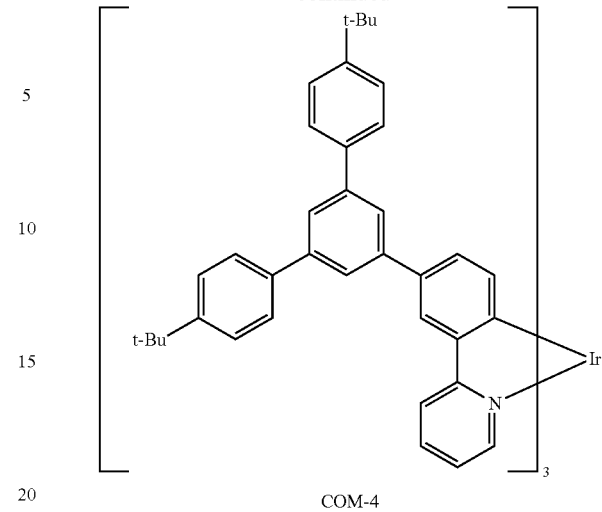
COM-4
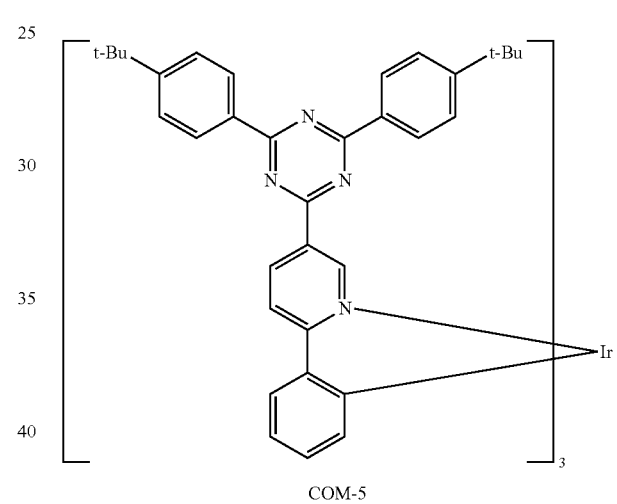
COM-5
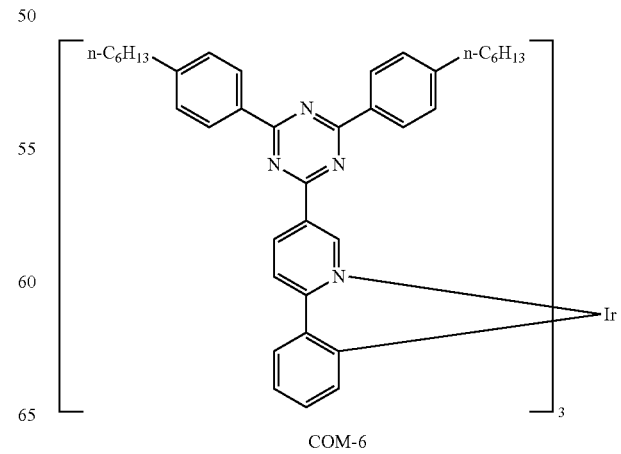
COM-6

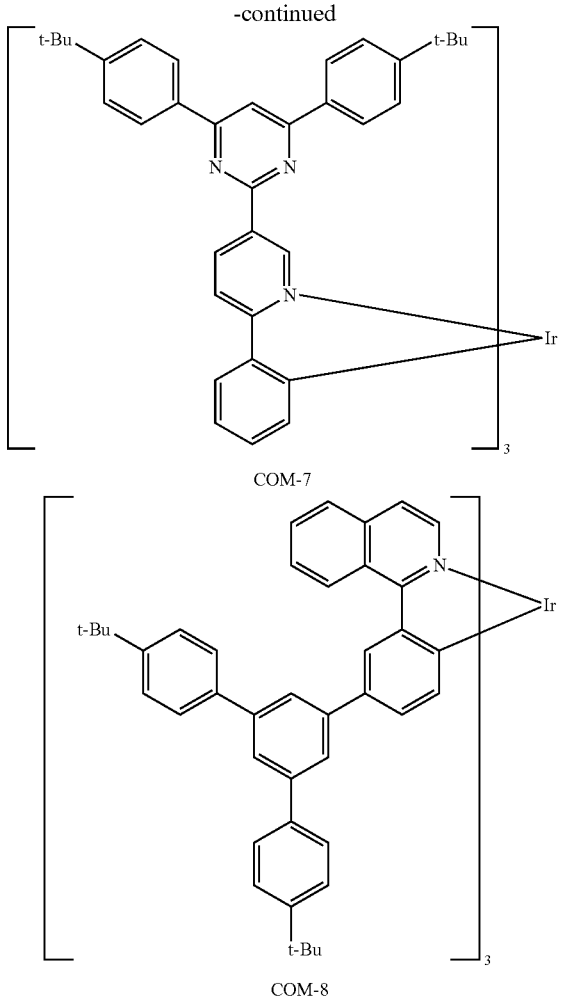

COM-7

COM-8

The triplet light emitting complex can also be linked to the main chain, the side chain or the end of a polymer compound of the present invention.

The additive for elongating luminance life of a light emitting device includes, for example, bipyridyls such as 2,2'-bipyridyl, 3,3'-bipyridyl, 4,4'-bipyridyl and the like, and bipyridyl derivatives such as 4-methyl-2,2'-bipyridyl, 5-methyl-2,2'-bipyridyl, 5,5'-dimethyl-2,2'-bipyridyl and the like.

The thickness of a light emitting layer shows the optimum value varying depending on the material used and may advantageously be selected so as to give suitable driving voltage and light emission efficiency, and it is usually 1 nm to 1 µm, preferably 5 nm to 200 nm, more preferably 50 nm to 150 nm.

The method of forming a light emitting layer includes, for example, a method by film formation from a solution. For film formation from a solution, coating methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method, a capillary coat method, a nozzle coat method and the like can be used.

As the solvent used for film formation from a solution, exemplified are chlorine-based solvents such as chloroform, methylene chloride, 1,2-dichloroethane, 1,1,2-trichloroethane, chlorobenzene, o-dichlorobenzene and the like, ether solvents such as tetrahydrofuran, dioxane and the like, aromatic hydrocarbon solvents such as toluene, xylene, mesitylene, ethylbenzene, n-hexylbenzene, cyclohexylbenzene, anisole, 4-methylanisole and the like, aliphatic hydrocarbon solvents such as cyclohexane, methylcyclohexane, n-pentane, n-hexane, n-heptane, n-octane, n-nonane, n-decane and the like, ketone solvents such as acetone, methylethyl ketone, cyclohexanone and the like, ester solvents such as ethyl acetate, butyl acetate, ethylcellosolve acetate and the like, poly-hydric alcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol and the like and derivatives thereof, alcohol solvents such as methanol, ethanol, propanol, isopropanol, cyclohexanol and the like, sulfoxide solvents such as dimethyl sulfoxide and the like, and amide solvents such as N-methyl-2-pyrrolidone, N,N-dimethylformamide and the like. These solvents may be used singly or two or more of them may be used in combination.

The light emitting device includes, for example, a light emitting device having an electron transporting layer disposed between a cathode and a light emitting layer, a light emitting device having a hole transporting layer disposed between an anode and a light emitting layer, and a light emitting device having an electron transporting layer disposed between a cathode and a light emitting layer and having a hole transporting layer disposed between an anode and a light emitting layer.

The structure of such a light emitting device includes structures a) to d) exemplified below.
a) anode/light emitting layer/cathode
b) anode/hole transporting layer/light emitting layer/cathode
c) anode/light emitting layer/electron transporting layer/cathode
d) anode/hole transporting layer/light emitting layer/electron transporting layer/cathode
(wherein, / means adjacent lamination of layers, the same shall apply hereinafter)

In each of these structures, an interlayer layer may be disposed adjacent to a light emitting layer between the light emitting layer and an anode. The structure of such a light emitting device includes structures a') to d') exemplified below.
a') anode/interlayer layer/light emitting layer/cathode
b') anode/hole transporting layer/interlayer layer/light emitting layer/cathode
c') anode/interlayer layer/light emitting layer/electron transporting layer/cathode
d') anode/hole transporting layer/interlayer layer/light emitting layer/electron transporting layer/cathode When a light emitting device has a hole transporting layer, the hole transporting layer usually contains a hole transporting material (compound of high molecular weight, compound of low molecular weight).

Exemplified as the compound of high molecular weight among hole transporting materials are polyvinylcarbazole and derivatives thereof, polysilane and derivatives thereof, polysiloxane derivatives having an aromatic amine in the side chain or main chain, pyrazoline derivatives, arylamine derivatives, stilbene derivatives, triphenyldiamine derivatives, polyaniline and derivatives thereof, polythiophene and derivatives thereof, polypyrrole and derivatives thereof, poly(p-phenylenevinylene) and derivatives thereof, and poly(2,5-thienylenevinylene) and derivatives thereof.

Exemplified as the compound of low molecular weight among hole transporting materials are pyrazoline derivatives, arylamine derivatives, stilbene derivatives and triphenyldiamine derivatives. It is preferable that the compound of low molecular weight is dispersed in a polymer binder.

As the polymer binder, compounds which do not extremely disturb charge transportation and show no strong absorption for visible light are preferable, and examples thereof include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride and polysiloxane.

As the method of film formation of a hole transporting layer, a method by film formation from a mixed solution with a polymer binder is exemplified when a compound of low molecular weight is used. When a compound of high molecular weight is used, a method by film formation from a solution is exemplified.

As the solvent used for film formation from a solution, those capable of dissolving or uniformly dispersing a hole transporting material are preferable. Exemplified as the solvent are chlorine-based solvents such as chloroform, methylene chloride, 1,2-dichloroethane, 1,1,2-trichloroethane, chlorobenzene, o-dichlorobenzene and the like, ether solvents such as tetrahydrofuran, dioxane and the like, aromatic hydrocarbon solvents such as toluene, xylene, mesitylene, ethylbenzene, n-hexylbenzene, cyclohexylbenzene, anisole, 4-methylanisole and the like, aliphatic hydrocarbon solvents such as cyclohexane, methylcyclohexane, n-pentane, n-hexane, n-heptane, n-octane, n-nonane, n-decane and the like, ketone solvents such as acetone, methylethyl ketone, cyclohexanone and the like, ester solvents such as ethyl acetate, butyl acetate, ethylcellosolve acetate and the like, poly-hydric alcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol and the like and derivatives thereof, alcohol solvents such as methanol, ethanol, propanol, isopropanol, cyclohexanol and the like, sulfoxide solvents such as dimethyl sulfoxide and the like, and amide solvents such as N-methyl-2-pyrrolidone, N,N-dimethylformamide and the like. The solvents may be used singly or two or more of them may be used in combination.

For film formation from a solution, coating methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method, a capillary coat method, a nozzle coat method and the like can be used.

The thickness of a hole transporting layer shows the optimum value varying depending on the material used and may advantageously be selected so as to give suitable driving voltage and light emission efficiency, and it is usually 1 nm to 1 μm, preferably 2 to 500 nm, more preferably 5 to 200 nm.

When a light emitting device has an electron transporting layer, the electron transporting layer contains usually an electron transporting material (compound of high molecular weight, compound of low molecular weight).

Exemplified as the electron transporting material are, for example, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof and polyfluorene and derivatives thereof.

As the method of film formation of an electron transporting layer, a vacuum vapor deposition method from a powder or a method by film formation from a solution or melted condition is exemplified when a compound of low molecular weight is used. When a compound of high molecular weight is used, a method by film formation from a solution or melted condition is exemplified. In the method by film formation from a solution or melted condition, the above-described polymer binder may be used together.

As the solvent used for film formation from a solution, solvents capable of dissolving or uniformly dispersing an electron transporting material and/or a polymer binder are preferable. The solvents are the same as explained and exemplified in the section of a hole transporting layer. The solvents may be used singly or two or more of them may be used in combination.

For film formation from a solution or melted condition, the same coating methods as explained and exemplified in the section of a hole transporting layer can be used.

The thickness of an electron transporting layer shows the optimum value varying depending on the material used and may advantageously be selected so as to give suitable driving voltage and light emission efficiency, and it is usually 1 nm to 1 μm, preferably 2 to 500 nm, more preferably 5 to 200 nm.

The hole injection layer and the electron injection layer are a charge transporting layer which is disposed adjacent to an electrode and having a function of improving charge injection efficiency from the electrode and having an effect of lowering the driving voltage of a light emitting device.

For improving close adhesion to an electrode and for an improvement in charge injection from an electrode, a charge injection layer or an insulation layer (usually having an average thickness of 0.5 to 4.0 nm, the same shall apply hereinafter) may be disposed adjacent to the electrode. For improving close adhesion of an interface and for protecting mixing thereof, a thin buffer layer may be inserted into an interface of a charge transporting layer and a light emitting layer.

The order and the number of layers to be laminated and the thickness of each layer may be advantageously adjusted in view of light emission efficiency and device life.

In the present embodiment, examples of the light emitting device having a charge injection layer disposed include a light emitting device having a charge injection layer disposed adjacent to a cathode and a light emitting device having a charge injection layer disposed adjacent to an anode. The structure of such a light emitting device includes the following structures e) to p).

e) anode/charge injection layer/light emitting layer/cathode
f) anode/light emitting layer/charge injection layer/cathode
g) anode/charge injection layer/light emitting layer/charge injection layer/cathode
h) anode/charge injection layer/hole transporting layer/light emitting layer/cathode
i) anode/hole transporting layer/light emitting layer/charge injection layer/cathode
j) anode/charge injection layer/hole transporting layer/light emitting layer/charge injection layer/cathode k) anode/charge injection layer/light emitting layer/electron transporting layer/cathode
l) anode/light emitting layer/electron transporting layer/charge injection layer/cathode
m) anode/charge injection layer/light emitting layer/electron transporting layer/charge injection layer/cathode
n) anode/charge injection layer/hole transporting layer/light emitting layer/electron transporting layer/cathode
o) anode/hole transporting layer/light emitting layer/electron transporting layer/charge injection layer/cathode
p) anode/charge injection layer/hole transporting layer/light emitting layer/electron transporting layer/charge injection layer/cathode Also exemplified are structures having an interlayer layer disposed adjacent to a light emitting layer between the light emitting layer and an anode in each of the above-described structures. In this case, the interlayer layer may also function as a hole injection layer and/or a hole transporting layer.

The charge injection layer includes, for example, a layer containing an electrically conductive polymer, a layer disposed between an anode and a hole transporting layer and having ionization potential of a value between that of an anode material and that of a hole transporting material contained in the hole transporting layer, and a layer disposed between a cathode and an electron transporting layer and having electron affinity of a value between that of a cathode material and that of an electron transporting material contained in the electron transporting layer.

When the charge injection layer is a layer containing an electrically conductive polymer, the electrically conductive polymer has an electric conductivity of preferably $1 \times 10^{-5}$ to $1 \times 10^3$ S/cm, further, since leak current between light emission picture elements can be decreased, more preferably $1 \times 10^{-5}$ to $1 \times 10^2$ S/cm, further preferably $1 \times 10^{-5}$ to $1 \times 10^1$ S/cm. Usually, for the electrically conductive polymer to have electric conductivity in such a range, the electrically conductive polymer is doped with a suitable amount of ions.

The kind of ions to be doped is an anion in the case of a hole injection layer and is a cation in the case of an electron injection layer. Exemplified as the anion are a polystyrenesulfonic ion, an alkylbenzenesulfonic ion and a camphorsulfonic ion. Exemplified as the cation are a lithium ion, a sodium ion, a potassium ion and a tetrabutylammonium ion.

The material used in the charge injection layer may advantageously be selected depending on the relation with materials of electrodes and adjacent layers. Exemplified as the material used in the charge injection layer are electrically conductive polymers such as polyaniline and derivatives thereof, polythiophene and derivatives thereof, polypyrrole and derivatives thereof, polyphenylenevinylene and derivatives thereof, polythienylenevinylene and derivatives thereof, polyquinoline and derivatives thereof, polyquinoxaline and derivatives thereof, polymers containing an aromatic amine structure in the main chain or side chain, and the like; metal phthalocyanines (copper phthalocyanine and the like) and carbon.

The material of the insulation layer includes, for example, metal fluorides, metal oxides and organic insulation materials. The light emitting device having the insulation layer disposed includes, for example, a light emitting device having an insulation layer disposed adjacent to a cathode and a light emitting device having an insulation layer disposed adjacent to an anode.

The structure of such a light emitting device includes the following structures q) to ab).
q) anode/insulation layer/light emitting layer/cathode
r) anode/light emitting layer/insulation layer/cathode
s) anode/insulation layer/light emitting layer/insulation layer/cathode
t) anode/insulation layer/hole transporting layer/light emitting layer/cathode
u) anode/hole transporting layer/light emitting layer/insulation layer/cathode
v) anode/insulation layer/hole transporting layer/light emitting layer/insulation layer/cathode
w) anode/insulation layer/light emitting layer/electron transporting layer/cathode
x) anode/light emitting layer/electron transporting layer/insulation layer/cathode
y) anode/insulation layer/light emitting layer/electron transporting layer/insulation layer/cathode
z) anode/insulation layer/hole transporting layer/light emitting layer/electron transporting layer/cathode
aa) anode/hole transporting layer/light emitting layer/electron transporting layer/insulation layer/cathode
ab) anode/insulation layer/hole transporting layer/light emitting layer/electron transporting layer/insulation layer/cathode Also exemplified are structures having an interlayer layer disposed adjacent to a light emitting layer between the light emitting layer and an anode in each of the above-described structures. In this case, the interlayer layer may also function as a hole injection layer and/or a hole transporting layer.

When the interlayer layer is applied to the above-described structures a) to ab), it is preferable that the interlayer layer is disposed between an anode and a light emitting layer and is constituted of a material having ionization potential of a value between that of the anode or a hole injection layer or a hole transporting layer, and that of a polymer compound constituting the light emitting layer.

As the material used in the interlayer layer, exemplified are polymers containing a residue of an aromatic amine such as polyvinylcarbazole and derivatives thereof, polyarylene derivatives having an aromatic amine in the side chain or main chain, arylamine derivatives, triphenyldiamine derivative and the like.

The method of forming the interlayer layer includes, for example, a method by film formation from a solution in the case of use of a material of high molecular weight.

As the solvent used for film formation from a solution, those capable of dissolving or uniformly dispersing the material used in the interlayer layer are preferable. The solvents are the same as explained and exemplified in the section of a hole transporting layer. The solvents may be used singly or two or more of them may be used in combination.

For film formation from a solution, the same coating methods as explained and exemplified in the section of a hole transporting layer can be used.

The thickness of the interlayer layer shows the optimum value varying depending on the material used and may advantageously be selected so as to give suitable driving voltage and light emission efficiency. It is usually 1 nm to 1 μm, preferably 2 to 500 nm, more preferably 5 to 200 nm.

When a light emitting layer is formed by a coating method after forming an interlayer layer by a coating method, examples of a method of decreasing mixing of two materials include a method in which an interlayer layer is formed by a coating method, this interlayer layer is heated to become insolubilizable in an organic solvent to be used for fabrication of a light emitting layer, then, the light emitting layer is formed. The heating temperature is usually 150 to 300° C. The heating time is usually 1 minute to 1 hour. In this case, it is recommendable, after heating and before formation of a light emitting layer, to rinse the interlayer layer with a solvent used in forming a light emitting layer, to remove a component not becoming insolubilizable in a solvent by heating. When insolubilization in a solvent is sufficiently attained by heating, rinsing can be omitted. For sufficient insolubilization in a solvent by heating, it is preferable to use a compound containing a polymerizable group in the molecule as the compound of high molecular weight used in the interlayer layer. Further, it is preferable that the proportion of the number of polymerizable groups is 5% or more with respect to the number of constitutional units in the molecule.

The substrate in a light emitting device may advantageously be a substrate on which an electrode can be formed and which does not chemically change in forming a layer of an organic material, and exemplified are substrates composed of a material such as glass, plastic, polymer film, silicon and the like. In the case of an opaque substrate, it is preferable that the opposite electrode is transparent or semi-transparent.

At least one of an anode and a cathode of alight emitting device is usually transparent or semi-transparent, and it is preferable that the anode side is transparent or semi-transparent.

The anode material includes, for example, electrically conductive metal oxide films and semi-transparent metal films. Specifically mentioned are films fabricated by using an electrically conductive compound such as indium oxide, zinc oxide, tin oxide and, composites thereof: indium.tin.oxide (ITO), indium.zinc.oxide and the like, NESA, gold, platinum, silver and copper, and preferable are ITO, indium.zinc.oxide and tin oxide. The anode fabrication method includes, for example, a vacuum vapor deposition method, a sputtering method, an ion plating method and a plating method. As the anode, a transparent electrically conductive film composed of an organic material such as polyaniline and derivatives thereof, polythiophene and derivatives thereof and the like may be used. Further, the anode may take a laminated structure composed of two or more layers.

The thickness of the anode can be selected in view of light permeability and electric conductivity, and it is usually 10 nm to 10 μm, preferably 20 nm to 1 μm, more preferably 40 to 500 nm.

On the anode, a layer composed of a phthalocyanine derivative, an electrically conductive polymer, carbon and the like or an insulation layer composed of a metal oxide, a metal fluoride, an organic insulation material and the like may be provided, for making charge injection easy.

As the cathode material, materials having small work function are preferable, and use is made of, for example, metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, or alloys composed of two or more of them, or alloys composed of at least one of them and at least one of gold, silver, platinum, copper, manganese, titanium, cobalt, nickel, tungsten and tin, and graphite and graphite intercalation compounds and the like. Examples of the alloy include a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy. The cathode may take a laminated structure composed of two or more layers.

The thickness of the cathode may advantageously be adjusted in view of electric conductivity and durability, and it is usually 10 nm to 10 μm, preferably 20 nm to 1 μm, more preferably 50 to 500 nm.

The cathode fabrication method includes, for example, a vacuum vapor deposition method, a sputtering method and a laminate method of thermally compression bonding a metal film. Between a cathode and an organic layer, a layer composed of an electrically conductive polymer or a layer having an average thickness of 2 nm or less composed of a metal oxide, a metal fluoride, an organic insulation material and the like may be provided, and after cathode fabrication, a protective layer for protecting a light emitting device may be mounted. For use of a light emitting device stably for a long period of time, it is preferable to mount a protective layer and/or a protective cover, for protecting the light emitting device from outside.

As the protective layer, for example, compounds of high molecular weight, metal oxides, metal fluorides and metal borides can be used. As the protective cover, for example, a metal plate, a glass plate, and a plastic plate having the surface on which a treatment for lowering coefficient of water permeability has been performed can be used. For example, a method in which a protective cover is pasted to a substrate with a thermosetting resin or a photo-curable resin, thereby attaining seal, is suitably used. If a space is maintained using a spacer, it is easy to prevent damage of a light emitting device. If this space is filled with an inert gas such as a nitrogen gas, an argon gas and the like, oxidation of a cathode can be prevented. Further, by placing a desiccant such as barium oxide and the like in this space, it becomes easy to suppress moisture adsorbed in a production step or a trace amount of moisture infiltrated through a resin from imparting damage to a device.

For obtaining planar light emission using a light emitting device, it may be advantageous to place a planar anode and a planar cathode so as to overlap. For obtaining light emission in the form of pattern, there are a method in which a mask having a window in the form of pattern is placed on the surface of a planar light emitting device, a method in which a layer to be a non-light emitting part is formed with extremely large thickness to give substantially no light emission, and a method in which either anode or cathode, or both electrodes are formed in the form of pattern. By forming a pattern by any of these methods, and placing several electrodes so that on/off thereof is independently possible, a display of segment type is obtained which can display digits, letters, simple marks and the like. Further, for providing a dot matrix display, it may be advantageous that both an anode and a cathode are formed in the form of stripe, and placed so as to cross. By using a method in which several polymer compounds showing different emission colors are painted separately or a method in which a color filter or a fluorescence conversion filter is used, partial color display and multi-color display are made possible. In the case of a dot matrix display, passive driving is possible, and active driving may also be carried out in combination with TFT and the like. These displays can be used in a computer, a television, a portable terminal, a cellular telephone, a car navigation, a view finder of video camera, and the like. A planar light emitting device is of self emitting and thin type, and can be suitably used as a planar light source for back light of a liquid crystal display, or as a planar light source for illumination. If a flexible substrate is used, it can also be used as a curved light source or display.

[Compound]
The first compound of the present invention is a compound represented by the above-described formula (a), typically is a compound represented by the above-described formula (b).
The compound represented by the formula (a) includes, for example, compounds represented by the following formulae (N-1) to (N-9).
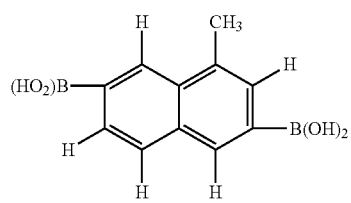
(N-1)
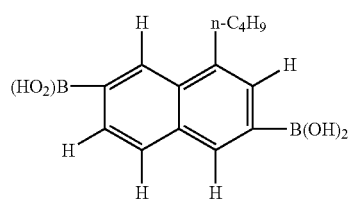
(N-2)
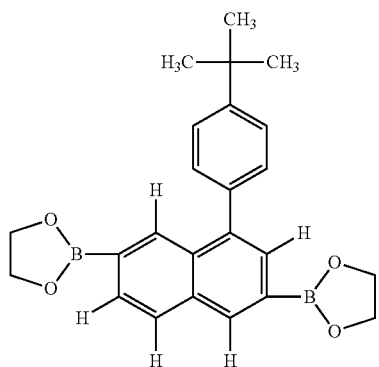
(N-3)
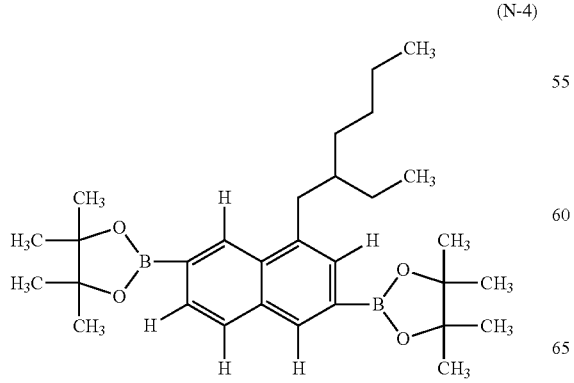
(N-4)
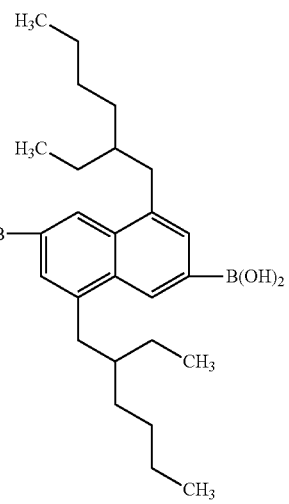
(N-5)
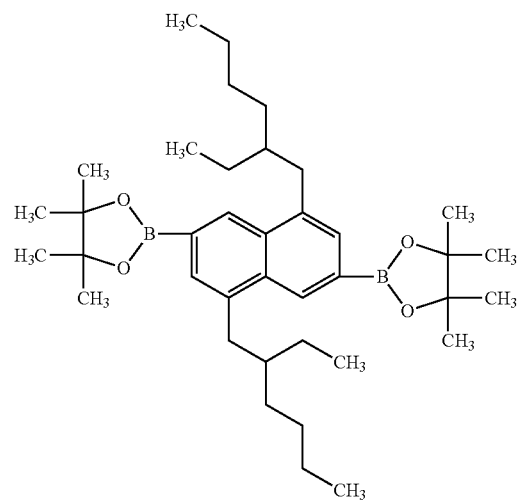
(N-6)
(N-7)

-continued

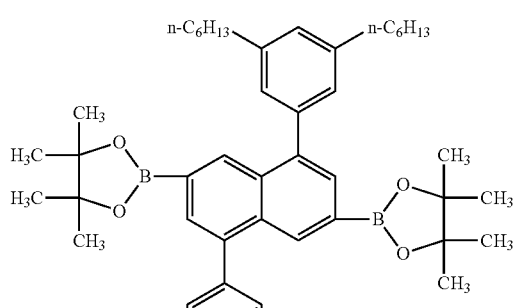

(N-8)

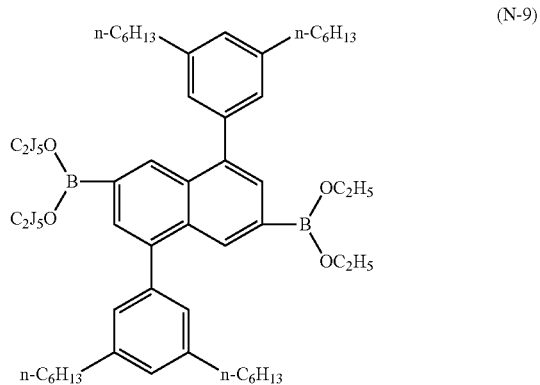

(N-9)

[Method of Producing Compound]

The compound represented by the above-described formula (a) may be produced by any method, and for example, can be produced by a method comprising reacting a compound represented by the above-described formula (c) with at least one compound selected from the group consisting of a compound represented by the above-described formula (d) and a compound represented by the above-described formula (e).

In the above-described formula (a) and the above-described formula (c), $R^1$ represents the same meaning as described above.

In the above-described formula (a) and the above-described formula (c), $R^{17}$ represents a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group. The definitions and examples of these unsubstituted or substituted alkyl group, unsubstituted or substituted aryl group, unsubstituted or substituted mono-valent aromatic heterocyclic group, unsubstituted or substituted alkoxy group and unsubstituted or substituted aryloxy group are the same as the definitions and examples of the unsubstituted or substituted alkyl group, the unsubstituted or substituted aryl group, the unsubstituted or substituted mono-valent aromatic heterocyclic group, the unsubstituted or substituted alkoxy group and the unsubstituted or substituted aryloxy group represented by $R^1$ and $R^2$.

In the above-described formula (a), $Z^1$ and $Z^2$ represent the same meaning as described above.

The compound represented by the above-described formula (c) includes, for example, compounds obtained by substituting a boric acid residue and a borate residue in compounds represented by the above-described (N-1) to (N-9) by a hydrogen atom.

In the above-described formula (d), the definitions and examples of the unsubstituted or substituted alkyl group and the unsubstituted or substituted aryl group represented by $R^A$ and $R^B$ are the same as the definitions and examples of the unsubstituted or substituted alkyl group and the unsubstituted or substituted aryl group represented by $R^1$ and $R^2$.

The compound represented by the above-described formula (d) includes, for example, compounds represented by the following formulae (d-1) to (d-4).

(d-1)

(d-2)

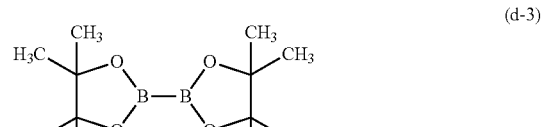

(d-3)

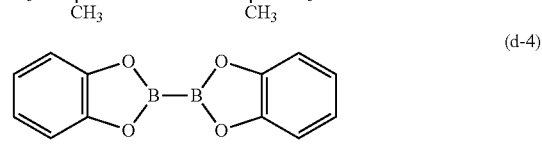

(d-4)

In the above-described formula (e), $R^A$ represents the same meaning as described above.

The compound represented by the above-described formula (e) includes, for example, compounds represented by the following formulae (e-1) to (e-4).

(e-1)

(e-2)

(e-3)

(e-4)

As the method of reacting
a compound represented by the above-described formula (c) with
at least one selected from the group consisting of a compound represented by the above-described formula (d) and a compound represented by the above-described formula (e), a method described, for example, in Chem. Commun., 2005, 2172-2174. can be applied.

In production of a compound represented by the above-described formula (a),
the use amount of at least one compound selected from the group consisting of a compound represented by the above-described formula (d) and a compound represented by the above-described formula (e) with respect to 1 mol of a compound represented by the above-described formula (c) is usually 1.0 to 100 mol, preferably 1.8 to 50 mol, more preferably 2.0 to 30 mol.

The compound represented by the above-described formula (b) may be produced by any method, and for example, can be produced by a method comprising reacting
a compound represented by the above-described formula (f) with
at least one selected from the group consisting of a compound represented by the above-described formula (d) and a compound represented by the above-described formula (e).

The compound represented by the above-described formula (f) includes, for example, compounds obtained by substituting a boric acid residue and a borate residue in compounds represented by the above-described (N-5) to (N-9) by a hydrogen atom.

As the method of reacting
a compound represented by the above-described formula (f) with
at least one selected from the group consisting of a compound represented by the above-described formula (d) and a compound represented by the above-described formula (e), a method described, for example, in Chem. Commun., 2005, 2172-2174. can be applied.

In production of a compound represented by the above-described formula (b),
the use amount of at least one compound selected from the group consisting of a compound represented by the above-described formula (d) and a compound represented by the above-described formula (e) with respect to 1 mol of a compound represented by the above-described formula (f) is usually 1.0 to 100 mol, preferably 1.8 to 50 mol, more preferably 2.0 to 30 mol.

The compound represented by the above-described formula (g) may be produced by any method, and for example, can be produced by a method comprising reacting a compound represented by the above-described formula (a) and a halogenating agent.

The compound represented by the above-described formula (h) may be produced by any method, and for example, can be produced by a method comprising reacting a compound represented by the above-described formula (b) and a halogenating agent.

The halogenating agent includes, for example, a combination of a copper salt and a halogen compound. When the copper salt is a copper(II) halide, a halogen compound may not be used.

The copper salt includes, for example, copper(I) salts and copper(II) salts.

The copper(I) salt includes, for example, copper(I) halides and copper(I) acetate.

The copper(II) salt includes, for example, copper(II) halides, copper(II) nitrate and copper(II) sulfate.

The copper(I) halide includes, for example, copper(I) chloride, copper(I) bromide and copper(I) iodide.

The copper(II) halide includes, for example, copper(II) fluoride, copper(II) chloride, copper(II) bromide and copper(II) iodide.

As the halogenating agent, preferable are copper(II) halides, more preferable are copper(II) chloride, copper(II) bromide and copper(II) iodide, further preferable is copper(II) bromide, since handling thereof is easy.

In production of a compound represented by the above-described formula (g), the use amount of the halogenating agent is usually 1 to 100 mol, preferably 1.8 to 80 mol, more preferably 2.0 to 50 mol with respect to 1 mol of a compound represented by the formula (a). Here, when the halogenating agent is a copper salt and the use amount of the copper salt in the halogenating agent is 2 mol or less with respect to 1 mol of a compound represented by the formula (a), it is preferable to use a halogen compound together.

In production of a compound represented by the above-described formula (h), the use amount of a halogenating agent is usually 1 to 100 mol, preferably 1.8 to 80 mol, more preferably 2.0 to 50 mol with respect to 1 mol of a compound represented by the formula (b). Here, when the halogenating agent is a copper salt and the use amount of the copper salt in the halogenating agent is 2 mol or less with respect to 1 mol of a compound represented by the formula (b), it is preferable to use a halogen compound together.

The halogen compound includes, for example, a chlorine molecule, a bromine molecule, an iodine molecule, N-chlorosuccinimide, N-bromosuccinimide, N-iodosuccinimide and 1,3-dibromo-5,5-dimethylhydantoin, and salts composed of a lithium ion, a sodium ion, a potassium ion, a rubidium ion or a cesium ion and a fluoride ion, a chloride ion, a bromide ion or an iodide ion.

When a halogen compound is used together, the use amount of the halogen compound is usually 1 to 100 mol, preferably 2 to 80 mol, more preferably 2 to 50 mol, with respect to 1 mol of a compound represented by the formula (a) or a compound represented by the formula (b).

In production of a compound represented by the above-described formula (g) and a compound represented by the above-described formula (h), it is preferable to use a solvent.

The solvent includes, for example, alcohol solvents such as methanol, ethanol, isopropanol and the like, ether solvents such as tetrahydrofuran, 1,4-dioxane and the like, hydrocarbon solvents such as hexane, toluene, xylene and the like, amide solvents such as N,N-dimethylformamide, N,N-diethylformamide, N,N-dimethylacetamide, 1-methyl-2-pyrrolidone and the like, acetonitrile and acetone, and owing to excellent reaction activity, preferable are ether solvents or amide solvents, more preferable are mixed solvents of ether solvents and amide solvents.

The use amount of the above-described solvent is preferably 1 to 500 parts by weight, more preferably 3 to 100 parts by weight, with respect to 1 part by weight of a compound represented by the formula (a) or a compound represented by the formula (b). When the above-described solvent is a mixed solvent, the mixing ratio thereof is not restricted.

When the halogenating agent is a copper(II) halide, it is preferable to allow water such as ion exchanged water, distilled water and the like to co-exist, in addition to the above-described solvent, since excellent reaction activity is obtained. The use amount of water is preferably 0.1 part by weight or more, more preferably 0.5 parts by weight or more, further preferably 0.5 to 100 parts by weight, particularly preferably 1 to 50 parts by weight, with respect to 1 part by weight of a compound represented by the formula (a) or a compound represented by the formula (b), since excellent reaction activity is obtained.

In production of a compound represented by the above-described formula (a), a compound represented by the above-described formula (b), a compound represented by the above-described formula (g) and a compound represented by the above-described formula (h), the reaction temperature is preferably 0 to 250° C., more preferably 0 to 200° C., further preferably 20 to 180° C.

For suppressing side reactions in production of a compound represented by the above-described formula (a), a compound represented by the above-described formula (b), a compound represented by the above-described formula (g) and a compound represented by the above-described formula (h), it is preferable to carry out the reaction under an atmosphere of an inert gas such as a nitrogen gas, an argon gas or the like which has been deoxidized.

In production of a compound represented by the above-described formula (a), a compound represented by the above-described formula (b), a compound represented by the above-described formula (g) and a compound represented by the above-described formula (h), the reaction time is usually 10 minutes or more, preferably 10 minutes to 100 hours, more preferably 10 minutes to 60 hours.

After completion of the reaction, purification is carried out by distillation off of unnecessary components under reduced pressure, removal by washing with a solvent, extraction of a product, column chromatographic purification, re-crystallization, distillation, sublimation and the like, depending on needs. In the case of use of a copper salt as the halogenating agent, it is effective to carry out a treatment with an acid or a metal scavenger, for removal of a copper component.

EXAMPLES

The present invention will be illustrated further in detail by examples below, but the present invention is not limited to these examples.

[Method of Measuring LC-MS]

In the present examples, measurement of LC-MS was carried out by the following method. The measurement sample was dissolved in chloroform or tetrahydrofuran so as to give a concentration of about 2 mg/mL, and about 1 μL of the solution was injected in LC-MS (manufactured by Agilent Technologies, trade name: 1100LCMSD). As the mobile phase of LC-MS, acetonitrile and tetrahydrofuran were used while changing the ratio thereof and allowed to flow at a flow rate of 0.2 mL/min. As the column, L-column 2 ODS (3 μm) (manufactured by Chemicals Evaluation and Research Institute, Japan, internal diameter: 2.1 mm, length: 100 mm, particle diameter: 3 μm) was used.

[Method of Measuring NMR]

In the present examples, measurement of NMR was carried out by the following method. Five to ten milligrams (5 to 10 mg) of a measurement sample was dissolved in about 0.5 mL of deuterated chloroform or deuterated tetrahydrofuran, and subjected to measurement using NMR (manufactured by Varian, trade name: MERCURY 300, or manufactured by Bruker, trade name: AVANCE600 TCI cryoprobe).

[Method of Measuring Number-Average Molecular Weight and Weight-Average Molecular Weight]

In the present examples, polystyrene-equivalent number-average molecular weight and weight-average molecular weight were measured by gel permeation chromatography (GPC, manufactured by Shimadzu Corp., trade name: LC-10Avp). The polymer compound to be measured was dissolved in tetrahydrofuran so as to give a concentration of about 0.5% by weight, and 30 μL of the solution was injected in GPC. As the mobile phase of GPC, tetrahydrofuran was used, and allowed to flow at a flow rate of 0.6 mL/min. As the column, two columns of TSKgel SuperHM-H (manufactured by Tosoh Corp.) and one column of TSKgel SuperH2000 (manufactured by Tosoh Corp.) were serially connected. As the detector, an UV detector (detection wavelength: 254 nm) was used.

<Synthesis Example 1> (Synthesis of Compound 2)

A nitrogen gas atmosphere was prepared in a reaction vessel, then, 1,5-naphthylbis(trifluoromethane sulfonate) (compound 1, 25.0 g), [1,1'-bis(diphenylphosphino)ferrocene]dichloropalladium(II) dichloromethylene adduct (0.24 g) and tert-butyl methyl ether (410 mL) were charged therein, 2-ethylhexylmagnesium bromide (1 mol/L diethyl ether solution, 173 mL) was dropped at 10° C. or lower, and the mixture was stirred at room temperature for 4 hours. After completion of the reaction, the reaction solution was poured into a mixed liquid of water and 2 N hydrochloric acid, the aqueous layer was extracted with ethyl acetate, then, the resultant organic layer was washed with a sodium chloride aqueous solution. The washed organic layer was dried over magnesium sulfate, then, the solvent was distilled off under reduced pressure. The residue was purified by silica gel column chromatography (developing solvent: hexane), to obtain 21.3 g of a compound 2 as a pale yellow oil.

MS (ESI, positive): [M$^+$]353

$^1$H-NMR (300 MHz, CDCl$_3$): δ (ppm)=0.75-1.00 (12H, m), 1.10-1.50 (16H, m), 1.69-1.85 (2H, m), 2.90-3.05 (4H, m), 7.24-7.38 (3H, m), 7.35-7.44 (3H, m), 7.90-7.95 (3H, m).

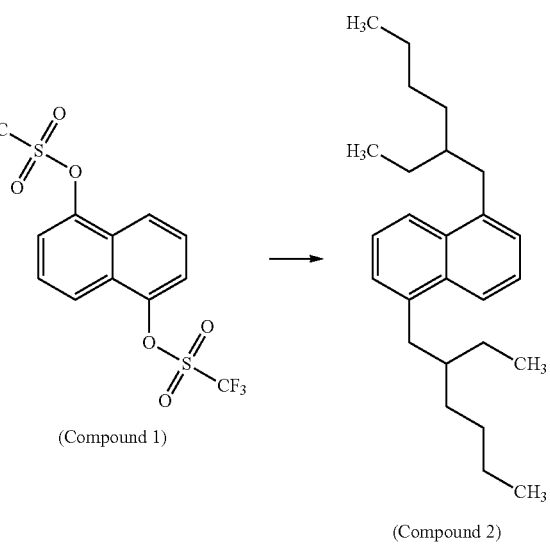

(Compound 1)

(Compound 2)

<Example 1> (Synthesis of Compound 3)

A nitrogen gas atmosphere was prepared in a reaction vessel, then, a mixture of the compound 2 (21.3 g), bis(pinacolato)diboron (4,4,4',4',5,5,5',5'-octamethyl-2,2'-bi-1,3,2-dioxaborolane) (46.0 g), bis(1,5-cyclooctadiene)di-μ-methoxydiiridium(I) (0.24 g) (manufactured by Aldrich), 4,4'-di-tert-butyl-2,2'-dipyridyl (0.19 g) and dioxane (140 mL) was stirred at 100° C. for 3 hours. After cooling, dioxane was distilled off under reduced pressure, methanol was added to the residue, and the deposited solid was isolated by filtration and dried. This solid was dissolved in toluene, activated clay was added, and the mixture was stirred at 60° C. for 30 minutes. Thereafter, the mixture was hot-filtrated on a filter pre-coated with silica gel, and the filtrate was concentrated under reduced pressure. To the resultant concentrated residue was added methanol, and the deposited solid was isolated by filtration and dried, to obtain 28.0 g of a compound 3 as a white powder.

LC-MS (ESI, positive): [M$^+$] 605

$^1$H-NMR (300 MHz, CDCl$_3$): δ (ppm)=0.85-0.95 (12H, m), 1.24-1.50 (16H, m), 1.66-1.85 (2H, m), 2.90-3.18 (4H, m), 7.60 (2H, s), 8.47 (2H, s).

<Example 2> (Synthesis of Compound 4)

A nitrogen gas atmosphere was prepared in a reaction vessel, then, into a mixture of the compound 3 (28.0 g), dioxane (420 mL), DMF (N,N-dimethylformamide) (420 mL) and water (210 mL) was added copper(II) bromide (62.7 g), and the mixture was stirred at 95° C. for 2 hours. Thereafter, copper(II) bromide (31.4 g) was added at the same temperature, and the mixture was stirred for 1.5 hours, then, copper(II) bromide (31.4 g) was additionally added, and the mixture was stirred for 1.5 hours. Then, the reaction solution was cooled, hexane was added to this and the mixture was stirred. Thereafter, the organic layer was separated, dried over magnesium sulfate, then, the solvent was distilled off under reduced pressure. The residue was purified by silica gel column chromatography (developing solvent: hexane), and concentrated to obtain a solid (21.0 g). This solid was dissolved in toluene, activated carbon was added, and the mixture was stirred at 60° C. for 30 minutes. Then, the mixture was hot-filtrated on a filter pre-coated with Celite, and the filtrate was concentrated under reduced pressure. The resultant concentrated residue was re-crystallized from a mixed liquid of toluene and methanol, to obtain 13.2 g of a compound 4 as a white solid.

MS (ESI, positive) [M$^+$] 511

$^1$H-NMR (300 MHz, CDCl$_3$): δ (ppm)=0.80-0.98 (12H, m), 1.20-1.44 (16H, m), 1.64-1.80 (2H, m), 2.77-2.95 (4H, m), 7.37 (2H, s), 8.00 (2H, s).

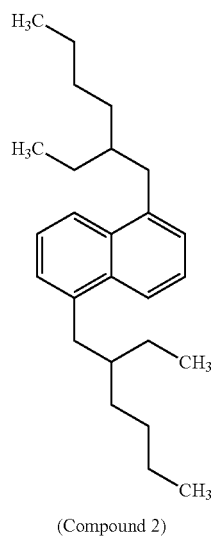

(Compound 2)

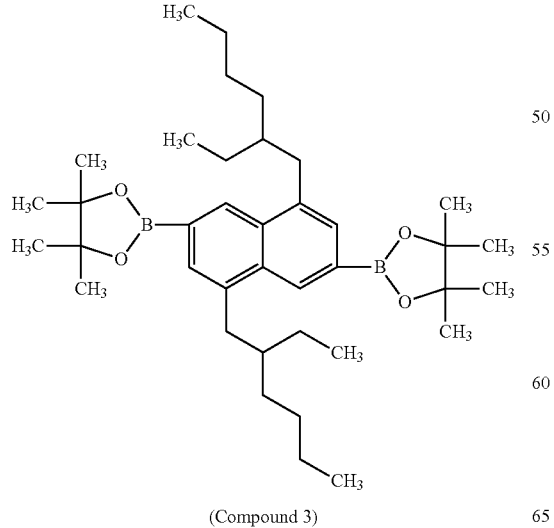

(Compound 3)

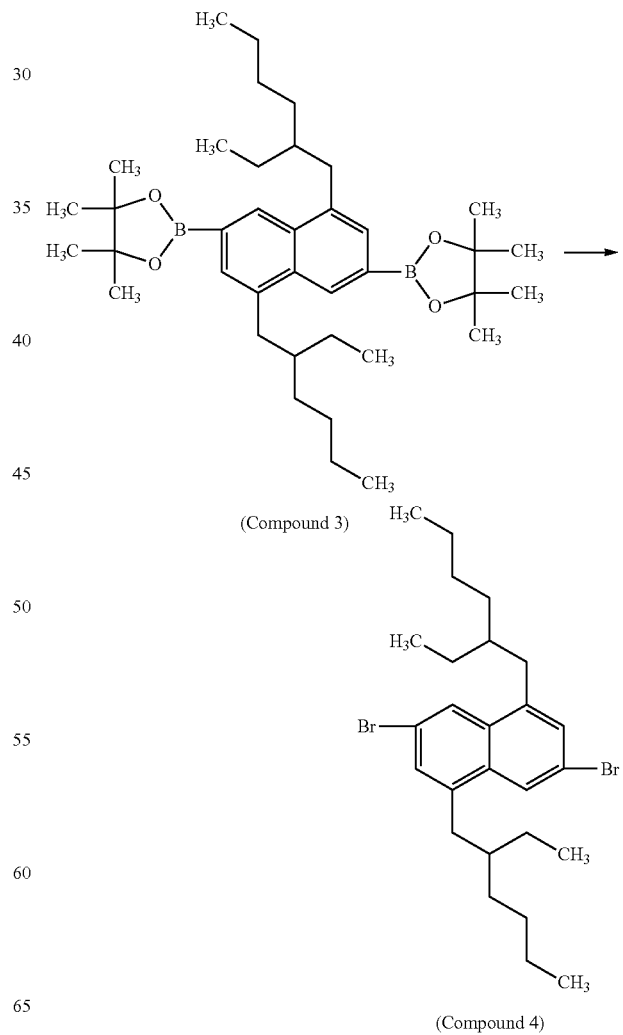

(Compound 3)

(Compound 4)

<Example 3> (Synthesis of Compound 6)

An argon gas atmosphere was prepared in a reaction vessel, then, 24 g of 1,5-dimethylnaphthalene (compound 5), 229 g of bis(pinacolato)diboron(4,4,4',4',5,5,5',5'-octamethyl-2,2'-bi-1,3,2-dioxaborolane), 0.6 g of bis(1,5-cyclooctadiene)di-μ-methoxydiiridium(I), 0.5 g of 4,4'-di-tert-butyl-2,2'-dipyridyl and 1,4-dioxane (412 mL) were charged therein, and the mixture was stirred at 85° C. for 2 hours. The reaction product was cooled down to room temperature, then, concentrated under reduced pressure, and the deposited solid was filtrated, and washed with methanol. Thereafter, the resultant solid was dissolved in toluene, activated clay was added, and the mixture was stirred, then, filtrated and concentrated under reduced pressure. The resultant solid was re-crystallized from toluene, to obtain 39.8 g of a compound 6 as a white solid.

LC-MS (APPI, positive): [M+H]⁺ 408

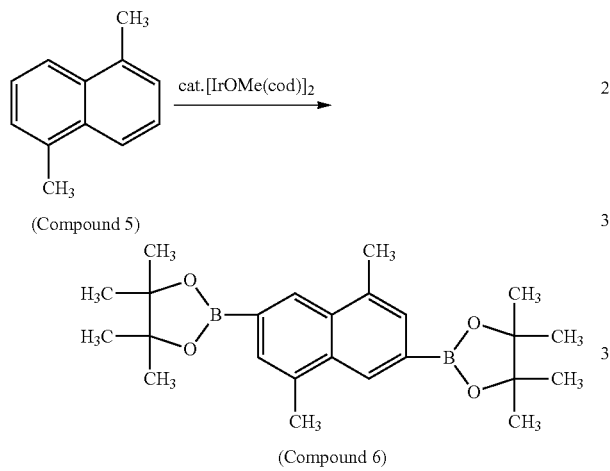

<Example 4> (Synthesis of Compound 7)

An argon gas atmosphere was prepared in a reaction vessel, then, into a mixed liquid of the compound 6 (1.00 g), dioxane (30 mL), DMF (15 mL) and water (3 mL) was added copper (II) bromide (0.5 g), and the mixture was stirred at 95° C. for 7 hours. Thereafter, copper(II) bromide (1.0 g) was additionally added at the same temperature, and the mixture was stirred for 10 hours, then, copper(II) bromide (1.0 g) was additionally added, and the mixture was stirred for 10 hours. After cooling, to the reaction solution were added toluene and water, and the mixture was stirred. Thereafter, the mixture was filtrated on a filter pre-coated with Celite, and the organic layer was washed with water, with 1 N hydrochloric acid and with water in this order. The resultant organic layer was dried over magnesium sulfate, filtrated, and the filtrate was concentrated under reduced pressure. The resultant concentrated residue was re-crystallized from a mixed liquid of toluene and methanol, to obtain a compound 7 as a pale brown solid.

MS (ESI, positive) [M⁺] 312

¹H-NMR (300 MHz, CDCl₃): δ (ppm)=2.62 (6H, s), 7.43 (2H, s), 7.95 (2H, s).

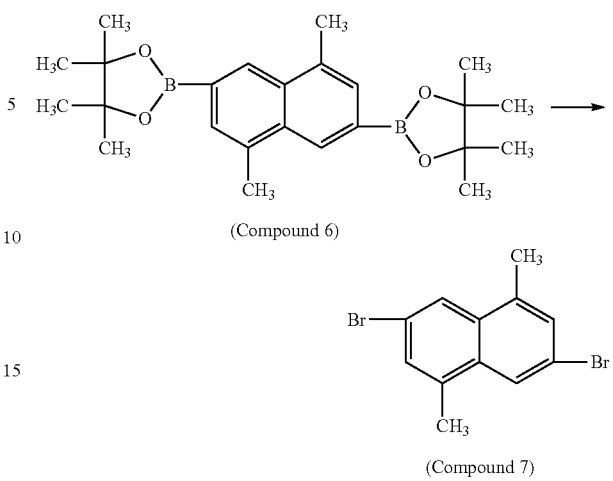

<Example 5> (Synthesis of Compound 9)

An argon gas atmosphere was prepared in a reaction vessel, then, 3 g of 1-methylnaphthalene (compound 8), 10.7 g of bis(pinacolato)diboron(4,4,4',4',5,5,5',5'-octamethyl-2, 2'-bi-1,3,2-dioxaborolane), 0.08 g of bis(1,5-cyclooctadiene)di-μ-methoxydiiridium(I), 0.07 g of 4,4'-di-tert-butyl-2, 2'-dipyridyl and 1,4-dioxane (36 mL) were charged therein, and the mixture was heated at 85° C. for 3 hours. The reaction solution was cooled down to room temperature, then, concentrated under reduced pressure, chloroform was added to the resultant concentrated residue, and the mixture was washed with water twice. Thereafter, the organic layer was dried over magnesium sulfate, filtrated, then, concentrated under reduced pressure. Ethanol was added to the resultant concentrated residue to find deposition of a solid, and the solid was filtrated and dried, to obtain 3.2 g of a compound 9 as a white solid.

¹H-NMR (300 MHz, CDCl₃): δ (ppm)=1.28-1.50 (24H, m), 2.75 (3H, s), 7.68 (1H, s), 7.78-7.85 (2H, m), 8.22 (1H, s), 8.50 (1H, s).

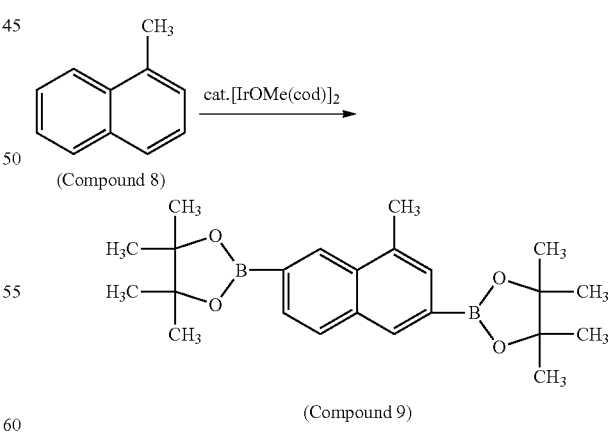

<Synthesis Example 2> (Synthesis of Compound 24)

A nitrogen gas atmosphere was prepared in a reaction vessel, then, magnesium (27.7 g) and tetrahydrofuran (800 mL) were charged therein, a tetrahydrofuran (200 mL) solution of 3,5-di(n-hexyl)bromobenzene (compound 23, 250 g) was dropped, and the mixture was refluxed with heating (hereinafter, referred to as "3,5-di(n-hexyl)phenylmagnesium bromide solution").

A nitrogen gas atmosphere was prepared in another reaction vessel, then, 1,3-dibromopropane (206 g), tetrahydrofuran (60.0 mL), hexamethylphosphoric triamide (60.0 mL) and copper(I) bromide (5.51 g) were charged therein, and the mixture was refluxed with heating. Then, the 3,5-di(n-hexyl) phenylmagnesium bromide solution prepared previously was dropped, and the mixture was stirred for 3 hours. After completion of the reaction, the reaction solution was poured into a mixed liquid of water and 2 N hydrochloric acid, and the aqueous layer was extracted with hexane, then, the resultant organic layer was washed with water. The organic layer washed was dried over magnesium sulfate, then, the solvent and excess 1,3-dibromopropane were distilled off under reduced pressure. The residue was purified by silica gel column chromatography (developing solvent: hexane), to obtain 232 g of a compound 24 as a colorless transparent liquid.

LC-MS (APPI, positive): [M+] 366

$^1$H-NMR (300 MHz, CDCl$_3$): δ (ppm)=0.83-0.94 (8H, m), 1.30-1.35 (8H, m), 1.53-1.61 (6H, m), 2.10-2.20 (2H, m), 2.52-2.59 (4H, m), 2.69-2.71 (2H, m), 3.37-3.40 (2H, m), 6.81 (2H, s), 6.84 (1H, s).

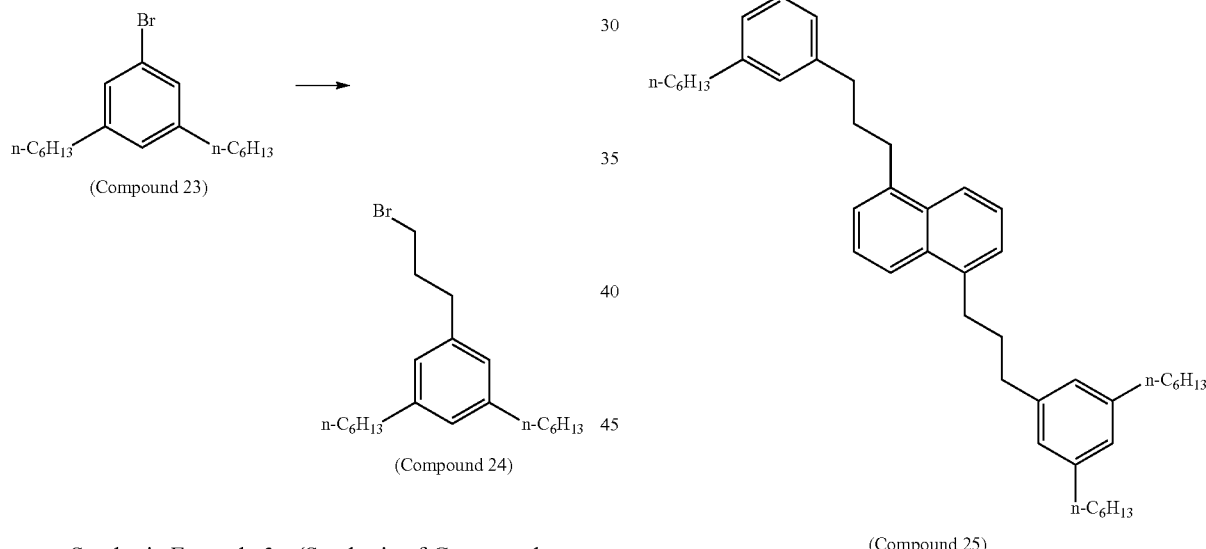

(Compound 23)

(Compound 24)

<Synthesis Example 3> (Synthesis of Compound 25)

A nitrogen gas atmosphere was prepared in a reaction vessel, then, magnesium (2.45 g) and diethyl ether (7.5 mL) were charged therein, a diethyl ether (27.0 mL) solution of the compound 24 (25.0 g) was dropped, and the mixture was fluxed with heating, to prepare a solution G-1.

A nitrogen gas atmosphere was prepared in another reaction vessel, then, 1,5-naphthylbis(trifluoromethane sulfonate) (compound 1, 5.77 g), [1,1'-bis(diphenylphosphino)ferrocene]dichloropalladium(II) dichloromethylene adduct (0.56 g) and diethyl ether (100 mL) were charged therein, and the solution G-1 prepared above was dropped at room temperature, then, the mixture was refluxed with heating for 3 hours. After completion of the reaction, the reaction solution was poured into a mixed liquid of water and 2 N hydrochloric acid, and the aqueous layer was extracted with ethyl acetate, then, the resultant organic layer was washed with a sodium chloride aqueous solution. The organic layer washed was dried over magnesium sulfate, then, the solvent was distilled off under reduced pressure. The residue was purified by silica gel column chromatography (developing solvent: hexane), to obtain 6.19 g of a compound 25 as a colorless oil.

MS (APPI, positive): [M+] 701

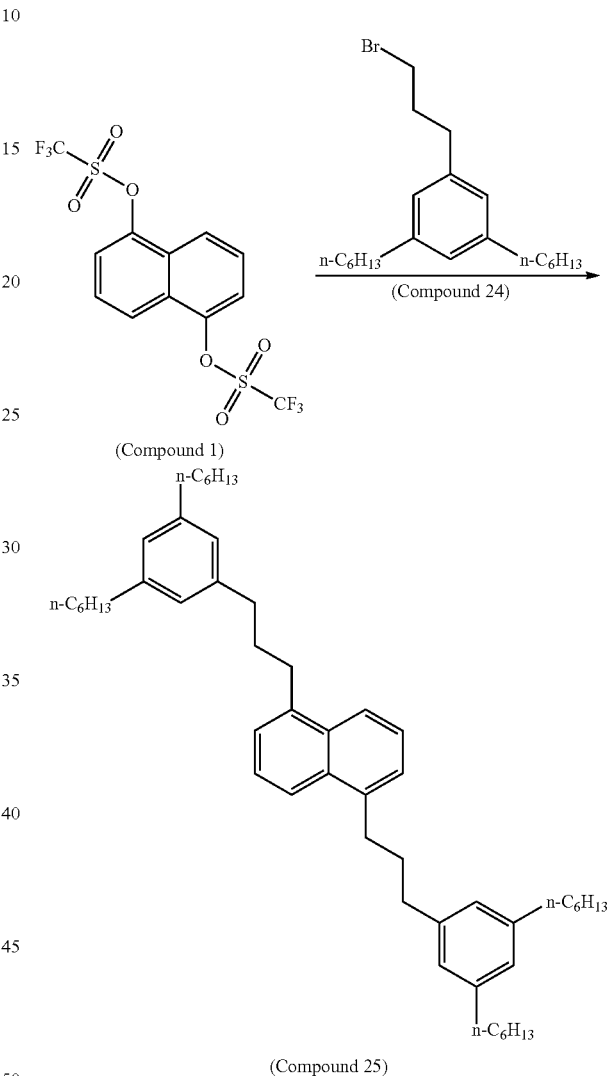

(Compound 1)

(Compound 24)

(Compound 25)

<Example 6> (Synthesis of Compound 26)

A nitrogen gas atmosphere was prepared in a reaction vessel, then, a mixture of the compound 25 (8.00 g), bis(pinacolato)diboron (4,4,4',4',5,5,5',5'-octamethyl-2,2'-bi-1,3,2-dioxaborolane) (8.69 g), bis(1,5-cyclooctadiene)di-µ-methoxydiiridium(I) ([Ir(OMe) (cod)]$_2$, 0.11 g) (manufactured by Aldrich), 4,4'-di-tert-butyl-2,2'-dipyridyl (0.09 g) and dioxane (80 mL) was stirred at 100° C. for 1.5 hours. The reaction solution was cooled down to room temperature, then, filtrated through Celite, washed with ethyl acetate, then, concentrated under reduced pressure. The resultant crude product was dissolved in hexane (100 mL), activated carbon (1.20 g) was added, and the mixture was refluxed with heating for 1 hour. Thereafter, the mixture was filtrated through Celite, and the filtrate was concentrated under reduced pressure. The resultant concentrated residue was re-crystallized from hexane-ethanol, and the deposited solid was isolated by filtration and dried, to obtain 7.3 g of a compound 26 as a white powder.

LC-MS (APPI, positive): [M⁻] 926

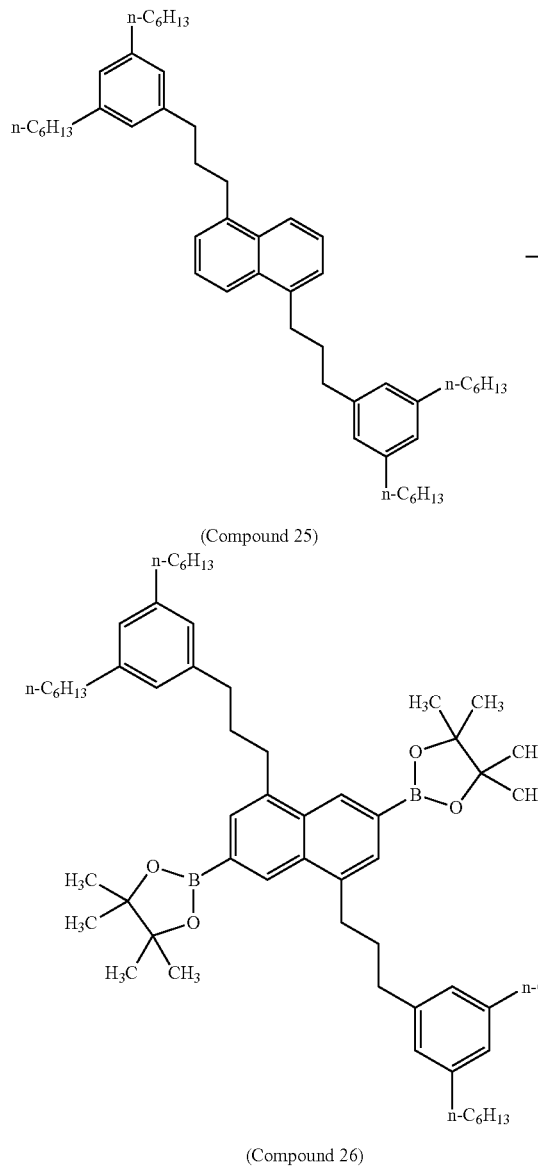

(Compound 25)

(Compound 26)

<Synthesis Example 4> (Synthesis of Compound 27)

A nitrogen gas atmosphere was prepared in a reaction vessel, then, 1,5-naphthylbis(trifluoromethane sulfonate) (compound 1, 12.7 g), [1,1'-bis(diphenylphosphino)ferrocene]dichloropalladium(II) dichloromethylene adduct (0.12 g) and tert-butyl methyl ether (137 mL) were charged therein, further, 1-decylmagnesium bromide (90 mL of 1 mol/L diethyl ether solution) was dropped at 30° C., and the mixture was stirred for 3 hours under reflux with heating. After completion of the reaction, the reaction solution was poured into a mixed liquid of water and 2 N hydrochloric acid, and the aqueous layer was extracted with hexane. The organic layer was dried over magnesium sulfate, then, the solvent was distilled off under reduced pressure. The residue was re-crystallized from a mixed liquid of hexane and isopropanol, to obtain 10.3 g of a compound 27 as a pale yellow solid.

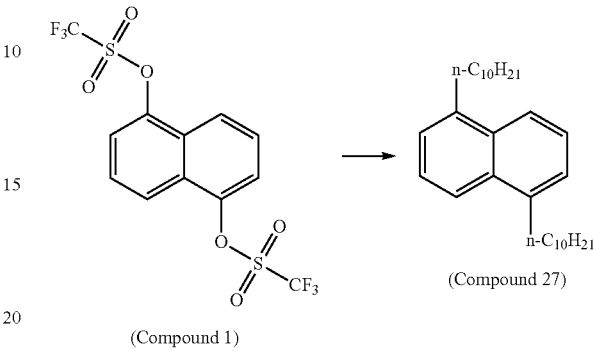

(Compound 1) (Compound 27)

<Example 7> (Synthesis of Compound 28)

A nitrogen gas atmosphere was prepared in a reaction vessel, then, a mixture of the compound 27 (10.0 g), bis(pinacolato)diboron(4,4,4',4',5,5,5',5'-octamethyl-2,2'-bi-1,3,2-dioxaborolane) (24.9 g), bis(1,5-cyclooctadiene)di-μ-methoxydiiridium(I) (0.13 g) (manufactured by Aldrich), 4,4'-di-tert-butyl-2,2'-dipyridyl (0.11 g) and dioxane (147 mL) was stirred at 100° C. for 3 hours. The reaction solution was cooled, then, dioxane was distilled off under reduced pressure, methanol was added to the residue, and the deposited solid was isolated by filtration and dried. Thereafter, this solid was dissolved in toluene, activated clay was added, and the mixture was stirred at 60° C. for 30 minutes. Thereafter, the mixture was hot-filtrated on a filter pre-coated with silica gel, and the filtrate was concentrated under reduced pressure. The resultant concentrated residue was re-crystallized from a mixed liquid of toluene and hexane, to obtain 13.3 g of a compound 28 as a white solid.

LC-MS (ESI, positive): [M+K⁺] 699

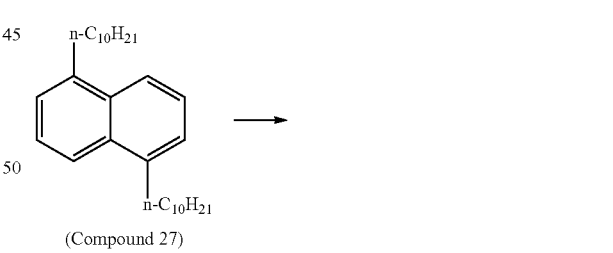

(Compound 27)

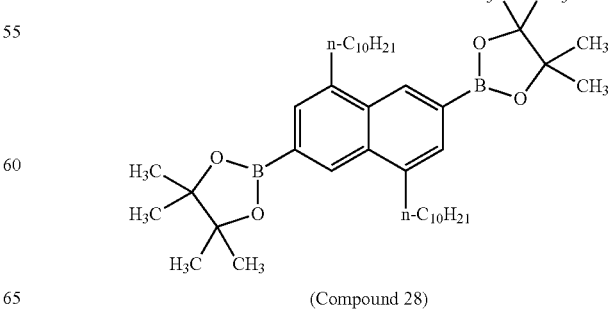

(Compound 28)

<Synthesis Example 5> (Synthesis of Compound 29)

A nitrogen gas atmosphere was prepared in a reaction vessel, then, at room temperature, magnesium (4.8 g) and diethyl ether (75 mL) were charged therein, further, iodine (0.01 g) was added, and the mixture was stirred for 10 minutes. A mixed liquid of (2-bromoethyl)cyclohexane (37.2 g) and diethyl ether (152 mL) was dropped into this over a period of 1 hour. Thereafter, the mixture was refluxed with heating for 1 hour, then, the reaction solution was cooled down to room temperature, to prepare a solution G-2.

A nitrogen gas atmosphere was prepared in another reaction vessel, then, 1,5-naphthylbis(trifluoromethane sulfonate) (compound 1, 25.0 g), [1,1'-bis(diphenylphosphino)ferrocene]dichloropalladium(II) dichloromethylene adduct (0.24 g) and tert-butyl methyl ether (270 mL) were charge therein, further, the solution G-2 was dropped at 30° C., then, the mixture was stirred for 3 hours under reflux with heating. After completion of the reaction, the reaction solution was poured into a mixed liquid of water and 2 N hydrochloric acid, and extracted with hexane. The organic layer was dried over magnesium sulfate, then, the solvent was distilled off under reduced pressure. The residue was re-crystallized from a mixed liquid of hexane and isopropanol, to obtain 18.0 g of a compound 29 as a white solid.

bis(pinacolato)diboron(4,4,4',4',5,5,5',5'-octamethyl-2,2'-bi-1,3,2-dioxaborolane) (39.3 g), bis(1,5-cyclooctadiene)di-µ-methoxydiiridium(I) (0.21 g) (manufactured by Aldrich), 4,4'-di-tert-butyl-2,2'-dipyridyl (0.17 g) and dioxane (135 g) was stirred at 100° C. for 3 hours. The reaction solution was cooled down to room temperature, then, acetonitrile was added, and the deposited solid was isolated by filtration and dried. This solid was re-crystallized from toluene, to obtain 24.5 g of a compound 30 as a white solid.

LC-MS (ESI, positive): [M+K$^+$] 639

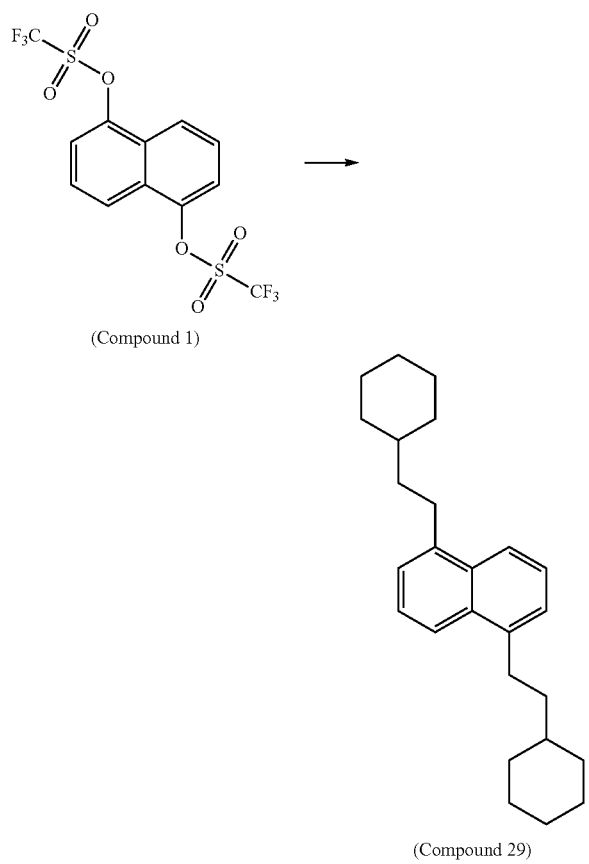

(Compound 1)

(Compound 29)

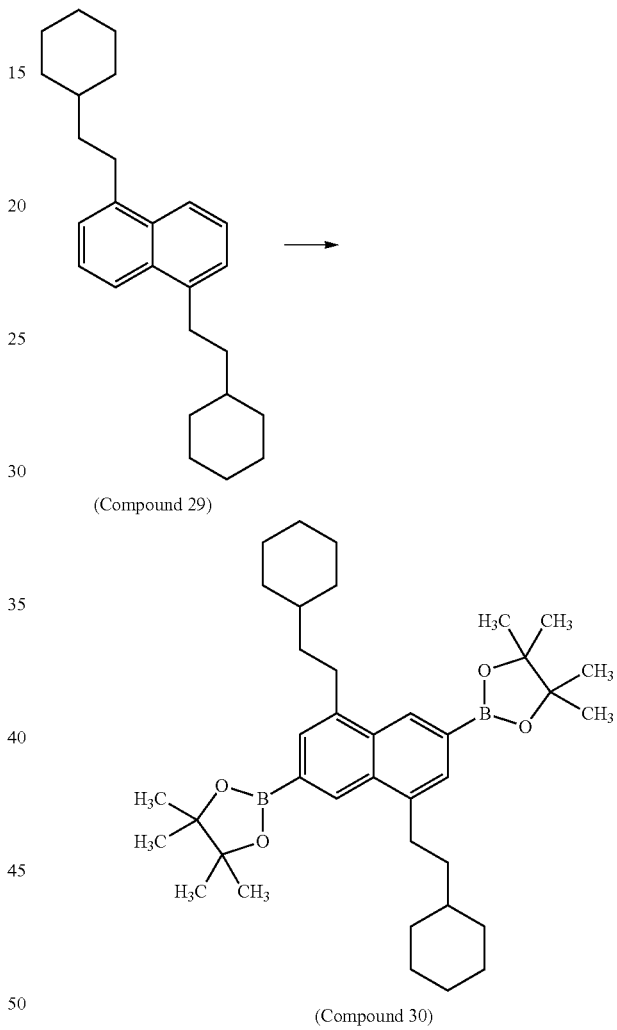

(Compound 29)

(Compound 30)

<Example 8> (Synthesis of Compound 30)

A nitrogen gas atmosphere was prepared in a reaction vessel, then, a mixture of the compound 29 (18.0 g), <Synthesis Example 6> (Synthesis of Compound 31)

A nitrogen gas atmosphere was prepared in a reaction vessel, then, copper(I) bromide (4.4 g), lithium chloride (2.6 g) and tetrahydrofuran (440 mL) were charged therein, and the mixture was stirred for 30 minutes. Thereafter, the mixed solution was cooled to 0° C., and ethyl trans-2-hexenoate (43.3 g) and chlorotrimethylsilane (36.4 g) were added. Further, 1-butylmagnesium chloride (2.0M tetrahydrofuran solution, 175 mL) was dropped over a period of 1 hour, then, the mixture was stirred for 1 hour. After completion of the reaction, the reaction solution was poured into a mixed liquid of water and 2 N hydrochloric acid. The mixed solution was extracted with hexane added, the organic layer was washed with water, then, the solvent was distilled off under reduced pressure, and the residue was purified by silica gel column chromatography (developing solvent: hexane/ethyl acetate), to obtain 54.5 g of a compound 31 as a pale yellow oil.

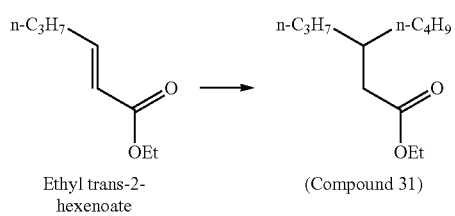

Ethyl trans-2-hexenoate    (Compound 31)

<Synthesis Example 7> (Synthesis of Compound 32)

A nitrogen gas atmosphere was prepared in a reaction vessel, then, lithium aluminum hydride (2.7 g) and tetrahydrofuran (63 mL) were charged therein, then, a mixed solution of the compound 31 (7.0 g) and THF (24 mL) was dropped over a period of 30 minutes. Then, the mixture was refluxed with heating for 5 hours, then, the reaction solution was cooled down to room temperature, and sodium sulfate decahydrate (45 g) was charged as a solid itself in divided portions over a period of 1 hour. Hexane was added to the resultant mixed solution to cause deposition of a solid, the solid was separated by filtration, and the solvent was distilled off under reduced pressure. The residue was purified by silica gel column chromatography (developing solvent: hexane/ethyl acetate), to obtain 5.1 g of a compound 32 as a colorless oil.

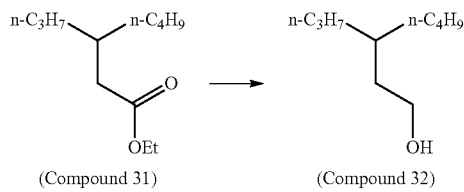

(Compound 31)    (Compound 32)

<Synthesis Example 8> (Synthesis of Compound 33)

A nitrogen gas atmosphere was prepared in a reaction vessel, then, the compound 32 (30.0 g), triphenylphosphine (59.7 g) and chloroform (61 mL) were charged therein, and cooled down to 0° C. Thereafter, N-bromosuccinimide (40.5 g) was charged over a period of 1 hour, then, the mixture was stirred for 1 hour at room temperature. To the resultant mixed solution were added a 10% by weight sodium carbonate aqueous solution (81 mL) and chloroform, and the solution was separated. From the resultant organic layer, the solvent was distilled off under reduced pressure. Thereafter, hexane was added to cause deposition of a solid, the deposited solid was separated by filtration, and the solvent was distilled off under reduced pressure. The residue was purified by silica gel column chromatography (developing solvent: hexane), further, distilled under reduced pressure, to obtain 33.1 g of a compound 33 as a colorless oil. The boiling point was 93° C. under 1.0 kPa.

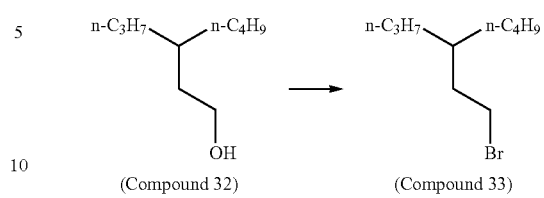

(Compound 32)    (Compound 33)

<Synthesis Example 9> (Synthesis of Compound 34)

A nitrogen gas atmosphere was prepared in a reaction vessel, then, at room temperature, to a mixture of magnesium (2.6 g) and diethyl ether (40 mL) was added iodine (0.01 g), and the mixture was stirred for 10 minutes. Into the resultant reaction solution, a mixed liquid of the compound 33 (23.0 g) and ether (82 mL) was dropped over a period of 1 hour, then, the mixture was refluxed with heating for 1 hour, and the reaction solution was cooled down to room temperature, to give a solution G-3.

A nitrogen gas atmosphere was prepared in another reaction vessel, then, 1,5-naphthylbis(trifluoromethane sulfonate) (compound 1, 13.4 g), [1,1'-bis(diphenylphosphino) ferrocene]dichloropalladium(II) dichloromethylene adduct (0.13 g) and tert-butyl methyl ether (144 mL) were charged therein, further, the solution G-3 was dropped at 30° C., then, the mixture was stirred for 3 hours under reflux with heating. After completion of the reaction, the reaction solution was poured into a mixed liquid of water and 2 N hydrochloric acid, and the aqueous layer was extracted with hexane. The organic layer was dried over magnesium sulfate, then, the solvent was distilled off under reduced pressure. The residue was purified by silica gel column chromatography (developing solvent: hexane), to obtain 11.6 g of a compound 34 as a colorless oil.

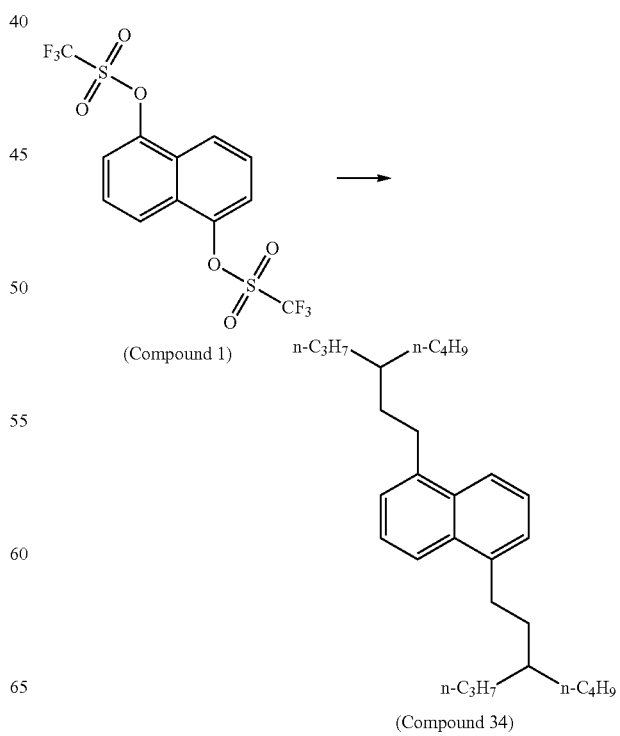

(Compound 1)

(Compound 34)

<Example 9> (Synthesis of Compound 35)

A nitrogen gas atmosphere was prepared in a reaction vessel, then, a mixture of the compound 34 (11.5 g), bis(pinacolato)diboron(4,4,4',4',5,5,5',5'-octamethyl-2,2'-bi-1,3,2-dioxaborolane) (20.4 g), bis(1,5-cyclooctadiene)di-μ-methoxydiiridium(I) (0.11 g) (manufactured by Aldrich), 4,4'-di-tert-butyl-2,2'-dipyridyl (0.09 g) and dioxane (86 g) was stirred at 100° C. for 3 hours. The reaction solution was cooled down to room temperature, then, acetonitrile (46 g) was added, further, methanol (23 g) was dropped, and the solution was cooled down to 0° C. to cause deposition of a solid, and the deposited solid was isolated by filtration and dried. This solid was re-crystallized from a mixed liquid of toluene and acetonitrile, to obtain 11.5 g of a compound 35 as a white solid.

LC-MS (ESI, positive): [M+K$^+$] 699

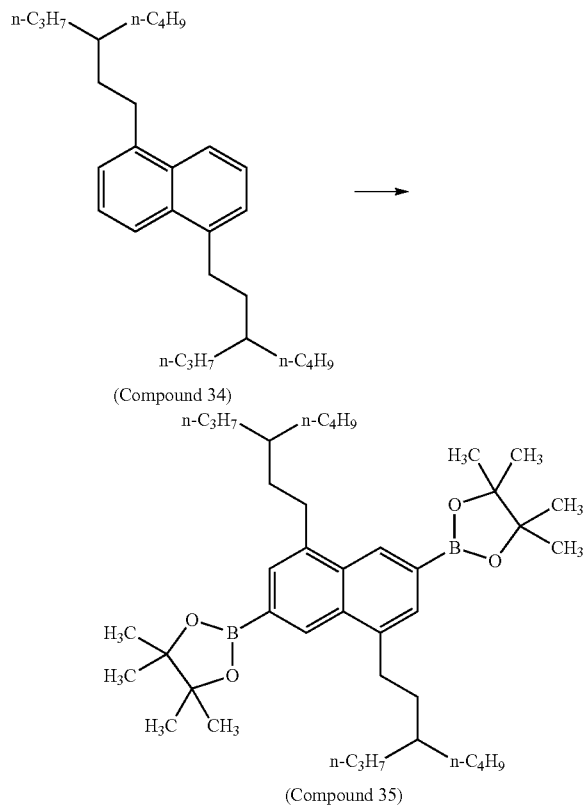

(Compound 34)

(Compound 35)

<Synthesis Example 10> (Synthesis of Compound 36)

A nitrogen gas atmosphere was prepared in a reaction vessel, then, cyclopentyl methyl ether (400 ml), 2-ethylhexylmagnesium bromide (1 mol/L diethyl ether solution, 232 mL) and [1,1'-bis(diphenylphosphino)ferrocene]dichloropalladium(II) dichloromethylene adduct (0.32 g) were charged therein, and under temperatures of 40° C. to 50° C., a mixed solution of 1-bromonaphthalene (40 g) and cyclopentyl methyl ether (100 ml) was dropped, then, the mixture was stirred at 50° C. for 2 hours. After completion of the reaction, the reaction solution was cooled down to 0° C., and a mixed liquid of water (80 ml) and 2 N hydrochloric acid (40 ml) was dropped. Then, the mixture was extracted with toluene (200 ml), then, washed with water, and the washed organic layer was dried over magnesium sulfate, then, the solvent was distilled off under reduced pressure. The residue was purified by silica gel column chromatography (developing solvent: hexane), to obtain 47.6 g of a compound 36 as a colorless oil.

$^1$H-NMR (300 MHz, CDCl$_3$): δ (ppm)=0.82-0.95 (6H, m), 1.20-1.45 (8H, m), 1.70-1.85 (1H, m), 2.80-3.05 (2H, m), 7.25-7.55 (4H, m), 7.70 (1H, d), 7.85 (1H, d), 8.05 (1H, d).

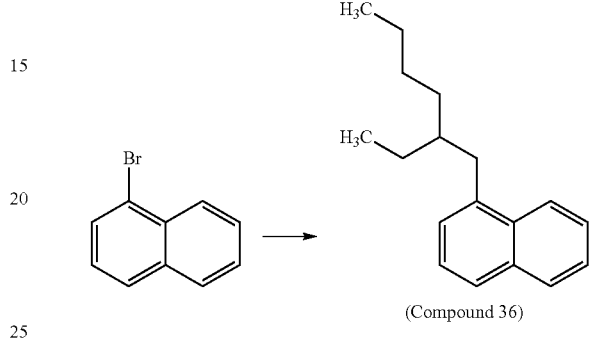

(Compound 36)

<Example 10> (Synthesis of Compound 37)

A nitrogen gas atmosphere was prepared in a reaction vessel, then, a mixture of the compound 36 (48.0 g), bis(pinacolato)diboron (101.8 g), bis(1,5-cyclooctadiene)di-μ-methoxydiiridium(I) (0.79 g) (manufactured by Aldrich), 4,4'-di-tert-butyl-2,2'-dipyridyl (0.69 g) and dioxane (348 mL) was stirred at 100° C. for 1.5 hours. The reaction solution was cooled down to room temperature, then, dioxane was distilled off under reduced pressure, and to the residue were added toluene (700 ml) and activated clay (98.3 g), and the mixture was stirred at 60° C. for 0.5 hours. Thereafter, the mixture was filtrated on a filter paved with silica gel and Celite, and toluene was distilled off under reduced pressure. Methanol was added to the residue to cause deposition of a solid, and the deposited solid was isolated by filtration and dried. Thereafter, the resultant solid was re-crystallized from a mixed liquid of toluene and acetonitrile, to obtain 23.2 g of a compound 37 as a white solid.

LC-MS (ESI, positive): [M$^+$] 492

$^1$H-NMR (300 MHz, CDCl$_3$): δ (ppm)=0.85-0.95 (6H, m), 1.20-1.40 (8H, m), 1.75-1.85 (1H, m), 2.90-3.15 (2H, m), 7.60 (1H, s), 7.75-7.90 (2H, m), 8.20 (1H, s), 8.55 (1H, s).

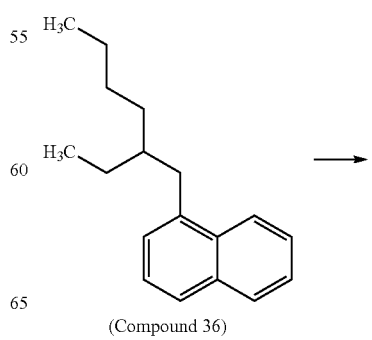

(Compound 36)

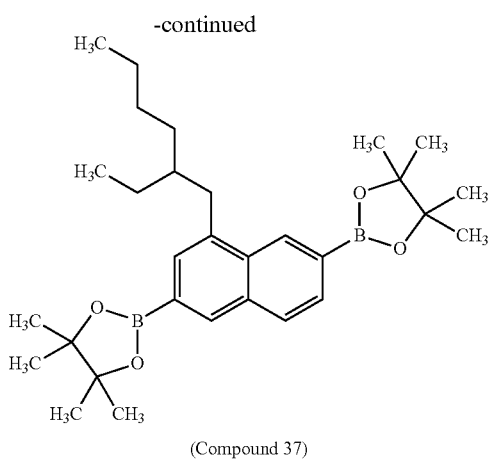

(Compound 37)

<Synthesis Example 11> (Synthesis of Compound 38)

A nitrogen gas atmosphere was prepared in a reaction vessel, then, 1,5-naphthylbis(trifluoromethane sulfonate) (compound 1, 15.0 g), [1,1'-bis(diphenylphosphino)ferrocene]dichloropalladium(II) dichloromethylene adduct (0.144 g) and tert-butyl methyl ether (162 mL) were charged therein, and at a temperature of 10° C. or lower, 2,2-ethylbutylmagnesium bromide (1 mol/L diethyl ether solution, 136 mL) was dropped, then, the mixture was stirred at 40° C. for 3.5 hours. After completion of the reaction, the reaction solution was poured into a mixed liquid of water and 2 N hydrochloric acid, and the aqueous layer was extracted with hexane, then, the resultant organic layer was washed with a 5% by weight sodium hydrogen carbonate aqueous solution. The washed organic layer was dried over magnesium sulfate, then, the solvent was distilled off under reduced pressure. The residue was purified by silica gel column chromatography (developing solvent: hexane), to obtain 9.27 g of a compound 38 as a pale yellow oil.

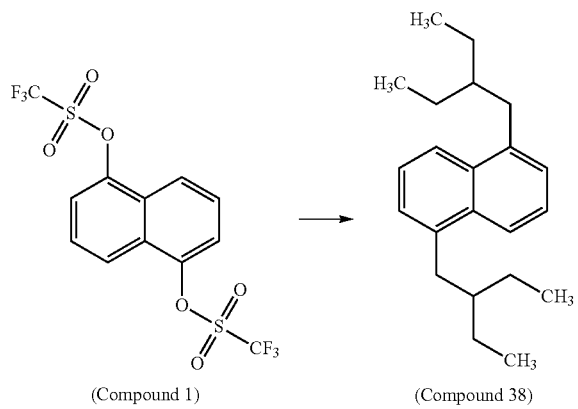

(Compound 1)   (Compound 38)

<Example 11> (Synthesis of Compound 39)

A nitrogen gas atmosphere was prepared in a reaction vessel, then, a mixture of the compound 38 (8.75 g), bis(pinacolato)diboron (4,4,4',4',5,5,5',5'-octamethyl-2,2'-bi-1,3,2-dioxaborolane) (22.5 g), bis(1,5-cyclooctadiene)di-µ-methoxydiiridium(I) (0.0951 g) (manufactured by Aldrich), 4,4'-di-tert-butyl-2,2'-dipyridyl (0.117 g) and cyclopentyl methyl ether (65.6 g) was stirred at 100° C. for 8 hours. The reaction solution was cooled down to room temperature, then, acetonitrile (35 mL) was added to cause deposition of a solid, and the deposited solid was isolated by filtration and dried. Thereafter, this solid was dissolved in toluene (120 mL), activated clay (1.2 g) was added, and the mixture was stirred at 60° C. for 1 hour. Thereafter, the resultant mixture was hot-filtrated on a filter pre-coated with silica gel, and the filtrate was concentrated under reduced pressure. The resultant concentrated residue was re-crystallized from a mixed liquid of toluene and acetonitrile, to obtain 11.5 g of a compound 39 as a white solid.

LC-MS (ESI, positive): [M$^+$] 549

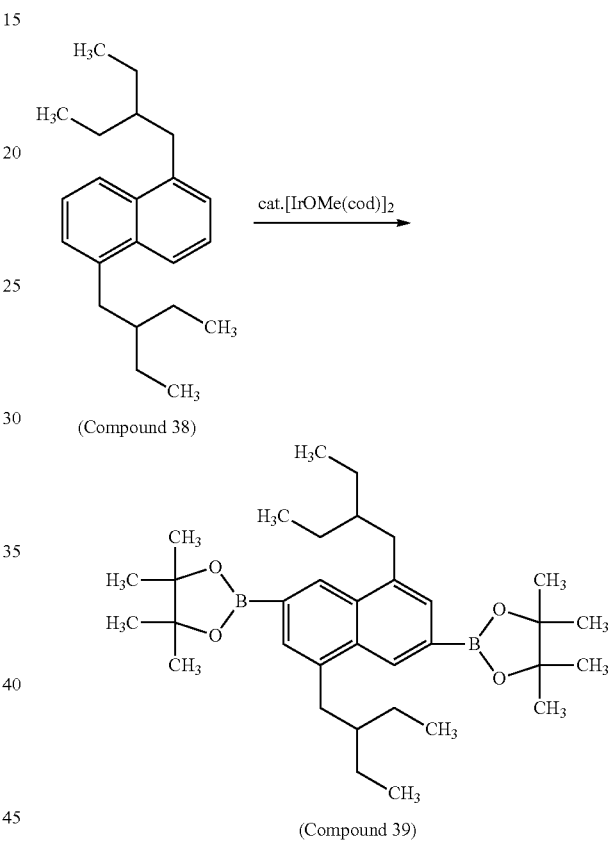

(Compound 38)

(Compound 39)

<Synthesis Example 12> (Synthesis of Compound 40)

A nitrogen gas atmosphere was prepared in a reaction vessel, then, 1,5-naphthylbis(trifluoromethane sulfonate) (compound 1, 82.4 g), 1-(4,4,5,5-tetramethyl-1,3,2-dioxaborolan-2-yl)-3,5-dihexyl benzene (193.0 g) and toluene (1137 mL) were charged therein, then, bis(triphenylphosphine) palladium (II) dichloride (2.7 g) was added, then, tetraethylammonium hydroxide (20% by weight aqueous solution, 424.1 g) was dropped at 80° C., then, mixture was stirred at 80° C. for 5 hours. After completion of the reaction, the resultant reaction solution was extracted with water and toluene poured. The resultant organic layer was dried over magnesium sulfate, then, the solvent was distilled off under reduced pressure. The residue was purified by silica gel column chromatography (developing solvent: hexane), to obtain 132.8 g of a compound 40 as a slightly yellow oil.

TLC-MS (ESI, positive): [M$^-$] 617

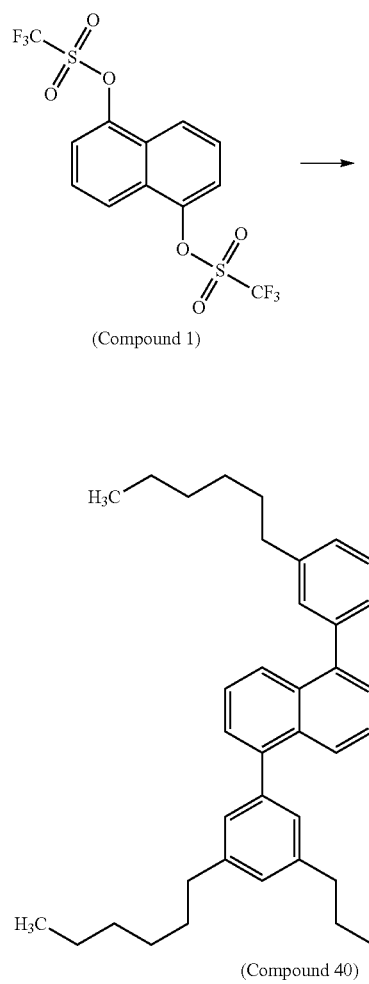

(Compound 1)

(Compound 40)

<Example 12> (Synthesis of Compound 41)

A nitrogen gas atmosphere was prepared in a reaction vessel, then, a mixture of the compound 40 (132.8 g), bis(pinacolato)diboron (4,4,4',4',5,5,5',5'-octamethyl-2,2'-bi-1,3,2-dioxaborolane) (147.8 g), bis(1,5-cyclooctadiene)di-μ-methoxydiiridium(I) (3.86 g) (manufactured by Aldrich), 4,4'-di-tert-butyl-2,2'-dipyridyl (3.12 g) and dioxane (2 L) was stirred at 80° C. overnight. The reaction solution was cooled down to room temperature, then, dioxane was distilled off under reduced pressure. The resultant residue was dissolved with toluene added, activated carbon was added, and the mixture was stirred at 50° C. for 30 minutes. Thereafter, the resultant mixture was hot-filtrated on a filter pre-coated with Celite, and the filtrate was concentrated under reduced pressure. The resultant concentrated residue was dissolved in toluene, then, methanol was added to cause deposition of a solid, and the deposited solid was isolated by filtration and dried. Thereafter, hexane was added to the resultant solid which was then dissolved with heating, then, cooled down to room temperature to cause deposition of a solid, and the deposited solid was isolated by filtration and dried, to obtain 123.0 g of a compound 41 as a white powder.

LC-MS (APPI, positive): [M⁻] 868

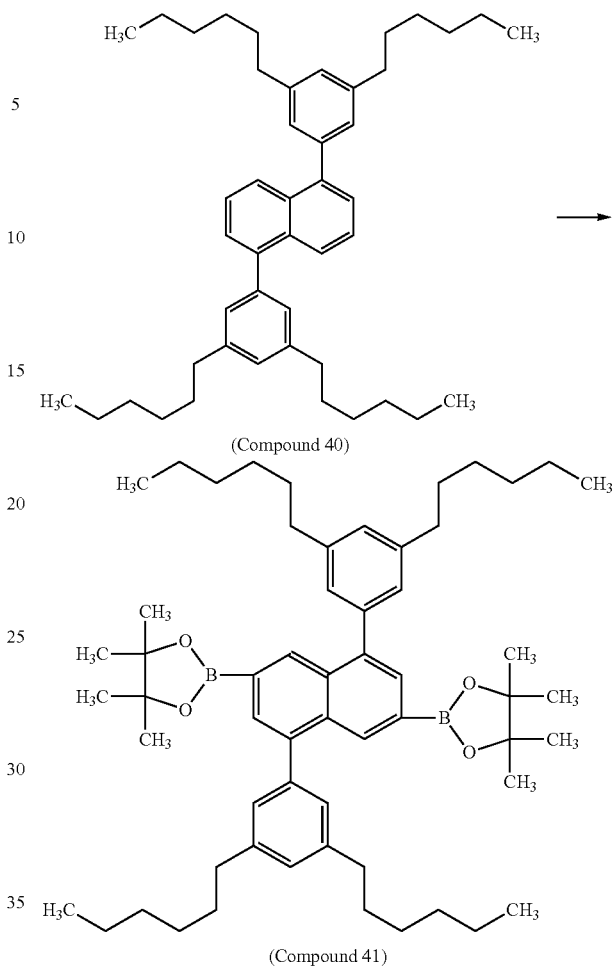

(Compound 40)

(Compound 41)

<Example 13> (Synthesis of Compound 42)

A nitrogen gas atmosphere was prepared in a reaction vessel, then, to a mixed solution of the compound 41 (63.5 g), dioxane (667 mL), N,N-dimethylformamide (667 mL) and water (333 mL) was added copper(II) bromide (48.7 g), and the mixture was stirred at 95° C. for 2 hours. Thereafter, copper(II) bromide (243.5 g) was added in divided portions at the same temperature, then, the mixture was stirred for 1 hour. Then, the reaction solution was cooled down to room temperature, then, hexane was added and the mixture was stirred. Thereafter, the organic layer was separated, and saturated sodium chloride water was added to the organic layer and the mixture was stirred. Thereafter, the organic layer was separated, dried over magnesium sulfate, then, the solvent was distilled off under reduced pressure. Thereafter, to a mixed solution of the resultant residue, dioxane (667 mL), N,N-dimethylformamide (667 mL) and water (333 mL) was added copper(II) bromide (48.7 g), and the mixture was stirred at 95° C. for 2 hours. Copper (II) bromide (559.9 g) was added in divided portions at the same temperature, then, the mixture was stirred for 1 hour. The resultant reaction solution was cooled down to room temperature, and hexane was added to this and the mixture was stirred. Thereafter, the organic layer was separated, saturated sodium chloride water was added to this and the mixture was stirred. Thereafter, the organic layer was separated, dried over magnesium sulfate, then, the solvent was distilled off under reduced pressure. The residue was purified by silica gel column chromatography (developing solvent: hexane), and concentrated, to obtain a solid (54.3 g). The resultant solid was re-crystallized from a mixed liquid of toluene and acetonitrile, to obtain 65.3 g of a compound 42 as a white solid.

MS (APPI, positive) [M$^+$] 772

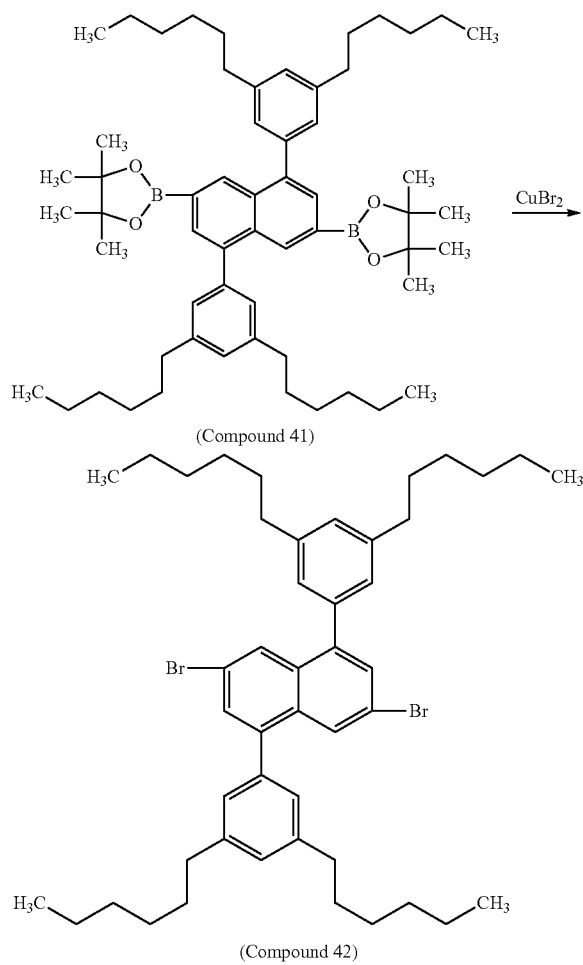

(Compound 41)

(Compound 42)

<Synthesis Example 13> (Synthesis of Compound 43)

A nitrogen gas atmosphere was prepared in a reaction vessel, then, 1,5-naphthylbis(trifluoromethane sulfonate) (compound 1, 63.6 g), 2-(4,4-bis(1,1-dimethylethyl) (1,1,3,1-terphenyl)-5-yl)-4,4,5,5-tetramethyl-1,3,2-dioxaborolane (161.4 g) and toluene (900 mL) were charged therein, then, bis(triphenylphosphine)palladium(II) dichloride (2.10 g) was added, then, tetraethylammonium hydroxide (20% by weight aqueous solution, 331.0 g) was dropped at 80° C., then, the mixture was stirred at 90° C. for 5 hours. After completion of the reaction, the resultant reaction solution was extracted with water and toluene poured. Thereafter, the resultant organic layer was dried over magnesium sulfate, and the solvent was distilled off under reduced pressure, to obtain a residue. Further, a crystal deposited in the aqueous layer after extraction with toluene described above was extracted with chloroform, the resultant organic layer was dried over magnesium sulfate, then, the solvent was distilled off under reduced pressure, to obtain a residue. These residues were combined, and re-crystallized from a mixed liquid of toluene and isopropanol, to obtain 121.9 g of a compound 43 as a white powdery solid.

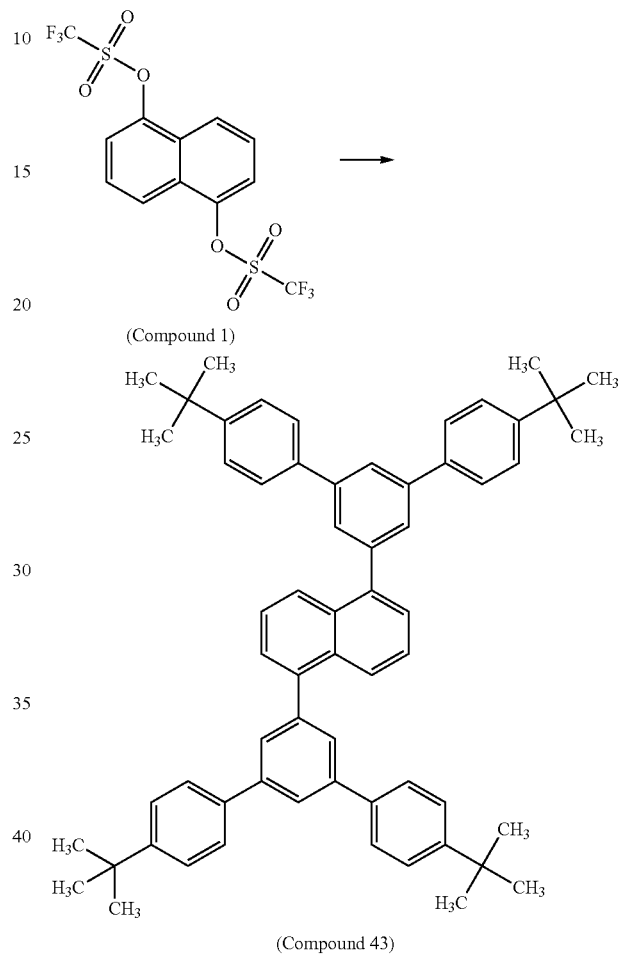

(Compound 1)

(Compound 43)

<Example 14> (Synthesis of Compound 44)

A nitrogen gas atmosphere was prepared in a reaction vessel, then, a mixture of the compound 43 (70.0 g), bis(pinacolato)diboron(4,4,4',4',5,5,5',5'-octamethyl-2,2'-bi-1,3,2-dioxaborolane) (1131.8 g), bis(1,5-cyclooctadiene)di-μ-methoxydiiridium(I) (1.72 g) (manufactured by Aldrich), 4,4'-di-tert-butyl-2,2'-dipyridyl (1.39 g) and dioxane (2365 mL) was stirred at 100° C. for 2 hours. The resultant reaction solution was cooled to cause deposition of a solid, and the deposited solid was isolated by filtration, washed with dioxane and hexane, then, dried, to obtain 101.3 g of a compound 44 as a white powder.

LC-MS (ESI-KCl, positive): [M+K$^+$] 1100

$^1$H-NMR (300 MHz, CDCl$_3$): δ (ppm)=1.34-1.39 (32H, d), 1.55-1.56 (36H, d), 7.49-7.52 (8H, d), 7.69-7.72 (8H, d), 7.78 (4H, s), 7.86-7.87 (2H, d), 7.95 (2H, s), 8.72 (2H, s).

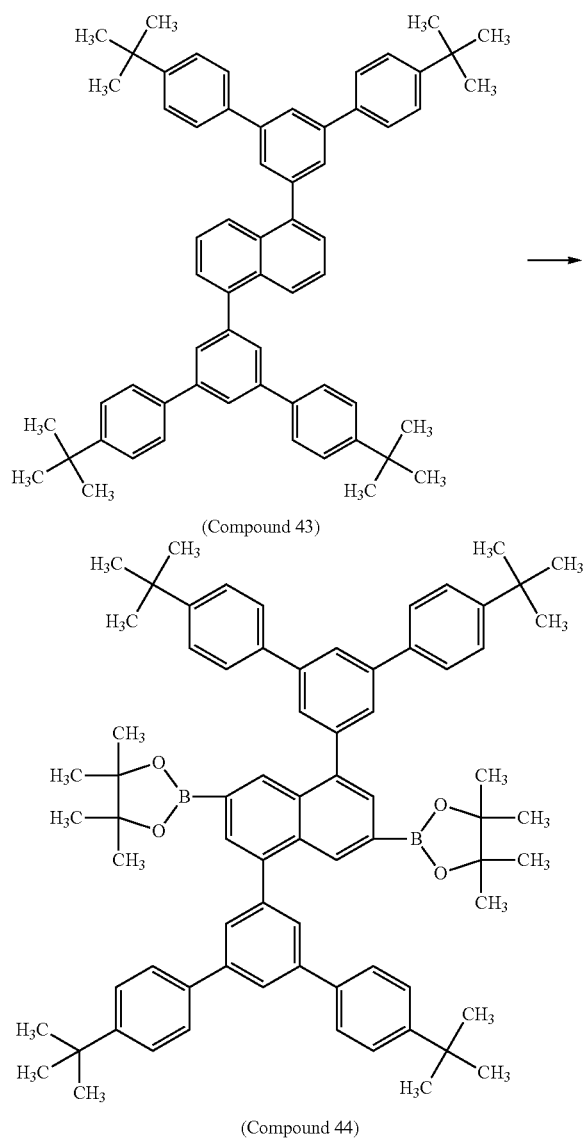

(Compound 43)

(Compound 44)

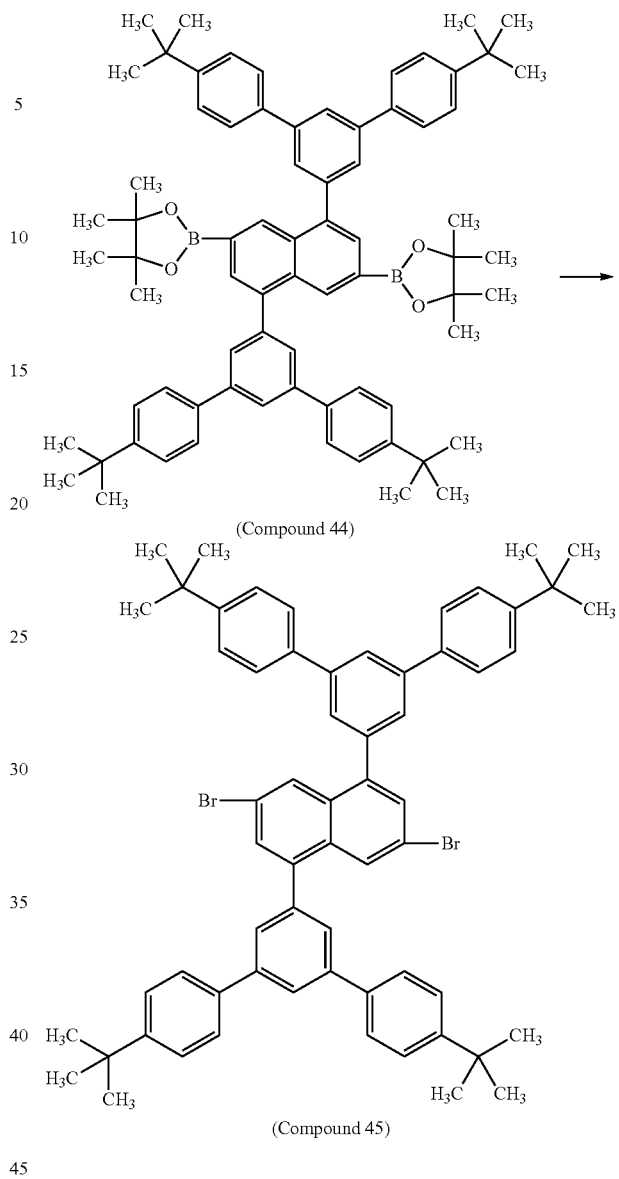

(Compound 44)

(Compound 45)

<Example 15> (Synthesis of Compound 45)

A nitrogen gas atmosphere was prepared in a reaction vessel, then, to a mixture of the compound 44 (1.11 g), dioxane (110 mL), N,N-dimethylformamide (55 mL) and water (11 mL) was added copper(II) bromide (4.49 g), thereafter, the mixture was stirred at 100° C. for 26 hours. Copper(II) bromide (6.74 g) was added in divided portions at the same temperature, then, the mixture was stirred for 14 hours. The resultant reaction solution was cooled down to room temperature, and to this was added 150 mL of water to cause deposition of a crystal. The deposited crystal was filtrated, and the resultant solid was washed with 20% by weight hydrochloric acid water and methanol. The solid was dried under reduced pressure, then, purified by silica gel column chromatography (developing solvent: hexane/toluene=90/10), to obtain 0.15 g of a compound 45 as a white solid.

MS (ESI-KCl, positive) [M$^+$] 1005

<Synthesis Example 14> (Synthesis of Compound 21)

A nitrogen gas atmosphere was prepared in a reaction vessel, then, into a mixture of 2,6-dibromo-1,5-dihydroxynaphthalene (73.7 g, 0.231 mol), ethanol (884 mL) and sodium ethoxide (40.70 g, 0.60 mol), a solution composed of n-hexyl bromide (98.71 g, 0.60 mol) and ethanol (147 mL) was dropped at room temperature over a period of 15 minutes, then, and the mixture was stirred for 8 hours with setting the temperature of an oil bath at 100° C. The resultant reaction solution was added to water (1500 mL) at room temperature, and the mixture was stirred, then, dichloromethane was added, and the mixture was stirred, and the resultant organic layer was concentrated by allowing to stand still, and dried to cause solidification thereof. Thereafter, the resultant solid was subjected to silica gel column chromatography using hexane as a developing solvent, then, to re-crystallization using a mixed liquid of toluene and methanol, to obtain 93.44 g of the intended compound 21 (yield: 42%).

¹H-NMR (300 MHz, CDCl₃): δ (ppm)=0.90-1.00 (6H, m), 1.35-1.45 (36H, m), 1.50-1.65 (4H, m), 4.02 (4H, t), 7.75 (2H, d), 7.95 (2H, d).

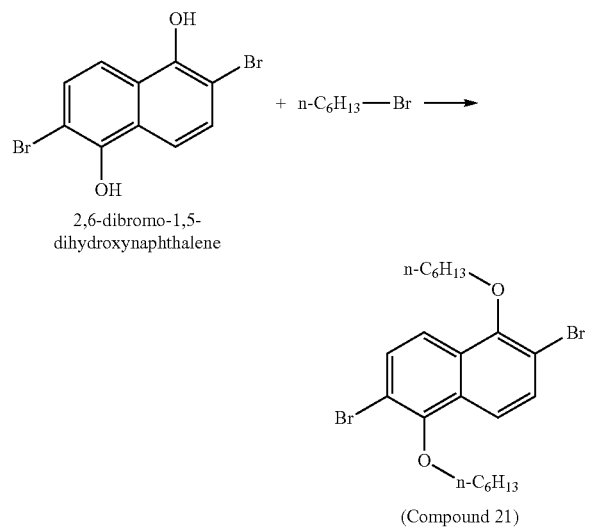

2,6-dibromo-1,5-dihydroxynaphthalene (Compound 21)

<Synthesis Example 15> (Synthesis of Compound 20)

A nitrogen gas atmosphere was prepared in a reaction vessel, then, the compound 21 (60.97 g, 0.13 mol), bis(pinacolato)diboron(4,4,4',4',5,5,5',5'-octamethyl-2,2'-bi-1,3,2-dioxaborolane) (319.64 g, 1.25 mol), [1,1'-bis(diphenylphosphino)ferrocene]palladium(II) dichloride.dichloromethane complex (PdCl₂(dppf)•CH₂Cl₂, 5.12 g, 6.3 mmol), 1,1'-bis(diphenylphosphino)ferrocene (3.48 g, 6.3 mmol), potassium acetate (184.57 g, 1.88 mol) and 1,4-dioxane (1829 mL) were mixed, and the mixture was stirred at 100° C. for 8 hours. Thereafter, 1,4-dioxane was distilled off by concentrating at room temperature. Thereafter, toluene, activated carbon and activated clay were added, then, the mixture was stirred at 70° C., then, filtrated to obtain the filtrate which was then concentrated, and dried to cause solidification thereof. Thereafter, re-crystallization was performed from a mixed liquid of acetonitrile and methanol, further, re-crystallization was performed from a mixed liquid of toluene and methanol, to obtain 30.47 g of the intended compound 20 (yield: 42%).

¹H-NMR (300 MHz, CDCl₃): δ (ppm)=0.85-1.00 (6H, m), 1.25-1.40 (8H, m), 1.50-1.65 (4H, m), 1.85-2.00 (4H, m), 4.05 (4H, t), 7.60 (2H, d), 7.75 (2H, d).

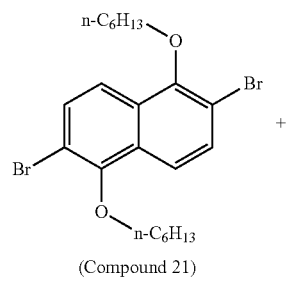

(Compound 21)

-continued

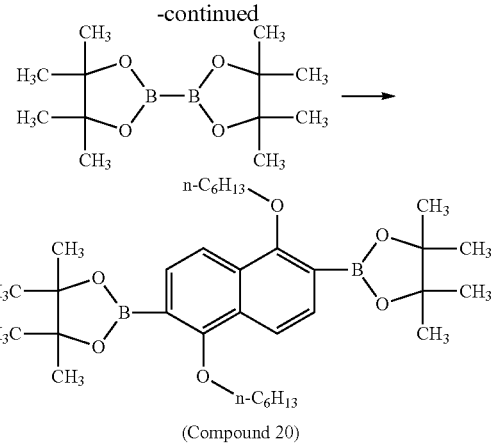

(Compound 20)

<Synthesis Example 16> (Synthesis of Polymer Compound 1)

An inert atmosphere was prepared in a reaction vessel, then, a compound 10 (2.6882 g, 2.96 mmol) represented by the following formula;

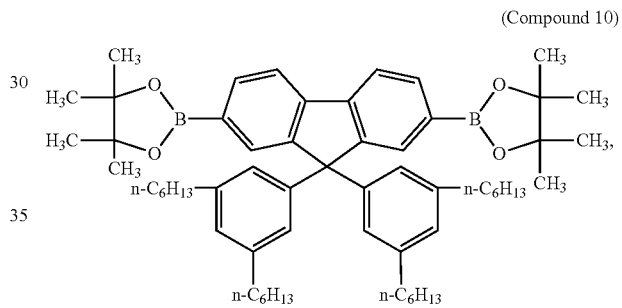

(Compound 10)

a compound 11 (0.4245 g, 0.75 mmol) represented by the following formula;

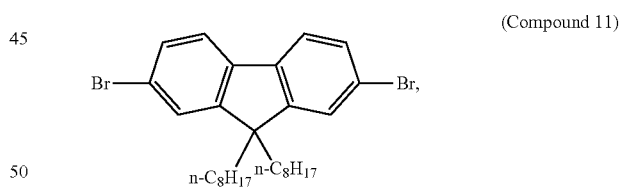

(Compound 11)

a compound 12 (1.6396 g, 1.80 mmol) represented by the following formula;

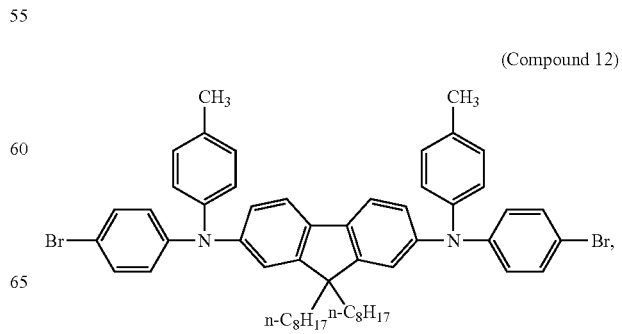

(Compound 12)

a compound 13 (0.2377 g, 0.45 mmol) represented by the following formula;

(Compound 13)

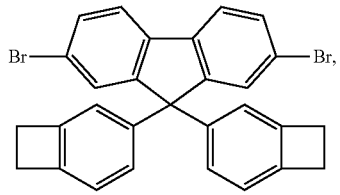

dichlorobis(triphenylphosphine)palladium (2.1 mg) and toluene (62 mL) were mixed, and the mixture was heated at 105° C.

Into the reaction solution, a 20% by weight tetraethylammonium hydroxide aqueous solution (10 mL) was dropped, and the mixture was refluxed for 4.5 hours. After the reaction, to this were added phenylboronic acid (36.8 mg) and dichlorobis(triphenylphosphine)palladium (2.1 mg), and the mixture was refluxed for 16.5 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, to find generation of a precipitate. The precipitate was isolated by filtration, to obtain the precipitated material.

This precipitated material was dissolved in toluene, and purified by passing through an alumina column and a silica gel column in series. The resultant solution was dropped into methanol, stirred, then, the resultant precipitated material was isolated by filtration, and dried, to obtain 3.12 g of a polymer compound 1. The polymer compound 1 had a polystyrene-equivalent number-average molecular weight of $7.8 \times 10^4$ and a polystyrene-equivalent weight-average molecular weight of $2.6 \times 10^5$.

The polymer compound 1 is a copolymer constituted of a constitutional unit represented by the following formula (J1), a constitutional unit represented by the following formula (J2), a constitutional unit represented by the following formula (J3) and a constitutional unit represented by the following formula (J4) at a molar ratio of 50:12.5:30:7.5, according to the theoretical value calculated from the amounts of the charged raw materials.

(J1)

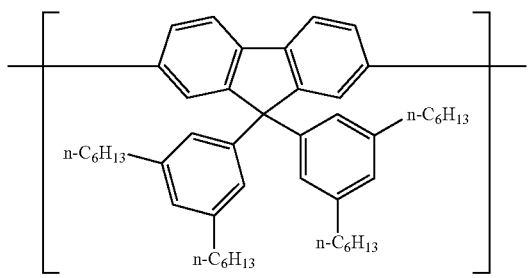

(J2)

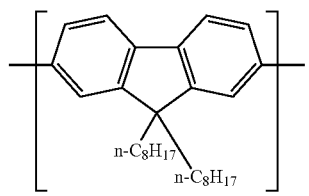

(J3)

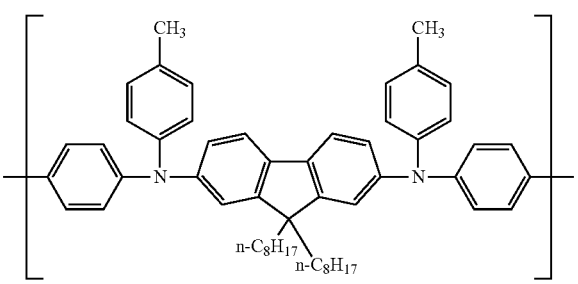

(J4)

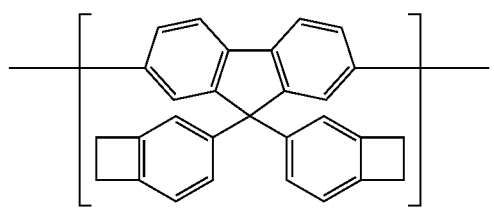

<Example 16> (Synthesis of Polymer Compound 2)

An inert gas atmosphere was prepared in a reaction vessel, then, the compound 3 (1.1946 g, 1.98 mmol), a compound 14 (1.0499 g, 1.76 mmol) represented by the following formula;

(Compound 14)

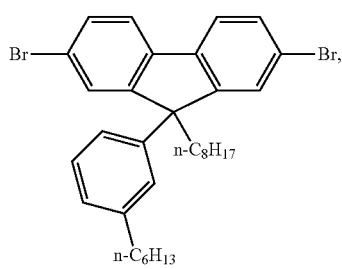

a compound 15 (0.1773 g, 0.24 mmol) represented by the following formula:

(Compound 15)

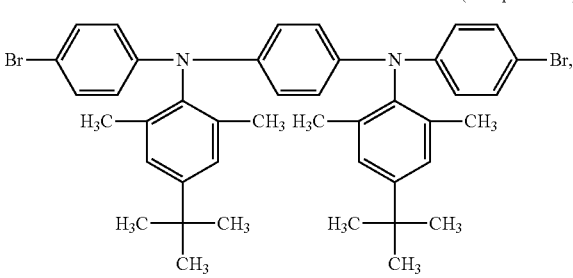

dichlorobis(triphenylphosphine)palladium (1.4 mg) and toluene (47 mL) were mixed, and the mixture was heated at 105° C. Into the reaction solution, a 20% by weight tetraethylammonium hydroxide aqueous solution (7.5 mL) was dropped, and the mixture was refluxed for 3.5 hours. After the reaction, to this were added phenylboronic acid (25 mg), a 20% by weight tetraethylammonium hydroxide aqueous solution (7.5 mL) and dichlorobis(triphenylphosphine)palladium (1.5 mg), further, the mixture was refluxed for 17 hours. Then, to this was added a sodium diethyldithiacarbamate aqueous solution, and the mixture was stirred at 80° C. for 2 hours. After cooling, the reaction solution was washed with water twice, with a by weight acetic acid aqueous solution twice and with water twice, the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.03 g of a polymer compound 2. The polymer compound 2 had a polystyrene-equivalent number-average molecular weight of $8.5 \times 10^4$ and a polystyrene-equivalent weight-average molecular weight of $2.4 \times 10^5$.

The polymer compound 2 is a copolymer constituted of a constitutional unit represented by the following formula:

a constitutional unit represented by the following formula:

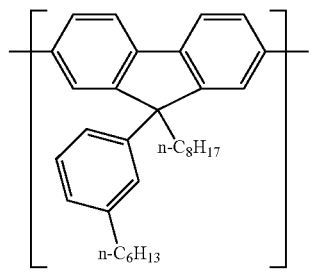

and a constitutional unit represented by the following formula:

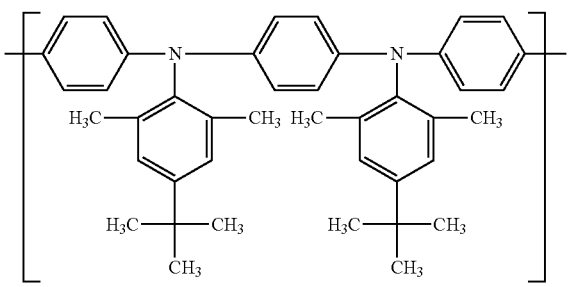

at a molar ratio of 50:44:6, and is a polymer compound constituted of a constitutional unit represented by the following formula:

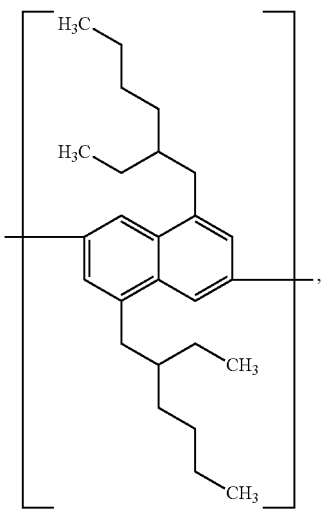

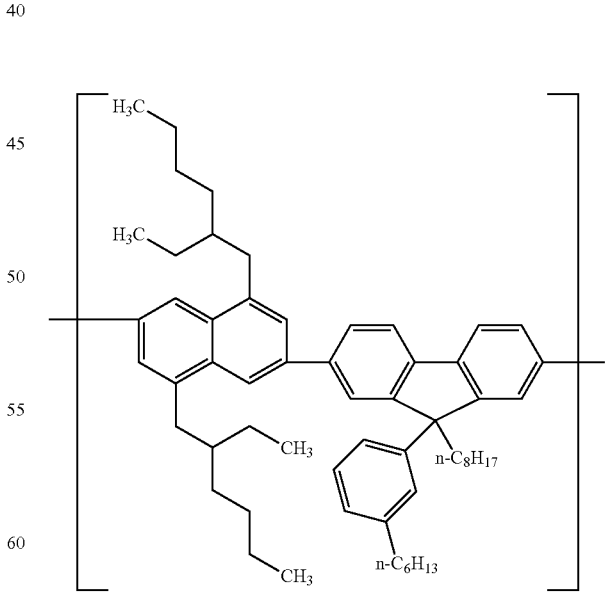

and a constitutional unit represented by the following formula:

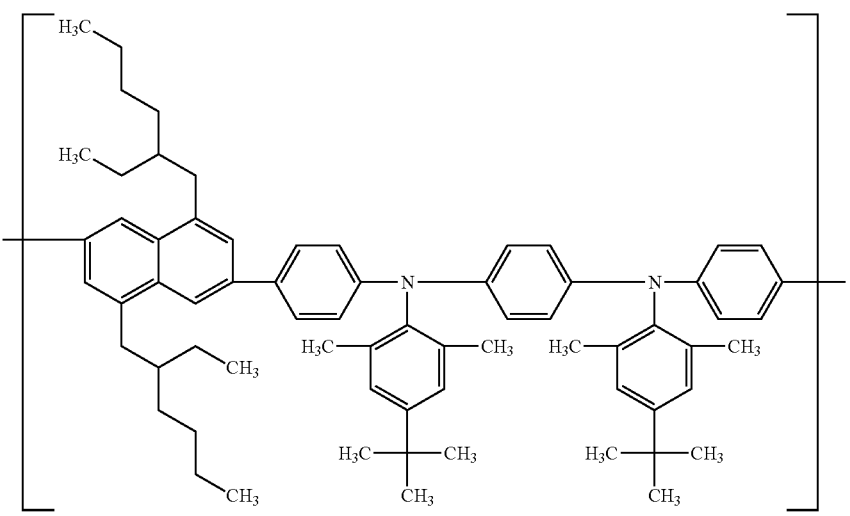

at a ratio of 88:12, according to the theoretical value calculated from the charged raw materials.

<Comparative Example 1> (Synthesis of Polymer Compound 7)

An inert gas atmosphere was prepared in a reaction vessel, then, the compound 20 (1.1399 g, 1.96 mmol), the compound 14 (1.0498 g, 1.76 mmol), the compound 15 (0.1772 g, 0.24 mmol), dichlorobis(triphenylphosphine)palladium (1.4 mg) and toluene (42 mL) were mixed, and the mixture was heated at 105° C. Into the reaction solution, a 20% by weight tetraethylammonium hydroxide aqueous solution (6.9 g) was dropped, and the mixture was refluxed for 24 hours. After the reaction, to this were added phenylboronic acid (24 mg), a 20% by weight tetraethylammonium hydroxide aqueous solution (6.9 g) and dichlorobis(triphenylphosphine)palladium (1.4 mg), further, the mixture was refluxed for 22 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.13 g of a polymer compound 7. The polymer compound 7 had a polystyrene-equivalent number-average molecular weight of $6.0 \times 10^3$ and a polystyrene-equivalent weight-average molecular weight of $8.4 \times 10^4$.

The polymer compound 7 is a copolymer constituted of a constitutional unit represented by the following formula:

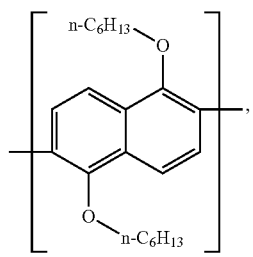

a constitutional unit represented by the following formula:

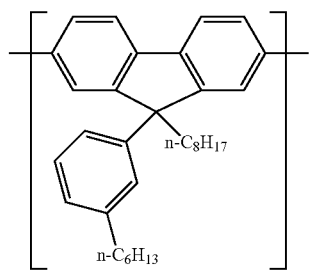

and a constitutional unit represented by the following formula:

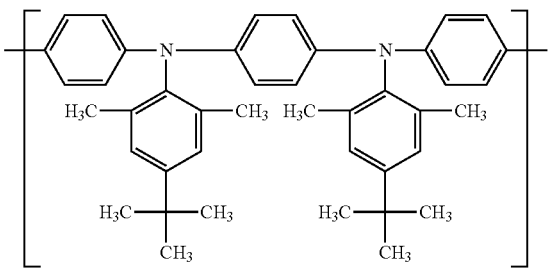

at a molar ratio of 50:44:6, and is a polymer compound constituted of a constitutional unit represented by the following formula:

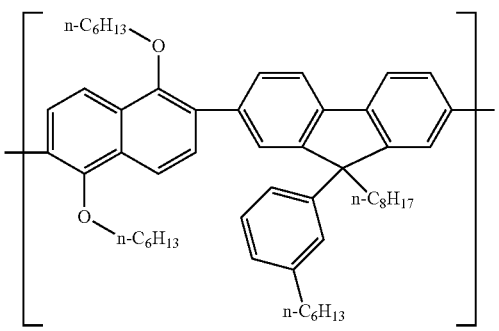

and a constitutional unit represented by the following formula:

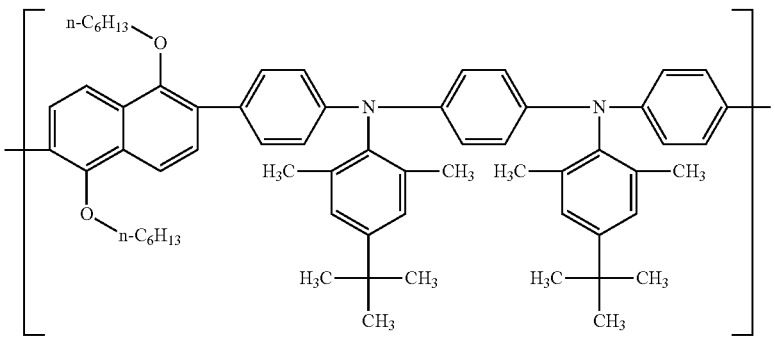

at a ratio of 88:12, according to the theoretical value calculated from the charged raw materials.

<Example D1> (Fabrication of Light Emitting Device D1)

On a glass substrate having an ITO film with a thickness of 45 nm formed thereon by a sputtering method, AQ-1200 (trade name) as a polythiophene.sulfonic acid type hole injection agent available from Plextronics was spin-coated so as to form a film with a thickness of 35 nm, and the film was dried on a hot plate at 170° C. for 15 minutes, to fabricate a substrate for light emitting device.

Next, on this substrate for light emitting device, a solution of the polymer compound 1 dissolved at a concentration of 0.7% by weight in a xylene solvent was spin-coated so as to form a film with a thickness of about 20 nm. Thereafter, the resultant film was heated on a hot plate at 180° C. for 60 minutes under a nitrogen atmosphere.

Next, a solution of the polymer compound 2 dissolved at a concentration of 1.0% by weight in chlorobenzene was prepared, and spin-coated on a substrate for light emitting device at a rotation rate of 2000 rpm to form a film. The thickness was about 60 nm. This was dried at 130° C. for 10 minutes under a nitrogen atmosphere, then, sodium fluoride was vapor-deposited with a thickness of about 3 nm, then, aluminum was vapor-deposited with a thickness of about 80 nm, as a cathode, thereby fabricating a light emitting device (hereinafter, referred to as "light emitting device D1"). After the degree of vacuum reached $1 \times 10^{-4}$ Pa or less, vapor-deposition of a metal was initiated.

Voltage was applied to the light emitting device D1, to observe EL light emission showing a peak at 460 nm derived mainly from the polymer compound 2. The device started light emission from 2.7 V, and the maximum light emission efficiency thereof was 8.2 cd/A. The results are shown in Table 1.

The light emitting device D1 was driven at constant current after setting the current value so as to give an initial luminance of 5000 cd/m$^2$, and the time change of luminance was measured. As a result, it became 60% based on the initial luminance after 36 hours. The results are shown in Table 1.

<Comparative Example CD1> (Fabrication of Light Emitting Device CD1)

A light emitting device was fabricated in the same manner as in Example D1 excepting that a solution of the polymer compound 7 dissolved at a concentration of 1.2% by weight in chlorobenzene, instead of the polymer compound 2 in Example D1, was prepared, and spin-coated on a substrate for light emitting device at a rotation rate of 1800 rpm so as to form a film with a thickness of about 60 nm (hereinafter, referred to as "light emitting device CD1").

Voltage was applied to the light emitting device CD1, to observe EL light emission showing a peak at 450 nm derived mainly from the polymer compound 7. The device started light emission from 3.1V, and the maximum light emission efficiency thereof was 5.2 cd/A. The results are shown in Table 1.

The light emitting device CD1 was driven at constant current after setting the current value so as to give an initial luminance of 5000 cd/m$^2$, and the time change of luminance was measured. As a result, it became 60% based on the initial luminance after 0.2 hours. The results are shown in Table 1.

TABLE 1

| | Polymer compound | Luminance life (time until becoming 60% of initial luminance) | Maximum light emission efficiency |
|---|---|---|---|
| Example D1 | polymer compound 2 | 36 hours | 8.2 cd/A |
| Comparative Example CD1 | polymer compound 7 | 0.2 hours | 5.2 cd/A |

<Example 17> (Synthesis of Polymer Compound 3)

An inert gas atmosphere was prepared in a reaction vessel, then, the compound 3 (1.1969 g, 1.98 mmol), the compound 14 (1.0737 g, 1.80 mmol), a compound 16 (0.2197 g, 0.20 mmol) represented by the following formula:

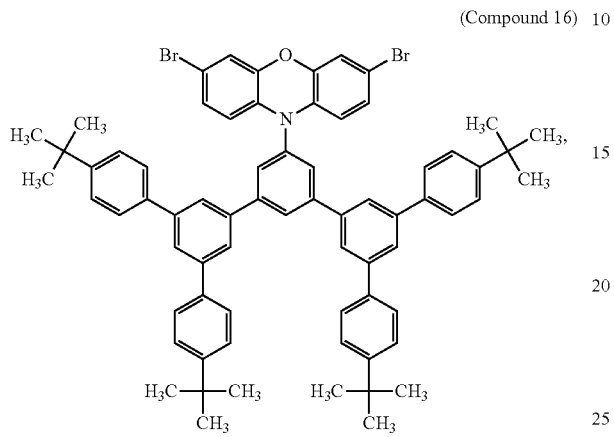

(Compound 16)

dichlorobis(triphenylphosphine)palladium (1.4 mg) and toluene (47 mL) were mixed, and the mixture was heated at 105° C. Into the reaction solution, a 20% by weight tetraethylammonium hydroxide aqueous solution (6.6 mL) was dropped, and the mixture was refluxed for 3.5 hours. After the reaction, to this were added phenylboronic acid (24 mg), a 20% by weight tetraethylammonium hydroxide aqueous solution (6.6 mL) and dichlorobis(triphenylphosphine)palladium (1.4 mg), and the mixture was refluxed for 16.5 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.12 g of a polymer compound 3. The polymer compound 3 had a polystyrene-equivalent number-average molecular weight of $7.5 \times 10^4$ and a polystyrene-equivalent weight-average molecular weight of $2.7 \times 10^5$.

The polymer compound 3 is a copolymer constituted of a constitutional unit represented by the following formula:

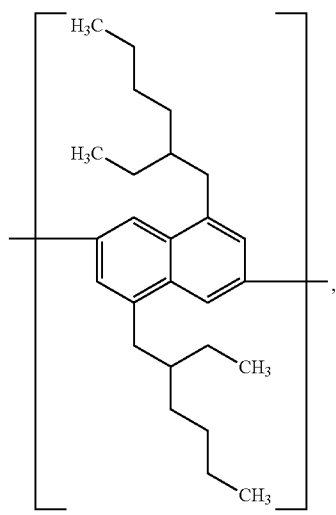

a constitutional unit represented by the following formula:

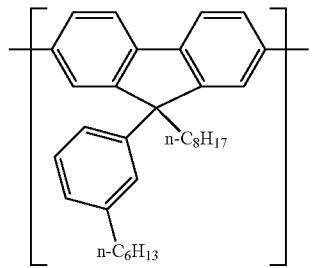

and a constitutional unit represented by the following formula:

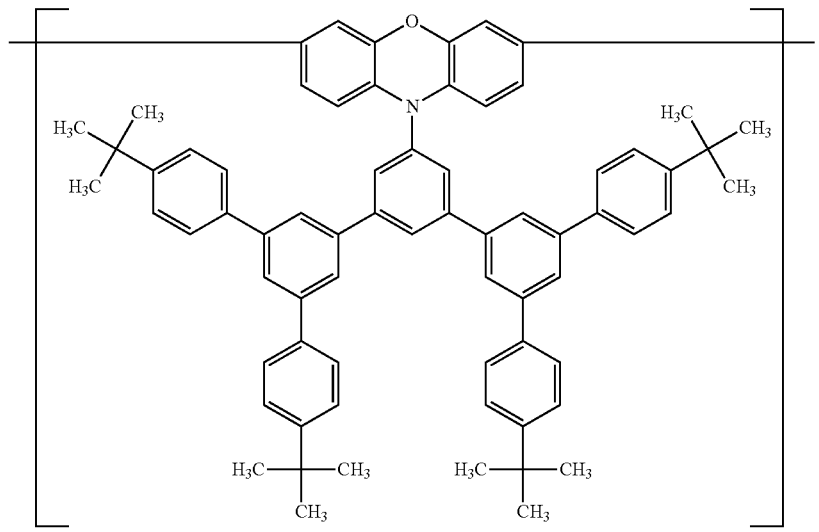

at a molar ratio of 50:45:5, and is a polymer compound constituted of a constitutional unit represented by the following formula:

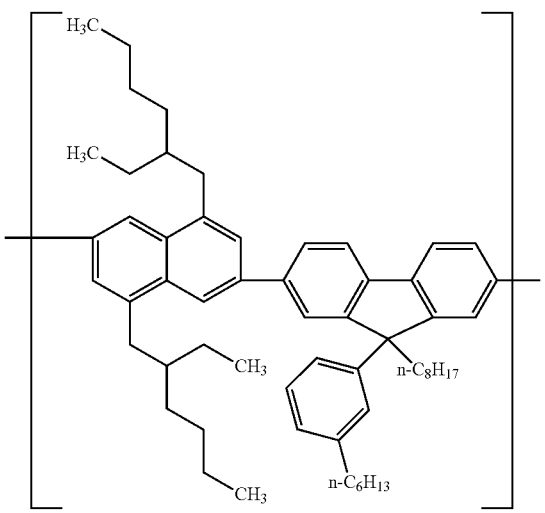

and a constitutional unit represented by the following formula:

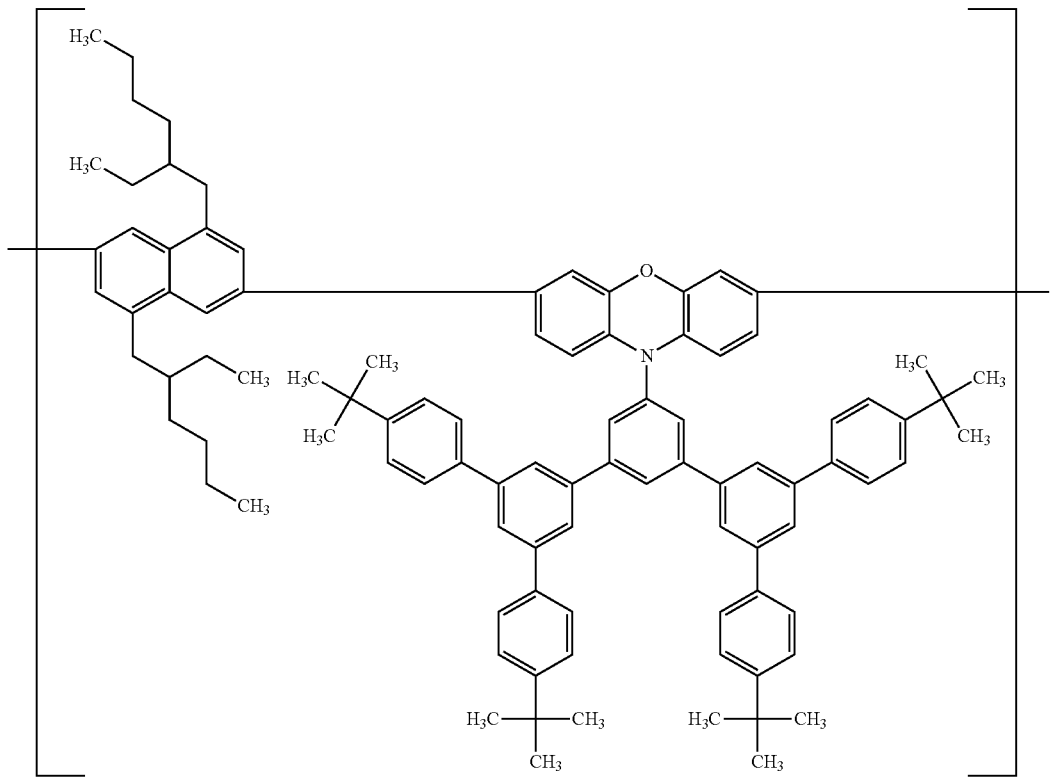

at a ratio of 90:10, according to the theoretical value calculated from the charged raw materials.

<Example 18> (Synthesis of Polymer Compound 8)

An inert gas atmosphere was prepared in a reaction vessel, then, the compound 41 (1.7117 g, 1.97 mmol), the compound 14 (1.0736 g, 1.80 mmol), the compound 16 (0.2196 g, 0.20 mmol), dichlorobis(triphenylphosphine)palladium (1.4 mg) and toluene (59 mL) were mixed, and the mixture was heated at 105° C. Into the reaction solution, a 20% by weight tetraethylammonium hydroxide aqueous solution (6.9 g) was dropped, and the mixture was refluxed for 3 hours. After the reaction, to this were added phenylboronic acid (24 mg), a 20% by weight tetraethylammonium hydroxide aqueous solution (6.9 g) and dichlorobis(triphenylphosphine)palladium (1.4 mg), and the mixture was refluxed for 20 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.69 g of a polymer compound 8. The polymer compound 8 had a polystyrene-equivalent number-average molecular weight of $7.6 \times 10^4$ and a polystyrene-equivalent weight-average molecular weight of $2.2 \times 10^5$.

The polymer compound 8 is a copolymer constituted of a constitutional unit represented by the following formula:

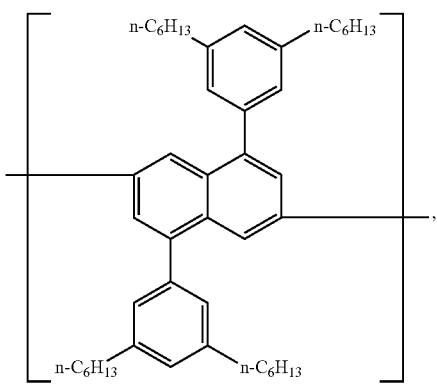
a constitutional unit represented by the following formula:
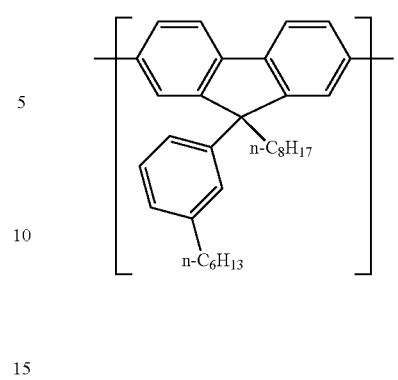
and a constitutional unit represented by the following formula:
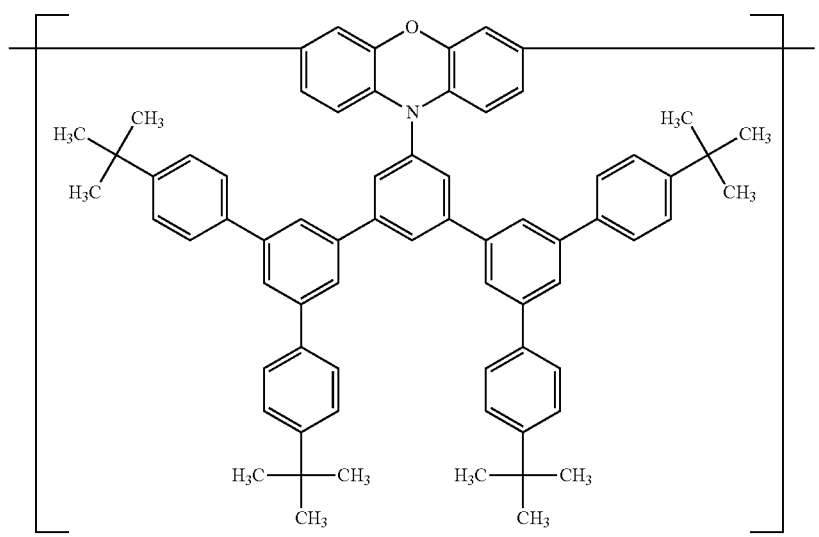

at a molar ratio of 50:45:5, and is a polymer compound constituted of a constitutional unit represented by the following formula:

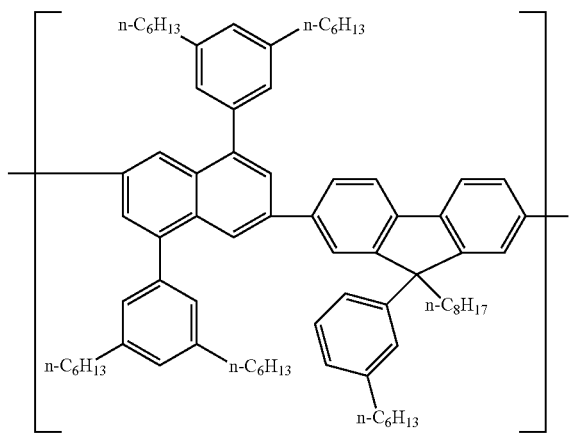

and a constitutional unit represented by the following formula:

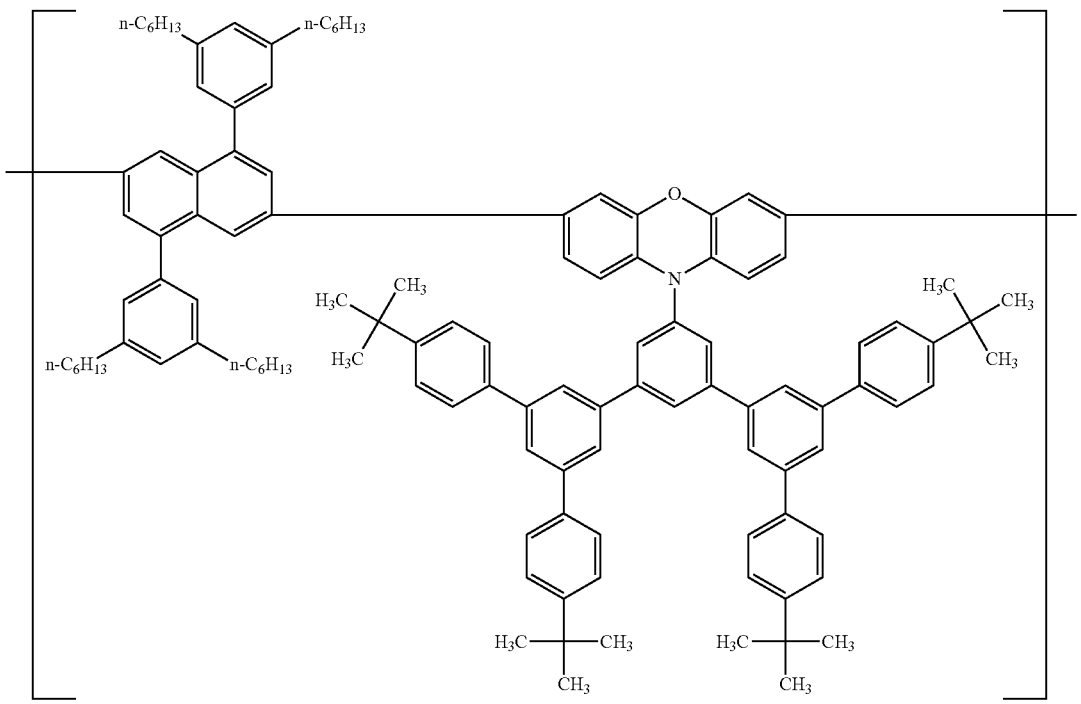

at a ratio of 90:10, according to the theoretical value calculated from the charged raw materials.

<Comparative Example 2> (Synthesis of Polymer Compound 9)

An inert gas atmosphere was prepared in a reaction vessel, then, the compound 20 (1.1400 g, 1.96 mmol), the compound 14 (1.0736 g, 1.80 mmol), the compound 16 (0.2196 g, 0.20 mmol), dichlorobis(triphenylphosphine)palladium (2.8 mg) and toluene (44 mL) were mixed, and the mixture was heated at 105° C. Into the reaction solution, a 20% by weight tetraethylammonium hydroxide aqueous solution (6.9 g) was dropped, and the mixture was refluxed for 7 hours. After the reaction, to this were added phenylboronic acid (24 mg), a 20% by weight tetraethylammonium hydroxide aqueous solution (6.9 g) and dichlorobis(triphenylphosphine)palladium (1.4 mg), and the mixture was refluxed for 16 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 0.95 g of a polymer compound 9. The polymer compound 9 had a polystyrene-equivalent number-average molecular weight of $9.0 \times 10^3$ and a polystyrene-equivalent weight-average molecular weight of $4.4 \times 10^4$.

The polymer compound 9 is a copolymer constituted of a constitutional unit represented by the following formula:

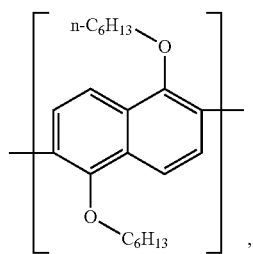

a constitutional unit represented by the following formula:
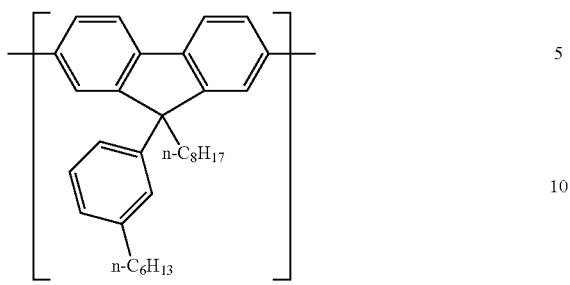
and a constitutional unit represented by the following formula:
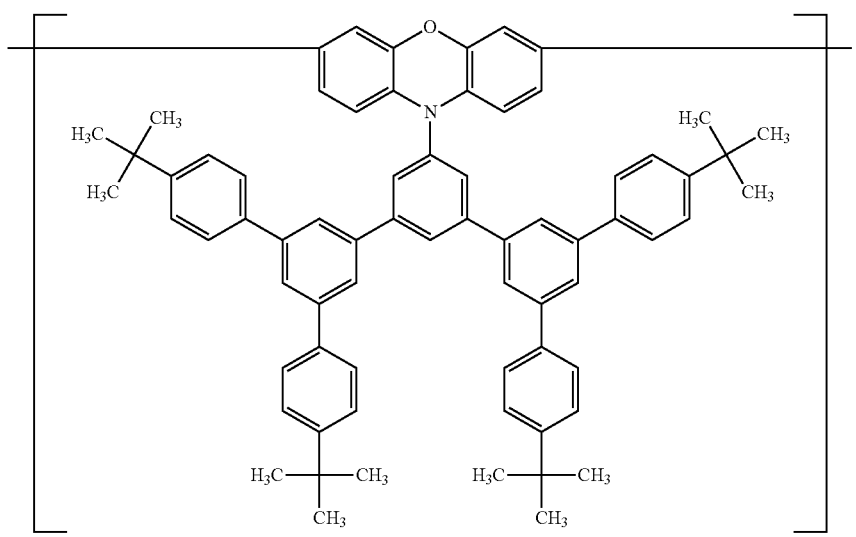
at a molar ratio of 50:45:5, and is a polymer compound constituted of a constitutional unit represented by the following formula:
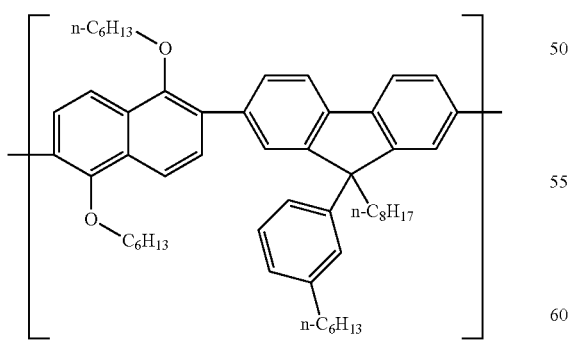
and a constitutional unit represented by the following formula:

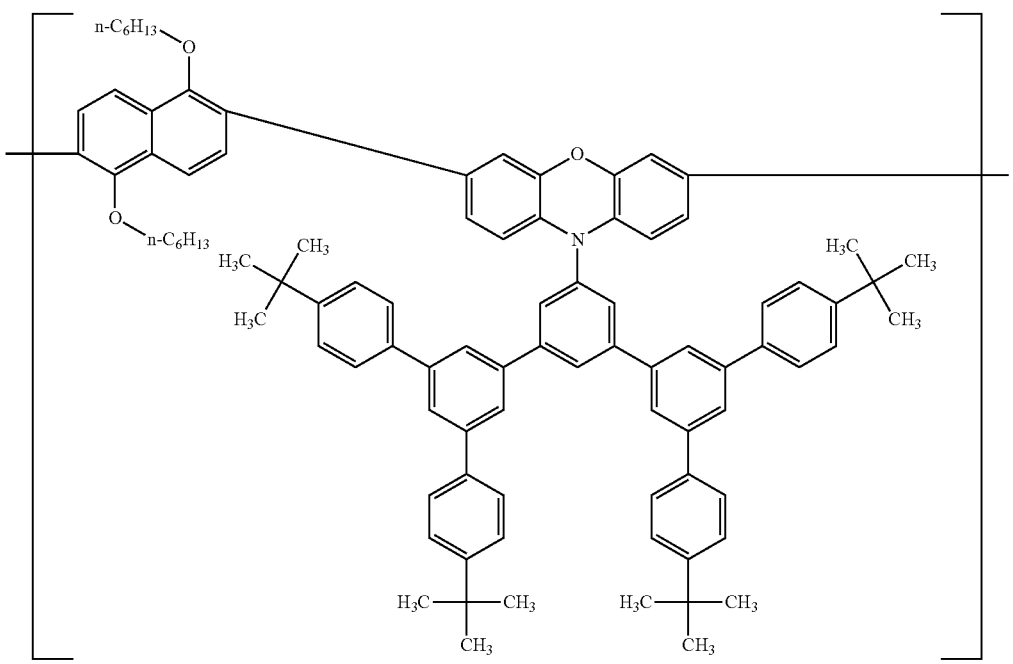

at a ratio of 90:10, according to the theoretical value calculated from the charged raw materials.

<Example D2> (Fabrication of Light Emitting Device D2)

A light emitting device was fabricated in the same manner as in Example D1 excepting that a solution of the polymer compound 3 dissolved at a concentration of 1.0% by weight in chlorobenzene, instead of the polymer compound 2 in Example D1, was prepared, and spin-coated on a substrate for light emitting device at a rotation rate of 3000 rpm so as to form a film with a thickness of about 60 nm (hereinafter, referred to as "light emitting device D2").

Voltage was applied to the light emitting device D2, to observe EL light emission showing a peak at 465 nm derived mainly from the polymer compound 3. The device started light emission from 2.6 V, and the maximum light emission efficiency thereof was 9.2 cd/A. The results are shown in Table 2.

The light emitting device D2 was driven at constant current after setting the current value so as to give an initial luminance of 5000 cd/m$^2$, and the time change of luminance was measured. As a result, it became 60% based on the initial luminance after 69 hours. The results are shown in Table 2.

<Example D3> (Fabrication of Light Emitting Device D3)

A light emitting device was fabricated in the same manner as in Example D1 excepting that a solution of the polymer compound 8 dissolved at a concentration of 0.9% by weight in chlorobenzene, instead of the polymer compound 2 in Example D1, was prepared, and spin-coated on a substrate for light emitting device at a rotation rate of 1100 rpm so as to form a film with a thickness of about 60 nm (hereinafter, referred to as "light emitting device D3").

Voltage was applied to the light emitting device D3, to observe EL light emission showing a peak at 465 nm derived mainly from the polymer compound 8. The device started light emission from 2.6 V, and the maximum light emission efficiency thereof was 10.1 cd/A. The results are shown in Table 2.

The light emitting device D3 was driven at constant current after setting the current value so as to give an initial luminance of 5000 cd/m$^2$, and the time change of luminance was measured. As a result, it became 60% based on the initial luminance after 18 hours. The results are shown in Table 2.

<Comparative Example CD2> (Fabrication of Light Emitting Device CD2)

A light emitting device was fabricated in the same manner as in Example D1 excepting that a solution of the polymer compound 9 dissolved at a concentration of 1.5% by weight in chlorobenzene, instead of the polymer compound 2 in Example D1, was prepared, and spin-coated on a substrate for light emitting device at a rotation rate of 3500 rpm so as to form a film with a thickness of about 60 nm (hereinafter, referred to as "light emitting device CD2").

Voltage was applied to the light emitting device CD2, to observe EL light emission showing a peak at 450 nm derived mainly from the polymer compound 9. The device 8 started light emission from 3.3 V, and the maximum light emission efficiency thereof was 3.9 cd/A. The results are shown in Table 2.

The light emitting device CD2 was driven at constant current after setting the current value so as to give an initial luminance of 5000 cd/m$^2$, and the time change of luminance was measured. As a result, it became 60% based on the initial luminance after 0.2 hours. The results are shown in Table 2.

TABLE 2

|  | Polymer compound | Luminance life (time until becoming 60% of initial luminance) | Maximum light emission efficiency |
|---|---|---|---|
| Example D2 | polymer compound 3 | 69 hours | 9.2 cd/A |
| Example D3 | polymer compound 8 | 18 hours | 10.1 cd/A |
| Comparative Example CD2 | polymer compound 9 | 0.2 hours | 3.9 cd/A |

<Example 19> (Synthesis of Polymer Compound 4)

An inert gas atmosphere was prepared in a reaction vessel, then, a compound 17 (1.3425 g, 1.98 mmol) represented by the following formula;

(Compound 17)

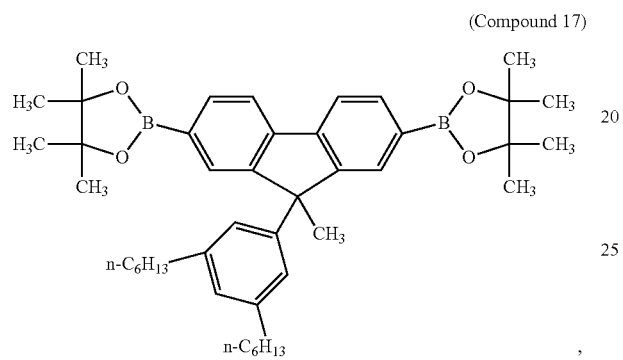

the compound 4 (0.8983 g, 1.76 mmol), the compound 15 (0.1772 g, 0.24 mmol), dichlorobis(triphenylphosphine)palladium (1.4 mg) and toluene (50 mL) were mixed, and the mixture was heated at 105° C. Into the reaction solution, a 20% by weight tetraethylammonium hydroxide aqueous solution (7.5 mL) was dropped, and the mixture was refluxed for 3.5 hours. After the reaction, to this were added phenylboronic acid (27 mg), a 20% by weight tetraethylammonium hydroxide aqueous solution (7.5 mL) and dichlorobis(triphenylphosphine)palladium (1.4 mg), and the mixture was refluxed for 17 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.15 g of a polymer compound 4. The polymer compound 4 had a polystyrene-equivalent number-average molecular weight of $5.6 \times 10^4$ and a polystyrene-equivalent weight-average molecular weight of $2.0 \times 10^5$.

The polymer compound 4 is a copolymer constituted of a constitutional unit represented by the following formula:

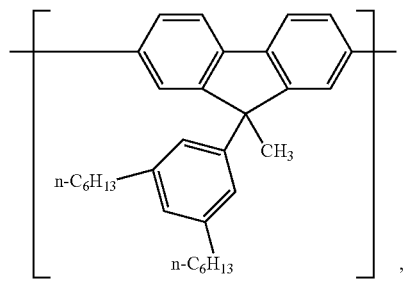

a constitutional unit represented by the following formula:

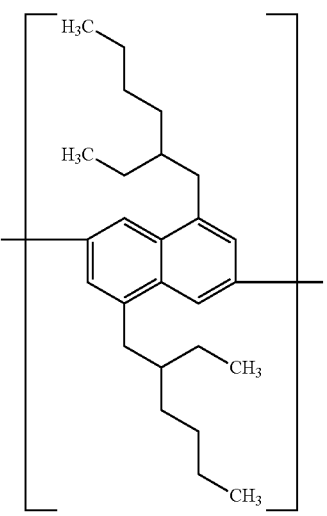

and a constitutional unit represented by the following formula:

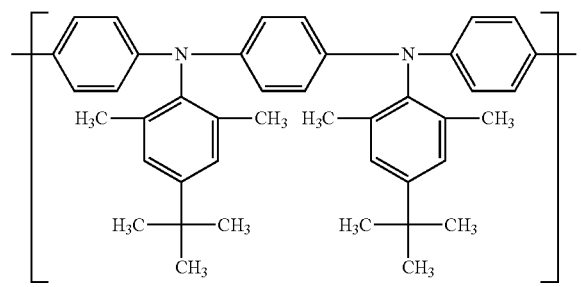

at a molar ratio of 50:44:6, and is a polymer compound constituted of a constitutional unit represented by the following formula:

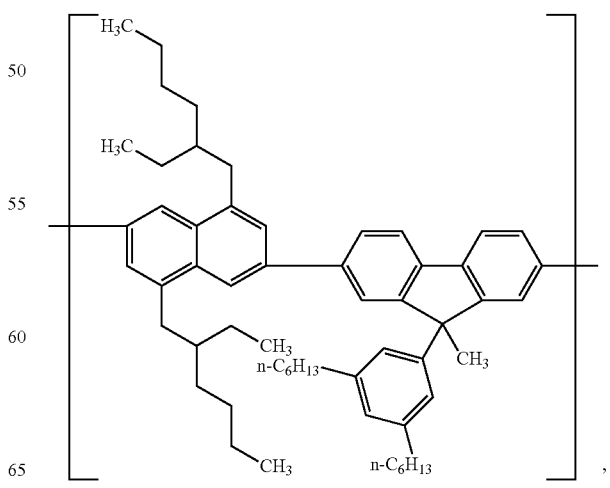

a constitutional unit represented by the following formula:

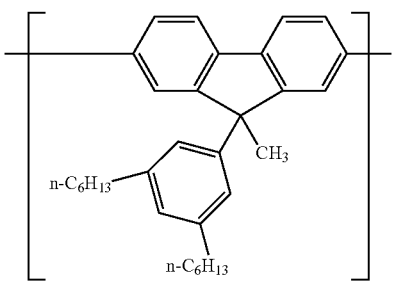

and a constitutional unit represented by the following formula;

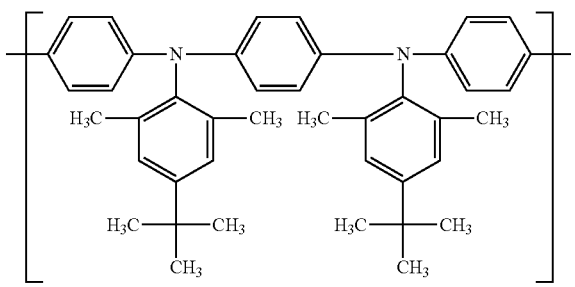

at a ratio of 78.6:10.7:10.7, according to the theoretical value calculated from the charged raw materials.

<Comparative Example 3> (Synthesis of Polymer Compound 10)

An inert gas atmosphere was prepared in a reaction vessel, then, the compound 17 (1.3328 g, 1.97 mmol), the compound 21 (0.8559 g, 1.76 mmol), the compound 15 (0.1773 g, 0.24 mmol), dichlorobis(triphenylphosphine)palladium (1.4 mg) and toluene (42 mL) were mixed in the vessel, and heated at 105° C. Into the reaction solution, a 20% by weight tetraethylammonium hydroxide aqueous solution (6.9 g) was dropped, and the mixture was refluxed for 3.5 hours. Since polymerization had not progressed and a polymer compound had not been obtained at this point, dichlorobis (triphenylphosphine)palladium (1.4 mg) was additionally added, and further, the mixture was refluxed for 3.5 hours, however, polymerization did not progress and a polymer compound was not obtained.

<Example D4> (Fabrication of Light Emitting Device D4)

A light emitting device was fabricated in the same manner as in Example D1 excepting that a solution of the polymer compound 4 dissolved at a concentration of 1.2% by weight in a xylene solvent, instead of the polymer compound 2 in Example D1, was prepared, and spin-coated on a substrate for light emitting device at a rotation rate of 1500 rpm so as to form a film with a thickness of about 60 nm (hereinafter, referred to as "light emitting device D4").

Voltage was applied to the light emitting device D4, to observe EL light emission showing a peak at 455 nm derived mainly from the polymer compound 4. The device started light emission from 2.7 V, and the maximum light emission efficiency thereof was 6.5 cd/A. The results are shown in Table 3.

The light emitting device D4 was driven at constant current after setting the current value so as to give an initial luminance of 5000 cd/m$^2$, and the time change of luminance was measured. As a result, it became 60% based on the initial luminance after 12 hours. The results are shown in Table 3.

TABLE 3

| | Polymer compound | Luminance life (time until becoming 60% of initial luminance) | Maximum light emission efficiency |
|---|---|---|---|
| Example D4 | polymer compound 4 | 12 hours | 6.5 cd/A |

<Synthesis Example 17> (Synthesis of Polymer Compound 5)

An inert gas atmosphere was prepared in a reaction vessel, then, a compound 18 (2.2749 g, 2.97 mmol) represented by the following formula:

(Compound 18)

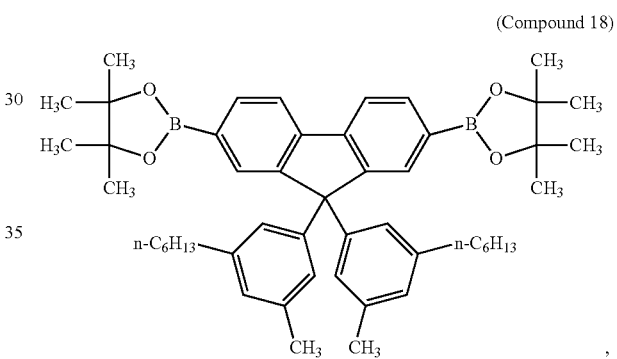

a compound 19 (1.2375 g, 1.92 mmol) represented by the following formula:

(Compound 19)

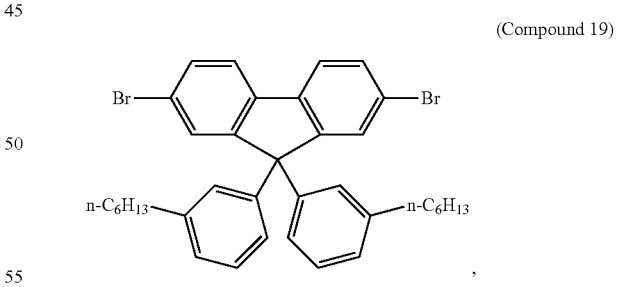

the compound 11 (0.3290 g, 0.60 mmol), the compound 15 (0.1330 g, 0.18 mmol), the compound 16 (0.3295 g, 0.30 mmol), dichlorobis(triphenylphosphine)palladium (2.1 mg) and toluene (76 mL) were mixed in the vessel, and heated at 105° C. Into the reaction solution, a 20% by weight tetraethylammonium hydroxide aqueous solution (10 mL) was dropped, and the mixture was refluxed for 1.5 hours. After the reaction, to this were added phenylboronic acid (37 mg), a 20% by weight tetraethylammonium hydroxide aqueous solution (10 mL) and dichlorobis(triphenylphosphine)palladium (2.1 mg), and the mixture was refluxed for 17 hours.

Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol to find generation of a precipitated material which was then isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 2.42 g of a polymer compound 5. The polymer compound 5 had a polystyrene-equivalent number-average molecular weight of $1.1 \times 10^5$ and a polystyrene-equivalent weight-average molecular weight of $2.9 \times 10^5$.

The polymer compound 5 is a copolymer constituted of a constitutional unit represented by the following formula:

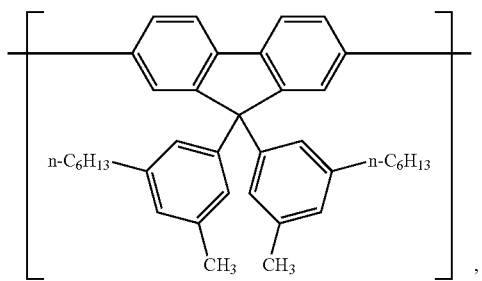

a constitutional unit represented by the following formula:

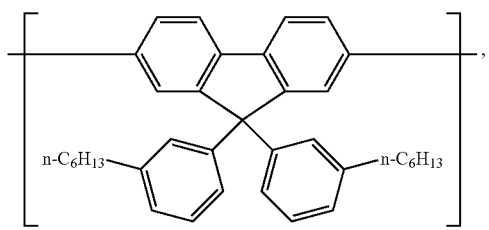

a constitutional unit represented by the following formula:

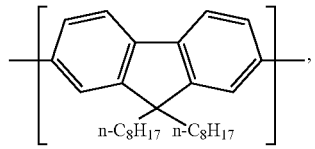

a constitutional unit represented by the following formula:

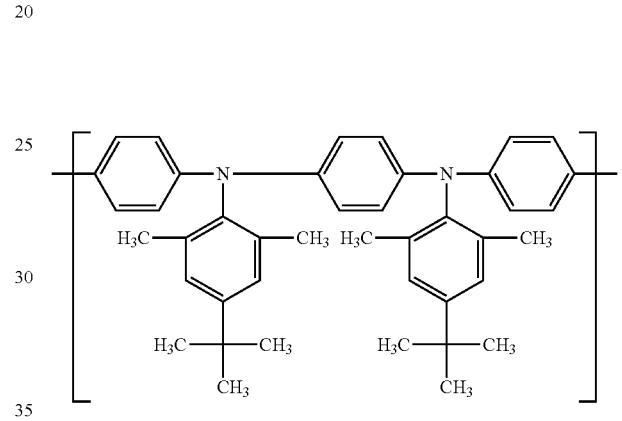

and a constitutional unit represented by the following formula:

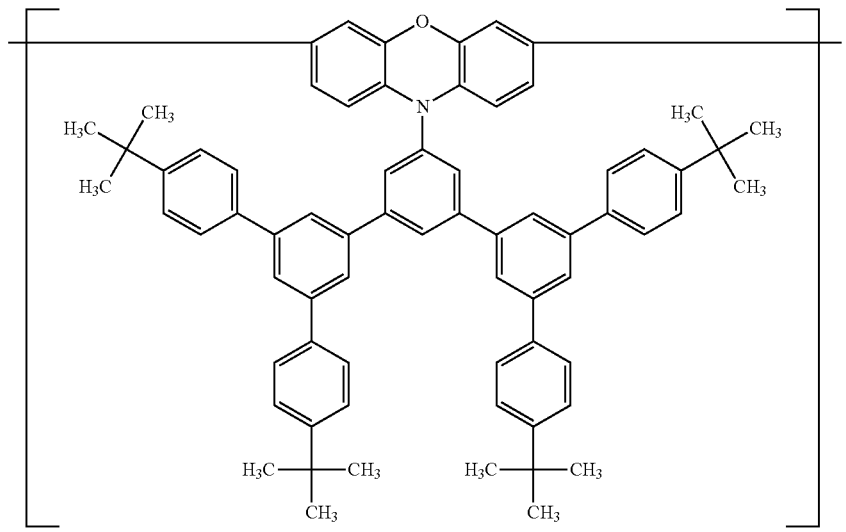

at a molar ratio of 50:32:10:3:5, according to the theoretical value calculated from the charged raw materials.

<Example 20> (Synthesis of Polymer Compound 6)

An inert gas atmosphere was prepared in a reaction vessel, then, the compound 3 (2.9470 g, 4.87 mmol), the compound 4 (2.5520 g, 5.00 mmol), dichlorobis(tris-o-methoxyphenylphosphine) (4.5 mg) and toluene (91 mL) were mixed in the vessel, and heated at 105° C. Into the reaction solution, a 20% by weight tetraethylammonium hydroxide aqueous solution (18 mL) was dropped, and the mixture was refluxed for 1 hour and 40 minutes. After the reaction, to this were added phenylboronic acid (62 mg), a 20% by weight tetraethylammonium hydroxide aqueous solution (18 mL) and dichlorobis(triphenylphosphine)palladium (4.4 mg), and the mixture was refluxed for 17 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol to find generation of a precipitated material which was then isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 3.14 g of a polymer compound 6. The polymer compound 6 had a polystyrene-equivalent number-average molecular weight of $9.0 \times 10^4$ and a polystyrene-equivalent weight-average molecular weight of $3.5 \times 10^5$.

The polymer compound 6 is a polymer compound consisting only of a constitutional unit represented by the following formula:

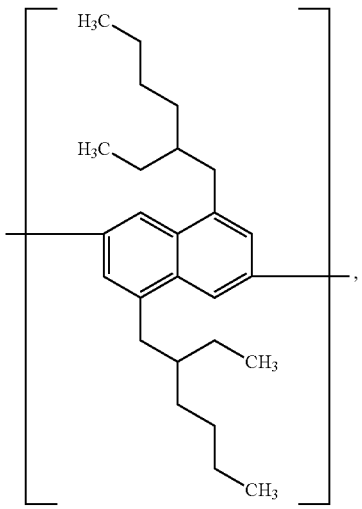

according to the theoretical value calculated from the charged raw materials.

<Comparative Example 4> (Synthesis of Polymer Compound 11)

An inert gas atmosphere was prepared in a reaction vessel, then, the compound 20 (1.4396 g, 2.48 mmol), the compound 21 (1.2157 g, 2.50 mmol), dichlorobis(triphenylphosphine)palladium (1.8 mg) and toluene (44 mL) were mixed in the vessel, and heated at 105° C. Into the reaction solution, a 20% by weight tetraethylammonium hydroxide aqueous solution (8.7 g) was dropped, and the mixture was refluxed for 3.5 hours. Since polymerization had not progressed and a polymer compound had not been obtained at this point, dichlorobis(triphenylphosphine)palladium (0.9 mg) was additionally added, and further, the mixture was refluxed for 3 hours, however, polymerization did not progress and a polymer compound was not obtained.

<Example D5> (Fabrication of Light Emitting Device D5)

A solution of the polymer compound 5 dissolved at a concentration of 1.0% by weight in chlorobenzene and a solution of the polymer compound 6 dissolved at a concentration of 1.0% by weight in chlorobenzene were mixed, at a weight ratio of polymer compound 5:polymer compound 6=90:10, to prepare a composition 1.

A light emitting device D5 was fabricated in the same manner as in Example D1 excepting that the composition 1 was used instead of the solution of the polymer compound 2 in Example D1, and spin-coated on a substrate for light emitting device at a rotation rate of 2600 rpm so as to form a film with a thickness of about 60 nm.

Voltage was applied to the light emitting device D5, to observe EL light emission showing a peak at 460 nm derived mainly from the polymer compound 5. The device started light emission from 2.7 V, and the maximum light emission efficiency thereof was 8.6 cd/A. The results are shown in Table 4.

The light emitting device D5 was driven at constant current after setting the current value so as to give an initial luminance of 5000 cd/m², and the time change of luminance was measured. As a result, it became 60% based on the initial luminance after 45 hours. The results are shown in Table 4.

TABLE 4

| | Polymer compound | Luminance life (time until becoming 60% of initial luminance) | Maximum light emission efficiency |
|---|---|---|---|
| Example D5 | polymer compound 5/ polymer compound 6 (weight ratio = 90/10) | 45 hours | 8.6 cd/A |

<Synthesis Example 18> (Synthesis of Polymer Compound 12)

An inert gas atmosphere was prepared in a reaction vessel, a compound 22 (1.4507 g, 1.96 mmol) represented by the following formula:

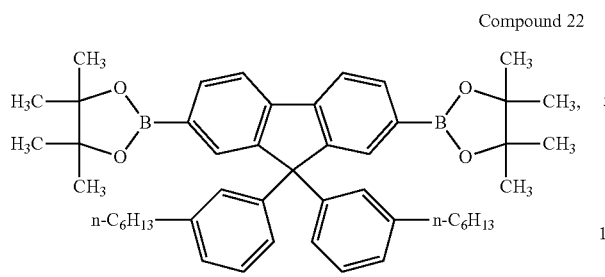

Compound 22

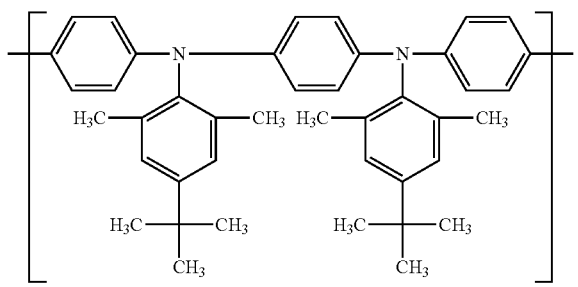

the compound 11 (0.9871 g, 1.80 mmol), the compound 15 (0.1478 g, 0.20 mmol), dichlorobis(triphenylphosphine)palladium (1.40 mg) and toluene (50 ml) were mixed in the vessel, and heated at 105° C.

Into the reaction solution, a 20% by weight tetraethylammonium hydroxide aqueous solution (7 ml) was dropped, and the mixture was refluxed for 2 hours and 20 minutes. After the reaction, to this were added phenylboronic acid (26 mg) and dichlorobis(triphenylphosphine)palladium (1.20 mg), and further, the mixture was refluxed for 17 hours. Then, to this was added a sodium diethyldithiacarbamate aqueous solution, and the mixture was stirred at 80 C.° for 2 hours. After cooling, the mixture was washed with water (26 ml) twice, with a 3% by weight acetic acid aqueous solution (26 ml) twice and with water (26 ml) twice, and the resultant solution was dropped into methanol (311 mL), and isolated by filtration, to obtain a precipitated material.

This precipitated material was dissolved in toluene (63 mL), and purified by passing through an alumina column and a silica gel column in series. The resultant solution was dropped into methanol (311 ml), stirred, then, the resultant precipitated material was isolated by filtration and dried, to obtain 1.49 g of a polymer compound 12. The polymer compound 12 had a polystyrene-equivalent number-average molecular weight of $1.1 \times 10^5$ and a polystyrene-equivalent weight-average molecular weight of $2.9 \times 10^5$.

The polymer compound 12 is a copolymer constituted of a constitutional unit represented by the following formula:

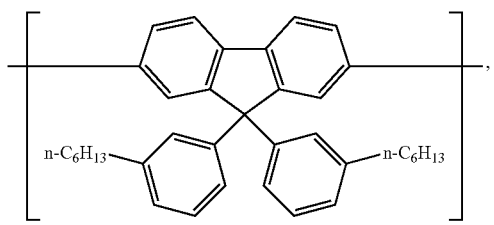

a constitutional unit represented by the following formula:

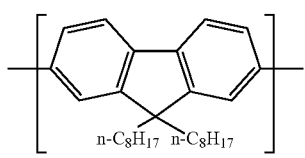

and a constitutional unit represented by the following formula:

at a molar ratio of 50:45:5, according to the theoretical value calculated from the amounts of the charged raw materials.

<Example D6> (Fabrication of Light Emitting Device D6)

A solution of the polymer compound 12 dissolved at a concentration of 0.9% by weight in chlorobenzene and a solution of the polymer compound 6 dissolved at a concentration of 0.9% by weight in chlorobenzene were mixed, at a weight ratio of polymer compound 12:polymer compound 6=90:10, to prepare a composition 2.

A light emitting device D6 was fabricated in the same manner as in Example D1 excepting that the composition 2 was used instead of the solution of the polymer compound 2 in Example D1, and spin-coated on a substrate for light emitting device at a rotation rate of 1900 rpm so as to form a film with a thickness of about 60 nm.

Voltage was applied to the light emitting device D6, to observe EL light emission showing a peak at 455 nm derived mainly from the polymer compound 12. The device started light emission from 2.7 V, and the maximum light emission efficiency thereof was 9.9 cd/A. The results are shown in Table 5.

The light emitting device D6 was driven at constant current after setting the current value so as to give an initial luminance of 5000 cd/m², and the time change of luminance was measured. As a result, it became 60% based on the initial luminance after 17 hours. The results are shown in Table 5.

<Example D7> (Fabrication of Light Emitting Device D7)

A solution of the polymer compound 12 dissolved at a concentration of 0.9% by weight in chlorobenzene and a solution of the polymer compound 6 dissolved at a concentration of 0.9% by weight in chlorobenzene were mixed, at a weight ratio of polymer compound 12:polymer compound 6=80:20, to prepare a composition 3.

A light emitting device D7 was fabricated in the same manner as in Example D1 excepting that the composition 3 was used instead of the solution of the polymer compound 2 in Example D1, and spin-coated on a substrate for light emitting device at a rotation rate of 2000 rpm so as to form a film with a thickness of about 60 nm.

Voltage was applied to the light emitting device D7, to observe EL light emission showing a peak at 455 nm derived mainly from the polymer compound 12. The device started light emission from 2.9V, and the maximum light emission efficiency thereof was 10.8 cd/A. The results are shown in Table 5.

The light emitting device D7 was driven at constant current after setting the current value so as to give an initial luminance of 5000 cd/m², and the time change of luminance was measured. As a result, it became 60% based on the initial luminance after 45 hours. The results are shown in Table 5.

<Comparative Example CD3> (Fabrication of Light Emitting Device CD3)

A light emitting device was fabricated in the same manner as in Example D1 excepting that a solution of the polymer compound 12 dissolved at a concentration of 0.9% by weight in chlorobenzene, instead of the polymer compound 2 in Example D1, was prepared, and spin-coated on a substrate for light emitting device at a rotation rate of 1700 rpm so as to form a film with a thickness of about 60 nm (hereinafter, referred to as "light emitting device CD3").

Voltage was applied to the light emitting device CD3, to observe EL light emission showing a peak at 455 nm derived mainly from the polymer compound 12. The device started light emission from 2.6 V, and the maximum light emission efficiency thereof was 7.6 cd/A. The results are shown in Table 5.

The light emitting device CD3 was driven at constant current after setting the current value so as to give an initial luminance of 5000 cd/m², and the time change of luminance was measured. As a result, it became 60% based on the initial luminance after 13 hours. The results are shown in Table 5.

TABLE 5

|  | Polymer compound | Luminance life (time until becoming 60% of initial luminance) | Maximum light emission efficiency |
|---|---|---|---|
| Example D6 | polymer compound 12/ polymer compound 6 (weight ratio = 90/10) | 17 hours | 9.9 cd/A |
| Example D7 | polymer compound 12/ polymer compound 6 (weight ratio = 80/20) | 45 hours | 10.8 cd/A |
| Comparative Example CD3 | polymer compound 12 | 13 hours | 7.6 cd/A |

<Example 21> (Synthesis of Polymer Compound 13)

An inert gas atmosphere was prepared in a reaction vessel, then, the compound 17 (1.3424 g, 1.98 mmol), the compound 4 (0.9187 g, 1.80 mmol), the compound 16 (0.2196 g, 0.20 mmol), dichlorobis(triphenylphosphine)palladium (1.4 mg) and toluene (47 mL) were mixed in the vessel, and heated at 105° C. Into the reaction solution, a 20% by weight tetraethylammonium hydroxide aqueous solution (6.6 mL) was dropped, and the mixture was refluxed for 2 hours and 40 minutes. After the reaction, to this were added phenylboronic acid (26 mg), a 20% by weight tetraethylammonium hydroxide aqueous solution (6.6 mL) and dichlorobis(triphenylphosphine)palladium (1.4 mg), and the mixture was refluxed for 18.5 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.2 g of a polymer compound 13. The polymer compound 13 had a polystyrene-equivalent number-average molecular weight of 8.4×10⁴ and a polystyrene-equivalent weight-average molecular weight of 2.5×10⁵.

The polymer compound 13 is a copolymer constituted of a constitutional unit represented by the following formula:

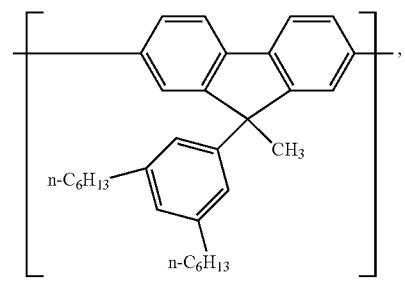

a constitutional unit represented by the following formula:

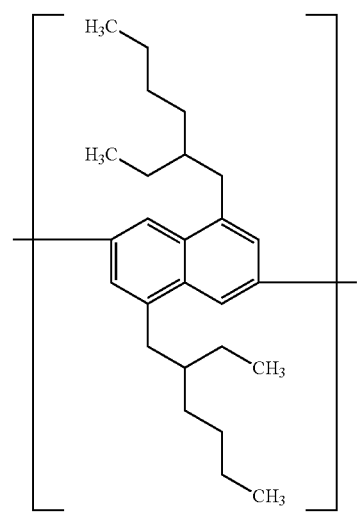

and a constitutional unit represented by the following formula:

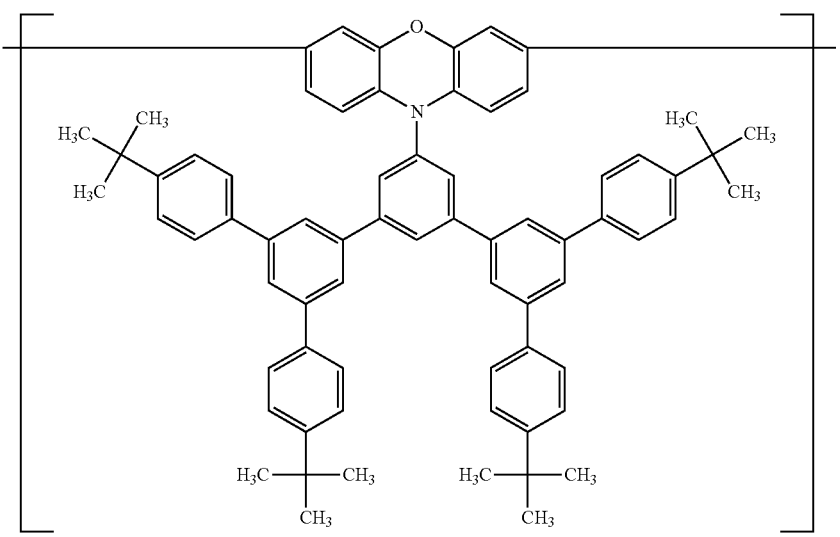
at a molar ratio of 50:45:5, and is a polymer compound constituted of a constitutional unit represented by the following formula:
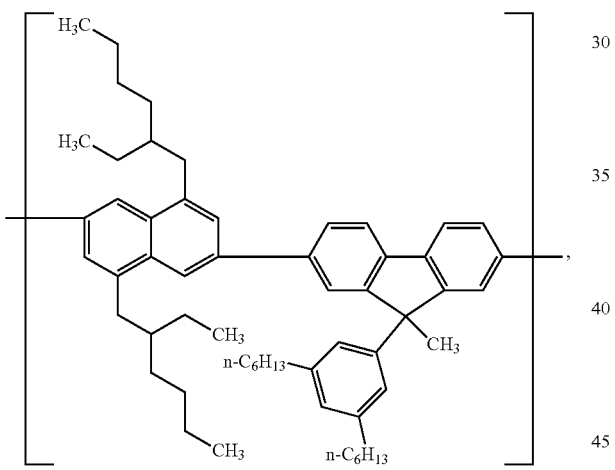
a constitutional unit represented by the following formula:
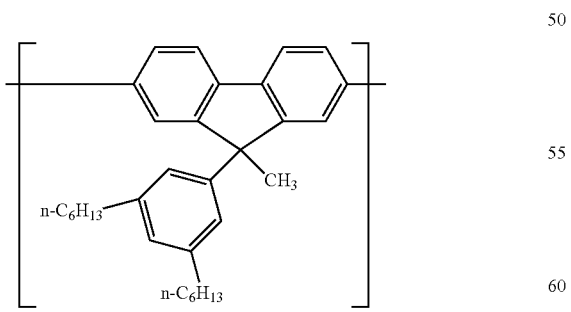
and a constitutional unit represented by the following formula:

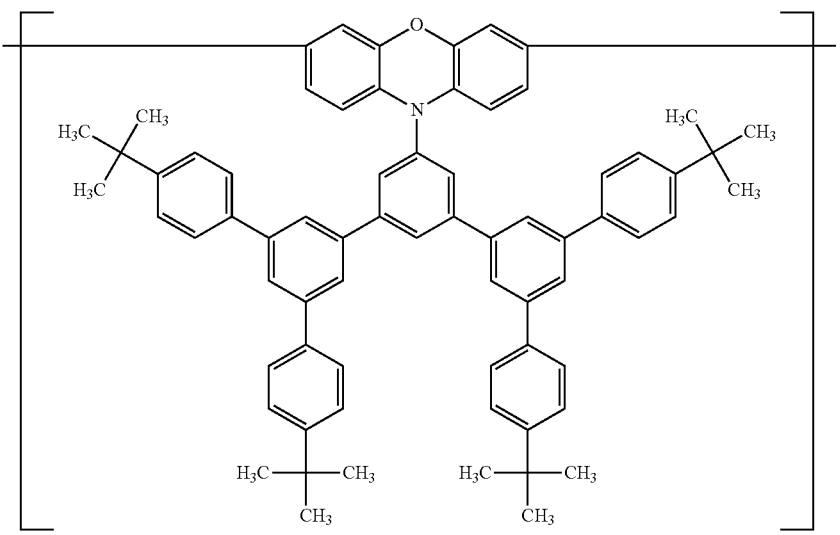

at a ratio of 82:9:9, according to the theoretical value calculated from the charged raw materials.

<Comparative Example 5> (Synthesis of Polymer Compound 14)

An inert gas atmosphere was prepared in a reaction vessel, then, the compound 17 (1.3369 g, 1.98 mmol), the compound 21 (0.8753 g, 1.80 mmol), the compound 16 (0.2196 g, 0.20 mmol), dichlorobis(triphenylphosphine)palladium (1.4 mg) and toluene (44 mL) were mixed in the vessel, and heated at 105° C. Into the reaction solution, a 20% by weight tetraethylammonium hydroxide aqueous solution (6.9 g) was dropped, and the mixture was refluxed for 22 hours. After the reaction, to this were added phenylboronic acid (24 mg), a 20% by weight tetraethylammonium hydroxide aqueous solution (6.9 g) and dichlorobis(triphenylphosphine) palladium (1.4 mg), and the mixture was refluxed for 21.5 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.13 g of a polymer compound 14. The polymer compound 14 had a polystyrene-equivalent number-average molecular weight of $6.9 \times 10^4$ and a polystyrene-equivalent weight-average molecular weight of $1.4 \times 10^5$.

The polymer compound 14 is a copolymer constituted of a constitutional unit represented by the following formula:

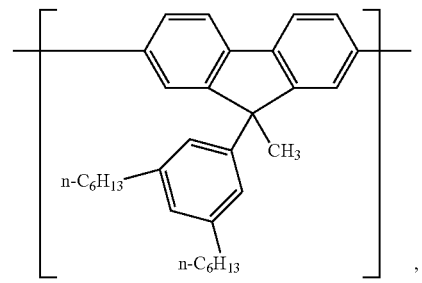

a constitutional unit represented by the following formula:

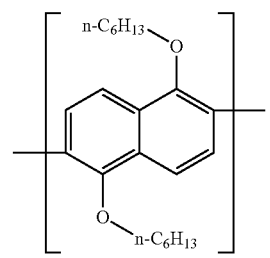

and a constitutional unit represented by the following formula:

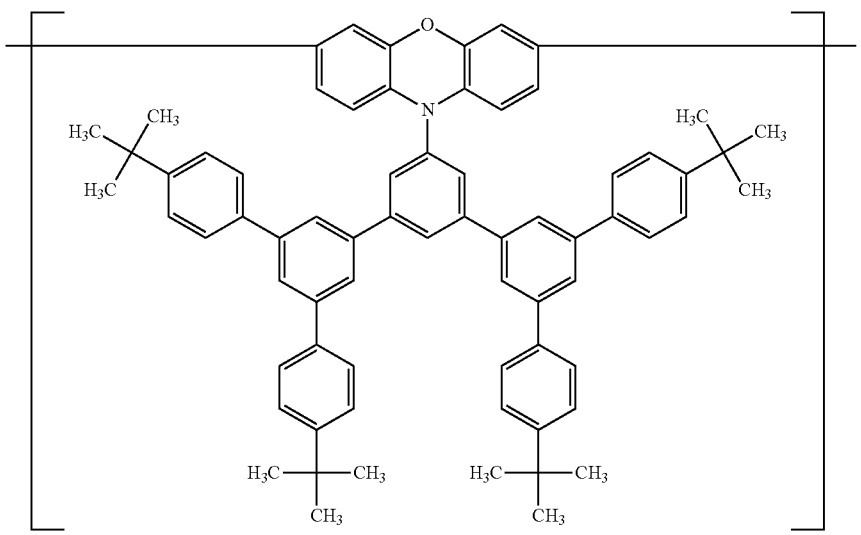
at a molar ratio of 50:45:5, and is a polymer compound constituted of a constitutional unit represented by the following formula:
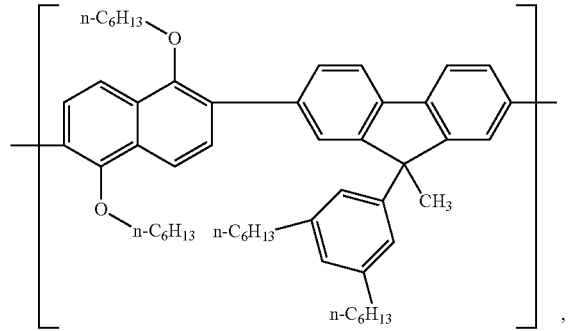
a constitutional unit represented by the following formula:
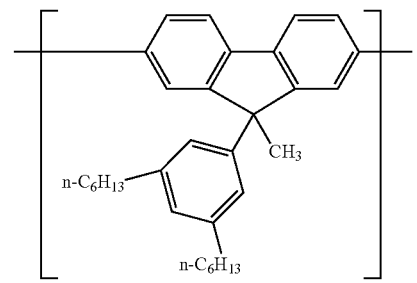
and a constitutional unit represented by the following formula:
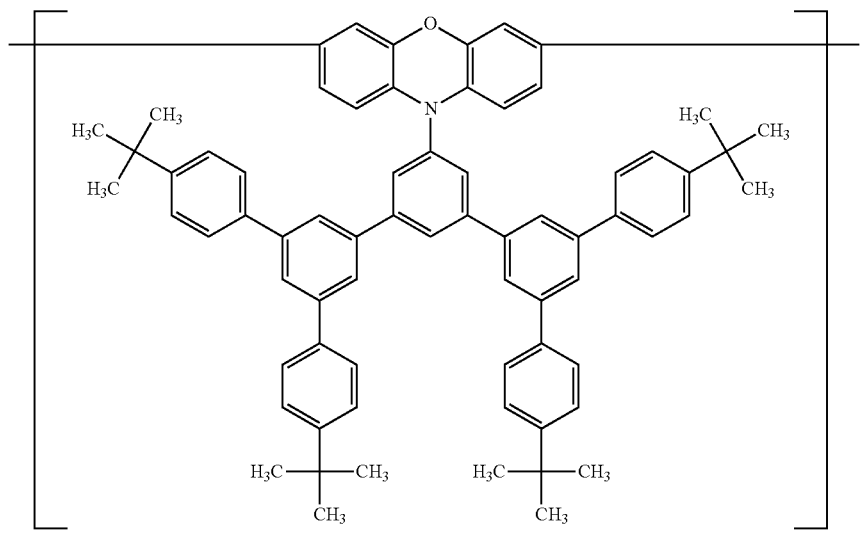

at a ratio of 82:9:9, according to the theoretical value calculated from the charged raw materials.

<Example D8> (Fabrication of Light Emitting Device D8)

A light emitting device was fabricated in the same manner as in Example D1 excepting that a solution of the polymer compound 13 dissolved at a concentration of 1.2% by weight in chlorobenzene, instead of the polymer compound 2 in Example D1, was prepared, and spin-coated on a substrate for light emitting device at a rotation rate of 2800 rpm so as to form a film with a thickness of about 60 nm (hereinafter, referred to as "light emitting device D8").

Voltage was applied to the light emitting device D8, to observe EL light emission showing a peak at 465 nm derived mainly from the polymer compound 13. The device started light emission from 2.7 V, and the maximum light emission efficiency thereof was 9.9 cd/A. The results are shown in Table 6.

The light emitting device D8 was driven at constant current after setting the current value so as to give an initial luminance of 5000 cd/m$^2$, and the time change of luminance was measured. As a result, it became 60% based on the initial luminance after 139 hours. The results are shown in Table 6.

<Comparative Example CD4> (Fabrication of Light Emitting Device CD4)

A light emitting device was fabricated in the same manner as in Example D1 excepting that a solution of the polymer compound 14 dissolved at a concentration of 1.0% by weight in chlorobenzene, instead of the polymer compound 2 in Example D1, was prepared, and spin-coated on a substrate for light emitting device at a rotation rate of 1500 rpm so as to form a film with a thickness of about 60 nm (hereinafter, referred to as "light emitting device CD4").

Voltage was applied to the light emitting device CD4, to observe EL light emission showing a peak at 460 nm derived mainly from the polymer compound 14. The device started light emission from 3.3 V, and the maximum light emission efficiency thereof was 8.7 cd/A. The results are shown in Table 6.

The light emitting device CD4 was driven at constant current after setting the current value so as to give an initial luminance of 5000 cd/m$^2$, and the time change of luminance was measured. As a result, it became 60% based on the initial luminance after 0.4 hours. The results are shown in Table 6.

TABLE 6

| | Polymer compound | Luminance life (time until becoming 60% of initial luminance) | Maximum light emission efficiency |
|---|---|---|---|
| Example D8 | polymer compound 13 | 139 hours | 9.9 cd/A |
| Comparative Example CD4 | polymer compound 14 | 0.4 hours | 8.7 cd/A |

<Example 22> (Synthesis of Polymer Compound 15)

An inert gas atmosphere was prepared in a reaction vessel, then, the compound 17 (1.3424 g, 1.98 mmol), the compound 4 (0.8983 g, 1.76 mmol), the compound 15 (0.1478 g, 0.20 mmol), the compound 16 (0.0439 g, 0.04 mmol), dichlorobis(triphenylphosphine)palladium (1.4 mg) and toluene (47 mL) were mixed in the vessel, and heated at 105° C. Into the reaction solution, a 20% by weight tetraethylammonium hydroxide aqueous solution (6.6 mL) was dropped, and the mixture was refluxed for 3 hours. After the reaction, to this were added phenylboronic acid (25 mg), a 20% by weight tetraethylammonium hydroxide aqueous solution (6.6 mL) and dichlorobis(triphenylphosphine)palladium (1.4 mg), and the mixture was refluxed for 17 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.22 g of a polymer compound 15. The polymer compound 15 had a polystyrene-equivalent number-average molecular weight of 7.4×10$^4$ and a polystyrene-equivalent weight-average molecular weight of 2.1× 10$^5$.

The polymer compound 15 is a copolymer constituted of a constitutional unit represented by the following formula:

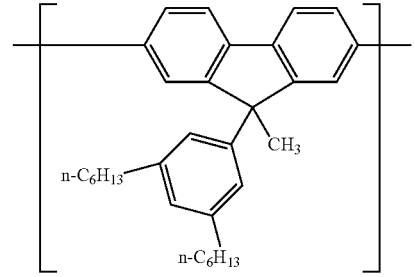

a constitutional unit represented by the following formula:

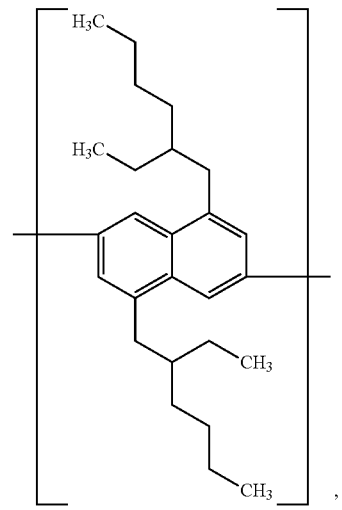

a constitutional unit represented by the following formula:

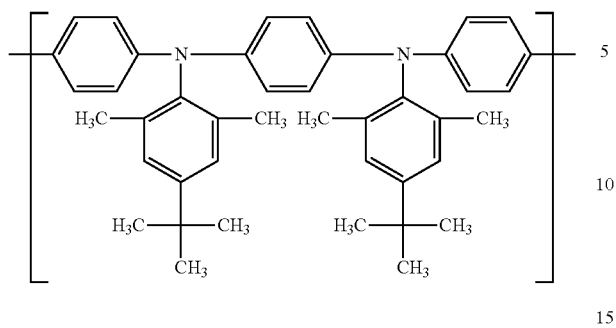

and a constitutional unit represented by the following formula:

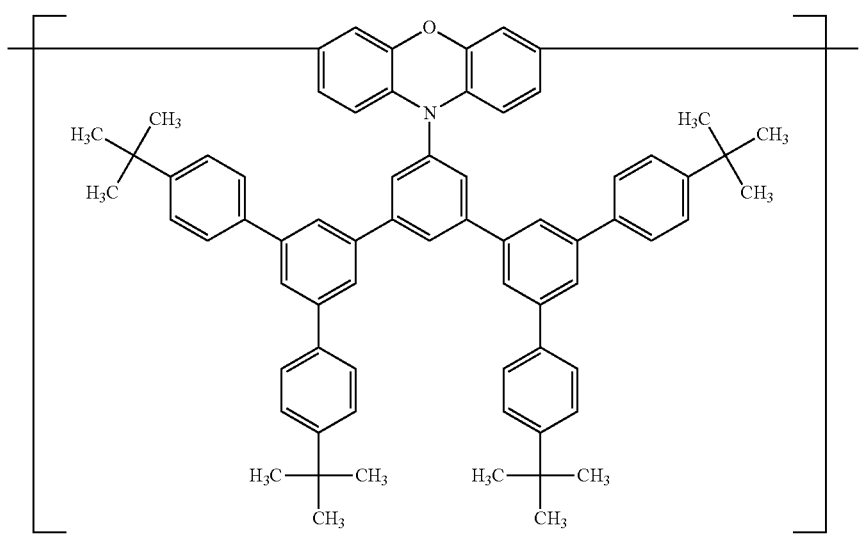

at a molar ratio of 50:44:5:1, and is a polymer compound constituted of a constitutional unit represented by the following formula:

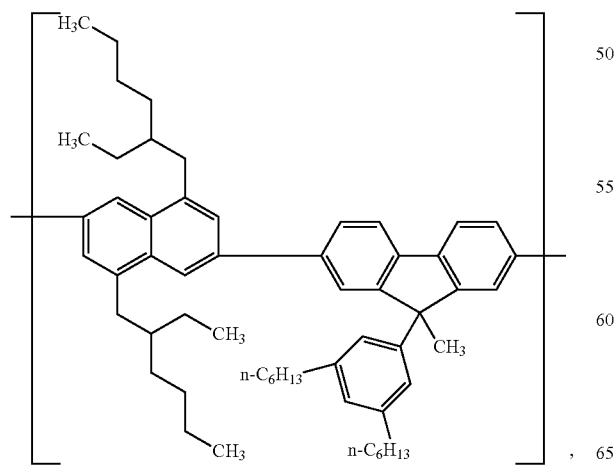

a constitutional unit represented by the following formula:

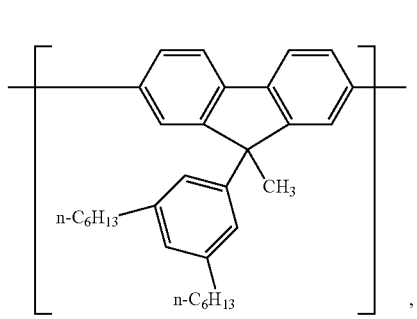

a constitutional unit represented by the following formula:

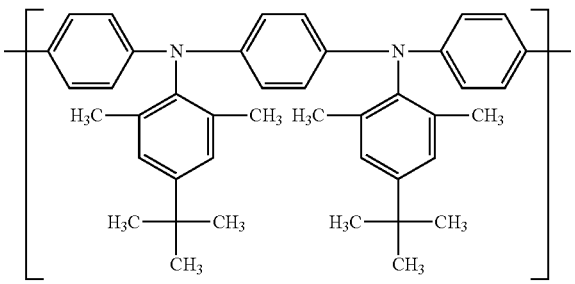

and a constitutional unit represented by the following formula:

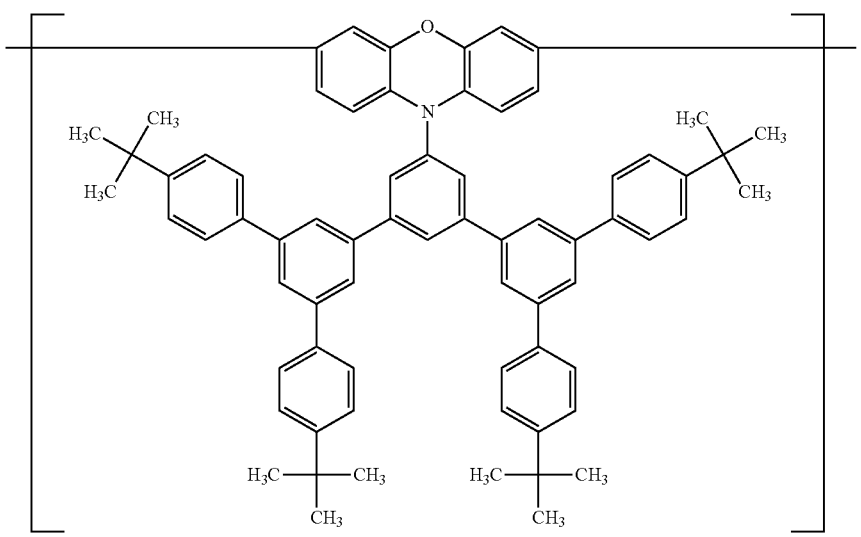

at a ratio of 79:11:9:2, according to the theoretical value calculated from the charged raw materials.

<Example 23> (Synthesis of Polymer Compound 16)

An inert gas atmosphere was prepared in a reaction vessel, then, the compound 3 (1.1957 g, 1.98 mmol), the compound 4 (0.8575 g, 1.68 mmol), the compound 15 (0.0886 g, 0.12 mmol), the compound 16 (0.2196 g, 0.20 mmol), dichlorobis(triphenylphosphine)palladium (1.4 mg) and toluene (47 mL) were mixed in the vessel, and heated at 105° C. Into the reaction solution, a 20% by weight tetraethylammonium hydroxide aqueous solution (6.6 mL) was dropped, and the mixture was refluxed for 2 hours. After the reaction, to this were added phenylboronic acid (25 mg), a 20% by weight tetraethylammonium hydroxide aqueous solution (6.6 mL) and dichlorobis(triphenylphosphine)palladium (1.4 mg), and the mixture was refluxed for 19 hours. Then, to this was added a sodium diethyldithiacarbamate aqueous solution, and the mixture was stirred at 80 C.° for 2 hours. After cooling, the reaction solution was washed with water twice, with a 3% by weight acetic acid aqueous solution twice and with water twice, and the resultant solution was dropped into methanol, and isolated by filtration, to obtain a precipitated material. This precipitated material was dissolved in toluene, and purified by passing through an alumina column and a silica gel column in series. The resultant solution was dropped into methanol, stirred, then, the resultant precipitated material was isolated by filtration and dried, to obtain 1.14 g of a polymer compound 16. The polymer compound 16 had a polystyrene-equivalent number-average molecular weight of $8.4 \times 10^4$ and a polystyrene-equivalent weight-average molecular weight of $2.5 \times 10^5$.

The polymer compound 16 is a copolymer constituted of a constitutional unit represented by the following formula:

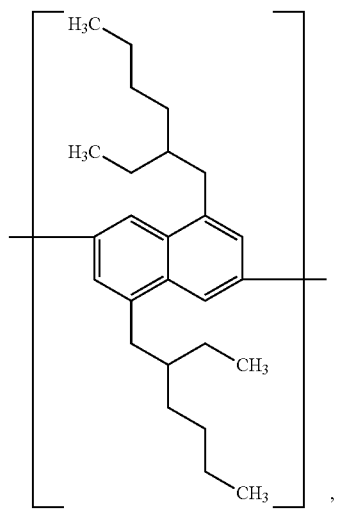

a constitutional unit represented by the following formula:

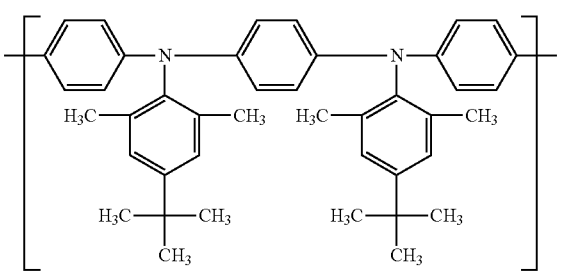

and a constitutional unit represented by the following formula:

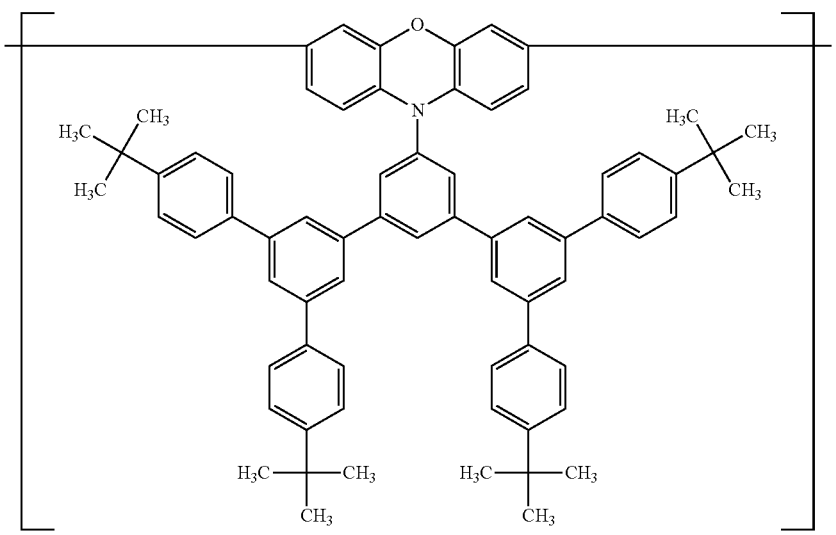
at a molar ratio of 92:3:5, and is a polymer compound constituted of a constitutional unit represented by the following formula:
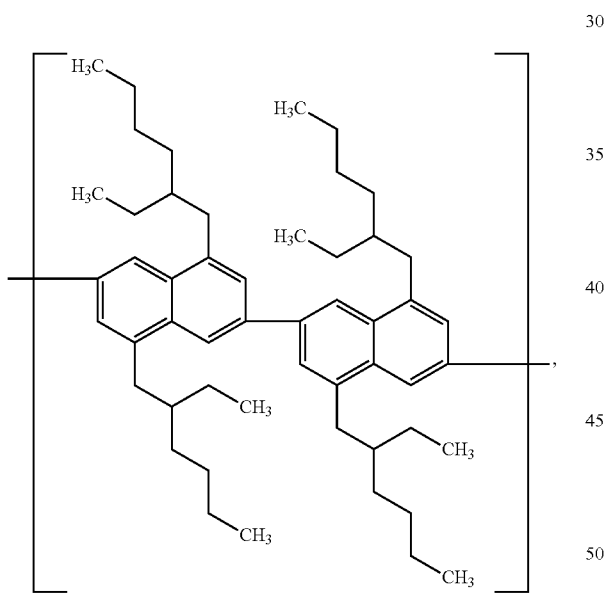
a constitutional unit represented by the following formula:

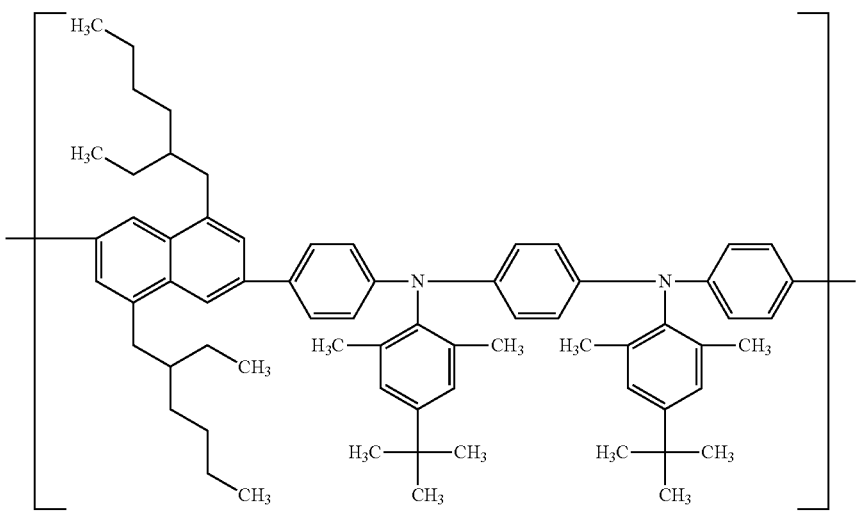
and a constitutional unit represented by the following formula:
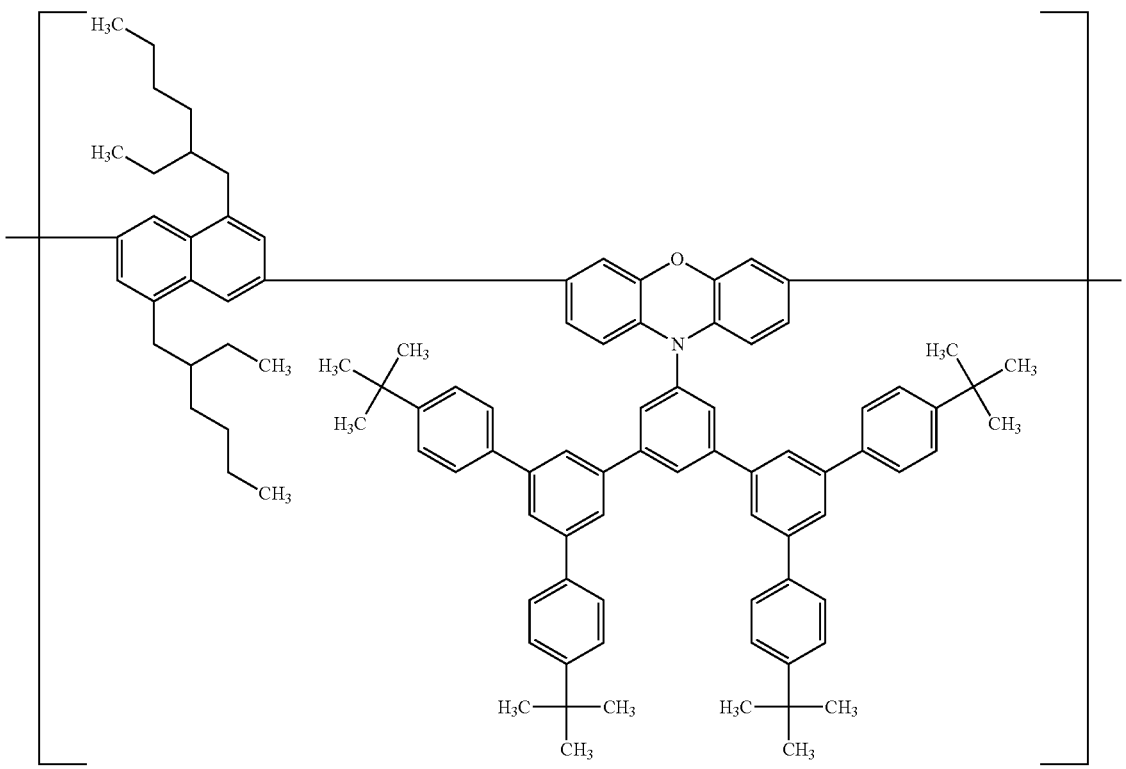

at a ratio of 84:6:10, according to the theoretical value calculated from the charged raw materials.

<Example D9> (Fabrication of Light Emitting Device D9)

A light emitting device was fabricated in the same manner as in Example D1 excepting that a solution of the polymer compound 15 dissolved at a concentration of 0.9% by weight in chlorobenzene, instead of the polymer compound 2 in Example D1, was prepared, and spin-coated on a substrate for light emitting device at a rotation rate of 1500 rpm so as to form a film with a thickness of about 60 nm (hereinafter, referred to as "light emitting device D9").

Voltage was applied to the light emitting device D9, to observe EL light emission showing a peak at 460 nm derived mainly from the polymer compound 15. The device started light emission from 2.6 V, and the maximum light emission efficiency thereof was 8.5 cd/A. The results are shown in Table 7.

The light emitting device D9 was driven at constant current after setting the current value so as to give an initial luminance of 5000 cd/m$^2$, and the time change of luminance was measured. As a result, it became 60% based on the initial luminance after 85 hours. The results are shown in Table 7.

<Example D10> (Fabrication of Light Emitting Device D10)

A light emitting device was fabricated in the same manner as in Example D1 excepting that a solution of the polymer compound 16 dissolved at a concentration of 1.0% by weight in chlorobenzene, instead of the polymer compound 2 in Example D1, was prepared, and spin-coated on a substrate for light emitting device at a rotation rate of 2500 rpm so as to form a film with a thickness of about 60 nm (hereinafter, referred to as "light emitting device D10").

Voltage was applied to the light emitting device D10, to observe EL light emission showing a peak at 465 nm derived mainly from the polymer compound 16. The device started light emission from 2.6 V, and the maximum light emission efficiency thereof was 10.9 cd/A. The results are shown in Table 7.

The light emitting device D10 was driven at constant current after setting the current value so as to give an initial luminance of 5000 cd/m$^2$, and the time change of luminance was measured. As a result, it became 60% based on the initial luminance after 66 hours. The results are shown in Table 7.

TABLE 7

| Polymer compound | Luminance life (time until becoming 60% of initial luminance) | Maximum light emission efficiency |
|---|---|---|
| Example D9 | polymer compound 15 | 85 hours | 8.5 cd/A |
| Example D10 | polymer compound 16 | 66 hours | 10.9 cd/A |

INDUSTRIAL APPLICABILITY

The polymer compound of the present invention gives, when used in fabrication of a light emitting device, excellent luminance life of the resulting light emitting device. Therefore, the polymer compound of the present invention is useful, for example, as an electronic material such as a light emitting material, a charge transporting material and the like. Further, the polymer compound and the light emitting device of the present invention are useful for backlights of liquid crystal displays, curved or flat light sources for illumination, segment type display devices, dot matrix type flat panel displays and the like.

The invention claimed is:
1. A polymer compound comprising a constitutional unit represented by the following formula (1) and a constitutional unit represented by the following formula (10):

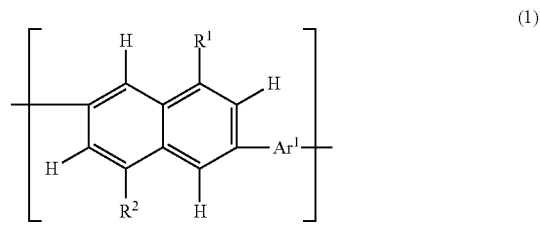

in the formula (1),
$R^1$ and $R^2$ represent each independently an unsubstituted or substituted alkyl group or an unsubstituted or substituted aryl group,
$Ar^1$ represents an unsubstituted or substituted arylene group, an unsubstituted or substituted di-valent condensed polycyclic aromatic heterocyclic group or a di-valent aromatic amine residue represented by the following formula (2),
with the proviso that the skeleton of a ring linked to a naphthalene ring in said unsubstituted or substituted di-valent condensed polycyclic aromatic heterocyclic group consists only of carbon atoms;

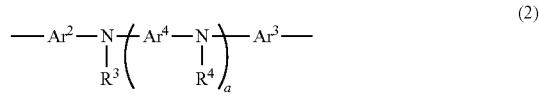

in the formula (2),
$Ar^2$, $Ar^3$ and $Ar^4$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups,
$R^3$ and $R^4$ represent each independently a hydrogen atom, an unsubstituted or substituted alkyl group, an unsubstituted or substituted aryl group or an unsubstituted or substituted mono-valent aromatic heterocyclic group, a is 0 or 1:

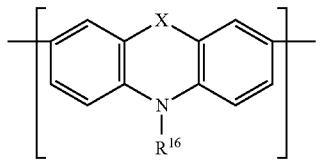
(10)

in the formula (10),
$R^{16}$ represents an unsubstituted or substituted alkyl group, an unsubstituted or substituted aryl group or an unsubstituted or substituted mono-valent aromatic heterocyclic group,
X represents a single bond, —O—, —S— or —C($R^a$)—, wherein $R^a$ represents an unsubstituted or substituted alkyl group or an unsubstituted or substituted aryl group, two $R^a$s may be the same or different.

2. The polymer compound according to claim 1, wherein $Ar^1$ is an unsubstituted or substituted arylene group.

3. The polymer compound according to claim 2, wherein $Ar^1$ is an unsubstituted or substituted fluorenediyl group or an unsubstituted or substituted naphthalenediyl group.

4. The polymer compound according to claim 3, wherein the constitutional unit represented by the formula (1) is a constitutional unit represented by the following formula (3):

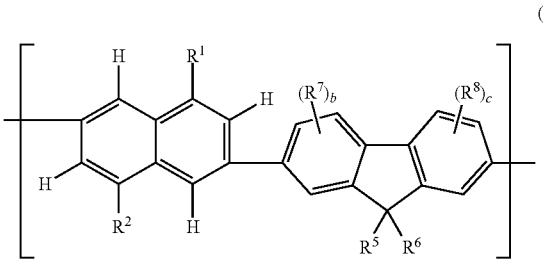
(3)

in the formula (3),
$R^1$ and $R^2$ represent the same meaning as described above,
$R^5$ and $R^6$ represent each independently a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group,
$R^7$ and $R^8$ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, when a plurality of $R^7$s and $R^8$s are present, each of them may be the same or different,
b and c represent each independently an integer of 0 to 3.

5. The polymer compound according to claim 4, wherein $R^5$ is an unsubstituted or substituted alkyl group and $R^6$ is an unsubstituted or substituted aryl group.

6. The polymer compound according to claim 4, wherein $R^5$ is an unsubstituted or substituted aryl group and $R^6$ is an unsubstituted or substituted aryl group.

7. The polymer compound according to claim 1, wherein $Ar^1$ is a di-valent aromatic amine residue represented by the formula (2).

8. The polymer compound according to claim 1, further comprising at least one constitutional unit selected from the group consisting of a constitutional unit represented by the following formula (4), and a constitutional unit represented by the following formula (6):

(4)

in the formula (4), $Ar^5$ represents an unsubstituted or substituted arylene group,

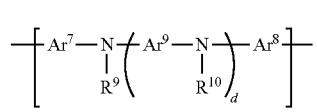
(6)

in the formula (6),
$Ar^7$, $Ar^8$ and $Ar^9$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups,
$R^9$ and $R^{10}$ represent each independently a hydrogen atom, an unsubstituted or substituted alkyl group, an unsubstituted or substituted aryl group or an unsubstituted or substituted mono-valent aromatic heterocyclic group,
d is 0 or 1.

9. The polymer compound according to claim 8, consisting of a constitutional unit represented by the formula (1), a constitutional unit represented by the formula (10), and at least one constitutional unit selected from the group consisting of a constitutional unit represented by the formula (4) and a constitutional unit represented by the formula (6).

10. The polymer compound according to claim 8, wherein $Ar^5$ is an unsubstituted or substituted phenylene group, an unsubstituted or substituted naphthalenediyl group or an unsubstituted or substituted fluorenediyl group.

11. The polymer compound according to claim 8, wherein the constitutional unit represented by the formula (4) is a constitutional unit represented by the following formula (7), a constitutional unit represented by the following formula (8) or a constitutional unit represented by the following formula (9):

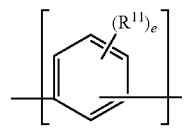
(7)

in the formula (7),
$R^{11}$ represents an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, when a plurality of $R^{11}$s are present, these may be the same or different, e is an integer of 0 to 4;

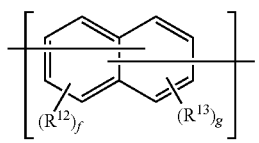
(8)

in the formula (8), $R^{12}$ and $R^{13}$ represent each independently an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group, when a plurality of $R^{12}$s and $R^{13}$s are present, each of them may be the same or different, f and g represent each independently an integer of 0 to 4, with the proviso that f+g is 6 or less;

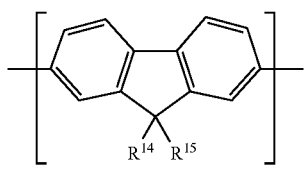
(9)

in the formula (9), $R^{14}$ and $R^{15}$ represent each independently a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.

12. The polymer compound according to claim 1, comprising a constitutional unit represented by the following formula (11):

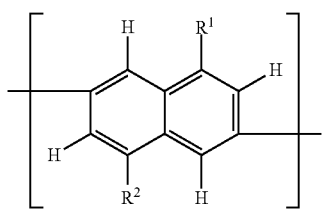
(11)

in the formula (11), $R^1$ and $R^2$ represent the same meaning as described above.

13. A composition comprising the polymer compound as described in claim 12 and a polymer compound consisting of at least one constitutional unit selected from the group consisting of a constitutional unit represented by the formula (5), a constitutional unit represented by the formula (6) and a constitutional unit represented by the formula (9) as a material selected from the group consisting of hole transporting materials, electron transporting materials and light emitting materials:

(5)

in the formula (5), $Ar^6$ represents an unsubstituted or substituted di-valent aromatic heterocyclic group;

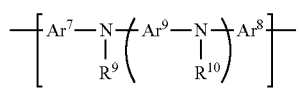
(6)

in the formula (6), $Ar^7$, $Ar^8$ and $Ar^9$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups, $R^9$ and $R^{10}$ represent each independently a hydrogen atom, an unsubstituted or substituted alkyl group, an unsubstituted or substituted aryl group or an unsubstituted or substituted mono-valent aromatic heterocyclic group, d is 0 or 1;

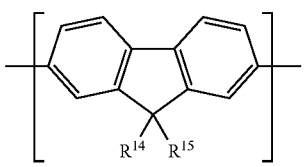
(9)

in the formula (9), $R^{14}$ and $R^{15}$ represent each independently a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.

14. A composition comprising at least one material selected from the group consisting of hole transporting materials, electron transporting materials and light emitting materials and the polymer compound as described in claim 1.

15. The composition according to claim 14, wherein the at least one material selected from the group consisting of hole transporting materials, electron transporting materials and light emitting materials is a polymer compound consisting of at least one constitutional unit selected from the group consisting of a constitutional unit represented by a constitutional unit represented by the formula (5), a constitutional unit represented by the formula (6) and a constitutional unit represented by the formula (9):

(5)

in the formula (5), $Ar^6$ represents an unsubstituted or substituted di-valent aromatic heterocyclic group;

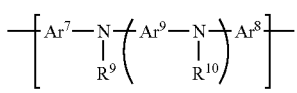 (6)

in the formula (6), $Ar^7$, $Ar^8$ and $Ar^9$ represent each independently an unsubstituted or substituted arylene group, an unsubstituted or substituted di-valent aromatic heterocyclic group or a group obtained by linking two or more groups selected from the group consisting of unsubstituted or substituted arylene groups and unsubstituted or substituted di-valent aromatic heterocyclic groups, $R^9$ and $R^{10}$ represent each independently a hydrogen atom, an unsubstituted or substituted alkyl group, an unsubstituted or substituted aryl group or an unsubstituted or substituted mono-valent aromatic heterocyclic group, d is 0 or 1;

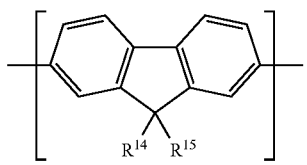 (9)

in the formula (9), $R^{14}$ and $R^{15}$ represent each independently a hydrogen atom, an unsubstituted or substituted alkyl group, an unsubstituted or substituted aryl group, an unsubstituted or substituted mono-valent aromatic heterocyclic group, an unsubstituted or substituted alkoxy group or an unsubstituted or substituted aryloxy group.

16. A liquid composition comprising the polymer compound as described in claim 1, and a solvent.

17. A film comprising the polymer compound as described in claim 1.

18. A light emitting device having electrodes consisting of an anode and a cathode and a layer containing the polymer compound as described in claim 1, disposed between the electrodes.

* * * * *